US010722564B2

United States Patent
Pinschewer et al.

(10) Patent No.: US 10,722,564 B2
(45) Date of Patent: Jul. 28, 2020

(54) TRI-SEGMENTED ARENAVIRUSES AS VACCINE VECTORS

(71) Applicant: UNIVERSITÉ DE GENÈVE, Genève (CH)

(72) Inventors: Daniel David Pinschewer, Binningen (CH); Doron Merkler, Geneva (CH); Sandra Margarete Kallert, Basel (CH); Mario Kreutzfeldt, Carouge (CH); Stéphanie Gabrielle Darbre Abdelrahman, Lausanne (CH); Nicolas Jean Page, Bonneville (FR)

(73) Assignee: UNIVERSITÉ DE GENÉVE, Geneva (CH)

( * ) Notice: Subject to any disclaimer, the term of this patent is extended or adjusted under 35 U.S.C. 154(b) by 510 days.

(21) Appl. No.: 15/526,211

(22) PCT Filed: Nov. 12, 2015

(86) PCT No.: PCT/EP2015/076458
§ 371 (c)(1),
(2) Date: May 11, 2017

(87) PCT Pub. No.: WO2016/075250
PCT Pub. Date: May 19, 2016

(65) Prior Publication Data
US 2017/0319673 A1    Nov. 9, 2017

Related U.S. Application Data

(60) Provisional application No. 62/079,493, filed on Nov. 13, 2014.

(51) Int. Cl.
*A61K 39/00* (2006.01)
*C12N 15/86* (2006.01)
*C12N 7/00* (2006.01)

(52) U.S. Cl.
CPC ............ *A61K 39/0011* (2013.01); *C12N 7/00* (2013.01); *C12N 15/86* (2013.01); *A61K 2039/5254* (2013.01); *A61K 2039/5256* (2013.01); *A61K 2039/545* (2013.01); *A61K 2039/572* (2013.01); *C12N 2760/10021* (2013.01); *C12N 2760/10034* (2013.01); *C12N 2760/10043* (2013.01); *C12N 2760/10062* (2013.01); *C12N 2840/85* (2013.01)

(58) Field of Classification Search
CPC .......... A61K 39/00; C12N 15/86; C12N 7/00; C12N 2760/10043
See application file for complete search history.

(56) References Cited

U.S. PATENT DOCUMENTS

| | | | |
|---|---|---|---|
| 5,057,540 A | 10/1991 | Kensil et al. | |
| 8,592,205 B2 | 11/2013 | Pinschewer et al. | |
| 9,309,289 B2 | 4/2016 | Pinschewer et al. | |
| 9,809,801 B2 | 11/2017 | Belnoue et al. | |
| 9,944,952 B2 | 4/2018 | Pinschewer et al. | |
| 10,111,945 B2 | 10/2018 | Orlinger et al. | |
| 2016/0206724 A1 | 7/2016 | De la Torre et al. | |
| 2018/0179257 A1 | 6/2018 | Orlinger et al. | |
| 2018/0319845 A1 | 11/2018 | Monath et al. | |
| 2018/0344830 A1 | 12/2018 | Schmidt et al. | |
| 2019/0062784 A1 | 2/2019 | Pinschewer et al. | |

FOREIGN PATENT DOCUMENTS

| | | |
|---|---|---|
| WO | WO 2007/109812 A2 | 9/2007 |
| WO | WO 2007/109813 A1 | 9/2007 |
| WO | WO 2009/083210 A1 | 7/2009 |
| WO | WO 2011/095760 A1 | 8/2011 |
| WO | WO 2012/162428 A1 | 11/2012 |
| WO | WO 2013/112549 A1 | 8/2013 |
| WO | WO 2014/140301 A1 | 9/2014 |
| WO | WO 2014/155076 A1 | 10/2014 |
| WO | WO 2015/082570 A1 | 6/2015 |
| WO | WO 2015/183895 A1 | 12/2015 |
| WO | WO 2016/048949 A1 | 3/2016 |
| WO | WO 2016/071683 A2 | 5/2016 |
| WO | WO 2016/075250 A1 | 5/2016 |
| WO | WO 2016/166285 A1 | 10/2016 |
| WO | WO 2016/198531 A2 | 12/2016 |
| WO | WO 2017/068190 A1 | 4/2017 |
| WO | WO 2017/076988 A1 | 5/2017 |
| WO | WO 2017/080920 A1 | 5/2017 |
| WO | WO 2017/198726 A1 | 11/2017 |

(Continued)

OTHER PUBLICATIONS

Albarino et al., "Efficient rescue of recombinant Lassa virus reveals the influence of S segment noncoding regions on virus replication and virulence," *J. Virol.*, 85(8):4020-4024 (2011).
Altman et al., "Phenotypic analysis of antigen-specific T lymphocytes," *Science*, 274:94-96 (1996).
Barton, "Lymphocytic choriomeningitis virus: a neglected central nervous system pathogen," *Clin. Infect. Dis.*, 22(1):197 (1996).
Bonilla et al., "Interpretation of lymphocyte proliferation tests," *Ann. Allergy Asthma Immunol.*, 101:101-104 (2008).
Bonilla et al., "Practice parameter for the diagnosis and management of primary immunodeficiency," *Ann. Allergy Asthma Innumol.*, 94(5 Supp 1):S1-63 (2005).
Brennan et al., "The consequences of reconfiguring the ambisense S genome segment of Rift Valley fever virus on viral replication in mammalian and mosquito cells and for genome packaging," *PLoS Pathog.*, 10(2):e1003922 (2014).

(Continued)

*Primary Examiner* — Antonio Galisteo Gonzalez
(74) *Attorney, Agent, or Firm* — Jones Day

(57) ABSTRACT

The present application relates to arenaviruses with rearrangements of their open reading frames ("ORF") in their genomes. In particular, described herein is a modified arenavirus genomic segment, wherein the arenavirus genomic segment is engineered to carry a viral ORF in a position other than the wild-type position of the ORF. Also described herein are trisegmented arenavirus particles comprising one L segment and two S segments or two L segments and one S segment. The arenavirus, described herein may be suitable for vaccines and/or treatment of diseases and/or for the use in immunotherapies.

Figure 1:
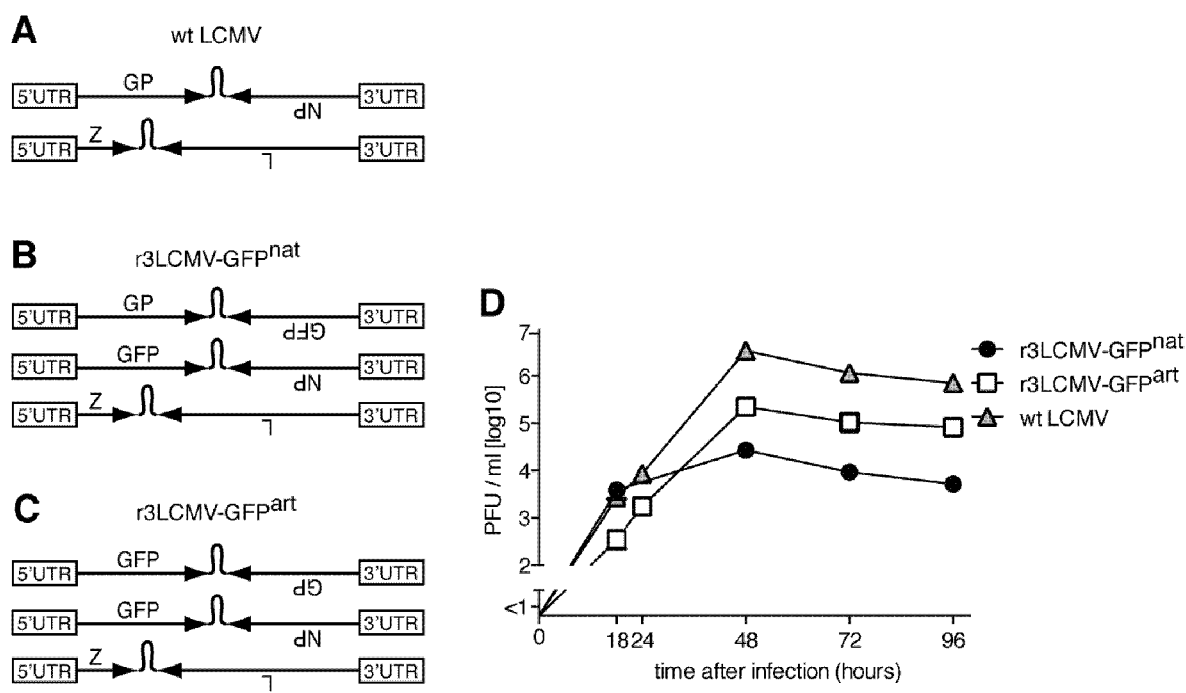

31 Claims, 14 Drawing Sheets
Specification includes a Sequence Listing.

(56) References Cited

FOREIGN PATENT DOCUMENTS

| WO | WO 2018/083220 A2 | 5/2018 |
| WO | WO 2018/185307 A1 | 10/2018 |

OTHER PUBLICATIONS

Buchmeier et al., "Protein structure of lymphocytic choriomeningitis virus: evidence for a cell-associated precursor of the virion glycopeptides," Virology, 99(1):111-120 (1979).
Buchmeier et al., "Arenaviridae: The Viruses and Their Replication," Fields Virol., 2:1635-1668 (2001).
Cao et al., "Identification of alpha-dystroglycan as a receptor for lymphocytic choriomeningitis virus and Lassa fever virus," Science, 282(5396):2079-2081 (1998).
Caruso et al., "Flow cytometric analysis of activation markers on stimulated T cells and their correlation with cell proliferation," Cytometry, 27:71-76 (1997).
Cheng et al., "Arenavirus Genome Rearrangement for the Development of Live Attenuated Vaccines," J. Virol., 89(14):7373-7384 (2015).
Cheng et al., "Generation of recombinant arenavirus for vaccine development in FDA-approved Vero cells," J. Vis. Exp., 78: 50662 (2013).
Czerkinsky et al., "A solid-phase enzyme-linked immunospot (ELISPOT) assay for enumeration of specific antibody-secreting cells," J. Immunol. Methods, 65:109-121 (1983).
Emonet et al., "Generation of recombinant lymphocytic choriomeningitis viruses with trisegmented genomes stably expressing two additional genes of interest," Proc. Natl. Acad. Sci. U.S.A., 106(9):3473-3478 (2009).
Emonet et al., "Arenavirus reverse genetics: new approaches for the investigation of arenavirus biology and development of antiviral strategies," Virology, 411(2):416-425 (2011).
Emonet et al., "Rescue from Cloned cDNAs and In Vivo Characterization of Recombinant Pathogenic Romero and Live-Attenuated Candid #1 Strains of Junin Virus, the Causative Agent of Argentine Hemorrhagic Fever Disease," J. Virol., 85(4):1473-1483 (2011).
Flatz et al., "Recovery of an arenavirus entirely from RNA polymerase I/II-driven cDNA," Proc. Natl. Acad. Sci. U.S.A., 103(12):4663-4668 (2006).
Flick et al., "Transient Bicistronic vRNA Segments for Indirect Selection of Recombinant Influenza Viruses," Virol., 262(1):93-103 (1999).
Garcia-Sastre et al., "Use of a mammalian internal ribosomal entry site element for expression of a foreign protein by a transfectant influenza virus," J. Virol., 68(10):6254-6261 (1994).
Geisbert et al., "Exotic emerging viral diseases: progress and challenges," Nat. Med., 10(12 Suppl): S110-S121 (2004).
Ghanekar et al., "Gamma interferon expression in CD8(+) T cells is a marker for circulating cytotoxic T lymphocytes that recognize an HLA A2-restricted epitope of human cytomegalovirus phosphoprotein pp65," Clin. Diagn. Lab Immunol., 8(3):628-631 (2001).
Hass et al., "Replicon system for Lassa virus," J. Virol., 78(24):13793-13803 (2004).
Hicks et al., "Age-related changes in mitogen-induced lymphocyte function from birth to old age," Am. J. Clin. Pathol., 80(2):159-163 (1983).
Hutchings et al., "The detection and enumeration of cytokine-secreting cells in mice and man and the clinical application of these assays," J. Immunol. Methods, 120(1):1-8 (1989).
Johnson et al., "Isolation of Machupo virus from wild rodent Calomys callosus," Am. J. Trop. Med. Hyg., 15(1):103-106 (1966).
Iwasaki et al., "General Molecular Strategy for Development of Arenavirus Live-Attenuated Vaccines," J. Virol., 89(23):12166-12177 (2015).
Kallert et al., "Replicating viral vector platform exploits alarmin signals for potent $CD8^+T$ cell-mediated tumour immunotherapy," Nat. Comm., 8:15327 (2017).
Lee et al., "Identification of the lymphocytic choriomeningitis virus (LCMV) proteins required to rescue LCMV RNA analogs into LCMV-like particles," J. Virol., 76(12):6393-6397 (2002).
Lee et al., "NP and L proteins of lymphocytic choriomeningitis virus (LCMV) are sufficient for efficient transcription and replication of LCMV genomic RNA analogs," J. Virol., 74(8):3470-3477 (2000).
Lopez et al., "Transcription and RNA replication of tacaribe virus genome and antigenome analogs require N and L proteins: Z protein is an inhibitor of these processes," J. Virol., 75(24):12241-12251 (2001).
Machado et al., "Expression of a foreign gene by stable recombinant influenza viruses harboring a dicistronic genomic segment with an internal promoter," Virol., 313(1):235-249 (2003).
Meyer et al., "Concurrent sequence analysis of 5' and 3' RNA termini by intramolecular circularization reveals 5' nontemplated bases and 3' terminal heterogeneity for lymphocytic choriomeningitis virus mRNAs," J. Virol., 67(5):2621-2627 (1993).
Mills et al., "Prevalence of infection with Junin virus in rodent populations in the epidemic area of Argentine hemorrhagic fever," Am. J trop. Med. Hyg., 51(5):554-562 (1994).
Murali-Krishna et al., "Counting antigen-specific CD8 T cells: a reevaluation of bystander activation during viral infection," Immunity, 8(2):177-187 (1998).
Nomura et al., "Optimization of whole blood antigen-specific cytokine assays for CD4(+) T cells," Cytometry, 40:60-68 (2000).
Oldstone, "Biology and pathogenesis of lymphocytic choriomeningitis virus infection," Curr. Top. Microbiol. Immunol., 263:83-117 (2002).
Ortiz-Riano et al., "Arenavirus reverse genetics for vaccine development," J. Gen. Virol., 94:1175-1188 (2013).
Percy et al., "Expression of a foreign protein by influenza A virus," J. Virol., 68(7):4486-4492 (1994).
Perez et al., "Characterization of the genomic promoter of the prototypic arenavirus lymphocytic choriomeningitis virus," J Virol., 77(2):1184-1194 (2003).
Perfetto et al., "Seventeen-colour flow cytometry: unravelling the immune system," Nat. Rev. Immunol., 4(8):648-655 (2004).
Pinschewer et al., "Dual role of the lymphocytic choriomeningitis virus intergenic region in transcription termination and virus propagation," J. Virol., 79(7):4519-4526 (2005).
Pinschewer et al., "Role of the virus nucleoprotein in the regulation of lymphocytic choriomeningitis virus transcription and RNA replication," J. Virol., 77(6):3882-3887 (2003).
Popkin et al., "Expanded Potential for Recombinant Trisegmented Lymphocytic Choriomeningitis Viruses: Protein Production, Antibody Production, and In Vivo Assessment of Biological Function of Genes of Interest," J. Virol., 85(15):7928-7932 (2011).
Rivers et al., "Meningitis in Man Caused by a Filterable Virus," Science, 81(2015):439-440 (1935).
Salvato et al., "Virus-lymphocyte interactions. IV. Molecular characterization of LCMV Armstrong (CTL+) small genomic segment and that of its variant, Clone 13 (CTL-)," Virology, 164(2):517-522 (1988).
Sanchez et al., "Rescue of the prototypic Arenavirus LCMV entirely from plasmid," Virology, 350(2):370-380 (2006).
Shimojima et al., "Cell surface molecules involved in infection mediated by lymphocytic choriomeningitis virus glycoprotein," J. Vet. Med. Sci., 74(1):1363-1366 (2012).
Shimojima et al., "Identification of cell surface molecules involved in dystroglycan-independent Lassa virus cell entry," J. Virol., 86(4):2067-2078 (2012).
Stoute et al., "A preliminary evaluation of a recombinant circumsporozoite protein vaccine against plasmodium falciparum malaria," N. Eng. J. Med., 336:86-91 (1997).
Suni et al., "Detection of antigen-specific T cell cytokine expression in whole blood by flow cytometry," J. Immunol. Methods, 212(1):89-98 (1998).
Tesh et al., "Field studies on the epidemiology of Venezuelan hemorrhagic fever: implication of the cotton rat Sigmodon alstoni as the probable rodent reservoir," Am. J. Trop. Med. Hyg., 49(2):227-235 (1993).
Wichgers et al., "Creation of Rift Valley fever viruses with four-segmented genomes reveals flexibility in bunyavirus genome packaging," J. Virol., 88(18):10883-10893 (2014).

(56) References Cited

OTHER PUBLICATIONS

Wright et al., "Congenital lymphocytic choriomeningitis virus syndrome: a disease that mimics congenital toxoplasmosis or Cytomegalovirus infection," *Pediatrics*, 100(1):E9 (1997).
Zinkernagel, "Lymphocytic choriomeningitis virus and immunology," *Curr. Top. Microbiol. Immunol.*, 263:1-5 (2002).

Figure 7

Figure 12

SEQUENCE LISTING

<160> NUMBER OF SEQ ID NOS: 24

<210> SEQ ID NO 1
<211> LENGTH: 3376
<212> TYPE: DNA
<213> ORGANISM: Lymphocytic choriomeningitis virus (LCMV)
<220> FEATURE:
<223> OTHER INFORMATION: cDNA sequence of LCMV seg

```
cttcaggggt ggagaatcca ggtggttatt gcctgaccaa atggatgatt cttgctgcag      960
agcttaagtg tttcgggaac acagcagttg cgaaatgcaa tgtaaatcat gatgccgaat     1020
tctgtgacat gctgcgacta attgactaca acaaggctgc tttgagtaag ttcaaagagg     1080
acgtagaatc tgccttgcac ttattcaaaa caacagtgaa ttctttgatt tcagatcaac     1140
tactgatgag gaaccacttg agagatctga tgggggtgcc atattgcaat tactcaaagt     1200
tttggtacct agaacatgca aagaccggcg aaactagtgt ccccaagtgc tggcttgtca     1260
ccaatggttc ttacttaaat gagacccact tcagtgatca aatcgaacag gaagccgata     1320
acatgattac agagatgttg aggaaggatt acataaagag gcaggggagt acccccctag     1380
cattgatgga ccttctgatg ttttccacat ctgcatatct agtcagcatc ttcctgcacc     1440
ttgtcaaaat accaacacac aggcacataa aaggtggctc atgtccaaag ccacaccgat     1500
taaccaacaa aggaatttgt agttgtggtg catttaaggt gcctggtgta aaaaccgtct     1560
ggaaaagacg ctgaagaaca gcgcctccct gactctccac ctcgaaagag gtggagagtc     1620
agggaggccc agagggtctt agagtgtcac aacatttggg cctctaaaaa ttaggtcatg     1680
tggcagaatt ttgtgaacag ttttcagatc tgggagcctt gctttggagg cgctttcaaa     1740
aatgatgcag tccatgagtg cacagtgcgg ggtgatctct ttcttctttt tgtcccttac     1800
tattccagta tgcatcttac acaaccagcc atatttgtcc cacactttgt cttcatactc     1860
cctcgaagct tccctggtca tttcaacatc gataagctta atgtccttcc tattctgtga     1920
gtccagaagc tttctgatgt catcggagcc ttgacagctt agaaccatcc cctgcggaag     1980
agcacctata actgacgagg tcaacccggg ttgcgcattg aagaggtcgg caagatccat     2040
gccgtgtgag tacttggaat cttgcttgaa ttgttttga tcaacgggtt ccctgtaaaa     2100
gtgtatgaac tgcccgttct gtggttggaa aattgctatt tccactggat cattaaatct     2160
accctcaatg tcaatccatg taggagcgtt ggggtcaatt cctcccatga ggtcttttaa     2220
aagcattgtc tggctgtagc ttaagcccac ctgaggtgga cctgctgctc caggcgctgg     2280
cctgggtgaa ttgactgcag gtttctcgct tgtgagatca attgttgtgt tttcccatgc     2340
tctccccaca atcgatgttc tacaagctat gtatggccat ccttcacctg aaaggcaaac     2400
tttatagagg atgttttcat aagggttcct gtccccaact tggtctgaaa caaacatgtt     2460
gagttttctc ttggccccga gaactgcctt caagaggtcc tcgctgttgc ttggcttgat     2520
caaaattgac tctaacatgt taccccccatc caacagggct gcccctgcct tcacggcagc     2580
accaagacta aagttatagc cagaaatgtt gatgctggac tgctgttcag tgatgacccc     2640
cagaactggg tgcttgtctt tcagccttc aagatcatta agatttggat acttgactgt     2700
gtaaagcaag ccaaggtctg tgagcgcttg tacaacgtca ttgagcggag tctgtgactg     2760
tttggccata caagccatag ttagacttgg cattgtgcca aattgattgt tcaaaagtga     2820
tgagtctttc acatcccaaa ctcttaccac accacttgca ccctgctgag gctttctcat     2880
cccaactatc tgtaggatct gagatctttg gtctagttgc tgtgttgtta agttccccat     2940 atataccccct gaagcctggg gccttttcaga cctcatgatc ttggccttca gcttctcaag     3000
gtcagccgca agagacatca gttcttctgc actgagcctc cccactttca aaacattctt     3060
ctttgatgtt gactttaaat ccacaagaga atgtacagtc tggttgagac ttctgagtct     3120
ctgtaggtct ttgtcatctc tcttttcctt cctcatgatc ctctgaacat tgctgacctc     3180
agagaagtcc aacccattca gaaggttggt tgcatcctta atgacagcag ccttcacatc     3240
```

| | |
|---|---|
| tgatgtgaag ctctgcaatt ctcttctcaa tgcttgcgtc cattggaagc tcttaacttc | 3300 |
| cttagacaag gacatcttgt tgctcaatgg tttctcaaga caaatgcgca atcaaatgcc | 3360 |
| taggatccac tgtgcg | 3376 |

<210> SEQ ID NO 2
<211> LENGTH: 3377
<212> TYPE: DNA
<213> ORGANISM: Lymphocytic choriomeningitis virus (LCMV)
<220> FEATURE:
<223> OTHER INFORMATION: LCMV clone 13 segment S complete sequence
      (GenBank: DQ361065.2)

<400> SEQUENCE: 2

| | |
|---|---|
| gcgcaccggg gatcctaggc tttttggatt gcgctttcct ctagatcaac tgggtgtcag | 60 |
| gccctatcct acagaaggat gggtcagatt gtgacaatgt ttgaggctct gcctcacatc | 120 |
| atcgatgagg tgatcaacat tgtcattatt gtgcttatcg tgatcacggg tatcaaggct | 180 |
| gtctacaatt ttgccacctg tgggatattc gcattgatca gtttcctact tctggctggc | 240 |
| aggtcctgtg gcatgtacgg tcttaaggga cccgacattt acaaggagt ttaccaattt | 300 |
| aagtcagtgg agtttgatat gtcacatctg aacctgacca tgcccaacgc atgttcagcc | 360 |
| aacaactccc accattacat cagtatgggg acttctggac tagaattgac cttcaccaat | 420 |
| gattccatca tcagtcacaa cttttgcaat ctgacctctg ccttcaacaa aagaccttt | 480 |
| gaccacacac tcatgagtat agtttcgagc ctacacctca gtatcagagg gaactccaac | 540 |
| tataaggcag tatcctgcga cttcaacaat ggcataacca tccaatacaa cttgacattc | 600 |
| tcagatgcac aaagtgctca gagccagtgt agaaccttca gaggtagagt cctagatatg | 660 |
| tttagaactg ccttcggggg gaaatacatg aggagtggct ggggctggac aggctcagat | 720 |
| ggcaagacca cctggtgtag ccagacgagt taccaatacc tgattataca aatagaacc | 780 |
| tgggaaaacc actgcacata tgcaggtcct tttgggatgt ccaggattct cctttcccaa | 840 |
| gagaagacta agttcctcac taggagacta gcgggcacat tcacctggac tttgtcagac | 900 |
| tcttcagggg tggagaatcc aggtggttat tgcctgacca atgatgat tcttgctgca | 960 |
| gagcttaagt gtttcgggaa cacagcagtt gcgaaatgca atgtaaatca tgatgaagaa | 1020 |
| ttctgtgaca tgctgcgact aattgactac aacaaggctg cttttgagtaa gttcaaagag | 1080 |
| gacgtagaat ctgccttgca cttattcaaa acaacagtga attctttgat ttcagatcaa | 1140 |
| ctactgatga ggaaccactt gagagatctg atgggggtgc catattgcaa ttactcaaag | 1200 |
| ttttggtacc tagaacatgc aaagaccggc gaaactagtg tccccaagtg ctggcttgtc | 1260 |
| accaatggtt cttacttaaa tgagacccac ttcagtgacc aaatcgaaca ggaagccgat | 1320 |
| aacatgatta cagagatgtt gaggaaggat tacataaaga gcaggggag tacccccta | 1380 |
| gcattgatgg accttctgat gttttccaca tctgcatatc tagtcagcat cttcctgcac | 1440 |
| cttgtcaaaa taccaacaca caggcacata aaggtggct catgtccaaa gccacaccga | 1500 |
| ttaaccaaca aaggaatttg tagttgtggt gcatttaagg tgcctggtgt aaaaaccgtc | 1560 |
| tggaaaagac gctgaagaac agcgcctccc tgactctcca cctcgaaaga ggtggagagt | 1620 |
| cagggaggcc cagagggtct tagagtgtca caacatttgg gcctctaaaa attaggtcat | 1680 |
| gtggcagaat gttgtgaaca gttttcagat ctgggagcct tgctttggag gcgctttcaa | 1740 |
| aaatgatgca gtccatgagt gcacagtgcg gggtgatctc tttcttcttt ttgtccctta | 1800 |
| ctattccagt atgcatctta cacaaccagc catatttgtc ccacactttg tcttcatact | 1860 |

```
cccctcgaagc ttccctggtc atttcaacat cgataagctt aatgtccttc ctattctgtg   1920
agtccagaag ctttctgatg tcatcggagc cttgacagct tagaaccatc ccctgcggaa   1980
gagcacctat aactgacgag gtcaacccgg gttgcgcatt gaagaggtcg gcaagatcca   2040
tgccgtgtga gtacttggaa tcttgcttga attgttttg atcaacgggt tcctgtaaa   2100
agtgtatgaa ctgcccgttc tgtggttgga aaattgctat ttccactgga tcattaaatc   2160
taccctcaat gtcaatccat gtaggagcgt tggggtcaat tcctcccatg aggtcttta   2220
aaagcattgt ctggctgtag cttaagccca cctgaggtgg acctgctgct ccaggcgctg   2280
gcctgggtga attgactgca ggtttctcgc ttgtgagatc aattgttgtg ttttcccatg   2340
ctctccccac aatcgatgtt ctacaagcta tgtatggcca tccttcacct gaaaggcaaa   2400
ctttatagag gatgttttca taaggttcc tgtccccaac ttggtctgaa acaaacatgt   2460
tgagttttct cttggcccg agaactgcct tcaagaggtc ctcgctgttg cttggcttga   2520
tcaaaattga ctctaacatg ttaccccccat ccaacagggc tgcccctgcc ttcacggcag   2580
caccaagact aaagttatag ccagaaatgt tgatgctgga ctgctgttca gtgatgaccc   2640
ccagaactgg gtgcttgtct ttcagccttt caagatcatt aagatttgga tacttgactg   2700
tgtaaagcaa gccaaggtct gtgagcgctt gtacaacgtc attgagcgga gtctgtgact   2760
gtttggccat acaagccata gttagacttg gcattgtgcc aaattgattg ttcaaaagtg   2820
atgagtcttt cacatcccaa actcttacca caccacttgc accctgctga ggctttctca   2880
tcccaactat ctgtaggatc tgagatcttt ggtctagttg ctgtgttgtt aagttcccca   2940
tatataccc tgaagcctgg ggcctttcag acctcatgat cttggccttc agcttctcaa   3000
ggtcagccgc aagagacatc agttcttctg cactgagcct ccccactttc aaaacattct   3060
tctttgatgt tgactttaaa tccacaagag aatgtacagt ctggttgaga cttctgagtc   3120
tctgtaggtc tttgtcatct ctcttttcct tcctcatgat cctctgaaca ttgctgacct   3180
cagagaagtc caacccattc agaaggttgg ttgcatcctt aatgacagca gccttcacat   3240
ctgatgtgaa gctctgcaat tctcttctca atgcttgcgt ccattggaag ctcttaactt   3300
ccttagacaa ggacatcttg ttgctcaatg gtttctcaag acaaatgcgc aatcaaatgc   3360
ctaggatcca ctgtgcg                                                 3377

<210> SEQ ID NO 3
<211> LENGTH: 7229
<212> TYPE: DNA
<213> ORGANISM: Lymphocytic choriomeningitis virus (LCMV)
<220> FEATURE:
<223> OTHER INFORMATION: LCMV clone 13 segment L complete sequence
      (GenBank: DQ361066.1)

<400> SEQUENCE: 3
gcgcaccggg gatcctaggc gtttagttgc gctgtttggt tgcacaactt tcttcgtgag     60
gctgtcagaa gtggacctgg ctgatagcga tgggtcaagg caagtccaga gaggagaaag    120
gcaccaatag tacaaacagg gccgaaatcc taccagatac cacctatctt ggcccttaa    180
gctgcaaatc ttgctggcag aaatttgaca gcttggtaag atgccatgac cactaccttt    240
gcaggcactg ttaaaacctt ctgctgtcag tatccgacag gtgtcctctt tgtaaatatc    300
cattaccaac cagattgaag atatcaacag ccccaagctc tccacctccc tacgaagagt    360
aacaccgtcc ggcccggcc ccgacaaaca gcccagcaca agggaaccgc acgtcaccca    420
acgcacacag acacagcacc caacacagaa cacgcacaca cacacacaca cacacccaca    480
```

```
cgcacgcgcc cccaccaccg gggggcgccc cccccggggg ggcggccccc cgggagcccg    540
ggcggagccc cacggagatg cccatcagtc gatgtcctcg gccaccgacc cgcccagcca    600
atcgtcgcag gacctcccct tgagtctaaa cctgcccccc actgtttcat acatcaaagt    660
gctcctagat ttgctaaaac aaagtctgca atccttaaag gcgaaccagt ctggcaaaag    720
cgacagtgga atcagcagaa tagatctgtc tatacatagt tcctggagga ttacacttat    780
ctctgaaccc aacaaatgtt caccagttct gaatcgatgc aggaagaggt tcccaaggac    840
atcactaatc ttttcatagc cctcaagtcc tgctagaaag actttcatgt ccttggtctc    900
cagcttcaca atgatatttt ggacaaggtt tcttccttca aaagggcac ccatctttac     960
agtcagtggc acaggctccc actcaggtcc aactctctca aagtcaatag atctaatccc    1020
atccagtatt cttttggagc ccaacaactc aagctcaaga gaatcaccaa gtatcaaggg    1080
atcttccatg taatcctcaa actcttcaga tctgatatca aagacaccat cgttcacctt    1140
gaagacagag tctgtcctca gtaagtggag gcattcatcc aacattcttc tatctatctc    1200
acccttaaag aggtgagagc atgataaaag ttcagccaca cctggattct gtaattggca    1260
cctaaccaag aatatcaatg aaaatttcct taaacagtca gtattattct gattgtgcgt    1320
aaagtccact gaaattgaaa actccaatac ccctttttgtg tagttgagca tgtagtccca   1380
cagatccttt aaggatttaa atgcctttgg gtttgtcagg ccctgcctaa tcaacatggc    1440
agcattacac acaacatctc ccattcggta agagaaccac ccaaaaccaa actgcaaatc    1500
attcctaaac ataggcctct ccacattttt gttcaccacc tttgagacaa atgattgaaa    1560
ggggcccagt gcctcagcac catcttcaga tggcatcatt tctttatgag gaaccatga    1620
aaaattgcct aatgtcctgg ttgttgcaac aaattctcga acaaatgatt caaaatacac    1680
ctgtttttaag aagttcttgc agacatccct cgtgctaaca acaaattcat caaccagact   1740
ggagtcagat cgctgatgag aattggcaag gtcagaaaac agaacagtgt aatgttcatc    1800
ccttttccac ttaacaacat gagaaatgag tgacaaggat tctgagttaa tatcaattaa    1860
aacacagagg tcaaggaatt taattctggg actccacctc atgtttttg agctcatgtc     1920
agacataaat ggaagaagct gatcctcaaa gatcttggga tatagccgcc tcacagattg    1980
aatcacttgg ttcaaattca ctttgtcctc cagtagcctt gagctctcag gctttcttgc    2040
tacataatca catgggttta agtgcttaag agttaggttc tcactgttat tcttcccttt    2100
ggtcggttct gctaggaccc aaacacccaa ctcaaaagag ttgctcaatg aaatacaaat    2160
gtagtcccaa agaagaggcc ttaaaaggca tatatgatca cggtgggctt ctggatgaga    2220
ctgtttgtca caaatgtaca gcgttatacc atcccgattg caaactcttg tcacatgatc    2280
atctgtggtt agatcctcaa gcagcttttt gatatacaga ttttcccat ttttgtttct     2340
cacacacctg cttcctagag ttttgcaaag gcctataaag ccagatgaga tacaactctg    2400
gaaagctgac ttgttgattg cttctgacag cagcttctgt gcaccccttg tgaatttact    2460
acaaagtttg ttctggagtg tcttgatcaa tgatgggatt ctttcctctt ggaaagtcat    2520
cactgatgga taaaccacct tttgtcttaa aaccatcctt aatgggaaca tttcattcaa    2580
attcaaccag ttaacatctg ctaactgatt cagatcttct tcaagaccga ggaggtctcc    2640
caattgaaga atggcctcct ttttatctct gttaaatagg tctaagaaaa attcttcatt    2700
aaattcacca tttttgagct tatgatgcag tttccttaca agctttctta caacctttgt    2760
ttcattagga cacagttcct caatgagtct ttgtattctg taacctctag aaccatccag    2820
ccaatctttc acatcagtgt tggtattcag tagaaatgga tccaaaggga aattggcata    2880
```

```
ctttaggagg tccagtgttc tcctttggat actattaact agggagactg ggacgccatt    2940
tgcgatggct tgatctgcaa ttgtatctat tgtttcacaa agttgatgtg gctctttaca    3000
cttgacattg tgtagcgctg cagatacaaa cttttgtgaga agagggactt cctcccccca   3060
tacatagaat ctagatttaa attctgcagc gaacctccca gccacacttt ttgggctgat    3120
aaatttgttt aacaagccgc tcagatgaga ttggaattcc aacaggacaa ggacttcctc    3180
cggatcactt acaaccaggt cactcagcct cctatcaaat aaagtgatct gatcatcact    3240
tgatgtgtaa gcctctggtc tttcgccaaa gataacacca atgcagtagt tgatgaacct    3300
ctcgctaagc aaaccataga agtcagaagc attatgcaag attccctgcc ccatatcaat    3360
aaggctggat atatgggatg gcactatccc catttcaaaa tattgtctga aaattctctc    3420
agtaacagtt gtttctgaac ccctgagaag ttttagcttc gacttgacat atgatttcat    3480
cattgcattc acaacaggaa aggggacctc gacaagctta tgcatgtgcc aagttaacaa    3540
agtgctaaca tgatctttcc cggaacgcac atactggtca tcacctagtt tgagattttg    3600
tagaaacatt aagaacaaaa atgggcacat cattggtccc catttgctgt gatccatact    3660
atagtttaag aacccttccc gcacattgat agtcattgac aagattgcat tttcaaattc    3720
cttatcattg tttaaacagg agcctgaaaa gaaacttgaa aaagactcaa ataatcttc    3780 tattaacctt gtgaacattt ttgtcctcaa atctccaata tagagttctc tatttccccc    3840
aacctgctct ttataagata gtgcaaattt cagccttcca gagtcaggac ctactgaggt    3900
gtatgatgtt ggtgattctt ctgagtagaa gcacagattt ttcaaagcag cactcataca    3960
ttgtgtcaac gacagagctt tactaaggga ctcagaatta ctttccctct cactgattct    4020
cacgtcttct tccagtttgt cccagtcaaa tttgaaattc aagccttgcc tttgcatatg    4080
cctgtatttc cctgagtacg catttgcatt catttgcaac agaatcatct tcatgcaaga    4140
aaaccaatca ttctcagaaa agaactttct acaaaggttt tttgccatct catcgaggcc    4200
acactgatct ttaatgactg aggtgaaata caaaggtgac agctctgtgg aaccctcaac    4260
agcctcacag ataaatttca tgtcatcatt ggttagacat gatgggtcaa agtcttctac    4320
taaatggaaa gatatttctg acaagataac ttttcttaag tgagccatct tccctgttag    4380
aataagctgt aaatgatgta gtccttttgt atttgtaagt ttttctccat ctcctttgtc    4440
attggccctc ctacctcttc tgtaccgtgc tattgtggtg ttgaccttt cttcgagact    4500 tttgaagaag cttgtctctt cttctccatc aaaacatatt tctgccaggt tgtcttccga    4560
tctccctgtc tcttctccct tggaaccgat gaccaatcta gagactaact tggaaacttt    4620
atattcatag tctgagtggc tcaacttata cttttgtttt cttacgaaac tctccgtaat    4680
ttgactcaca gcactaacaa gcaatttgtt aaagtcatat tccagaagtc gttctccatt    4740
tagatgctta ttaaccacca cacttttgtt actagcaaga tctaatgctg tcgcacatcc    4800
agagttagtc atgggatcta ggctgtttag cttcttctct cctttgaaaa ttaaagtgcc    4860
gttgttaaat gaagacacca ttaggctaaa ggcttccaga ttaacacctg gagttgtatg    4920
ctgacagtca atttctttac tagtgaatct cttcatttgc tcatagaaca cacattcttc    4980
ctcaggagtg attgcttcct tggggttgac aaaaaaacca aattgacttt tgggctcaaa    5040
gaacttttca aaacatttta tctgatctgt tagcctgtca ggggtctcct ttgtgatcaa    5100 atgcacagg tatgacacat tcaacataaa tttaaatttt gcactcaaca acaccttctc    5160
accagtacca aaaatagttt ttattaggaa tctaagcagc ttatacacca ccttctcagc    5220
```

```
aggtgtgatc agatcctccc tcaacttatc cattaatgat gtagatgaaa aatctgacac    5280
tattgccatc accaaatatc tgacactctg tacctgcttt tgatttctct ttgttgggtt    5340
ggtgagcatt agcaacaata gggtcctcag tgcaacctca atgtcggtga gacagtcttt    5400
caaatcagga catgatctaa tccatgaaat catgatgtct atcatattgt ataagacctc    5460
atctgaaaaa attggtaaaa agaaccttt aggatctgca tagaaggaaa ttaaatgacc    5520
atccgggcct tgtatggagt agcaccttga agattctcca gtcttctggt ataataggtg    5580
gtattcttca gagtccagtt ttattacttg gcaaaacact tctttgcatt ctaccacttg    5640
atatctcaca gaccctattt gattttgcct tagtctagca actgagctag ttttcatact    5700
gtttgttaag gccagacaaa cagatgataa tcttctcagg ctctgtatgt tcttcagctg    5760
ctctgtgctg ggttggaaat tgtaatcttc aaacttcgta taatacatta tcgggtgagc    5820
tccaattttc ataaagttct caaattcagt gaatggtatg tggcattctt gctcaaggtg    5880
ttcagacagt ccgtaatgct cgaaactcag tcccaccact aacaggcatt tttgaatttt    5940
tgcaatgaac tcactaatag atgccctaaa caattcctca aaagacacct ttctaaacac    6000
ctttgacttt tttctattcc tcaaaagtct aatgaactcc tctttagtgc tgtgaaagct    6060
taccagccta tcattcacac tactatagca acacccacc cagtgtttat catttttaa    6120 cccttgaat ttcgactgtt ttatcaatga ggaaagacac aaaacatcca gatttaacaa    6180
ctgtctcctt ctagtattca acagtttcaa actcttgact ttgttaaca tagagaggag    6240 cctctcatat tcagtgctag tctcacttcc cctttcgtgc ccatgggtct ctgcagttat    6300
gaatctcatc aaaggacagg attcgactgc ctccctgctt aatgttaaga tatcatcact    6360
atcagcaagg ttttcataga gctcagagaa ttccttgatc aagccttcag ggtttacttt    6420
ctgaaagttt ctctttaatt tcccactttc taaatctctt ctaaacctgc tgaaaagaga    6480
gtttattcca aaaaccacat catcacagct catgttgggg ttgatgcctt cgtggcacat    6540
cctcataatt tcatcattgt gagttgacct cgcatctttc agaattttca tagagtccat    6600
accggagcgc ttgtcgatag tagtcttcag ggactcacag agtctaaaat attcagactc    6660
ttcaaagact ttctcatttt ggttagaata ctccaaaagt ttgaataaaa ggtctctaaa    6720
tttgaagttt gcccactctg gcataaaact attatcataa tcacaacgac catctactat    6780
tggaactaat gtgacacccg caacagcaag gtcttccctg atgcatgcca atttgttagt    6840
gtcctctata aatttcttct caaaactggc tggagtgctc taacaaaac actcaagaag    6900 aatgagagaa ttgtctatca gcttgtaacc atcaggaatg ataagtggta gtcctgggca    6960
tacaattcca gactccacca aaattgtttc cacagactta tcgtcgtggt tgtgtgtgca    7020
gccactcttg tctgcactgt ctatttcaat gcagcgtgac agcaacttga gtccctcaat    7080
cagaaccatt ctgggttccc tttgtcccag aaagttgagt ttctgccttg acaacctctc    7140
atcctgttct atatagttta aacataactc tctcaattct gagatgattt catccattgc    7200
gcatcaaaaa gcctaggatc ctcggtgcg                                       7229
```

<210> SEQ ID NO 4
<211> LENGTH: 7205
<212> TYPE: DNA
<213> ORGANISM: Lymphocytic choriomeningitis virus (LCMV)
<220> FEATURE:
<223> OTHER INFORMATION: LCMV strain MP segment L complete sequence

<400> SEQUENCE: 4

```
gcgcaccggg gatcctaggc attttgttg cgcattttgt tgtgttattt gttgcacagc      60
```

```
ccttcatcgt gggaccttca caaacaaacc aaaccaccag ccatgggcca aggcaagtcc    120
aaagagggaa gggatgccag caatacgagc agagctgaaa ttctgccaga caccacctat    180
ctcggacctc tgaactgcaa gtcatgctgg cagagatttg acagtttagt cagatgccat    240
gaccactatc tctgcagaca ctgcctgaac ctcctgctgt cagtctccga caggtgccct    300
ctctgcaaac atccattgcc aaccaaactg aaaatatcca cggccccaag ctctccaccc    360
ccttacgagg agtgacgccc cgagcccaa caccgacaca aggaggccac caacacaacg     420
cccaacacgg aacacacaca cacacaccca cacacacatc cacacacacg cgcccccaca    480 acggggcgc ccccccgggg gtggccccc gggtgctcgg gcggagcccc acggagaggc      540
caattagtcg atctcctcga ccaccgactt ggtcagccag tcatcacagg acttgccctt    600
aagtctgtac ttgcccacaa ctgtttcata catcaccgtg ttctttgact tactgaaaca    660
tagcctacag tctttgaaag tgaaccagtc aggcacaagt gacagcggta ccagtagaat    720
ggatctatct atacacaact cttggagaat tgtgctaatt ccgacccct gtagatgctc     780 accagttctg aatcgatgta aagaaggct cccaaggacg tcatcaaaat ttccataacc     840
ctcgagctct gccaagaaaa ctctcatatc cttggtctcc agtttcacaa cgatgttctg    900
aacaaggctt cttccctcaa aaagagcacc cattctcaca gtcaagggca caggctccca    960
ttcaggccca atcctctcaa aatcaaggga tctgatcccg tccagtattt tccttgagcc   1020
tatcagctca agctcaagag agtcaccgag tatcagggg tcctccatat agtcctcaaa    1080
ctcttcagac ctaatgtcaa aaacaccatc gttcaccttg aagatagagt ctgatctcaa   1140
caggtggagg cattcgtcca agaaccttct gtccacctca cctttaaaga ggtgagagca   1200
tgataggaac tcagctacac ctggaccttg taactggcac ttcactaaaa agatcaatga   1260
aaacttcctc aaacaatcag tgttattctg gttgtgagtg aaatctactg taattgagaa   1320
ctctagcact ccctctgtat tatttatcat gtaatcccac aagtttctca aagacttgaa   1380
tgcctttgga tttgtcaagc cttgtttgat tagcatggca gcattgcaca caatatctcc   1440
caatcggtaa gagaaccatc caaatccaaa ttgcaagtca ttcctaaaca tgggcctctc   1500
catatttttg ttcactactt ttaagatgaa tgattggaaa ggccccaatg cttcagcgcc   1560
atcttcagat ggcatcatgt ctttatgagg gaaccatgaa aaacttccta gagttctgct   1620
tgttgctaca aattctcgta caaatgactc aaaatacact tgttttaaaa agttttttgca  1680 gacatccctt gtactaacga caaattcatc aacaaggctt gagtcagagc gctgatggga   1740
atttacaaga tcagaaaata gaacagtgta gtgttcgtcc ctcttccact taactacatg   1800
agaaatgagc gataaagatt ctgaattgat atcgatcaat acgcaaaggt caaggaattt   1860
gattctggga ctccatctca tgttttttga gctcatatca gacatgaagg gaagcagctg   1920
atcttcatag attttagggt acaatcgcct cacagattgg attacatggt ttaaacttat   1980
cttgtcctcc agtagccttg aactctcagg cttccttgct acataatcac atgggttcaa   2040
gtgcttgagg cttgagcttc cctcattctt ccctttcaca ggttcagcta agacccaaac   2100
acccaactca aaggaattac tcagtgagat gcaaatatag tcccaaagga ggggcctcaa   2160
gagactgatg tggtcgcagt gagcttctgg atgactttgc ctgtcacaaa tgtacaacat   2220
tatgccatca tgtctgtgga ttgctgtcac atgcgcatcc atagctagat cctcaagcac   2280
ttttctaatg tatagattgt ccctattttt atttctcaca catctacttc ccaaagttt    2340 gcaaagacct ataaagcctg atgagatgca actttgaaag gctgacttat tgattgcttc   2400
```

```
tgacagcaac ttctgtgcac ctcttgtgaa cttactgcag agcttgttct ggagtgtctt    2460
gattaatgat gggattcttt cctcttggaa agtcattact gatggataaa ccactttctg    2520
cctcaagacc attcttaatg ggaacaactc attcaaattc agccaattta tgtttgccaa    2580
ttgacttaga tcctcttcga ggccaaggat gtttcccaac tgaagaatgg cttcctttt     2640 atccctattg aagaggtcta agaagaattc ttcattgaac tcaccattct tgagcttatg    2700
atgtagtctc cttacaagcc ttctcatgac cttcgtttca ctaggacaca attcttcaat    2760
aagcctttgg attctgtaac ctctagagcc atccaaccaa tccttgacat cagtattagt    2820
gttaagcaaa aatgggtcca agggaaagtt ggcatatttt aagaggtcta atgttctctt    2880
ctggatgcag tttaccaatg aaactggaac accatttgca acagcttgat cggcaattgt    2940
atctattgtt tcacagagtt ggtgtggctc tttacactta acgttgtgta atgctgctga    3000
cacaattttt gttaaaagtg ggacctcttc cccccacaca taaaatctgg atttaaattc    3060
tgcagcaaat cgccccacca cacttttcgg actgatgaac ttgttaagca agccactcaa    3120
atgagaatga aattccagca atacaaggac ttcctcaggg tcactatcaa ccagttcact    3180
caatctccta tcaaataagg tgatctgatc atcacttgat gtgtaagatt ctggtctctc    3240
accaaaaatg acaccgatac aataattaat gaatctctca ctgattaagc cgtaaaagtc    3300
agaggcatta tgtaagattc cctgtcccat gtcaatgaga ctgcttatat gggaaggcac    3360
tattcctaat tcaaaatatt ctcgaaagat tctttcagtc acagttgtct ctgaaccct     3420 aagaagtttc agctttgatt tgatatatga tttcatcatt gcattcacaa caggaaaagg    3480
gacctcaaca agtttgtgca tgtgccaagt taataaggtg ctgatatgat cctttccgga    3540
acgcacatac tggtcatcac ccagtttgag attttgaagg agcattaaaa acaaaaatgg    3600
gcacatcatt ggcccccatt tgctatgatc catactgtag ttcaacaacc cctctcgcac    3660
attgatggtc attgatagaa ttgcatttc aaattctttg tcattgttta agcatgaacc     3720
tgagaagaag ctagaaaaag actcaaaata atcctctatc aatcttgtaa acattttgt     3780 tctcaaatcc ccaatataaa gttctctgtt tcctccaacc tgctctttgt atgataacgc    3840
aaacttcaac cttccggaat caggaccaac tgaagtgtat gacgttggtg actcctctga    3900
gtaaaaacat aaattcttta aagcagcact catgcatttt gtcaatgata gagccttact    3960
tagagactca gaattacttt ccctttcact aattctaaca tcttcttcta gtttgtccca    4020
gtcaaacttg aaattcagac cttgtctttg catgtgcctg tatttccctg agtatgcatt    4080
tgcattcatt tgcagtagaa tcattttcat acacgaaaac caatcaccct ctgaaaaaaa    4140
cttcctgcag aggttttttg ccatttcatc cagaccacat tgttctttga cagctgaagt    4200
gaaatacaat ggtgacagtt ctgtagaagt ttcaatagcc tcacagataa atttcatgtc    4260
atcattggtg agacaagatg ggtcaaaatc ttccacaaga tgaaaagaaa tttctgataa    4320
gatgaccttc cttaaatatg ccattttacc tgacaatata gtctgaaggt gatgcaatcc    4380
ttttgtattt tcaaaccca cctcatttttc cccttcattg gtcttcttgc ttctttcata    4440
ccgctttatt gtggagttga ccttatcttc taaattcttg aagaaacttg tctcttcttc    4500
cccatcaaag catatgtctg ctgagtcacc ttctagtttc ccagcttctg tttctttaga    4560
gccgataacc aatctagaga ccaactttga aaccttgtac tcgtaatctg agtggttcaa    4620
tttgtacttc tgcttctca tgaagctctc tgtgatctga ctcacagcac taacaagcaa     4680
tttgttaaaa tcatactcta ggagccgttc cccatttaaa tgtttgttaa caaccacact    4740
tttgttgctg gcaaggtcta atgctgttgc acacccagag ttagtcatgg gatccaagct    4800
```

```
attgagcctc ttctcccctt tgaaaatcaa agtgccattg ttgaatgagg acaccatcat   4860
gctaaaggcc tccagattga cacctggggt tgtgcgctga cagtcaactt ctttcccagt   4920
gaacttcttc atttggtcat aaaaaacaca ctcttcctca ggggtgattg actctttagg   4980
gttaacaaag aagccaaact cacttttagg ctcaaagaat ttctcaaagc atttaatttg   5040
atctgtcagc ctatcagggg tttcctttgt gattaaatga cacaggtatg acacattcaa   5100
catgaacttg aactttgcgc tcaacagtac cttttcacca gtcccaaaaa cagttttgat   5160
caaaaatctg agcaatttgt acactacttt ctcagcaggt gtgatcaaat cctccttcaa   5220
cttgtccatc aatgatgtgg atgagaagtc tgagacaatg ccatcacta aatacctaat    5280
gttttgaacc tgttttttgat tcctctttgt tgggttggtg agcatgagta ataatagggt   5340
tctcaatgca atctcaacat catcaatgct gtccttcaag tcaggacatg atctgatcca   5400
tgagatcatg gtgtcaatca tgttgtgcaa cacttcatct gagaagattg gtaaaaagaa   5460
cctttttggg tctgcataaa aagagattag atggccattg ggaccttgta tagaataaca   5520
ccttgaggat tctccagtct tttgatacag caggtgatat tcctcagagt ccaattttat   5580
cacttggcaa aatacctctt tacattccac cacttgatac cttacagagc ccaattggtt   5640
ttgtcttaat ctagcaactg aacttgtttt catactgttt gtcaaagcta gacagacaga   5700
tgacaatctt ttcaaactat gcatgttcct taattgttcc gtattaggct ggaaatcata   5760
atcttcaaac tttgtataat acattatagg atgagttccg gacctcatga aattctcaaa   5820
ctcaataaat ggtatgtggc actcatgctc aagatgttca gacagaccat agtgcccaaa   5880
actaagtccc accactgaca agcacctttg aacttttaaa atgaactcat ttatggatgt   5940
tctaaacaaa tcctcaagag ataccttttct atacgccttt gactttctcc tgttccttag   6000
aagtctgatg aactcttcct tggtgctatg aaagctcacc aacctatcat tcacactccc   6060
atagcaacaa ccaacccagt gcttatcatt ttttgaccct ttgagtttag actgtttgat   6120
caacgaagag agacacaaga catccaaatt cagtaactgt ctccttctgg tgttcaataa   6180
ttttaaactt ttaactttgt tcaacataga gaggagcctc tcatactcag tgctagtctc   6240
acttcctctc tcataaccat gggtatctgc tgtgataaat ctcatcaaag gacaggattc   6300
aactgcctcc ttgcttagtg ctgaaatgtc atcactgtca gcaagagtct cataaagctc   6360
agagaattcc ttaattaaat ttccgggggtt gatttttctga aaactcctct tgagcttccc   6420
agtttccaag tctcttctaa acctgctgta aagggagttt atgccaagaa ccacatcatc   6480
gcagttcatg tttgggttga caccatcatg gcacattttc ataatttcat cattgtgaaa   6540
tgatcttgca tctttcaaga ttttcataga gtctataccg gaacgcttat caacagtggt   6600
cttgagagat tcgcaaagtc tgaagtactc agattcctca aagactttct catccttggct   6660
agaatactct aaaagtttaa acagaaggtc tctgaacttg aaattcaccc actctggcat   6720
aaagctgtta tcataatcac accgaccatc cactattggg accaatgtga tacccgcaat   6780
ggcaaggtct tctttgatac aggctagttt attggtgtcc tctataaatt tcttctcaaa   6840
actagctggt gtgcttctaa cgaagcactc aagaagaatg agggaattgt caatcagttt   6900
ataaccatca ggaatgatca aaggcagtcc cgggcacaca atcccagact ctattagaat   6960
tgcctcaaca gatttatcat catggttgtg tatgcagccg ctcttgtcag cactgtctat   7020
ctctatacaa cgcgacaaaa gtttgagtcc ctctatcaat accattctgg gttctctttg   7080
ccctaaaaag ttgagcttct gccttgacaa cctctcatct tgttctatgt ggtttaagca   7140
```

```
caactctctc aactccgaaa tagcctcatc cattgcgcat caaaaagcct aggatcctcg    7200
gtgcg                                                                 7205

<210> SEQ ID NO 5
<211> LENGTH: 3359
<212> TYPE: DNA
<213> ORGANISM: Lymphocytic choriomeningitis virus (LCMV)
<220> FEATURE:
<223> OTHER INFORMATION: LCMV strain MP segment S complete sequence

<400> SEQUENCE: 5
cgcaccgggg atcctaggct ttttggattg cgctttcctc agctccgtct tgtgggagaa      60
tgggtcaaat tgtgacgatg tttgaggctc tgcctcacat cattgatgag gtcattaaca     120
ttgtcattat cgtgcttatt atcatcacga gcatcaaagc tgtgtacaat ttcgccacct     180
gcgggatact tgcattgatc agctttcttt ttctggctgg caggtcctgt ggaatgtatg     240
gtcttgatgg gcctgacatt tacaaagggg tttaccgatt caagtcagtg gagtttgaca     300
tgtcttacct taacctgacg atgcccaatg catgttcggc aaacaactcc catcattata     360
taagtatggg gacttctgga ttggagttaa ccttcacaaa tgactccatc atcacccaca     420
acttttgtaa tctgacttcc gccctcaaca agaggacttt tgaccacaca cttatgagta     480
tagtctcaag tctgcacctc agcattagag gggtccccag ctacaaagca gtgtcctgtg     540
attttaacaa tggcatcact attcaataca acctgtcatt ttctaatgca cagagcgctc     600
tgagtcaatg taagaccttc aggggagag tcctggatat gttcagaact gcttttggag     660
gaaagtacat gaggagtggc tggggctgga caggttcaga tggcaagact acttggtgca     720
gccagacaaa ctaccaatat ctgattatac aaaacaggac ttgggaaaac cactgcaggt     780
acgcaggccc tttcggaatg tctagaattc tcttcgctca agaaaagaca aggtttctaa     840
ctagaaggct tgcaggcaca ttcacttgga ctttatcaga ctcatcagga gtggagaatc     900
caggtggtta ctgcttgacc aagtggatga tcctcgctgc agagctcaag tgttttggga     960
acacagctgt tgcaaagtgc aatgtaaatc atgatgaaga gttctgtgat atgctacgac    1020
tgattgatta caacaaggct gctttgagta aattcaaaga gatgtagaa tccgctctac    1080 atctgttcaa gacaacagtg aattctttga tttctgatca gcttttgatg agaaatcacc    1140
taagagactt gatgggagtg ccatactgca attactcgaa attctggtat ctagagcatg    1200
caaagactgg tgagactagt gtccccaagt gctggcttgt cagcaatggt tcttatttga    1260
atgaaaccca tttcagcgac caaattgagc aggaagcaga taatatgatc acagaaatgc    1320
tgagaaagga ctacataaaa aggcaaggga gtacccctct agccttgatg gatctattga    1380
tgttttctac atcagcatat ttgatcagca tctttctgca tcttgtgagg ataccaacac    1440
acagacacat aaagggcggc tcatgcccaa aaccacatcg gttaaccagc aagggaatct    1500
gtagttgtgg tgcatttaaa gtaccaggtg tggaaaccac ctggaaaaga cgctgaacag    1560
cagcgcctcc ctgactcacc acctcgaaag aggtggtgag tcaggaggc ccagagggtc    1620 ttagagtgtt acgacatttg gacctctgaa gattaggtca tgtggtagga tattgtggac    1680
agttttcagg tcggggagcc ttgccttgga ggcgctttca aagatgatac agtccatgag    1740
tgcacagtgt ggggtgacct cttctttttt cttgtccctc actattccag tgtgcatctt    1800
gcatagccag ccatatttgt cccagacttt gtcctcatat tctcttgaag cttctttagt    1860
catctcaaca tcgatgagct taatgtctct tctgttttgt gaatctagga gtttcctgat    1920
gtcatcagat ccctgacaac ttaggaccat tccctgtgga agagcaccta ttactgaaga    1980
```

-continued

```
tgtcagccca ggttgtgcat tgaagaggtc agcaaggtcc atgccatgtg agtatttgga    2040
gtcctgcttg aattgttttt gatcagtggg ttctctatag aaatgtatgt actgcccatt    2100
ctgtggctga aatattgcta tttctaccgg gtcattaaat ctgccctcaa tgtcaatcca    2160
tgtaggagcg ttagggtcaa tacctcccat gaggtccttc agcaacattg tttggctgta    2220
gcttaagccc acctgaggtg ggcccgctgc cccaggcgct ggtttgggtg agttggccat    2280
aggcctctca tttgtcagat caattgttgt gttctcccat gctctcccta caactgatgt    2340
tctacaagct atgtatggcc acccctcccc tgaaagacag actttgtaga ggatgttctc    2400
gtaaggattc ctgtctccaa cctgatcaga aacaaacatg ttgagtttct tcttggcccc    2460
aagaactgct ttcaggagat cctcactgtt gcttggctta attaagatgg attccaacat    2520
gttaccccca tctaacaagg ctgcccctgc tttcacagca gcaccgagac tgaaattgta    2580
gccagatatg ttgatgctag actgctgctc agtgatgact cccaagactg ggtgcttgtc    2640
tttcagcctt tcaaggtcac ttaggttcgg tacttgact gtgtaaagca gcccaaggtc    2700
tgtgagtgct tgcacaacgt cattgagtga ggtttgtgat tgtttggcca tacaagccat    2760
tgttaagctt ggcattgtgc cgaattgatt gttcagaagt gatgagtcct tcacatccca    2820
gaccctcacc acaccatttg cactctgctg aggtctcctc attccaacca tttgcagaat    2880
ctgagatctt tggtcaagct gttgtgctgt taagttcccc atgtagactc cagaagttag    2940
aggcctttca gacctcatga ttttagcctt cagttttttca aggtcagctg caagggacat    3000
cagttcttct gcactaagcc tccctacttt tagaacattc ttttttgatg ttgactttag    3060
gtccacaagg gaatacacag tttggttgag gcttctgagt ctctgtaaat ctttgtcatc    3120
cctcttctct ttcctcatga tcctctgaac attgctcacc tcagagaagt ctaatccatt    3180
cagaaggctg gtggcatcct tgatcacagc agctttcaca tctgatgtga agccttgaag    3240
ctctctcctc aatgcctggg tccattgaaa gcttttaact tctttggaca gagacatttt    3300
gtcactcagt ggatttccaa gtcaaatgcg caatcaaaat gcctaggatc cactgtgcg     3359
```

<210> SEQ ID NO 6
<211> LENGTH: 552
<212> TYPE: PRT
<213> ORGANISM: Lymphocytic choriomeningitis virus (LCMV)
<220> FEATURE:
<223> OTHER INFORMATION: Amino acid sequence of the NP protein of the MP strain of LCMV

<400> SEQUENCE: 6

```
Met Ser Leu Ser Lys Glu Val Lys Ser Phe Gln Trp Thr Gln Ala Leu
1               5                   10                  15

Arg Arg Glu Leu Gln Gly Phe Thr Ser Asp Val Lys Ala Ala Val Ile
            20                  25                  30

Lys Asp Ala Thr Ser Leu Leu Asn Gly Leu Asp Phe Ser Glu Val Ser
        35                  40                  45

Asn Val Gln Arg Ile Met Arg Lys Glu Lys Arg Asp Asp Lys Asp Leu
    50                  55                  60

Gln Arg Leu Arg Ser Leu Asn Gln Thr Val Tyr Ser Leu Val Asp Leu
65                  70                  75                  80

Lys Ser Thr Ser Lys Lys Asn Val Leu Lys Val Gly Arg Leu Ser Ala
                85                  90                  95

Glu Glu Leu Met Ser Leu Ala Ala Asp Leu Glu Lys Leu Lys Ala Lys
            100                 105                 110
```

```
Ile Met Arg Ser Glu Arg Pro Leu Thr Ser Gly Val Tyr Met Gly Asn
            115                 120                 125

Leu Thr Ala Gln Gln Leu Asp Gln Arg Ser Gln Ile Leu Gln Met Val
        130                 135                 140

Gly Met Arg Arg Pro Gln Gln Ser Ala Asn Gly Val Val Arg Val Trp
145                 150                 155                 160

Asp Val Lys Asp Ser Ser Leu Leu Asn Asn Gln Phe Gly Thr Met Pro
                165                 170                 175

Ser Leu Thr Met Ala Cys Met Ala Lys Gln Ser Gln Thr Ser Leu Asn
            180                 185                 190

Asp Val Val Gln Ala Leu Thr Asp Leu Gly Leu Leu Tyr Thr Val Lys
        195                 200                 205

Tyr Pro Asn Leu Ser Asp Leu Glu Arg Leu Lys Asp Lys His Pro Val
210                 215                 220

Leu Gly Val Ile Thr Glu Gln Gln Ser Ser Ile Asn Ile Ser Gly Tyr
225                 230                 235                 240

Asn Phe Ser Leu Gly Ala Ala Val Lys Ala Gly Ala Ala Leu Leu Asp
                245                 250                 255

Gly Gly Asn Met Leu Glu Ser Ile Leu Ile Lys Pro Ser Asn Ser Glu
            260                 265                 270

Asp Leu Leu Lys Ala Val Leu Gly Ala Lys Lys Leu Asn Met Phe
        275                 280                 285

Asp Arg Asn Pro Tyr Glu Asn Ile Leu Tyr Lys Val Cys Leu Ser Gly
        290                 295                 300

Glu Gly Trp Pro Tyr Ile Ala Cys Arg Thr Ser Val Val Gly Arg Ala
305                 310                 315                 320

Trp Glu Asn Thr Thr Ile Asp Leu Thr Asn Glu Arg Pro Met Ala Asn
                325                 330                 335

Ser Pro Lys Pro Ala Pro Gly Ala Ala Gly Pro Pro Gln Val Gly Leu
            340                 345                 350

Ser Tyr Ser Gln Thr Met Leu Leu Lys Asp Leu Met Gly Gly Ile Asp
        355                 360                 365

Pro Asn Ala Pro Thr Trp Ile Asp Ile Glu Gly Arg Phe Asn Asp Pro
370                 375                 380

Val Glu Ile Ala Ile Phe Gln Pro Gln Asn Gly Gln Tyr Ile His Phe
385                 390                 395                 400

Tyr Arg Glu Pro Thr Asp Gln Lys Gln Phe Lys Gln Asp Ser Lys Tyr
                405                 410                 415

Ser His Gly Met Asp Leu Ala Asp Leu Phe Asn Ala Gln Pro Gly Leu
            420                 425                 430

Thr Ser Ser Val Ile Gly Ala Leu Pro Gln Gly Met Val Leu Ser Cys
        435                 440                 445

Gln Gly Ser Asp Asp Ile Arg Lys Leu Leu Asp Ser Gln Asn Arg Arg
450                 455                 460

Asp Ile Lys Leu Ile Asp Val Glu Met Thr Lys Glu Ala Ser Arg Glu
465                 470                 475                 480

Tyr Glu Asp Lys Val Trp Asp Lys Tyr Gly Trp Leu Cys Lys Met His
                485                 490                 495

Thr Gly Ile Val Arg Asp Lys Lys Lys Glu Val Thr Pro His Cys
            500                 505                 510

Ala Leu Met Asp Cys Ile Ile Phe Glu Ser Ala Ser Lys Ala Arg Leu
        515                 520                 525

Pro Asp Leu Lys Thr Val His Asn Ile Leu Pro His Asp Leu Ile Phe
```

```
                    530                 535                 540
Arg Gly Pro Asn Val Val Thr Leu
545                 550

<210> SEQ ID NO 7
<211> LENGTH: 498
<212> TYPE: PRT
<213> ORGANISM: Lymphocytic choriomeningitis virus (LCMV)
<220> FEATURE:
<223> OTHER INFORMATION: Amino acid sequence of the GP protein of the MP
      strain of LCMV

<400> SEQUENCE: 7

Met Gly Gln Ile Val Thr Met Phe Glu Ala Leu Pro His Ile Ile Asp
1               5                   10                  15

Glu Val Ile Asn Ile Val Ile Ile Val Leu Ile Ile Ile Thr Ser Ile
            20                  25                  30

Lys Ala Val Tyr Asn Phe Ala Thr Cys Gly Ile Leu Ala Leu Ile Ser
        35                  40                  45

Phe Leu Phe Leu Ala Gly Arg Ser Cys Gly Met Tyr Gly Leu Asp Gly
    50                  55                  60

Pro Asp Ile Tyr Lys Gly Val Tyr Arg Phe Lys Ser Val Glu Phe Asp
65                  70                  75                  80

Met Ser Tyr Leu Asn Leu Thr Met Pro Asn Ala Cys Ser Ala Asn Asn
                85                  90                  95

Ser His His Tyr Ile Ser Met Gly Thr Ser Gly Leu Glu Leu Thr Phe
            100                 105                 110

Thr Asn Asp Ser Ile Ile Thr His Asn Phe Cys Asn Leu Thr Ser Ala
        115                 120                 125

Leu Asn Lys Arg Thr Phe Asp His Thr Leu Met Ser Ile Val Ser Ser
    130                 135                 140

Leu His Leu Ser Ile Arg Gly Val Pro Ser Tyr Lys Ala Val Ser Cys
145                 150                 155                 160

Asp Phe Asn Asn Gly Ile Thr Ile Gln Tyr Asn Leu Ser Phe Ser Asn
                165                 170                 175

Ala Gln Ser Ala Leu Ser Gln Cys Lys Thr Phe Arg Gly Arg Val Leu
            180                 185                 190

Asp Met Phe Arg Thr Ala Phe Gly Gly Lys Tyr Met Arg Ser Gly Trp
        195                 200                 205

Gly Trp Thr Gly Ser Asp Gly Lys Thr Thr Trp Cys Ser Gln Thr Asn
    210                 215                 220

Tyr Gln Tyr Leu Ile Ile Gln Asn Arg Thr Trp Glu Asn His Cys Arg
225                 230                 235                 240

Tyr Ala Gly Pro Phe Gly Met Ser Arg Ile Leu Phe Ala Gln Glu Lys
                245                 250                 255

Thr Arg Phe Leu Thr Arg Arg Leu Ala Gly Thr Phe Thr Trp Thr Leu
            260                 265                 270

Ser Asp Ser Ser Gly Val Glu Asn Pro Gly Gly Tyr Cys Leu Thr Lys
        275                 280                 285

Trp Met Ile Leu Ala Ala Glu Leu Lys Cys Phe Gly Asn Thr Ala Val
    290                 295                 300

Ala Lys Cys Asn Val Asn His Asp Glu Glu Phe Cys Asp Met Leu Arg
305                 310                 315                 320

Leu Ile Asp Tyr Asn Lys Ala Ala Leu Ser Lys Phe Lys Glu Asp Val
                325                 330                 335
```

```
Glu Ser Ala Leu His Leu Phe Lys Thr Thr Val Asn Ser Leu Ile Ser
                340                 345                 350

Asp Gln Leu Leu Met Arg Asn His Leu Arg Asp Leu Met Gly Val Pro
            355                 360                 365

Tyr Cys Asn Tyr Ser Lys Phe Trp Tyr Leu Glu His Ala Lys Thr Gly
        370                 375                 380

Glu Thr Ser Val Pro Lys Cys Trp Leu Val Ser Asn Gly Ser Tyr Leu
385                 390                 395                 400

Asn Glu Thr His Phe Ser Asp Gln Ile Glu Gln Glu Ala Asp Asn Met
                405                 410                 415

Ile Thr Glu Met Leu Arg Lys Asp Tyr Ile Lys Arg Gln Gly Ser Thr
            420                 425                 430

Pro Leu Ala Leu Met Asp Leu Leu Met Phe Ser Thr Ser Ala Tyr Leu
        435                 440                 445

Ile Ser Ile Phe Leu His Leu Val Arg Ile Pro Thr His Arg His Ile
        450                 455                 460

Lys Gly Gly Ser Cys Pro Lys Pro His Arg Leu Thr Ser Lys Gly Ile
465                 470                 475                 480

Cys Ser Cys Gly Ala Phe Lys Val Pro Gly Val Glu Thr Thr Trp Lys
                485                 490                 495

Arg Arg

<210> SEQ ID NO 8
<211> LENGTH: 2201
<212> TYPE: PRT
<213> ORGANISM: Lymphocytic choriomeningitis virus (LCMV)
<220> FEATURE:
<223> OTHER INFORMATION: Amino acid sequence of the L protein of the MP
      strain of LCMV

<400> SEQUENCE: 8

Met Asp Glu Ala Ile Ser Glu Leu Arg Glu Leu Cys Leu Asn His Ile
1               5                   10                  15

Glu Gln Asp Glu Arg Leu Ser Arg Gln Lys Leu Asn Phe Leu Gly Gln
                20                  25                  30

Arg Glu Pro Arg Met Val Leu Ile Glu Gly Leu Lys Leu Leu Ser Arg
            35                  40                  45

Cys Ile Glu Ile Asp Ser Ala Asp Lys Ser Gly Cys Ile His Asn His
        50                  55                  60

Asp Asp Lys Ser Val Glu Ala Ile Leu Ile Glu Ser Gly Ile Val Cys
65                  70                  75                  80

Pro Gly Leu Pro Leu Ile Ile Pro Asp Gly Tyr Lys Leu Ile Asp Asn
                85                  90                  95

Ser Leu Ile Leu Leu Glu Cys Phe Val Arg Ser Thr Pro Ala Ser Phe
            100                 105                 110

Glu Lys Lys Phe Ile Glu Asp Thr Asn Lys Leu Ala Cys Ile Lys Glu
        115                 120                 125

Asp Leu Ala Ile Ala Gly Ile Thr Leu Val Pro Ile Val Asp Gly Arg
    130                 135                 140

Cys Asp Tyr Asp Asn Ser Phe Met Pro Glu Trp Val Asn Phe Lys Phe
145                 150                 155                 160

Arg Asp Leu Leu Phe Lys Leu Leu Glu Tyr Ser Ser Gln Asp Glu Lys
                165                 170                 175

Val Phe Glu Glu Ser Glu Tyr Phe Arg Leu Cys Glu Ser Leu Lys Thr
            180                 185                 190
```

-continued

```
Thr Val Asp Lys Arg Ser Gly Ile Asp Ser Met Lys Ile Leu Lys Asp
        195                 200                 205
Ala Arg Ser Phe His Asn Asp Glu Ile Met Lys Met Cys His Asp Gly
    210                 215                 220
Val Asn Pro Asn Met Asn Cys Asp Asp Val Val Leu Gly Ile Asn Ser
225                 230                 235                 240
Leu Tyr Ser Arg Phe Arg Arg Asp Leu Glu Thr Gly Lys Leu Lys Arg
                245                 250                 255
Ser Phe Gln Lys Ile Asn Pro Gly Asn Leu Ile Lys Glu Phe Ser Glu
            260                 265                 270
Leu Tyr Glu Thr Leu Ala Asp Ser Asp Ile Ser Ala Leu Ser Lys
        275                 280                 285
Glu Ala Val Glu Ser Cys Pro Leu Met Arg Phe Ile Thr Ala Asp Thr
    290                 295                 300
His Gly Tyr Glu Arg Gly Ser Glu Thr Ser Thr Glu Tyr Glu Arg Leu
305                 310                 315                 320
Leu Ser Met Leu Asn Lys Val Lys Ser Leu Lys Leu Leu Asn Thr Arg
                325                 330                 335
Arg Arg Gln Leu Leu Asn Leu Asp Val Leu Cys Leu Ser Ser Leu Ile
            340                 345                 350
Lys Gln Ser Lys Leu Lys Gly Ser Lys Asn Asp Lys His Trp Val Gly
        355                 360                 365
Cys Cys Tyr Gly Ser Val Asn Asp Arg Leu Val Ser Phe His Ser Thr
    370                 375                 380
Lys Glu Glu Phe Ile Arg Leu Leu Arg Asn Arg Lys Ser Lys Ala
385                 390                 395                 400
Tyr Arg Lys Val Ser Leu Glu Asp Leu Phe Arg Thr Ser Ile Asn Glu
                405                 410                 415
Phe Ile Leu Lys Val Gln Arg Cys Leu Ser Val Val Gly Leu Ser Phe
            420                 425                 430
Gly His Tyr Gly Leu Ser Glu His Leu Glu His Glu Cys His Ile Pro
        435                 440                 445
Phe Ile Glu Phe Glu Asn Phe Met Arg Ser Gly Thr His Pro Ile Met
    450                 455                 460
Tyr Tyr Thr Lys Phe Glu Asp Tyr Asp Phe Gln Pro Asn Thr Glu Gln
465                 470                 475                 480
Leu Arg Asn Met His Ser Leu Lys Arg Leu Ser Ser Val Cys Leu Ala
                485                 490                 495
Leu Thr Asn Ser Met Lys Thr Ser Ser Val Ala Arg Leu Arg Gln Asn
            500                 505                 510
Gln Leu Gly Ser Val Arg Tyr Gln Val Val Glu Cys Lys Glu Val Phe
        515                 520                 525
Cys Gln Val Ile Lys Leu Asp Ser Glu Glu Tyr His Leu Leu Tyr Gln
    530                 535                 540
Lys Thr Gly Glu Ser Ser Arg Cys Tyr Ser Ile Gln Gly Pro Asn Gly
545                 550                 555                 560
His Leu Ile Ser Phe Tyr Ala Asp Pro Lys Arg Phe Leu Pro Ile
                565                 570                 575
Phe Ser Asp Glu Val Leu His Asn Met Ile Asp Thr Met Ile Ser Trp
            580                 585                 590
Ile Arg Ser Cys Pro Asp Leu Lys Asp Ser Ile Asp Asp Val Glu Ile
        595                 600                 605
Ala Leu Arg Thr Leu Leu Leu Leu Met Leu Thr Asn Pro Thr Lys Arg
```

-continued

```
            610                 615                 620
Asn Gln Lys Gln Val Gln Asn Ile Arg Tyr Leu Val Met Ala Ile Val
625                 630                 635                 640

Ser Asp Phe Ser Ser Thr Ser Leu Met Asp Lys Leu Lys Glu Asp Leu
                    645                 650                 655

Ile Thr Pro Ala Glu Lys Val Val Tyr Lys Leu Leu Arg Phe Leu Ile
                660                 665                 670

Lys Thr Val Phe Gly Thr Gly Glu Lys Val Leu Leu Ser Ala Lys Phe
            675                 680                 685

Lys Phe Met Leu Asn Val Ser Tyr Leu Cys His Leu Ile Thr Lys Glu
        690                 695                 700

Thr Pro Asp Arg Leu Thr Asp Gln Ile Lys Cys Phe Glu Lys Phe Phe
705                 710                 715                 720

Glu Pro Lys Ser Glu Phe Gly Phe Phe Val Asn Pro Lys Glu Ser Ile
                725                 730                 735

Thr Pro Glu Glu Glu Cys Val Phe Tyr Asp Gln Met Lys Lys Phe Thr
                740                 745                 750

Gly Lys Glu Val Asp Cys Gln Arg Thr Thr Pro Gly Val Asn Leu Glu
            755                 760                 765

Met Met Val Ser Ser Phe Asn Asn Gly Thr Leu Ile Phe Lys Arg Leu
        770                 775                 780

Asn Ser Leu Asp Pro Met Thr Asn Ser Gly Cys Ala Thr Ala Leu Asp
785                 790                 795                 800

Leu Ala Ser Asn Lys Ser Val Val Asn Lys His Leu Asn Gly Glu
                805                 810                 815

Arg Leu Leu Glu Tyr Asp Phe Asn Lys Leu Leu Val Ser Ala Val Ser
                820                 825                 830

Gln Ile Thr Glu Ser Phe Met Arg Lys Gln Lys Tyr Lys Leu Asn His
            835                 840                 845

Ser Asp Tyr Glu Tyr Lys Val Ser Lys Leu Val Ser Arg Leu Val Ile
        850                 855                 860

Gly Ser Lys Glu Thr Glu Ala Gly Lys Leu Glu Gly Asp Ser Ala Asp
865                 870                 875                 880

Ile Cys Phe Asp Gly Glu Glu Thr Ser Phe Lys Asn Leu Glu
                885                 890                 895

Asp Lys Val Asn Ser Thr Ile Lys Arg Tyr Glu Arg Ser Lys Lys Thr
            900                 905                 910

Asn Glu Gly Glu Asn Glu Val Gly Phe Glu Asn Thr Lys Gly Leu His
        915                 920                 925

His Leu Gln Thr Ile Leu Ser Gly Lys Met Ala Tyr Leu Arg Lys Val
    930                 935                 940

Ile Leu Ser Glu Ile Ser Phe His Leu Val Glu Asp Phe Asp Pro Ser
945                 950                 955                 960

Cys Leu Thr Asn Asp Asp Met Lys Phe Ile Cys Glu Ala Ile Glu Thr
                965                 970                 975

Ser Thr Glu Leu Ser Pro Leu Tyr Phe Thr Ser Ala Val Lys Glu Gln
            980                 985                 990

Cys Gly Leu Asp Glu Met Ala Lys Asn Leu Cys Arg Lys Phe Phe Ser
        995                 1000                1005

Glu Gly Asp Trp Phe Ser Cys Met Lys Met Ile Leu Leu Gln Met
    1010                1015                1020

Asn Ala Asn Ala Tyr Ser Gly Lys Tyr Arg His Met Gln Arg Gln
    1025                1030                1035
```

-continued

Gly Leu Asn Phe Lys Phe Asp Trp Asp Lys Leu Glu Glu Asp Val
1040                1045                1050

Arg Ile Ser Glu Arg Glu Ser Asn Ser Glu Ser Leu Ser Lys Ala
1055                1060                1065

Leu Ser Leu Thr Lys Cys Met Ser Ala Ala Leu Lys Asn Leu Cys
1070                1075                1080

Phe Tyr Ser Glu Glu Ser Pro Thr Ser Tyr Thr Ser Val Gly Pro
1085                1090                1095

Asp Ser Gly Arg Leu Lys Phe Ala Leu Ser Tyr Lys Glu Gln Val
1100                1105                1110

Gly Gly Asn Arg Glu Leu Tyr Ile Gly Asp Leu Arg Thr Lys Met
1115                1120                1125

Phe Thr Arg Leu Ile Glu Asp Tyr Phe Glu Ser Phe Ser Ser Phe
1130                1135                1140

Phe Ser Gly Ser Cys Leu Asn Asn Asp Lys Glu Phe Glu Asn Ala
1145                1150                1155

Ile Leu Ser Met Thr Ile Asn Val Arg Glu Gly Leu Leu Asn Tyr
1160                1165                1170

Ser Met Asp His Ser Lys Trp Gly Pro Met Met Cys Pro Phe Leu
1175                1180                1185

Phe Leu Met Leu Leu Gln Asn Leu Lys Asp Asp Gln Tyr Val Arg
1190                1195                1200

Ser Gly Lys Asp His Ile Ser Thr Leu Leu Thr Trp His Met His
1205                1210                1215

Lys Leu Val Glu Val Pro Phe Pro Val Val Asn Ala Met Met Lys
1220                1225                1230

Ser Tyr Ile Lys Ser Lys Leu Lys Leu Leu Arg Gly Ser Glu Thr
1235                1240                1245

Thr Val Thr Glu Arg Ile Phe Arg Glu Tyr Phe Glu Leu Gly Ile
1250                1255                1260

Val Pro Ser His Ile Ser Ser Leu Ile Asp Met Gly Gln Gly Ile
1265                1270                1275

Leu His Asn Ala Ser Asp Phe Tyr Gly Leu Ile Ser Glu Arg Phe
1280                1285                1290

Ile Asn Tyr Cys Ile Gly Val Ile Phe Gly Glu Arg Pro Glu Ser
1295                1300                1305

Tyr Thr Ser Ser Asp Asp Gln Ile Thr Leu Phe Asp Arg Arg Leu
1310                1315                1320

Ser Glu Leu Val Asp Ser Asp Pro Glu Val Leu Val Leu Leu
1325                1330                1335

Glu Phe His Ser His Leu Ser Gly Leu Leu Asn Lys Phe Ile Ser
1340                1345                1350

Pro Lys Ser Val Val Gly Arg Phe Ala Ala Glu Phe Lys Ser Arg
1355                1360                1365

Phe Tyr Val Trp Gly Glu Glu Val Pro Leu Leu Thr Lys Phe Val
1370                1375                1380

Ser Ala Ala Leu His Asn Val Lys Cys Lys Glu Pro His Gln Leu
1385                1390                1395

Cys Glu Thr Ile Asp Thr Ile Ala Asp Gln Ala Val Ala Asn Gly
1400                1405                1410

Val Pro Val Ser Leu Val Asn Cys Ile Gln Lys Arg Thr Leu Asp
1415                1420                1425

```
Leu Leu Lys Tyr Ala Asn Phe Pro Leu Asp Pro Phe Leu Leu Asn
1430                1435                1440

Thr Asn Thr Asp Val Lys Asp Trp Leu Asp Gly Ser Arg Gly Tyr
1445                1450                1455

Arg Ile Gln Arg Leu Ile Glu Glu Leu Cys Pro Ser Glu Thr Lys
1460                1465                1470

Val Met Arg Arg Leu Val Arg Arg Leu His His Lys Leu Lys Asn
1475                1480                1485

Gly Glu Phe Asn Glu Glu Phe Phe Leu Asp Leu Phe Asn Arg Asp
1490                1495                1500

Lys Lys Glu Ala Ile Leu Gln Leu Gly Asn Ile Leu Gly Leu Glu
1505                1510                1515

Glu Asp Leu Ser Gln Leu Ala Asn Ile Asn Trp Leu Asn Leu Asn
1520                1525                1530

Glu Leu Phe Pro Leu Arg Met Val Leu Arg Gln Lys Val Val Tyr
1535                1540                1545

Pro Ser Val Met Thr Phe Gln Glu Glu Arg Ile Pro Ser Leu Ile
1550                1555                1560

Lys Thr Leu Gln Asn Lys Leu Cys Ser Lys Phe Thr Arg Gly Ala
1565                1570                1575

Gln Lys Leu Leu Ser Glu Ala Ile Asn Lys Ser Ala Phe Gln Ser
1580                1585                1590

Cys Ile Ser Ser Gly Phe Ile Gly Leu Cys Lys Thr Leu Gly Ser
1595                1600                1605

Arg Cys Val Arg Asn Lys Asn Arg Asp Asn Leu Tyr Ile Arg Lys
1610                1615                1620

Val Leu Glu Asp Leu Ala Met Asp Ala His Val Thr Ala Ile His
1625                1630                1635

Arg His Asp Gly Ile Met Leu Tyr Ile Cys Asp Arg Gln Ser His
1640                1645                1650

Pro Glu Ala His Cys Asp His Ile Ser Leu Leu Arg Pro Leu Leu
1655                1660                1665

Trp Asp Tyr Ile Cys Ile Ser Leu Ser Asn Ser Phe Glu Leu Gly
1670                1675                1680

Val Trp Val Leu Ala Glu Pro Val Lys Gly Lys Asn Glu Gly Ser
1685                1690                1695

Ser Ser Leu Lys His Leu Asn Pro Cys Asp Tyr Val Ala Arg Lys
1700                1705                1710

Pro Glu Ser Ser Arg Leu Leu Glu Asp Lys Ile Ser Leu Asn His
1715                1720                1725

Val Ile Gln Ser Val Arg Arg Leu Tyr Pro Lys Ile Tyr Glu Asp
1730                1735                1740

Gln Leu Leu Pro Phe Met Ser Asp Met Ser Ser Lys Asn Met Arg
1745                1750                1755

Trp Ser Pro Arg Ile Lys Phe Leu Asp Leu Cys Val Leu Ile Asp
1760                1765                1770

Ile Asn Ser Glu Ser Leu Ser Leu Ile Ser His Val Val Lys Trp
1775                1780                1785

Lys Arg Asp Glu His Tyr Thr Val Leu Phe Ser Asp Leu Val Asn
1790                1795                1800

Ser His Gln Arg Ser Asp Ser Ser Leu Val Asp Glu Phe Val Val
1805                1810                1815

Ser Thr Arg Asp Val Cys Lys Asn Phe Leu Lys Gln Val Tyr Phe
```

```
            1820                1825                1830

Glu Ser Phe Val Arg Glu Phe Val Ala Thr Ser Arg Thr Leu Gly
    1835                1840                1845

Ser Phe Ser Trp Phe Pro His Lys Asp Met Met Pro Ser Glu Asp
    1850                1855                1860

Gly Ala Glu Ala Leu Gly Pro Phe Gln Ser Phe Ile Leu Lys Val
    1865                1870                1875

Val Asn Lys Asn Met Glu Arg Pro Met Phe Arg Asn Asp Leu Gln
    1880                1885                1890

Phe Gly Phe Gly Trp Phe Ser Tyr Arg Leu Gly Asp Ile Val Cys
    1895                1900                1905

Asn Ala Ala Met Leu Ile Lys Gln Gly Leu Thr Asn Pro Lys Ala
    1910                1915                1920

Phe Lys Ser Leu Arg Asn Leu Trp Asp Tyr Met Ile Asn Asn Thr
    1925                1930                1935

Glu Gly Val Leu Glu Phe Ser Ile Thr Val Asp Phe Thr His Asn
    1940                1945                1950

Gln Asn Asn Thr Asp Cys Leu Arg Lys Phe Ser Leu Ile Phe Leu
    1955                1960                1965

Val Lys Cys Gln Leu Gln Gly Pro Gly Val Ala Glu Phe Leu Ser
    1970                1975                1980

Cys Ser His Leu Phe Lys Gly Glu Val Asp Arg Arg Phe Leu Asp
    1985                1990                1995

Glu Cys Leu His Leu Leu Arg Ser Asp Ser Ile Phe Lys Val Asn
    2000                2005                2010

Asp Gly Val Phe Asp Ile Arg Ser Glu Glu Phe Glu Asp Tyr Met
    2015                2020                2025

Glu Asp Pro Leu Ile Leu Gly Asp Ser Leu Glu Leu Glu Leu Ile
    2030                2035                2040

Gly Ser Arg Lys Ile Leu Asp Gly Ile Arg Ser Leu Asp Phe Glu
    2045                2050                2055

Arg Ile Gly Pro Glu Trp Glu Pro Val Pro Leu Thr Val Arg Met
    2060                2065                2070

Gly Ala Leu Phe Glu Gly Arg Ser Leu Val Gln Asn Ile Val Val
    2075                2080                2085

Lys Leu Glu Thr Lys Asp Met Arg Val Phe Leu Ala Glu Leu Glu
    2090                2095                2100

Gly Tyr Gly Asn Phe Asp Asp Val Leu Gly Ser Leu Leu Leu His
    2105                2110                2115

Arg Phe Arg Thr Gly Glu His Leu Gln Gly Ser Glu Ile Ser Thr
    2120                2125                2130

Ile Leu Gln Glu Leu Cys Ile Asp Arg Ser Ile Leu Leu Val Pro
    2135                2140                2145

Leu Ser Leu Val Pro Asp Trp Phe Thr Phe Lys Asp Cys Arg Leu
    2150                2155                2160

Cys Phe Ser Lys Ser Lys Asn Thr Val Met Tyr Glu Thr Val Val
    2165                2170                2175

Gly Lys Tyr Arg Leu Lys Gly Lys Ser Cys Asp Asp Trp Leu Thr
    2180                2185                2190

Lys Ser Val Val Glu Glu Ile Asp
    2195                2200
```

<210> SEQ ID NO 9

-continued

<211> LENGTH: 90
<212> TYPE: PRT
<213> ORGANISM: Lymphocytic choriomeningitis virus (LCMV)
<220> FEATURE:
<223> OTHER INFORMATION: amino acid sequence of the Z protein of the MP
      strain of LCMV

<400> SEQUENCE: 9

Met Gly Gln Gly Lys Ser Lys Glu Gly Arg Asp Ala Ser Asn Thr Ser
1               5                   10                  15

Arg Ala Glu Ile Leu Pro Asp Thr Thr Tyr Leu Gly Pro Leu Asn Cys
            20                  25                  30

Lys Ser Cys Trp Gln Arg Phe Asp Ser Leu Val Arg Cys His Asp His
        35                  40                  45

Tyr Leu Cys Arg His Cys Leu Asn Leu Leu Leu Ser Val Ser Asp Arg
    50                  55                  60

Cys Pro Leu Cys Lys His Pro Leu Pro Thr Lys Leu Lys Ile Ser Thr
65                  70                  75                  80

Ala Pro Ser Ser Pro Pro Pro Tyr Glu Glu
                85                  90

<210> SEQ ID NO 10
<211> LENGTH: 4604
<212> TYPE: DNA
<213> ORGANISM: Lymphocytic choriomeningitis virus (LCMV)
<220> FEATURE:
<223> OTHER INFORMATION: LCMV clone 13 S-Segment encoding HCMV strain
      Merlin gB (full-length wildtype)

<400> SEQUENCE: 10
gcgcaccggg gatcctaggc tttttggatt gcgctttcct ctagatcaac tgggtgtcag      60
gccctatcct acagaaggat ggaatccagg atctggtgcc tggtagtctg cgttaacttg     120
tgtatcgtct gtctgggtgc tgcggtttcc tcatcttcta ctcgtggaac ttctgctact     180
cacagtcacc attcctctca tacgacgtct gctgctcact ctcgatccgg ttcagtctct     240
caacgcgtaa cttcttccca acggtcagc catggtgtta acgagaccat ctacaacact     300
accctcaagt acggagatgt ggtggggtc aataccacca gtaccccta tcgcgtgtgt     360 tctatggccc agggtacgga tcttattcgc tttgaacgta atatcgtctg cacctcgatg     420
aagcccatca tgaagacct ggacgagggc atcatggtgg tctacaaacg caacatcgtc     480
gcgcacacct ttaaggtacg agtctaccag aaggttttga cgtttcgtcg tagctacgct     540
tacatccaca ccacttatct gctgggcagc aacacggaat acgtggcgcc tcctatgtgg     600
gagattcatc atatcaacag ccacagtcag tgctacagtt cctacagccg cgttatagca     660
ggcacggttt tcgtggctta tcatagggac agctatgaaa acaaaaccat gcaattaatg     720
cccgacgatt attccaacac ccacagtacc cgttacgtga cggtcaagga tcaatggcac     780
agccgcggca gcacctggct ctatcgtgag acctgtaatc tgaattgtat ggtgaccatc     840
actactgcgc gctccaaata tccttatcat tttttcgcca cttccacggg tgacgtggtt     900
gacatttctc ctttctacaa cggaaccaat cgcaatgcca gctactttgg agaaaacgcc     960
gacaagtttt tcattttcc gaactacact attgtctccg actttggaag accgaattct    1020
gcgttagaga cccacaggtt ggtggctttt cttgaacgtg cggactcggt gatctcctgg    1080
gatatacagg acgaaaagaa tgtcacttgt caactcactt tctgggaagc tcggaacgc    1140 accattcgtt ccgaagccga ggactcgtat cactttcttc tgccaaaat gaccgccact    1200 ttcttatcta agaagcaaga ggtgaacatg tccgactctg cgctggactg cgtacgtgat    1260

```
gaggctataa ataagttaca gcagattttc aatacttcat acaatcaaac atatgaaaaa    1320
tatggaaacg tgtccgtctt tgaaaccact ggtggtttgg tagtgttctg gcaaggtatc    1380
aagcaaaaat ctctggtgga actcgaacgt ttggccaacc gctccagtct gaatcttact    1440
cataatagaa ccaaaagaag tacagatggc aacaatgcaa ctcatttatc caacatggaa    1500
tcggtgcaca atctggtcta cgcccagctg cagttcacct atgacacgtt gcgcggttac    1560
atcaaccggg cgctggcgca aatcgcagaa gcctggtgtg tggatcaacg cgcacccta    1620 gaggtcttca aggaactcag caagatcaac ccgtcagcca ttctctcggc catttacaac    1680
aaaccgattg ccgcgcgttt catgggtgat gtcttgggcc tggccagctg cgtgaccatc    1740
aaccaaacca gcgtcaaggt gctgcgtgat atgaacgtga aggagtcgcc aggacgctgc    1800
tactcacgac ccgtggtcat ctttaatttc gccaacagct cgtacgtgca gtacggtcaa    1860
ctgggcgagg acaacgaaat cctgttgggc aaccaccgca ctgaggaatg tcagcttccc    1920
agcctcaaga tcttcatcgc cgggaactcg gcctacgagt acgtggacta cctcttcaaa    1980
cgcatgattg acctcagcag tatctccacc gtcgacagca tgatcgccct ggatatcgac    2040
ccgctggaaa ataccgactt cagggtactg gaactttact cgcagaaaga gctgcgttcc    2100
agcaacgttt ttgacctcga agagatcatg cgcgaattca actcgtacaa gcagcgggta    2160
aagtacgtgg aggacaaggt agtcgacccg ctaccgccct acctcaaggg tctggacgac    2220
ctcatgagcg gcctgggcgc cgcgggaaag gccgttggcg tagccattgg ggccgtgggt    2280
ggcgcggtgg cctccgtggt cgaaggcgtt gccaccttcc tcaaaaaccc cttcggagcg    2340
ttcaccatca tcctcgtggc catagctgta gtcattatca cttatttgat ctatactcga    2400
cagcggcgtt tgtgcacgca gccgctgcag aacctctttc cctatctggt gtccgccgac    2460
gggaccaccg tgacgtcggg cagcaccaaa gacacgtcgt tacaggctcc gccttcctac    2520
gaggaaagtg tttataattc tggtcgcaaa ggaccgggac caccgtcgtc tgatgcatcc    2580
acggcggctc cgccttacac caacgagcag gcttaccaga tgcttctggc cctggcccgt    2640
ctggacgcag agcagcgagc gcagcagaac ggtacagatt cttggacgg acggactggc    2700 acgcaggaca agggacagaa gcccaaccta ctagaccgac tgcgacatcg caaaaacggc    2760
taccgacact tgaaagactc tgacgaagaa gagaacgtct gaagaacagc gcctccctga    2820
ctctccacct cgaaagaggt ggagagtcag ggaggcccag agggtcttag agtgtcacaa    2880
catttgggcc tctaaaaatt aggtcatgtg gcagaatgtt gtgaacagtt ttcagatctg    2940
ggagccttgc tttggaggcg cttttcaaaaa tgatgcagtc catgagtgca cagtgcgggg    3000
tgatctcttt cttcttttg tcccttacta ttccagtatg catcttacac aaccagccat    3060
atttgtccca cactttatct tcatactccc tcgaagcttc cctggtcatt tcaacatcga    3120
taagcttaat gtccttccta ttttgtgagt ccagaagctt tctgatgtca tcggagcctt    3180
gacagcttag aaccatcccc tgcggaagag cacctataac tgacgaggtc aacccgggtt    3240
gcgcattgaa gaggtcggca agatccatgc cgtgtgagta cttggaatct tgcttgaatt    3300 gttttttgatc aacgggttcc ctgtaaaagt gtatgaactg cccgttctgt ggttggaaaa    3360
ttgctatttc cactggatca ttaaatctac cctcaatgtc aatccatgta ggagcgttgg    3420
ggtcaattcc tcccatgagg tcttttaaaa gcattgtctg gctgtagctt aagcccacct    3480
gaggtggacc tgctgctcca ggcgctggcc tgggtgagtt gactgcaggt ttctcgcttg    3540
tgagatcaat tgttgtgttt tcccatgctc tccccacaat cgatgttcta caagctatgt    3600
```

-continued

| | |
|---|---|
| atggccatcc ttcacctgaa aggcaaactt tatagaggat gttttcataa gggttcctgt | 3660 |
| ccccaacttg gtctgaaaca acatgttga gttttctctt ggccccgaga actgccttca | 3720 |
| agagatcctc gctgttgctt ggcttgatca aaattgactc taacatgtta ccccatcca | 3780 |
| acagggctgc ccctgccttc acggcagcac caagactaaa gttatagcca gaaatgttga | 3840 |
| tgctggactg ctgttcagtg atgaccccca gaactgggtg cttgtctttc agccttcaa | 3900 |
| gatcattaag atttggatac ttgactgtgt aaagcaagcc aaggtctgtg agcgcttgta | 3960 |
| caacgtcatt gagcggagtc tgtgactgtt tggccataca agccatagtt agacttggca | 4020 |
| ttgtgccaaa ttgattgttc aaaagtgatg agtctttcac atcccaaact cttaccacac | 4080 |
| cacttgcacc ctgctgaggc tttctcatcc caactatctg taggatctga gatctttggt | 4140 |
| ctagttgctg tgttgttaag ttccccatat atacccctga agcctgggc ctttcagacc | 4200 |
| tcatgatctt ggccttcagc ttctcaaggt cagccgcaag agacatcagt tcttctgcac | 4260 |
| tgagcctccc cactttcaaa acattcttct ttgatgttga cttaaatcc acaagagaat | 4320 |
| gtacagtctg gttgagactt ctgagtctct gtaggtcttt gtcatctctc tttccttcc | 4380 |
| tcatgatcct ctgaacattg ctgacctcag agaagtccaa cccattcaga aggttggttg | 4440 |
| catccttaat gacagcagcc ttcacatctg atgtgaagct ctgcaattct cttctcaatg | 4500 |
| cttgcgtcca ttggaagctc ttaacttcct tagacaagga catcttgttg ctcaatggtt | 4560 |
| tctcaagaca aatgcgcaat caaatgccta ggatccactg tgcg | 4604 |

<210> SEQ ID NO 11
<211> LENGTH: 35
<212> TYPE: DNA
<213> ORGANISM: Artificial Sequence
<220> FEATURE:
<223> OTHER INFORMATION: WE-specific primer

<400> SEQUENCE: 11
aatcgtctct aaggatgggt cagattgtga caatg     35

<210> SEQ ID NO 12
<211> LENGTH: 35
<212> TYPE: DNA
<213> ORGANISM: Artificial Sequence
<220> FEATURE:
<223> OTHER INFORMATION: WE specific fusion-primer carrying an overhang
      complementary to the WET-specific primer

<400> SEQUENCE: 12
aatcgtctct aaggatgggt cagattgtga caatg     35

<210> SEQ ID NO 13
<211> LENGTH: 37
<212> TYPE: DNA
<213> ORGANISM: Artificial Sequence
<220> FEATURE:
<223> OTHER INFORMATION: WET-specific primer

<400> SEQUENCE: 13
ctcggtgatc atgttatctg cttcttgttc gatttga     37

<210> SEQ ID NO 14
<211> LENGTH: 34
<212> TYPE: DNA
<213> ORGANISM: Artificial Sequence
<220> FEATURE:
<223> OTHER INFORMATION: WET-specific fusion-primer complementary to the
      WE-sequence -continued

<400> SEQUENCE: 14
aatcgtctct ttctttatct cctcttccag atgg                               34

<210> SEQ ID NO 15
<211> LENGTH: 23
<212> TYPE: DNA
<213> ORGANISM: Artificial Sequence
<220> FEATURE:
<223> OTHER INFORMATION: Primer specific for LCMV NP

<400> SEQUENCE: 15
ggctcccaga tctgaaaact gtt                                           23

<210> SEQ ID NO 16
<211> LENGTH: 22
<212> TYPE: DNA
<213> ORGANISM: Artificial Sequence
<220> FEATURE:
<223> OTHER INFORMATION: NP- and GP-specific primer

<400> SEQUENCE: 16
gctggcttgt cactaatggc tc                                            22

<210> SEQ ID NO 17
<211> LENGTH: 535
<212> TYPE: DNA
<213> ORGANISM: Artificial Sequence
<220> FEATURE:
<223> OTHER INFORMATION: Representative cDNA sequence obtained from
      animal #3 (r3LCMV-GFPnat #3) revealing a recombined S segment
      combining NP and GP sequences

<400> SEQUENCE: 17
aagaagcaga taacatgatc accgagatgc tgaggaagga ctacatcaag agacagggca    60 gcaccccct ggccctcatg gatctgctca tgttcagcac cagcgcctac ctcatcagca    120
tcttcctgca cctggtgaag atccccaccc acagacacat caagggcggc agctgcccca   180
agccccacag actcaccaac aagggcatct gcagctgcgg cgccttcaag gtgcccggcg   240
taaaaaccat ctggaagagg agataaagaa cagcgcctcc ctgactctcc acctcgaaag   300
aggtggagag tcagggaggc ccagagggtc ttacttgtac agctcgtcca tgccgagagt   360
gatcccggcg gcggtcacga actccagcag gaagaacagc gcctccctga ctctccacct   420
cgaaagaggt ggagagtcag ggaggcccag aggtcttaga gtgtcacaac atttgggcct   480
ctaaaaatta ggtcatgtgg cagaatgttg tgaacagttt tcagatctgg gagcc         535

<210> SEQ ID NO 18
<211> LENGTH: 2555
<212> TYPE: DNA
<213> ORGANISM: Artificial Sequence
<220> FEATURE:
<223> OTHER INFORMATION: S segment 1 of r3LCMV-P1A (containing NP)

<400> SEQUENCE: 18
gcgcaccggg gatcctaggc tttttggatt gcgctttcct ctagatcaac tgggtgtcag    60
gccctatcct acagaaggat gagcgacaac aagaagcccg acaaggccca ctctggcagc   120
ggcggagatg gcgacggcaa cagatgtaac ctgctgcaca gatacagcct ggaagagatc   180
ctgccctacc tggctggct ggtgttcgcc gtcgtgacaa caagcttcct ggccctgcag    240
atgttcatcg acgccctgta cgaggaacag tacgagaggg acgtggcctg gatcgccaga   300

-continued

```
cagagcaaga gaatgagcag cgtggacgag gacgaggatg atgaggacga cgaagatgac    360
tactacgacg atgaggatga cgacgacgac gccttctacg atgacgagga cgatgaagag    420
gaagaactgg aaaacctgat ggacgacgag tccgaggatg aggccgagga agagatgagc    480
gtggaaatgg gcgctggcgc cgaagagatg ggagccggcg ctaactgtgc ttgcgtgcca    540
ggacaccacc tgagaaagaa cgaagtgaag tgccggatga tctacttctt ccacgacccc    600
aactttctgg tgtccatccc cgtgaacccc aaagaacaga tggaatgcag atgcgagaac    660
gccgacgaag aggtggccat ggaagaagaa gaggaagagg aagaagaaga agaagaggaa    720
gaaatgggca accccgacgg cttcagcccc tgaagaacag cgcctccctg actctccacc    780
tcgaaagagg tggagagtca gggaggccca gagggtctta gagtgtcaca acatttgggc    840
ctctaaaaat taggtcatgt ggcagaatgt tgtgaacagt tttcagatct gggagccttg    900
ctttggaggc gcttttcaaaa atgatgcagt ccatgagtgc acagtgcggg gtgatctctt    960
tcttcttttt gtcccttact attccagtat gcatcttaca caaccagcca tatttgtccc   1020
acactttatc ttcatactcc ctcgaagctt ccctggtcat ttcaacatcg ataagcttaa   1080
tgtccttcct attttgtgag tccagaagct ttctgatgtc atcggagcct tgacagctta   1140
gaaccatccc ctgcggaaga gcacctataa ctgacgaggt caacccgggt tgcgcattga   1200
agaggtcggc aagatccatg ccgtgtgagt acttggaatc ttgcttgaat tgttttgat   1260
caacgggttc cctgtaaaag tgtatgaact gcccgttctg tggttggaaa attgctattt   1320
ccactggatc attaaatcta ccctcaatgt caatccatgt aggagcgttg gggtcaattc   1380
ctcccatgag gtcttttaaa agcattgtct ggctgtagct taagcccacc tgaggtggac   1440
ctgctgctcc aggcgctggc ctgggtgagt tgactgcagg tttctcgctt gtgagatcaa   1500
ttgttgtgtt ttcccatgct ctccccacaa tcgatgttct acaagctatg tatggccatc   1560
cttcacctga aaggcaaact ttatagagga tgttttcata agggttcctg tccccaactt   1620
ggtctgaaac aaacatgttg agttttctct tggccccgag aactgccttc aagagatcct   1680
cgctgttgct tggcttgatc aaaattgact ctaacatgtt accccatcc aacagggctg   1740
cccctgcctt cacggcagca ccaagactaa agttatagcc agaaatgttg atgctggact   1800
gctgttcagt gatgaccccc agaactgggt gcttgtcttt cagcctttca agatcattaa   1860
gatttggata cttgactgtg taaagcaagc caaggtctgt gagcgcttgt acaacgtcat   1920
tgagcggagt ctgtgactgt ttggccatac aagccatagt tagacttggc attgtgccaa   1980
attgattgtt caaaagtgat gagtctttca catcccaaac tcttaccaca ccacttgcac   2040
cctgctgagg ctttctcatc ccaactatct gtaggatctg agatctttgg tctagttgct   2100
gtgttgttaa gttccccata tataccctg aagcctgggg cctttcagac ctcatgatct   2160
tggccttcag cttctcaagg tcagccgcaa gagacatcag ttcttctgca ctgagcctcc   2220
ccactttcaa acattcttc tttgatgttg actttaaatc cacaagagaa tgtacagtct   2280
ggttgagact tctgagtctc tgtaggtctt tgtcatctct cttttccttc ctcatgatcc   2340
tctgaacatt gctgacctca gagaagtcca accattcag aaggttggtt gcatccttaa   2400
tgacagcagc cttcacatct gatgtgaagc tctgcaattc tcttctcaat gcttgcgtcc   2460
attggaagct cttaacttcc ttagacaagg acatcttgtt gctcaatggt ttctcaagac   2520
aaatgcgcaa tcaaatgcct aggatccact gtgcg                              2555
```

<210> SEQ ID NO 19
<211> LENGTH: 2375

```
<212> TYPE: DNA
<213> ORGANISM: Artificial Sequence
<220> FEATURE:
<223> OTHER INFORMATION: S segment 2 of r3LCMV-P1A (containing GP)

<400> SEQUENCE: 19
gcgcaccggg gatcctaggc tttttggatt gcgctttcct ctagatcaac tgggtgtcag      60
gccctatcct acagaaggat gagcgacaac aagaagcccg acaaggccca ctctggcagc     120
ggcggagatg gcgacggcaa cagatgtaac ctgctgcaca gatacagcct ggaagagatc     180
ctgccctacc tgggctggct ggtgttcgcc gtcgtgacaa caagcttcct ggccctgcag     240
atgttcatcg acgccctgta cgaggaacag tacgagaggg acgtggcctg gatcgccaga     300
cagagcaaga gaatgagcag cgtggacgag gacgaggatg atgaggacga cgaagatgac     360
tactacgacg atgaggatga cgacgacgac gccttctacg atgacgagga cgatgaagag     420
gaagaactgg aaaacctgat ggacgacgag tccgaggatg aggccgagga gagatgagc      480
gtggaaatgg gcgctggcgc cgaagagatg ggagccggcg ctaactgtgc ttgcgtgcca     540
ggacaccacc tgagaaagaa cgaagtgaag tgccggatga tctacttctt ccacgacccc     600
aactttctgg tgtccatccc cgtgaacccc aagaacaga tggaatgcag atgcgagaac      660
gccgacgaag aggtggccat ggaagaagaa gaggaagagg aagaagaaga agaagaggaa     720
gaaatgggca accccgacgg cttcagcccc tgaagaacag cgcctccctg actctccacc     780
tcgaaagagg tggagagtca gggaggccca gagggtctca gcgtctttc cagacggttt      840
ttacaccagg caccttaaat gcaccacaac tacaaattcc tttgttggtt aatcggtgtg     900
gctttggaca tgagccacct tttatgtgcc tgtgtgttgg tattttgaca aggtgcagga     960
agatgctgac tagatatgca gatgtggaaa acatcagaag gtccatcaat gctagggggg    1020
tactcccctg cctctttatg taatccttcc tcaacatctc tgtaatcatg ttatcggctt    1080
cctgttcgat ttggtcactg aagtgggtct catttaagta agaaccattg gtgacaagcc    1140
agcacttggg gacactagtt tcgccggtct ttgcatgttc taggtaccaa aactttgagt    1200
aattgcaata tggcaccccc atcagatctc tcaagtggtt cctcatcagt agttgatctg    1260
aaatcaaaga attcactgtt gttttgaata agtgcaaggc agattctacg tcctctttga    1320
acttactcaa agcagccttg ttgtagtcaa ttagtcgcag catgtcacag aattcttcat    1380
catgatttac attgcatttc gcaactgctg tgttcccgaa acacttaagc tctgcagcaa    1440
gaatcatcca tttggtcagg caataaccac ctggattctc caccctgaa gagtctgaca     1500
aagtccaggt gaatgtgccc gctagtctcc tagtggagaa cttagttttc tcttgggaaa    1560
ggagaatcct ggacatccca aaaggacctg catatgtgca gtggttttcc caggttctat    1620
tttgtataat caggtattgg taactcgtct ggctacacca ggtggtcttg ccatctgagc    1680
ctgtccagcc ccagccactc ctcatgtatt tcccccgaa ggcagttcta aacatatcta     1740
ggactctacc tctgaaggtt ctacactggc tctgagcact ttgtgcatct gagaatgtca    1800
agttgtattg gatggttatg ccattgttga agtcgcagga tactgcctta gttggagt      1860
tccctctgat actgaggtgt aggctcgaaa ctatactcat gagtgtgtgg tcaaaggtct    1920
ttttgttgaa ggcagaggtc agattgcaaa agttgtgact gatgatgaa tcattggtga     1980
aggtcaattc tagtccagaa gtccccatac tgatgtaatg gtgggagttg ttggctgaac    2040
atgcgttggg catggtcagg ttcagatgtg acatatcaaa ctccactgac ttaaattggt    2100
aaactccttt gtaaatgtcg ggtcccttaa gaccgtacat gccacaggac ctgccagcca    2160
```

| | |
|---|---|
| gaagtaggaa actgatcaat gcgaatatcc cacaggtggc aaaattgtag acagccttga | 2220 |
| tacccgtgat cacgataagc acaataatga caatgttgat cacctcatcg atgatgtgag | 2280 |
| gcagagcctc aaacattgtc acaatctgac ccatcttgtt gctcaatggt ttctcaagac | 2340 |
| aaatgcgcaa tcaaatgcct aggatccact gtgcg | 2375 |

```
<210> SEQ ID NO 20
<211> LENGTH: 7229
<212> TYPE: DNA
<213> ORGANISM: Artificial Sequence
<220> FEATURE:
<223> OTHER INFORMATION: L segment of r3LCMV-P1A

<400> SEQUENCE: 20
```

| | |
|---|---|
| gcgcaccggg gatcctaggc gtttagttgc gctgtttggt tgcacaactt tcttcgtgag | 60 |
| gctgtcagaa gtggacctgg ctgatagcga tgggtcaagg caagtccaga gaggagaaag | 120 |
| gcaccaatag tacaaacagg gccgaaatcc taccagatac cacctatctt ggcccttta a | 180 |
| gctgcaaatc ttgctggcag aaatttgaca gcttggtaag atgccatgac cactaccttt | 240 |
| gcaggcactg tttaaacctt ctgctgtcag tatccgacag gtgtcctctt tgtaaatatc | 300 |
| cattaccaac cagattgaag atatcaacag ccccaagctc tccacctccc tacgaagagt | 360 |
| aacaccgtcc ggccccggcc ccgacaaaca gcccagcaca agggaaccgc acgtcaccca | 420 |
| acgcacacag acacagcacc caacacagaa cacgcacaca cacacacaca cacacccaca | 480 |
| cgcacgcgcc cccaccaccg gggggcgccc cccccgggg gcggccccc cgggagcccg | 540 |
| ggcggagccc cacggagatg cccatcagtc gatgtcctcg gccaccgacc cgcccagcca | 600 |
| atcgtcgcag gacctcccct tgagtctaaa cctgcccccc actgtttcat acatcaaagt | 660 |
| gctcctagat ttgctaaaac aaagtctgca atccttaaag gcgaaccagt ctggcaaaag | 720 |
| cgacagtgga atcagcagaa tagatctgtc tatacatagt tcctggagga ttacacttat | 780 |
| ctctgaaccc aacaaatgtt caccagttct gaatcgatgc aggaagaggt tcccaaggac | 840 |
| atcactaatc tttcatagc cctcaagtcc tgctagaaag actttcatgt ccttggtctc | 900 |
| cagcttcaca atgatatttt ggacaaggtt tcttccttca aaagggcac ccatctttac | 960 |
| agtcagtggc acaggctccc actcaggtcc aactctctca aagtcaatag atctaatccc | 1020 |
| atccagtatt cttttggagc ccaacaactc aagctcaaga gaatcaccaa gtatcaaggg | 1080 |
| atcttccatg taatcctcaa actcttcaga tctgatatca aagacaccat cgttcacctt | 1140 |
| gaagacagag tctgtcctca gtaagtggag gcattcatcc acattcttc tatctatctc | 1200 |
| acccttaaag aggtgagagc atgataaaag ttcagccaca cctggattct gtaattggca | 1260 |
| cctaaccaag aatatcaatg aaaatttcct taaacagtca gtattattct gattgtgcgt | 1320 |
| aaagtccact gaaattgaaa actccaatac ccctttttgtg tagttgagca tgtagtccca | 1380 |
| cagatccttt aaggatttaa atgcctttgg gtttgtcagg ccctgcctaa tcaacatggc | 1440 |
| agcattacac acaacatctc ccattcggta agagaaccac ccaaaaccaa actgcaaatc | 1500 |
| attcctaaac ataggcctct ccacattttt gttcaccacc tttgagacaa atgattgaaa | 1560 |
| ggggcccagt gcctcagcac catcttcaga tggcatcatt tctttatgag gaaccatga | 1620 |
| aaaattgcct aatgtcctgg ttgttgcaac aaattctcga acaaatgatt caaaatacac | 1680 |
| ctgtttttaag aagttcttgc agacatccct cgtgctaaca acaaattcat caaccagact | 1740 |
| ggagtcagat cgctgatgag aattggcaag gtcagaaaac agaacagtgt aatgttcatc | 1800 |
| ccttttccac ttaacaacat gagaaatgag tgacaaggat tctgagttaa tatcaattaa | 1860 |

```
aacacagagg tcaaggaatt taattctggg actccacctc atgttttttg agctcatgtc   1920
agacataaat ggaagaagct gatcctcaaa gatcttggga tatagccgcc tcacagattg   1980
aatcacttgg ttcaaattca ctttgtcctc cagtagcctt gagctctcag gctttcttgc   2040
tacataatca catgggttta agtgcttaag agttaggttc tcactgttat tcttcccttt   2100
ggtcggttct gctaggaccc aaacacccaa ctcaaaagag ttgctcaatg aaatacaaat   2160
gtagtcccaa agaagaggcc ttaaaaggca tatatgatca cggtgggctt ctggatgaga   2220
ctgtttgtca caaatgtaca gcgttatacc atcccgattg caaactcttg tcacatgatc   2280
atctgtggtt agatcctcaa gcagcttttt gatatacaga ttttccctat ttttgtttct   2340
cacacacctg cttcctagag ttttgcaaag gcctataaag ccagatgaga tacaactctg   2400
gaaagctgac ttgttgattg cttctgacag cagcttctgt gcaccccttg tgaatttact   2460
acaaagtttg ttctggagtg tcttgatcaa tgatgggatt cttttcctctt ggaaagtcat   2520 cactgatgga taaaccacct tttgtcttaa aaccatcctt aatgggaaca tttcattcaa   2580
attcaaccag ttaacatctg ctaactgatt cagatcttct tcaagaccga ggaggtctcc   2640
caattgaaga atggcctcct ttttatctct gttaaatagg tctaagaaaa attcttcatt   2700
aaattcacca tttttgagct tatgatgcag tttccttaca agctttctta caacctttgt   2760
ttcattagga cacagttcct caatgagtct ttgtattctg taacctctag aaccatccag   2820
ccaatctttc acatcagtgt tggtattcag tagaaatgga tccaagggga aattggcata   2880
ctttaggagg tccagtgttc tcctttggat actattaact agggagactg ggacgccatt   2940
tgcgatggct tgatctgcaa ttgtatctat tgtttcacaa agttgatgtg gctctttaca   3000
cttgacattg tgtagcgctg cagatacaaa ctttgtgaga gagggactt cctcccccca   3060 tacatagaat ctagatttaa attctgcagc gaacctccca gccacacttt ttgggctgat   3120
aaatttgttt aacaagccgc tcagatgaga ttggaattcc aacaggacaa ggacttcctc   3180
cggatcactt acaaccaggt cactcagcct cctatcaaat aaagtgatct gatcatcact   3240
tgatgtgtaa gcctctggtc tttcgccaaa gataacacca atgcagtagt tgatgaacct   3300
ctcgctaagc aaaccataga agtcagaagc attatgcaag attccctgcc ccatatcaat   3360
aaggctggat atatgggatg gcactatccc catttcaaaa tattgtctga aaattctctc   3420
agtaacagtt gtttctgaac ccctgagaag ttttagcttc gacttgacat atgatttcat   3480
cattgcattc acaacaggaa aggggacctc gacaagctta tgcatgtgcc aagttaacaa   3540
agtgctaaca tgatctttcc cggaacgcac atactggtca tcacctagtt tgagattttg   3600
tagaaacatt aagaacaaaa atgggcacat cattggtccc catttgctgt gatccatact   3660
atagtttaag aacccttccc gcacattgat agtcattgac aagattgcat tttcaaattc   3720
cttatcattg tttaaacagg agcctgaaaa gaaacttgaa aaagactcaa ataatcttc   3780 tattaacctt gtgaacattt ttgtcctcaa atctccaata tagagttctc tatttccccc   3840
aacctgctct ttataagata gtgcaaattt cagccttcca gagtcaggac ctactgaggt   3900
gtatgatgtt ggtgattctt ctgagtagaa gcacagattt ttcaaagcag cactcataca   3960
ttgtgtcaac gacagagctt tactaaggga ctcagaatta ctttccctct cactgattct   4020
cacgtcttct tccagtttgt cccagtcaaa tttgaaattc aagccttgcc tttgcatatg   4080
cctgtatttc cctgagtacg catttgcatt catttgcaac agaatcatct tcatgcaaga   4140
aaaccaatca ttctcagaaa agaactttct acaaaggttt tttgccatct catcgaggcc   4200
```

```
acactgatct ttaatgactg aggtgaaata caaaggtgac agctctgtgg aaccctcaac      4260
agcctcacag ataaatttca tgtcatcatt ggttagacat gatgggtcaa agtcttctac      4320
taaatggaaa gatatttctg acaagataac ttttcttaag tgagccatct tccctgttag      4380
aataagctgt aaatgatgta gtccttttgt atttgtaagt ttttctccat ctcctttgtc      4440
attggccctc ctacctcttc tgtaccgtgc tattgtggtg ttgacctttt cttcgagact      4500
tttgaagaag cttgtctctt cttctccatc aaaacatatt tctgccaggt tgtcttccga      4560
tctccctgtc tcttctccct tggaaccgat gaccaatcta gagactaact tggaaacttt      4620
atattcatag tctgagtggc tcaacttata cttttgtttt cttacgaaac tctccgtaat      4680
ttgactcaca gcactaacaa gcaatttgtt aaagtcatat tccagaagtc gttctccatt      4740
tagatgctta ttaaccacca cacttttgtt actagcaaga tctaatgctg tcgcacatcc      4800
agagttagtc atgggatcta ggctgtttag cttcttctct cctttgaaaa ttaaagtgcc      4860
gttgttaaat gaagacacca ttaggctaaa ggcttccaga ttaacacctg gagttgtatg      4920
ctgacagtca atttctttac tagtgaatct cttcatttgc tcatagaaca cacattcttc      4980
ctcaggagtg attgcttcct tggggttgac aaaaaaacca aattgacttt tgggctcaaa      5040 gaactttta aaacatttta tctgatctgt tagcctgtca ggggtctcct ttgtgatcaa       5100
atgacacagg tatgcacat tcaacataaa tttaaatttt gcactcaaca acaccttctc       5160
accagtacca aaaatagttt ttattaggaa tctaagcagc ttatacacca ccttctcagc      5220
aggtgtgatc agatcctccc tcaacttatc cattaatgat gtagatgaaa atctgacac       5280 tattgccatc accaaatatc tgacactctg tacctgcttt tgatttctct tgttgggtt       5340 ggtgagcatt agcaacaata gggtcctcag tgcaacctca atgtcggtga gacagtcttt      5400
caaatcagga catgatctaa tccatgaaat catgatgtct atcatattgt ataagacctc      5460
atctgaaaaa attggtaaaa agaacctttt aggatctgca tagaaggaaa ttaaatgacc      5520
atccgggcct tgtatggagt agcaccttga agattctcca gtcttctggt ataataggtg      5580
gtattcttca gagtccagtt ttattacttg gcaaacact tctttgcatt ctaccacttg       5640
atatctcaca gacccatttt gattttgcct tagtctagca actgagctag ttttcatact      5700
gtttgttaag gccagacaaa cagatgataa tcttctcagg ctctgtatgt tcttcagctg      5760
ctctgtgctg ggttggaaat tgtaatcttc aaacttcgta taatacatta tcgggtgagc      5820
tccaattttc ataaagttct caaattcagt gaatggtatg tggcattctt gctcaaggtg      5880
ttcagacagt ccgtaatgct cgaaactcag tcccaccact aacaggcatt tttgaatttt      5940
tgcaatgaac tcactaatag atgccctaaa caattcctca aaagacacct ttctaaacac      6000
ctttgacttt tttctattcc tcaaaagtct aatgaactcc tctttagtgc tgtgaaagct      6060
taccagccta tcattcacac tactatagca acaacccacc cagtgtttat cattttttaa      6120
ccctttgaat ttcgactgtt ttatcaatga ggaaagacac aaaacatcca gatttaacaa      6180
ctgtctcctt ctagtattca acagtttcaa actcttgact ttgtttaaca tagagaggag      6240
cctctcatat tcagtgctag tctcacttcc cctttcgtgc ccatgggtct ctgcagttat      6300
gaatctcatc aaaggacagg attcgactgc ctccctgctt aatgttaaga tatcatcact      6360
atcagcaagg ttttcataga gctcagagaa ttccttgatc aagccttcag ggtttacttt      6420
ctgaaagttt ctctttaatt tcccactttc taaatctctt ctaaacctgc tgaaaagaga      6480
gtttattcca aaaaccacat catcacagct catgttgggg ttgatgcctt cgtggcacat      6540
cctcataatt tcatcattgt gagttgacct cgcatctttc agaattttca tagagtccat      6600
```

```
accggagcgc ttgtcgatag tagtcttcag ggactcacag agtctaaaat attcagactc    6660
ttcaaagact ttctcatttt ggttagaata ctccaaaagt ttgaataaaa ggtctctaaa    6720
tttgaagttt gcccactctg gcataaaact attatcataa tcacaacgac catctactat    6780
tggaactaat gtgacacccg caacagcaag gtcttccctg atgcatgcca atttgttagt    6840
gtcctctata aatttcttct caaaactggc tggagtgctc ctaacaaaac actcaagaag    6900
aatgagagaa ttgtctatca gcttgtaacc atcaggaatg ataagtggta gtcctgggca    6960
tacaattcca gactccacca aaattgtttc cacagactta tcgtcgtggt tgtgtgtgca    7020
gccactcttg tctgcactgt ctatttcaat gcagcgtgac agcaacttga gtccctcaat    7080
cagaaccatt ctgggttccc tttgtcccag aaagttgagt ttctgccttg acaacctctc    7140
atcctgttct atatagttta aacataactc tctcaattct gagatgattt catccattgc    7200
gcatcaaaaa gcctaggatc ctcggtgcg                                      7229

<210> SEQ ID NO 21
<211> LENGTH: 2628
<212> TYPE: DNA
<213> ORGANISM: Artificial Sequence
<220> FEATURE:
<223> OTHER INFORMATION: S segment 1 of r3JUNV-P1A (containing NP)

<400> SEQUENCE: 21
gcgcaccggg gatcctaggc gattttggtt acgctataat tgtaactgtt ttctgtttgg      60
acaacatcaa aaacatccat tgcacaatga gcgacaacaa gaagcccgac aaggcccact     120
ctggcagcgg cggagatggc gacggcaaca gatgtaacct gctgcacaga tacagcctgg     180
aagagatcct gccctacctg ggctggctgg tgttcgccgt cgtgacaaca agcttcctgg     240
ccctgcagat gttcatcgac gccctgtacg aggaacagta cgagagggac gtggcctgga     300
tcgccagaca gagcaagaga atgagcagcg tggacgagga cgaggatgat gaggacgacg     360
aagatgacta ctacgacgat gaggatgacg acgacgcgc cttctacgat gacgaggacg     420
atgaagagga gaactggaa acctgatgat gcgacgagtc cgaggatgag gccgaggaag     480
agatgagcgt ggaaatgggc gctggcgccg aagagatggg agccggcgct aactgtgctt     540
gcgtgccagg acaccacctg agaaagaacg aagtgaagtg ccggatgatc tacttcttcc     600 acgacccccaa ctttctggtg tccatccccg tgaaccccaa agaacagatg gaatgcagat     660
gcgagaacgc cgacgaagag gtggccatgg aagaagaaga ggaagaggaa gaagaagaag     720
aagaggaaga aatgggcaac cccgacggct tcagcccctg agacctcctg agggtcccca     780
ccagcccggg cactgcccgg gctggtgtgg cccccccagtc cgcggcctgg ccgcggactg     840
gggaggcact gcttacagtg cataggctgc cttcgggagg aacagcaagc tcggtggtaa     900
tagaggtgta ggttcctcct catagagctt cccatctagc actgactgaa acattatgca     960
gtctagcaga gcacagtgtg gttcactgga ggccaacttg aagggagtat ccttttccct    1020 cttttttctta ttgacaacca ctccattgtg atatttgcat aagtgaccat atttctccca    1080
gacctgttga tcaaactgcc tggcttgttc agatgtgagc ttaacatcaa ccagtttaag    1140
atctcttctt ccatggaggt caaacaactt cctgatgtca tcggatcctt gagtagtcac    1200
aaccatgtct ggaggcagca agccgatcac gtaactaaga actcctggca ttgcatcttc    1260
tatgtccttc attaagatgc cgtgagagtg tctgctacca tttttaaacc ctttctcatc    1320
atgtggtttt ctgaagcagt gaatgtactg cttacctgca ggttggaata atgccatctc    1380
```

```
aacagggtca gtggctggtc cttcaatgtc gagccaaagg gtgttggtgg ggtcgagttt    1440
ccccactgcc tctctgatga cagcttcttg tatctctgtc aagttagcca atctcaaatt    1500
ctgaccgttt ttttccggct gtctaggacc agcaactggt ttccttgtca gatcaatact    1560
tgtgttgtcc catgacctgc ctgtgatttg tgatctagaa ccaatataag gccaaccatc    1620
gccagaaaga caaagtttgt acaaaaggtt ttcataagga tttctattgc ctggtttctc    1680
atcaataaac atgccttctc ttcgtttaac ctgaatggtt gattttatga gggaagagaa    1740
gttttctggg gtgactctga ttgtttccaa catgtttcca ccatcaagaa tagatgctcc    1800
agcctttact gcagctgaaa gactgaagtt gtaaccagaa atattgatgg agctttcatc    1860
tttagtcaca atctgaaggc agtcatgttc ctgagtcagt ctgtcaaggt cacttaagtt    1920
tggatacttc acagtgtata aagcccaag tgaggttaaa gcttgtatga cactgttcat    1980
tgtctcacct ccttgaacag tcatgcatgc aattgtcaat gcaggaacag agccaaactg    2040
attgtttagc tttgaagggg cttaacatc ccatatcctc accacaccat ttcccccagt    2100
cccttgctgt tgaaatccca gtgttctcaa tatctctgat cttttagcaa gttgtgactg    2160
ggacaagtta cccatgtaaa cccctgaga gcctgtctct gctcttctta tcttgttttt    2220
taatttctca aggtcagacg ccaactccat cagttcatcc ctcccagat ctcccacctt    2280 gaaaactgtg tttcgttgaa cactcctcat ggacatgagt ctgtcaacct ctttattcag    2340
gtccctcaac ttgttgagat cttcttcccc cttttagtc tttctgagtg cccgctgcac    2400
ctgtgccact tggttgaagt cgatgctgtc agcaattagc ttggcgtcct tcaaaacatc    2460
tgacttgaca gtctgagtga attggctcaa acctctcctt aaggactgag tccatctaaa    2520
gcttggaacc tccttggagt gtgccatgcc agaagttctg gtgattttga tctagaatag    2580
agttgctcag tgaaagtgtt agacactatg cctaggatcc actgtgcg    2628
```

<210> SEQ ID NO 22
<211> LENGTH: 2391
<212> TYPE: DNA
<213> ORGANISM: Artificial Sequence
<220> FEATURE:
<223> OTHER INFORMATION: S segment 2 of r3JUNV-P1A (containing GP)

<400> SEQUENCE: 22

```
gcgcaccggg gatcctaggc gattttggtt acgctataat tgtaactgtt ttctgtttgg     60
acaacatcaa aaacatccat tgcacaatga gcgacaacaa gaagcccgac aaggcccact    120
ctggcagcgg cggagatggc gacggcaaca gatgtaacct gctgcacaga tacagcctgg    180
aagagatcct gccctacctg ggctggctgg tgttcgccgt cgtgacaaca agcttcctgg    240
ccctgcagat gttcatcgac gccctgtacg aggaacagta cgagagggac gtggcctgga    300
tcgccagaca gagcaagaga atgagcagcg tggacgagga cgaggatgat gaggacgacg    360
aagatgacta ctacgacgat gaggatgacg acgacgacgc cttctacgat gacgaggacg    420
atgaagagga agaactggaa aacctgatgg acgacgagtc cgaggatgag gccgaggaag    480
agatgagcgt ggaaatgggc gctggcgccg aagagatggg agccggcgct aactgtgctt    540
gcgtgccagg acaccacctg agaaagaacg aagtgaagtg ccggatgatc tacttcttcc    600
acgaccccaa ctttctggtg tccatccccg tgaaccccaa agaacagatg gaatgcagat    660
gcgagaacgc cgacgaagag gtggccatgg aagaagaaga ggaagaggaa gaagaagaag    720
aagaggaaga aatgggcaac cccgacggct tcagcccctg agacctcctg agggtcccca    780
ccagcccggg cactgcccgg gctggtgtgg ccccccagtc cgcggcctgg ccgcggactg    840
```

```
gggaggcact gcatggggca gttcattagc ttcatgcaag aaataccaac cttttttgcag    900
gaggctctga acattgctct tgttgcagtc agtctcattg ccatcattaa gggtatagtg    960
aacttgtaca aaagtggttt attccaattc tttgtattcc tagcgcttgc aggaagatcc   1020
tgcacagaag aagctttcaa aatcggactg cacactgagt tccagactgt gtccttctca   1080
atggtgggtc tcttttccaa caatccacat gacctacctt tgttgtgtac cttaaacaag   1140
agccatcttt acattaaggg gggcaatgct tcatttcaga tcagctttga tgatattgca   1200
gtattgttgc cacagtatga tgttataata caacatccag cagatatgag ctggtgttcc   1260
aaaagtgatg atcaaatttg gttgtctcag tggttcatga atgctgtggg acatgattgg   1320
catctagacc caccatttct gtgtaggaac cgtgcaaaga cagaaggctt catctttcaa   1380
gtcaacacct ccaagactgg tgtcaatgga aattatgcta agaagtttaa gactggcatg   1440
catcatttat atagagaata tcctgaccct tgcttgaatg gcaaactgtg cttaatgaag   1500
gcacaaccta ccagttggcc tctccaatgt ccactcgacc acgttaacac attacacttc   1560
cttacaagag gtaaaaacat tcaacttcca aggaggtcct tgaaagcatt cttctcctgg   1620
tctttgacag actcatccgg caaggatacc cctggaggct attgtctaga agagtggatg   1680
ctcgtagcag ccaaaatgaa gtgttttggc aatactgctg tagcaaaatg caatttgaat   1740
catgactctg aattctgtga catgttgagg ctctttgatt acaacaaaaa tgctatcaaa   1800
accctaaatg atgaaactaa gaaacaagta atctgatggg ggcagacaat caatgccctg   1860
atatctgaca atttattgat gaaaaacaaa attagggaac tgatgagtgt cccttactgc   1920
aattacacaa aattttggta tgtcaaccac acactttcag gacaacactc attaccaagg   1980
tgctggttaa taaaaaacaa cagctatttg aacatctctg acttccgtaa tgactggata   2040
ttagaaagtg acttcttaat ttctgaaatg ctaagcaaag agtattcgga caggcagggt   2100
aaaactcctt tgactttagt tgacatctgt attttggagca cagtattctt cacagcgtca   2160
ctcttccttc acttggtggg tataccctcc cacagacaca tcaggggcga agcatgccct   2220
ttgccacaca ggttgaacag cttgggtggt tgcagatgtg gtaagtaccc caatctaaag   2280
aaaccaacag tttggcgtag aggacactaa gccagaagtt ctggtgattt tgatctagaa   2340
tagagttgct cagtgaaagt gttagacact atgcctagga tccactgtgc g             2391
```

<210> SEQ ID NO 23
<211> LENGTH: 7115
<212> TYPE: DNA
<213> ORGANISM: Artificial Sequence
<220> FEATURE:
<223> OTHER INFORMATION: L segment of r3JUNV-P1A

<400> SEQUENCE: 23

```
gcgcaccggg gatcctaggc gtaacttcat cattaaaatc tcagattctg ctctgagtgt     60
gacttactgc gaagaggcag acaaatgggc aactgcaacg gggcatccaa gtctaaccag    120
ccagactcct caagagccac acagccagcc gcagaattta ggagggtagc tcacagcagt    180
ctatatggta gatataactg taagtgctgc tggtttgctg ataccaattt gataacctgt    240
aatgatcact accctttgttt aaggtgccat cagggtatgt taaggaattc agatctctgc    300
aatatctgct ggaagcccct gcccaccaca atcacagtac cggtggagcc aacagcacca    360
ccaccatagg cagactgcac agggtcagac ccgacccccc gggggcccc catgggggacc     420
ccccgtgggg gaaccccggg ggtgatgcgc cattagtcaa tgtctttgat ctcgactttg    480
```

```
tgcttcagtg gcctgcatgt caccccttc aatctgaact gcccttgggg atctgatatc    540
agcaggtcat ttaaagatct gctgaatgcc accttgaaat ttgagaattc caaccagtca   600
ccaaatttat caagtgaacg atcaactgc tctttgtgta gatcataaac gaggacaaag    660
tcctcttgct gaaataatat tgtttgtgat gttgttttta gataaggcca tagttggctt   720
aataaggttt ccacactatc aatgtcctct agtgctccaa ttgccttgac tatgacatcc   780
ccagacaact caactctata tgttgacaac ctttcattac ctctgtaaaa gatacctct    840
ttcaagacaa gaggttctcc tgggttatct ggcccaatga ggtcatatgc atacttgtta   900
cttagttcag aataaaagtc accaaagttg aacttaacat ggctcagaat attgtcatca   960
tttgtcgcag cgtagcctgc atcaataaac aagccagcta ggtcaaagct ctcatggcct  1020
gtgaacaatg gtaggctagc gataaccagt gcaccatcca acaatgagtg gcttccctca  1080
gacccagaaa cacattgact cattgcatcc acattcagct ctaattcagg ggtaccgaca  1140
tcatccactc ctagtgaact gacaatggtg taactgtaca ccatctttct tctaagttta  1200
aattttgtcg aaactcgtgt gtgttctact tgaatgatca attttagttt cacagcttct  1260
tggcaagcaa cattgcgcaa cacagtgtgc aggtccatca tgtcttcctg aggcaacaag  1320
gagatgttgt caacagagac accctcaagg aaaaccttga tattatcaaa gctagaaact  1380
acataaccca ttgcaatgtc ttcaacaaac attgctcttg atactttatt attcctaact  1440
gacaaggtaa aatctgtgag ttcagctaga tctacttgac tgtcatcttc tagatctaga  1500
acttcattga accaaaagaa ggatttgaga cacgatgttg acatgactag tgggtttatc  1560
atcgaagata agacaacttg caccatgaag ttcctgcaaa cttgctgtgg gctgatgcca  1620
acttcccaat ttgtatactc tgactgtcta acatgggctg aagcgcaatc actctgtttc  1680
acaatataaa cattattatc tcttactttc aataagtgac ttataatccc taagttttca  1740
ttcatcatgt ctagagccac acagacatct agaaacttga gtcttccact atccaaagat  1800
ctgttcactt gaagatcatt cataaagggt gccaaatgtt cttcaaatag tttggggtaa  1860
tttcttcgta tagaatgcaa tacatggttc atgcctaatt ggtcttctat ctgtcgtact  1920
gctttgggtt taacagccca gaagaaattc ttattacata agaccagagg ggcctgtgga  1980
ctcttaatag cagaaaacac ccactcccct aactcacagg catttgtcag caccaaagag  2040
aagtaatccc acaaaattgg tttagaaaat tggttaactt ctttaagtga ttttgacag   2100
taaataactt taggctttct ctcacaaatt ccacaaagac atggcattat tcgagtaaat  2160
atgtccttta tatacagaaa tccgccttta ccatccctaa cacacttact ccccatactc  2220
ttacaaaacc caatgaagcc tgaggcaaca gaagactgaa atgcagattt gttgattgac  2280
tctgccaaga tcttcttcac gccttttgtg aaatttcttg acagcctgga ctgtattgtc  2340
cttatcaatg ttggcatctc ttctttctct aacactcttc gacttgtcat gagtttggtc  2400
ctcaagacca acctcaagtc cccaaagctc gctaaattga cccatctgta gtctagagtt  2460
tgtctgattt catcttcact acacccggca tattgcagga atccggataa agcctcatcc  2520
cctcccctgc ttatcaagtt gataaggttt cctcaaaga tttttgcctct cttaatgtca  2580
ttgaacactt tcctcgcgca gttccttata aacattgtct ccttatcatc agaaaaaata  2640
gcttcaattt tcctctgtag acggtaccct ctagacccat caacccagtc tttgacatct  2700
tgttcttcaa tagctccaaa cggagtctct ctgtatccag agtatctaat caattggttg  2760
actctaatgg aaatctttga cactatatga gtgctaaccc cattagcaat acattgatca  2820
caaattgtgt ctatggtctc tgacagttgt gttggagttt tacacttaac gttgtgtaga  2880
```

```
gcagcagaca caaacttggt gagtaaagga gtctcttcac ccatgacaaa aaatcttgac    2940
ttaaactcag caacaaaagt tcctatcaca ctctttgggc tgataaactt gtttaattta    3000
gaagataaga attcatggaa gcacaccatt tccagcagtt ctgtcctgtc ttgaaacttt    3060
tcatcactaa ggcaaggaat ttttataagg ctaacctggt catcgctgga ggtataagtg    3120
acaggtatca catcatacaa taagtcaagt gcataacaca gaaattgttc agtaattagc    3180
ccatataaat ctgatgtgtt gtgcaagatt ccctggccca tgtccaagac agacattata    3240
tggctgggga cctggtccct tgactgcaga tactggtgaa aaactcttc accaacacta     3300 gtacagtcac aacccattaa acctaaagat ctcttcaatt tccctacaca gtaggcttct    3360
gcaacattaa ttggaacttc aacgacctta tgaagatgcc atttgagaat gttcattact    3420
ggttcaagat tcacctttgt tctatctctg ggattcttca attctaatgt gtacaaaaaa    3480
gaaaggaaaa gtgctgggct catagttggt ccccatttgg agtggtcata tgaacaggac    3540
aagtcaccat tgttaacagc catttttcata tcacagattg cacgttcgaa ttcctttct     3600 gaattcaagc atgtgtattt cattgaacta cccacagctt ctgagaagtc ttcaactaac    3660
ctggtcatca gcttagtgtt gaggtctccc acatacagtt ctctatttga gccaacctgc    3720
tccttataac ttagtccaaa tttcaagttc cctgtatttg agctgatgct tgtgaactct    3780
gtaggagagt cgtctgaata gaaacataaa ttccgtaggg ctgcatttgt aaaataactt    3840
ttgtctagct tatcagcaat ggcttcagaa ttgctttccc tggtactaag ccgaacctca    3900
tcctttagtc tcagaacttc actggaaaag cccaatctag atctacttct atgctcataa    3960
ctacccaatt tctgatcata atgtccttga attaaaagat acttgaagca ttcaaagaat    4020
tcatcttctt ggtaggctat tgttgtcaaa ttttttaata acaaacccaa agggcagatg    4080
tcctgcggtg cttcaagaaa ataagtcaat ttaaatggag atagataaac agcatcacat    4140
aactctttat acacatcaga cctgagcaca tctggatcaa aatccttcac ctcatgcatt    4200
gacacctctg ctttaatctc tctcaacact ccaaaagggg cccacaatga ctcaagagac    4260
tctcgctcat caacagatgg atttttttgat ttcaacttgg tgatctcaac tttttgtcccc   4320 tcactattag ccatcttggc tagtgtcatt tgtacgtcat ttctaatacc ctcaaaggcc    4380
cttacttgat cctctgttaa actctcatac atcactgata attcttcttg attggttctg    4440
gttcttgaac cggtgctcac aagacctgtt agatttttta atattaagta gtccatggaa    4500
tcaggatcaa gattatacct gccttttgtt ttaaacctct cagccatagt agaaacgcat    4560
gttgaaacaa gtttctcctt atcataaaca gaaagaatat ttccaagttc gtcgagcttg    4620
gggattacca cacttttatt gcttgacaga tccagagctg tgctagtgat gttaggcctg    4680
tagggattgc ttttcagttc acctgtaact ttaagtcttc ctctattgaa gagagaaatg    4740
cagaaggaca aaatctcttt acacactcct ggaatttgag tatctgagga agtcttagcc    4800
tctttggaaa agaatctgtc caatcctctt atcatggtgt cctcttgttc cagtgttaga    4860
ctcccactta gagggggtt tacaacaaca caatcaaact tgactttggg ctcaataaac     4920
ttctcaaaac actttatttg atctgtcagg cgatcaggtg tctctttggt taccaagtga    4980
cacagataac taacatttaa tagatattta aaccttcttg caaagtaaag atctgcatct    5040
tccccttcac ccaaaattgt ctggaaaagt tccacagcca tcctctgaat cagcacctct    5100
gatccagaca tgcagtcgac ccttaacttt gacatcaaat ccacatgatg gatttgattt    5160
gcatatgcca tcaagaaata tcttagacct tgtaaaaatg tctggttcct tttggaaggg    5220
```

| | |
|---|---|
| gaacagagta cagctaacac taacaatctt aatattggcc ttgtcattgt catgagttcg | 5280 |
| tggctaaaat ccaaccagct ggtcatttcc tcacacattt caattaacac atcctccgaa | 5340 |
| aatataggca ggaaaaatct ctttggatca cagtaaaaag agccttgttc ttccaatacc | 5400 |
| ccattgatgg atagatagat agaatagcac cttgacttct cacctgtttt ttggtaaaac | 5460 |
| aagagaccaa atgtattctt tgtcagatga atctttgta cataacactc tcttagtcta | 5520 |
| acattcccaa atatctaga atactctctt tcattgatta acaatcggga ggaaaatgat | 5580 |
| gtcttcatcg agttgaccaa tgcaagggaa atggaggaca aaatcctaaa taatttcttc | 5640 |
| tgctcacctt ccactaagct gctgaatggc tgatgtctac agatttctc aaattccttg | 5700 |
| ttaatagtat atctcatcac tggtctgtca gaaacaagtg cctgagctaa atcatcaag | 5760 |
| ctatccatat cagggtgttt tattagtttt tccagctgtg accagagatc ttgatgagag | 5820 |
| ttcttcaatg ttctggaaca cgcttgaacc cacttggggc tggtcatcaa tttcttcctt | 5880 |
| attagtttaa tcgcctccag aatatctaga agtctgtcat tgactaacat taacatttgt | 5940 |
| ccaacaacta ttcccgcatt tcttaacctt acaattgcat catcatgcgt tttgaaaaga | 6000 |
| tcacaaagta aattgagtaa aactaagtcc agaaacagta aagtgtttct cctggtgttg | 6060 |
| aaaacttta gaccttcac tttgttacac acggaaaggg cttgaagata cacctctct | 6120 |
| acagcatcaa tagatataga attctcatct gactggcttt ccatgttgac ttcatctatt | 6180 |
| ggatgcaatg cgatagagta gactacatcc atcaacttgt ttgcacaaaa agggcagctg | 6240 |
| ggcacatcac tgtctttgtg gcttcctaat aagatcaagt catttataag cttagacttt | 6300 |
| tgtgaaaatt tgaatttccc caactgcttg tcaaaaatct ccttcttaaa ccaaaacctt | 6360 |
| aactttatga gttcttctct tatgacagat tctctaatgt ctcctctaac cccaacaaag | 6420 |
| agggattcat ttaacctctc atcataaccc aaagaattc ttttcaagca ttcgatgttt | 6480 |
| tctaatccca agctctggtt ttttgtgttg gacaaactat ggatcaatcg ctggtattct | 6540 |
| tgttcttcaa tattaatctc ttgcataaat tttgatttct ttaggatgtc gatcagcaac | 6600 |
| caccgaactc tttcaacaac ccaatcagca aggaatctat tgctgtagct agatctgcca | 6660 |
| tcaaccacag gaaccaacgt aatccctgcc ttagtaggg cggactttag gtttaagagc | 6720 |
| tttgacatgt cactcttcca ttttctctca aactcatcag gattgaccct aacaaaggtt | 6780 |
| tccaatagga tgagtgtttt ccctgtgagt ttgaagccat ccggaatgac ttttggaagg | 6840 |
| gtgggacata gtatgccata gtcagacagg atcacatcaa caaacttctg atctgaattg | 6900 |
| atctgacagg cgtgtgcctc acaggactca agctctacta aacttgacag aagtttgaac | 6960 |
| ccttccaaca acagagagct ggggtgatgt tgagataaaa agatgtccct ttggtatgct | 7020 |
| agctcctgtc tttctggaaa atgctttcta ataaggcttt ttatttcatt tactgattcc | 7080 |
| tccatgctca agtgccgcct aggatcctcg gtgcg | 7115 |

<210> SEQ ID NO 24
<211> LENGTH: 224
<212> TYPE: PRT
<213> ORGANISM: Artificial Sequence
<220> FEATURE:
<223> OTHER INFORMATION: Amino acid sequence of a P815 mouse
      mastocytoma-derived self antigen P1A

<400> SEQUENCE: 24

Met Ser Asp Asn Lys Lys Pro Asp Lys Ala His Ser Gly Ser Gly Gly
1               5                   10                  15

Asp Gly Asp Gly Asn Arg Cys Asn Leu Leu His Arg Tyr Ser Leu Glu

-continued

```
                    20                  25                  30
Glu Ile Leu Pro Tyr Leu Gly Trp Leu Val Phe Ala Val Val Thr Thr
            35                  40                  45

Ser Phe Leu Ala Leu Gln Met Phe Ile Asp Ala Leu Tyr Glu Glu Gln
    50                  55                  60

Tyr Glu Arg Asp Val Ala Trp Ile Ala Arg Gln Ser Lys Arg Met Ser
65                  70                  75                  80

Ser Val Asp Glu Asp Glu Asp Asp Glu Asp Asp Glu Asp Asp Tyr Tyr
                85                  90                  95

Asp Asp Glu Asp Asp Asp Asp Ala Phe Tyr Asp Asp Glu Asp Asp
                100                 105                 110

Glu Glu Glu Glu Leu Glu Asn Leu Met Asp Asp Glu Ser Glu Asp Glu
            115                 120                 125

Ala Glu Glu Glu Met Ser Val Glu Met Gly Ala Gly Ala Glu Glu Met
        130                 135                 140

Gly Ala Gly Ala Asn Cys Ala Cys Val Pro Gly His His Leu Arg Lys
145                 150                 155                 160

Asn Glu Val Lys Cys Arg Met Ile Tyr Phe Phe His Asp Pro Asn Phe
                165                 170                 175

Leu Val Ser Ile Pro Val Asn Pro Lys Glu Gln Met Glu Cys Arg Cys
            180                 185                 190

Glu Asn Ala Asp Glu Glu Val Ala Met Glu Glu Glu Glu Glu Glu
        195                 200                 205

Glu Glu Glu Glu Glu Glu Glu Met Gly Asn Pro Asp Gly Phe Ser Pro
    210                 215                 220
```

TRI-SEGMENTED ARENAVIRUSES AS VACCINE VECTORS

This application is a U.S. National Stage Application under 35 U.S.C. § 371 of International Patent Application No. PCT/EP2015/076458, filed Nov. 12, 2015, which claims benefit of priority from U.S. provisional application No. 62/079,493 filed on Nov. 13, 2014, which is incorporated herein by reference in its entirety.

1. INTRODUCTION

The present application relates to arenaviruses with rearrangements of their open reading frames ("ORF") in their genomes. In particular, described herein is a modified arenavirus genomic segment, wherein the arenavirus genomic segment is engineered to carry a viral ORF in a position other than the wild-type position of the ORF. Also described herein are tri-segmented arenavirus particles comprising one L segment and two S segments or two L segments and one S segment. The arenavirus, described herein may be suitable for vaccines and/or treatment of diseases and/or for the use in immunotherapies.

2. BACKGROUND

2.1 Lymphocytic Choriomeningitis Virus Research and Human Disease

Lymphocytic choriomeningitis virus (LCMV), a member of the family arenaviridae, is a prototypic mouse model virus in research on viral infections. Since its isolation in the 1930s (Rivers and McNair Scott, 1935, Science, 81(2105): 439-440) studies using this virus have uncovered many key concepts in viral immunology and pathogenesis (summarized in Zinkernagel, 2002, Curr Top Microbiol Immunol, 263:1-5; Oldstone, 2002, Curr Top Microbiol Immunol, 263:83-117). LCMV has been extensively used to investigate viral molecular biology and immune responses particularly in the context of persistent infection. The natural host of LCMV are mice, however, several reports revealed that LCMV might also be a neglected human pathogen (Barton, 1996, Clin. Infect. Dis, 22(1):197; Wright et al., 1997, Pediatrics 100(1): E9). Moreover, numerous other members of the arenavirus family have been found in rodent populations around the world. In addition to the Old World arenavirus Lassa virus (LASV), which can be found in Africa, several New World arenaviruses like Junin (JUNV), Guanarito or Machupo are prevalent in diverse rodent populations of South America (Johnson et al., 1966, Am J Trop Med Hyg, 15(1): 103-106; Tesh et al., 1993, Am J Trop Med Hyg 49(2):227-235; Mills et al., 1994, Trop Med Hyg 51(5): 554-562). Upon transmission to humans, many of those viruses can cause viral hemorrhagic fever associated with high mortality (Geisbert and Jahrling, 2004, Nat Med 10(12 Suppl): S110-121).

2.2 Genomic Organization of Lymphocytic Choriomeningitis Virus

Arenaviruses are enveloped viruses. Their genome consists of two segments of single-stranded RNA of negative sense (L: 7.2 kb, S: 3.4 kb). Each segment encodes for two viral genes in opposite orientations. The short segment (S segment) encodes the viral glycoprotein (GP) precursor (GP-C; 75 kDa) and the nucleoprotein (NP; 63 kDa) (Salvato et al., 1988, Virology 164(2): 517-522). The long segment (L segment) expresses the RNA-dependent RNA polymerase (RdRp; L protein; approximately 200 kDa) and the matrix protein Z (protein Z), a RING finger protein (11 kDa) (FIG. 1A) (Salvato et al., 1988, Virology 164(2): 517-522). The GP precursor GP-C is post-translationally cleaved into GP-1 and GP-2, which remain non-covalently associated (Buchmeier and Oldstone 1979, Virology 99(1): 111-120). Trimers of GP-1 and GP-2 are assembled as spikes on the surface of virions and are essential for mediating entry into the host cells by interaction with the cellular surface receptors. Binding and entry of the virus into host cells was long claimed to be mediated by interaction of the LCMV GP with the cellular receptor α-Dystroglycan as the only cellular receptor for LCMV (Cao et al., 1998, Science, 282(5396):2079-2081). Only very recently three additional human molecules (Axl and Tyro3 from the TAM family and dendritic cell-specific intracellular adhesion molecule 3-grabbing nonintegrin) were postulated as additional receptors for LCMV and LASV, a close relative of LCMV, which enable entry of LCMV into cells independently of α-Dystroglycan (Shimojima and Kawaoka 2012, J Vet Med, 74(10):1363-1366; Shimojima et al., 2012, J Virol 86(4): 2067-2078). NP binds to the viral RNA, forming the nucleocapsid, which serves as a template for the viral L protein. The nucleocapsid associated with the viral L protein forms the so-called ribonucleoprotein complex, which is active both in replication and transcription and represents the minimum unit of viral infectivity. It has been shown, that NP and the L protein are the minimal trans-acting factors necessary for viral RNA transcription and replication (Lee et al., 2000, J Virol 74(8): 3470-3477). The two genes on each segment are separated by a non-coding intergenic region (IGR) and flanked by 5' and 3' untranslated regions (UTR). The IGR forms a stable hairpin structure and has been shown to be involved in structure-dependent termination of viral mRNA transcription (Pinschewer et al., 2005, J Virol 79(7): 4519-4526). The terminal nucleotides of the UTR show a high degree of complementarity, resulting in the formation of secondary structures. These panhandle structures are known to serve as the viral promoter for transcription and replication, and their analysis by site-directed mutagenesis has revealed sequence- and structure-dependence, tolerating not even minor sequence changes (Perez and de la Torre, 2003, Virol 77(2): 1184-1194).

2.3 Reverse Genetic System

Isolated and purified RNAs of negative-strand viruses like LCMV cannot directly serve as mRNA i.e., cannot be translated when introduced into cells. Consequently transfection of cells with viral RNA does not lead to production of infectious viral particles. In order to generate infectious viral particles of negative-stranded RNA viruses from cDNA in cultured permissive cells, the viral RNA segment(s) must be trans-complemented with the minimal factors required for transcription and replication. With the help of a minigenome system which has been published several years ago, viral cis-acting elements and transacting factors involved in transcription, replication and formation of viral particles could finally be analyzed (Lee et al., 2000, J Virol 74(8): 3470-3477; Lee et al., 2002, J Virol 76(12): 6393-6397; Perez and de la Torre 2003, J Virol 77(2): 1184-1194; Pinschewer et al., 2003, J Virol 77(6): 3882-3887; Pinschewer et al., 2005, J Virol 79(7): 4519-4526). Also for other arenaviruses like LASV and Tacaribe virus reverse genetic systems have been established (Lopez et al., 2001, J Virol 75(24): 12241-12251; Hass et al., 2004, J Virol 78(24): 13793-13803). Two publications showed the recovery of infectious LCMV entirely from cDNA using pol-I/-II or T7/pol-II-driven plasmids, respectively (referred to as "viral rescue") (Flatz et al., 2006, Proc Natl Acad Sci USA 103(12): 4663-4668; Sanchez and de la Torre, 2006, Virology 350(2): 370-380).

2.4 Recombinant LCMV Expressing Genes of Interest

The generation of recombinant negative-stranded RNA viruses expressing foreign genes of interest has been pursued for a long time. Different strategies have been published for other viruses (Garcia-Sastre et al., 1994, J Virol 68(10): 6254-6261; Percy et al., 1994, J Virol 68(7): 4486-4492; Flick and Hobom, 1999, Virology 262(1): 93-103; Machado et al., 2003, Virology 313(1): 235-249). In the past it has been shown that it is possible to introduce additional foreign genes into the genome of bi-segmented LCMV particles (Emonet et al., 2009, PNAS, 106(9):3473-3478). Two foreign genes of interest were inserted into the bi-segmented genome of LCMV, resulting in tri-segmented LCMV particles (r3LCMV) with two S segments and one L segment. In the tri-segmented virus, published by Emonet et al., (2009), both NP and GP were kept in their respective natural position in the S segment and thus were expressed under their natural promoters in the flanking UTR (FIG. 1B). However, the present application reveals that the tri-segmented LCMV particle disclosed by Emonet et al., assembles predominately bi-segmented particles (i.e., the arenavirus only packages one instead of two S segments), resulting in attenuated growth and strong selection pressure to recombine the two S segments. As further shown in the present application, such recombination is reproducibly found and results in phenotypic reversion to wild-type virus and transgene loss.

2.5 Replication-Defective Arenavirus

Recently, it has been shown that an infectious arenavirus particle can be engineered to contain a genome with the ability to amplify and express its genetic material in infected cells but unable to produce further progeny in normal, not genetically engineered cells (i.e., an infectious, replication-deficient arenavirus particle) (International Publication No.: WO 2009/083210 A1 and International Publication No.: WO 2014/140301 A1).

3. SUMMARY OF THE INVENTION

The present application, relates to arenaviruses with rearrangements of their ORFs in their genomes. In particular, the present application relates to an arenavirus genomic segment that has been engineered to carry an arenavirus ORF in a position other than the wild-type position. The present application also provides a tri-segmented arenavirus particle comprising one L segment and two S segments or two L segments and one S segment that do not recombine into a replication-competent bi-segmented arenavirus particle. The present application demonstrates that the tri-segmented arenavirus particle can be engineered to improve genetic stability and ensure lasting transgene expression.

In certain embodiments, a viral vector as provided herein is infectious, i.e., is capable of entering into or injecting its genetic material into a host cell. In certain more specific embodiments, a viral vector as provided herein is infectious, i.e., is capable of entering into or injecting its genetic material into a host cell followed by amplification and expression of its genetic information inside the host cell. In certain embodiments, the viral vector is an infectious, replication-deficient arenavirus viral vector engineered to contain a genome with the ability to amplify and express its genetic information in infected cells but unable to produce further infectious progeny particles in normal, not genetically engineered cells. In certain embodiments, the infectious arenavirus viral vector is replication-competent and able to produce further infectious progeny particles in normal, not genetically engineered cells. In certain more specific embodiments, such a replication-competent viral vector is attenuated relative to the wild type virus from which the replication-competent viral vector is derived.

3.1 Non-Natural Open Reading Frame

Accordingly, in one aspect, provided herein is an arenavirus genomic segment. In certain embodiments, the genomic segment is engineered to carry a viral ORF in a position other than the wild-type position of the ORF. In some embodiments, the arenavirus genomic segment is selected from the group consisting of:

(i) an S segment, wherein the ORF encoding the NP is under control of an arenavirus 5' UTR;
(ii) an S segment, wherein the ORF encoding the Z protein is under control of an arenavirus 5' UTR;
(iii) an S segment, wherein the ORF encoding the L protein is under control of an arenavirus 5' UTR;
(iv) an S segment, wherein the ORF encoding the GP is under control of an arenavirus 3' UTR;
(v) an S segment, wherein the ORF encoding the L protein is under control of an arenavirus 3' UTR;
(vi) an S segment, wherein the ORF encoding the Z protein is under control of an arenavirus 3' UTR;
(vii) an L segment, wherein the ORF encoding the GP is under control of an arenavirus 5' UTR;
(viii) an L segment, wherein the ORF encoding the NP is under control of an arenavirus 5' UTR;
(ix) an L segment, wherein the ORF encoding the L protein is under control of an arenavirus 5' UTR;
(x) an L segment, wherein the ORF encoding the GP is under control of an arenavirus 3' UTR;
(xi) an L segment, wherein the ORF encoding the NP is under control of an arenavirus 3' UTR; and
(xii) an L segment, wherein the ORF encoding the Z protein is under control of an arenavirus 3' UTR.

In some embodiments, the arenavirus 3' UTR is the 3' UTR of the arenavirus S segment or the arenavirus L segment. In certain embodiments, the arenavirus 5' UTR is the 5' UTR of the arenavirus S segment or the arenavirus L segment.

Also provided herein is an isolated cDNA of an arenavirus genomic segment provided herein. Also provided herein, is a DNA expression vector comprising a cDNA of the arenavirus genomic segment.

Also provided herein, is a host cell comprising the arenavirus genomic segment, a cDNA of the arenavirus genomic segment, or the vector comprising a cDNA of the arenavirus genomic segment.

Also provided herein, is an arenavirus particle comprising the arenavirus genomic segment and a second arenavirus genomic segment so that the arenavirus particle comprises an S segment and an L segment.

In certain embodiments, the arenavirus particle is infectious and replication competent. In some embodiments, the arenavirus particle is attenuated. In other embodiments, the arenavirus particle is infectious but unable to produce further infectious progeny in non-complementing cells.

In certain embodiments, at least one of the four ORFs encoding GP, NP, Z protein, and L protein is removed or functionally inactivated.

In certain embodiments, at least one of the four ORFs encoding GP, NP, Z protein and L protein is removed and replaced with a heterologous ORF from an organism other than an arenavirus. In other embodiments, only one of the four ORFs encoding GP, NP, Z protein and L protein is removed and replaced with a heterologous ORF from an organism other than an arenavirus. In a more specific embodiment, the ORF encoding GP is removed and replaced with a heterologous ORF from an organism other than an arenavirus. In other embodiments, the ORF encoding NP is removed and replaced with a heterologous ORF from an organism other than an arenavirus. In some embodiments, the ORF encoding the Z protein is removed and replaced with a heterologous ORF from an organism other than an arenavirus. In other embodiments, the ORF encoding the L protein is removed and replaced with a heterologous ORF from an organism other than an arenavirus.

In certain embodiments, the heterologous ORF encodes a reporter protein. In some embodiments, the heterologous ORF encodes an antigen derived from an infectious organism, tumor, or allergen. In other embodiments, the heterologous ORF encoding an antigen is selected from human immunodeficiency virus antigens, hepatitis C virus antigens, hepatitis B surface antigen, varizella zoster virus antigens, cytomegalovirus antigens, *Mycobacterium tuberculosis* antigens, and tumor associated antigens.

In certain embodiments, the growth or infectivity of the arenavirus particle is not affected by the heterologous ORF from an organism other than an arenavirus.

Also provided herein is a method of producing the arenavirus genomic segment. In certain embodiments, the method comprises transcribing the cDNA of the arenavirus genomic segment.

Also provided herein is a method of generating the arenavirus particle. In certain embodiments the method of generating the arenavirus particle comprises:
  (i) transfecting into a host cell the cDNA of the arenavirus genomic segment;
  (ii) transfecting into the host cell a plasmid comprising the cDNA of the second arenavirus genomic segment;
  (iii) maintaining the host cell under conditions suitable for virus formation; and
  (iv) harvesting the arenavirus particle.

In certain embodiments, the transcription of the L segment and the S segment is performed using a bidirectional promoter.

In certain embodiments, the method further comprises transfecting into a host cell one or more nucleic acids encoding an arenavirus polymerase. In yet more specific embodiments, the polymerase is the L protein. In other embodiments, the method further comprises transfecting into the host cell one or more nucleic acids encoding the NP.

In certain embodiments, transcription of the L segment, and the S segment are each under the control of a promoter selected from the group consisting of:
  (i) a RNA polymerase I promoter;
  (ii) a RNA polymerase II promoter; and
  (iii) a T7 promoter.

In another embodiment, provided herein is a vaccine comprising an arenavirus particle, wherein at least one of the four ORFs encoding GP, NP, Z protein, and L protein is removed or functionally inactivated; or wherein at least one ORF encoding GP, NP, Z protein, and L protein is removed and replaced with a heterologous ORF from another organism other than an arenavirus; or wherein only one of the four ORFs encoding GP, NP, Z protein, and L protein is removed and replaced with a heterologous ORF from an organism other than an arenavirus. In more specific embodiments, the vaccine further comprises a pharmaceutically acceptable carrier.

In another embodiment, provided herein is a pharmaceutical composition comprising an arenavirus particle, wherein at least one of the four ORFs encoding GP, NP, Z protein, and L protein is removed or functionally inactivated; or wherein at least one ORF encoding GP, NP, Z protein, and L protein is removed and replaced with a heterologous ORF from another organism other than an arenavirus; or wherein only one of the four ORFs encoding GP, NP, Z protein, and L protein is removed and replaced with a heterologous ORF from an organism other than an arenavirus. In more specific embodiments, the pharmaceutically acceptable carrier further comprises a pharmaceutically acceptable carrier.

In certain embodiments, the arenavirus genomic segment or the arenavirus particle is derived from LCMV. In some embodiments, the arenavirus genomic segment or arenavirus particle is derived from the LCMV MP strain, Armstrong strain, or Armstrong Clone 13 strain. In other embodiments, the arenavirus genomic segment or the arenavirus particle is derived from Junin virus vaccine Candid #1, or Junin virus vaccine XJ Clone 3 strain.

3.2 Tri-Segmented Arenavirus

In one aspect, provided herein is a tri-segmented arenavirus particle comprising one L segment and two S segments. In some embodiments, propagation of the tri-segmented arenavirus particle does not result in a replication-competent bi-segmented viral particle after 70 days of persistent infection in mice lacking type I interferon receptor, type II interferon receptor and recombination activating gene 1 (RAG1), and having been infected with $10^4$ PFU of the tri-segmented arenavirus particle. In certain embodiments, inter-segmental recombination of the two S segments, uniting two arenavirus ORFs on only one instead of two separate segments, abrogates viral promoter activity.

In another aspect, provided herein is a tri-segmented arenavirus particle comprising two L segments and one S segment. In certain embodiments, propagation of the tri-segmented arenavirus particle does not result in a replication-competent bi-segmented viral particle after 70 days of persistent infection in mice lacking type I interferon receptor, type II interferon receptor and recombination activating gene 1 (RAG1), and having been infected with $10^4$ PFU of the tri-segmented arenavirus particle. In certain embodiments, inter-segmental recombination of the two L segments, uniting two arenavirus ORFs on only one instead of two separate segments, abrogates viral promoter activity.

In certain embodiments, one of the two S segments is selected from the group consisting of:
  (i) an S segment, wherein the ORF encoding the NP is under control of an arenavirus 5' UTR
  (ii) an S segment, wherein the ORF encoding the Z protein is under control of an arenavirus 5' UTR;
  (iii) an S segment, wherein the ORF encoding the L protein is under control of an arenavirus 5' UTR;
  (iv) an S segment, wherein the ORF encoding the GP is under control of an arenavirus 3' UTR;
  (v) an S segment, wherein the ORF encoding the L protein is under control of an arenavirus 3' UTR; and
  (vi) an S segment, wherein the ORF encoding the Z protein is under control of an arenavirus 3' UTR.

In certain embodiments, one of the two L segments is selected from the group consisting of:
  (i) an L segment, wherein the ORF encoding the GP is under control of an arenavirus 5' UTR;
  (ii) an L segment, wherein the ORF encoding the NP is under control of an arenavirus 5' UTR;
  (iii) an L segment, wherein the ORF encoding the L protein is under control of an arenavirus 5' UTR;
  (iv) an L segment, wherein the ORF encoding the GP is under control of an arenavirus 3' UTR;

(v) an L segment, wherein the ORF encoding the NP is under control of an arenavirus 3' UTR; and (vi) an L segment, wherein the ORF encoding the Z protein is under control of an arenavirus 3' UTR.

In certain embodiments, the tri-segmented arenavirus particle 3' UTR is the 3' UTR of the arenavirus S segment or the arenavirus L segment. In other embodiments, the tri-segmented arenavirus particle 5' UTR is the 5' UTR of the arenavirus S segment or the arenavirus L segment.

In certain embodiments, the two S segments comprise (i) one or two heterologous ORFs from an organism other than an arenavirus; or (ii) one or two duplicated arenavirus ORFs; or (iii) one heterologous ORF from an organism other than an arenavirus and one duplicated arenavirus ORF.

In certain embodiments, the two L segments comprise (i) one or two heterologous ORFs from an organism other than an arenavirus; or (ii) one or two duplicated arenavirus ORFs; or (iii) one heterologous ORF from an organism other than an arenavirus and one duplicated arenavirus ORF.

In certain embodiments, the heterologous ORF encodes an antigen derived from an infectious organism, tumor, or allergen. In other embodiments, the heterologous ORF encoding an antigen is selected from human immunodeficiency virus antigens, hepatitis C virus antigens, hepatitis B surface antigen, varizella zoster virus antigens, cytomegalovirus antigens, *Mycobacterium tuberculosis* antigens, and tumor associated antigens.

In certain embodiments, at least one heterologous ORF encodes a fluorescent protein. In other embodiments the fluorescent protein is a green fluorescent protein (GFP) or red fluorescent protein (RFP).

In certain embodiments, the tri-segmented arenavirus particle comprises all four arenavirus ORFs. In some embodiments the tri-segmented arenavirus particle is infectious and replication competent.

In certain embodiments, the tri-segmented arenavirus particle lacks one or more of the four arenavirus ORFs. In other embodiments, the tri-segmented arenavirus particle is infectious but unable to produce further infectious progeny in non-complementing cells.

In certain embodiments, the tri-segmented arenavirus particle lacks one of the four arenavirus ORFs, wherein the tri-segmented arenavirus particle is infectious but unable to produce further infectious progeny in non-complementing cells.

In some embodiments, the tri-segmented arenavirus particle lacks the GP ORF.

In a further aspect, provided herein is a tri-segmented arenavirus particle comprising one L segment and two S segments. In certain embodiments, a first S segment is engineered to carry an ORF encoding GP in a position under control of an arenavirus 3' UTR and an ORF encoding a first gene of interest in a position under control of an arenavirus 5' UTR. In some embodiments, a second S segment is engineered to carry an ORF encoding the NP in a position under control of an arenavirus 3' UTR and an ORF encoding a second gene of interest in a position under control of an arenavirus 5' UTR.

In yet another aspect, provided herein, is a tri-segmented arenavirus particle comprising one L segment and two S segments. In certain embodiments, a first S segment is engineered to carry an ORF encoding GP in a position under control of an arenavirus 5' UTR and an ORF encoding a first gene of interest in a position under control of an arenavirus 3' UTR. In some embodiments, a second S segment is engineered to carry an ORF encoding NP in a position under control of an arenavirus 5' UTR and an ORF encoding a second gene of interest in a position under control of an arenavirus 3' UTR.

In certain embodiments, the gene of interest encodes an antigen derived from an infectious organism, tumor, or allergen. In other embodiments, the gene of interest encodes an antigen selected from human immunodeficiency virus antigens, hepatitis C virus antigens, hepatitis B surface antigen, varizella zoster virus antigens, cytomegalovirus antigens, *Mycobacterium tuberculosis* antigens, and tumor associated antigens. In yet another embodiment, at least one gene of interest encodes a fluorescent protein. In a specific embodiment, the fluorescent protein is GFP or RFP.

Also provided herein is an isolated cDNA of the genome of the tri-segmented arenavirus particle. Also provided herein, is a DNA expression vector comprising a cDNA of the genome of the tri-segmented arenavirus particle. Also provided herein is one or more DNA expression vectors comprising either individually or in their totality the cDNA of the tri-segmented arenavirus.

Also provided herein, is a host cell comprising the tri-segmented arenavirus particle, the cDNA of the genome of the tri-segmented arenavirus particle, or the vector comprising the cDNA of the genome of the tri-segmented arenavirus particle.

In certain embodiments, the tri-segmented arenavirus particle is attenuated

Also provided herein is a method of generating the tri-segmented arenavirus particle. In certain embodiments the method of generating the arenavirus particle comprises:

(i) transfecting into a host cell one or more cDNAs of one L segment and two S segments;

(ii) maintaining the host cell under conditions suitable for virus formation; and (iii) harvesting the arenavirus particle.

Also provided herein is a method of generating the tri-segmented arenavirus particle. In certain embodiments the method of generating the tri-segmented arenavirus particle comprises:

(i) transfecting into a host cell one or more cDNAs of two L segments and one S segment;

(ii) maintaining the host cell under conditions suitable for virus formation; and (iii) harvesting the arenavirus particle.

In certain embodiments, the transcription of the one L segment and two S segment is performed using a bidirectional promoter. In some embodiments, the transcription of the two L segments and one S segment is performed using a bidirectional promoter.

In certain embodiments, the method further comprises transfecting into a host cell one or more nucleic acids encoding an arenavirus polymerase. In yet more specific embodiments, the polymerase is the L protein. In other embodiments, the method further comprises transfecting into the host cell one or more nucleic acids encoding the NP protein.

In certain embodiments, transcription of the one L segment, and two S segments are each under the control of a promoter selected from the group consisting of:

(i) a RNA polymerase I promoter;

(ii) a RNA polymerase II promoter; and (iii) a T7 promoter.

In certain embodiments, transcription of the two L segments, and one S segment are each under the control of a promoter selected from the group consisting of:

(i) a RNA polymerase I promoter;

(ii) a RNA polymerase II promoter; and (iii) a T7 promoter.

In certain embodiments, the tri-segmented arenavirus particle has the same tropism as the bi-segmented arenavirus particle. In other embodiments, the tri-segmented arenavirus particle is replication deficient.

In another embodiment, provided herein is a vaccine comprising a tri-segmented arenavirus particle and a pharmaceutically acceptable carrier.

In another embodiment, provided herein is a pharmaceutical composition comprising a tri-segmented arenavirus particle and a pharmaceutically acceptable carrier.

In certain embodiments, the tri-segmented arenavirus particle is derived from LCMV. In some embodiments, the tri-segmented arenavirus particle is derived from the LCMV MP strain, Armstrong strain, or Armstrong Clone 13 strain. In other embodiments, the tri-segmented arenavirus particle is derived from Junin virus vaccine Candid #1, or Junin virus vaccine XJ Clone 3 strain.

3.3 Conventions and Abbreviations

| Abbreviation | Convention |
| --- | --- |
| APC | Antigen presenting cell |
| art | Artificial |
| CAT | Chloramphenicol acetyltransferase |
| CMI | cell-mediated immunity |
| CD8 | Cluster of differentiation 8 |
| CD4 | Cluster of differentiation 4 |
| GFP | Green fluorescent protein |
| GP | Glycoprotein |
| IGR | Intergenic region |
| JUNV | Junin virus |
| LCMV | Lymphocytic choriomeningitis virus |
| L protein | RNA-dependent RNA polymerase |
| L segment | Long segment |
| MHC | Major Histocompatibility Complex |
| Z protein | Matrix protein Z |
| nat | Natural |
| NP | Nucleoprotein |
| ORF | Open reading frame |
| RFP | Red fluorescent protein |
| r2JUNV | Recombinant bi-segmented JUNV |
| r3JUNV | Recombinant tri-segmented JUNV |
| r2LCMV | Recombinant bi-segmented LCMV |
| r3LCMV | Recombinant tri-segmented LCMV |
| S segment | Short segment |
| UTR | Untranslated region |
| VSV | Vesicular Stomatitis Virus |

4. BRIEF DESCRIPTION OF THE FIGURES

FIG. 1: Recombinant tri-segmented viruses show impaired growth compared to wild-type LCMV independently of the position of the GP ORF in the genome. (AC) Schematic representation of the genomic organization of bi- and tri-segmented LCMV. The bi-segmented genome of wild-type LCMV consists of one S segment encoding the GP and NP and one L segment encoding the Z protein and the L protein (A). Both segments are flanked by the respective 5' and 3' UTRs. The genome of recombinant tri-segmented LCMVs (r3LCMV) consists of one L and two S segments with one position where to insert a gene of interest (here GFP) into each one of the S segments. (B) r3LCMV-GFP$^{natural}$ (nat) has all viral genes in their natural position whereas the GP ORF in r3LCMV-GFP$^{artificial}$ (art) is artificially juxtaposed to and expressed under control of the 3' UTR (C). (D) Growth kinetics of the indicated viruses in BHK-21 cells, infected at a multiplicity of infection (moi) of 0.01 (wild-type LCMV: grey triangles; r3LCMV-GFP$^{nat}$: black circles; r3LCMV-GFP$^{art}$: white squares). Supernatant was taken at the indicated time points after infection and viral titers were determined by focus forming assay. Symbols and bars represent the mean±SEM of three replicates per group. Error bars are hidden in the symbol size.

Figure 2:
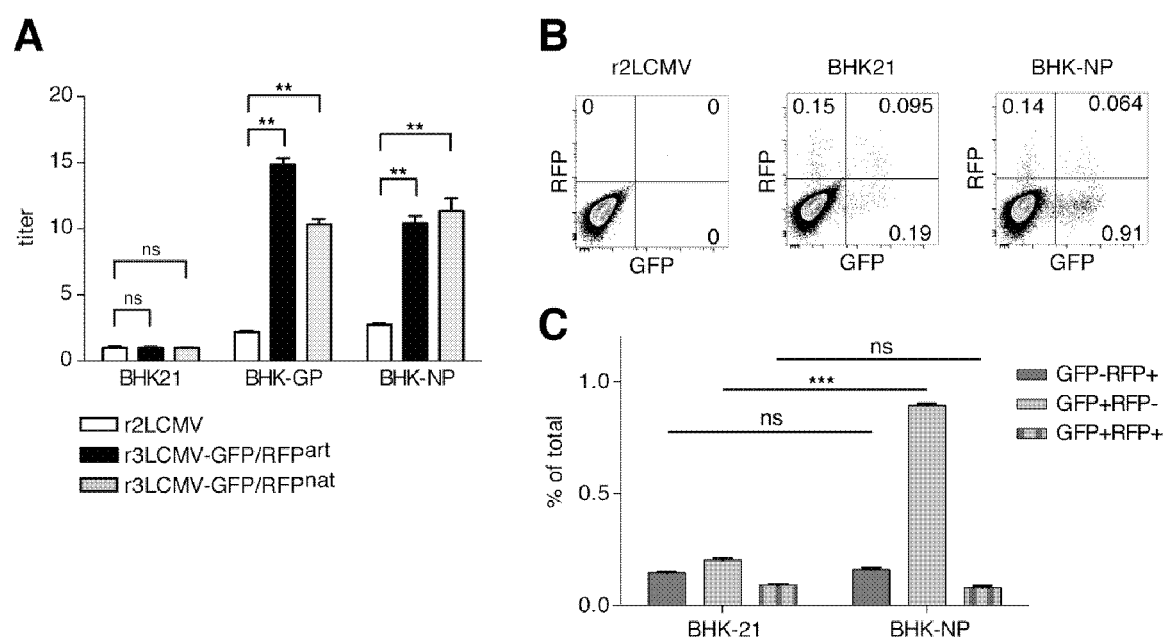

FIG. 2: Tri-segmented virus preparations contain a majority of bi-segmented replication-deficient particles (r2LCMV). (A) r2LCMV (white bars), r3LCMV-GFP/RF-P$^{art}$ (black bars, GFP-GP, RFP-NP) and r3LCMV-GFP/RFP$^{nat}$ (grey bars, GP-GFP, RFP-NP) were grown on wild-type BHK-21 cells and the infectivity of supernatant was determined on wild-type non-complementing BHK-21 cells (BHK21), GP-expressing (BHK-GP) or NP-expressing (BHK-NP) BHK-21 cells. Titers on BHK-21 and BHK-GP cells were determined by staining NP-positive viral foci. Titers on NP-complementing BHK-21 cells were determined by counting GP-positive foci. Titers were normalized to the average titer obtained when assessed on BHK-21 cells, and thus are expressed as a multiple thereof. Bars represent the mean±SEM of six replicates per group. ns.: not statistically significant (p≥0.05); : p<0.01 by 1-way ANOVA followed by Dunnett's post-test using r2LCMV as a reference. (B) r2LCMV (left plot) or r3LCMV-GFP/RFP$^{art}$ (middle and right plot) were grown on wild-type BHK-21 cells (BHK21; left and middle plot) or NP-expressing BHK-21 cells (BHK-NP, right plot) and fluorescence was assessed 12 hours after infection by flow cytometry. r2LCMV infected cells were used as gating control. One representative plot per condition is shown. (C) Quantification of GFP+, RFP+ or GFP+RFP+ double positive cells 12 hours after infection with r3LCMV-GFP/RFP$^{art}$ on BHK-21 or BHK-NP cells. Bars represent the mean±SEM of three replicates per group. ns.: not statistically significant (p≥0.05); *: p<0.001 by unpaired two-tailed student's t test.

Figure 3:
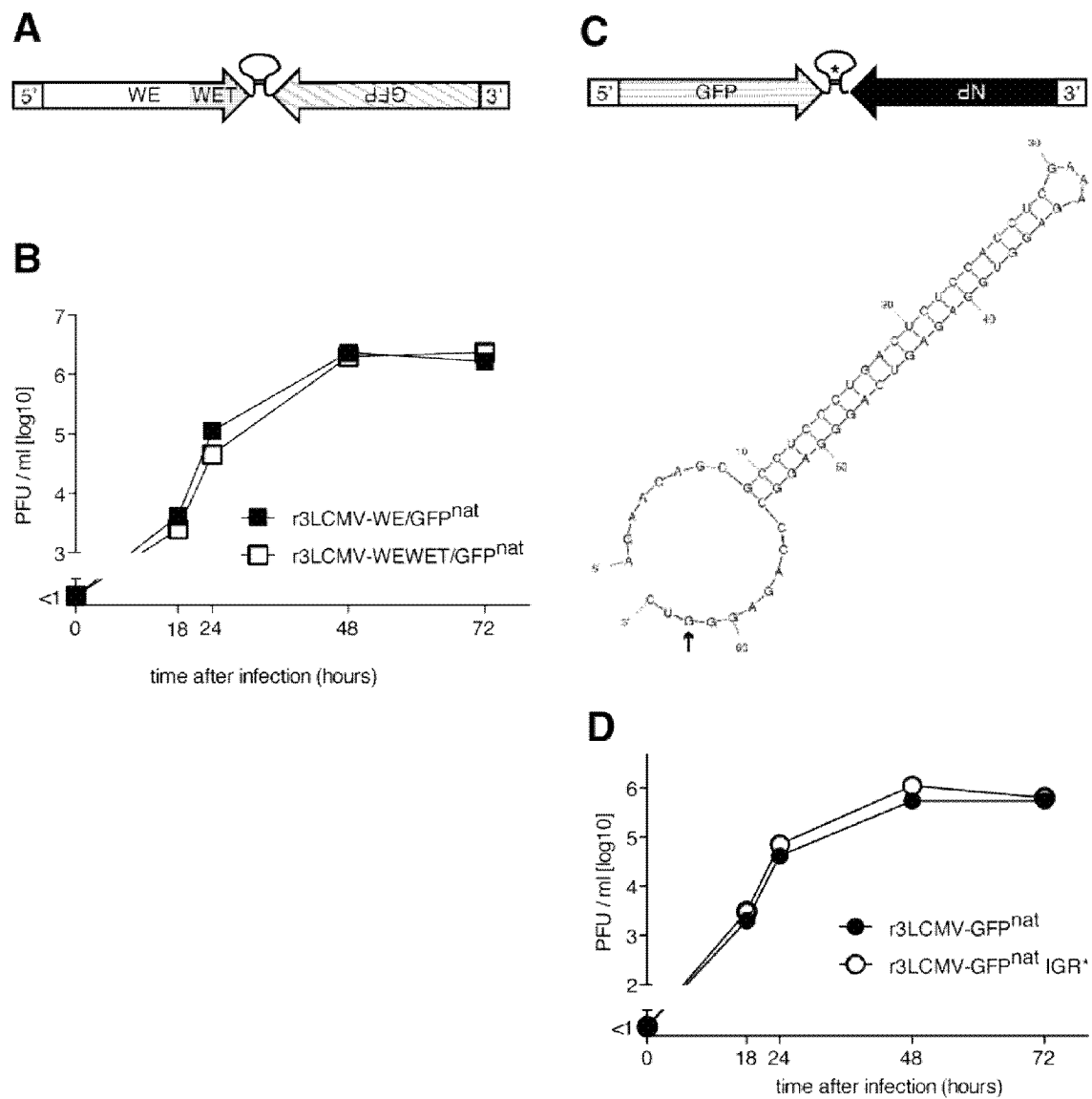

FIG. 3: Design and growth kinetics of recombinant tri-segmented viruses carrying a partially codon-optimized GP ORF or a genetic tag in the IGR of the S segment. (A) Schematic of genetically engineered S segment wherein the 255 C-terminal base pairs of GP are codon-optimized and NP is replaced for GFP (GP ORF referred to as "WE/WET"). Growth kinetics of the tri-segmented r3LCMV-WEWET/GFP$^{nat}$ consisting of two S and one L segment as detailed in FIG. 1B, with modification of the GP-containing S segment as shown in (A) were performed on BHK-21 cells. Supernatant was taken at the indicated time points after infection at moi=0.01 and viral titers were determined by focus forming assay (B). Symbols and bars represent the mean±SEM of three replicates per group. Error bars are hidden in the symbol size. (C) Schematic of the NP-encoding S segment wherein one base pair of the IGR has been deleted in order to genetically "tag" this non-coding RNA element. The deleted G residue (indicated by an arrow) lies outside the critical stem-loop structure of the IGR. Comparative growth kinetics of tri-segmented viruses with or without genetic tag in the IGR of the NP-encoding S segment (r3LCMV-GFP$^{nat}$: black circles; r3LCMV-GFP$^{nat}$ IGR*: white circles) were performed on BHK-21 cells at a moi of 0.01. Supernatant was collected at the indicated time points after infection and viral titers were determined by focus forming assay. Symbols and bars represent the mean±SEM of three replicates per group. Representative data from one of two independent experiments are shown.

Figure 4:
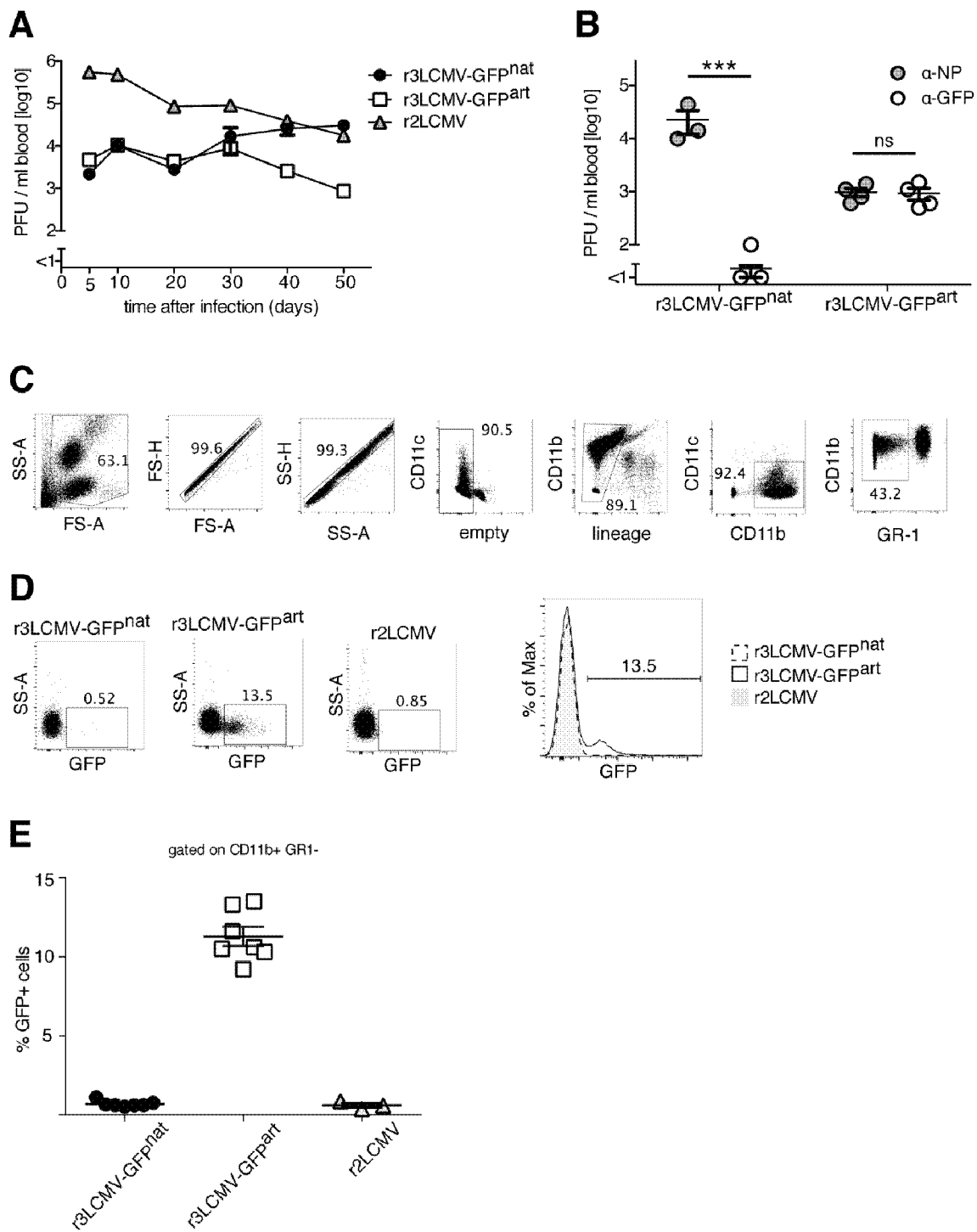

FIG. 4: r3LCMV-GFP$^{nat}$ but not r3LCMV-GFP$^{art}$ persistent infection in immunodeficient mice reaches viremia levels equivalent to bi-segmented wild-type virus and results in loss of GFP expression. (A) AGRAG mice were infected intravenously with 1×10$^4$ PFU of r3LCMV-GFP$^{nat}$ (black circles), r3LCMV-GFP$^{art}$ (white squares) or control bisegmented r2LCMV (grey triangles) and viremia was monitored over time. Symbols represent the mean±SEM of 3-7 mice per group. (B) LCMV viremia on day 127 after intravenous infection of AGRAG mice with 1×10$^4$ PFU of r3LCMV-GFP$^{nat}$ or r3LCMV-GFP$^{art}$ is shown. Immunofocus assays were performed to detect either nucleoprotein NP (grey circles) or GFP (white circles). Symbols represent individual mice. ns.: not statistically significant (p≥0.05); ***: p<0.001 (unpaired two-tailed student's t test). (C-E) Blood from AGRAG mice infected with r3LCMV-GFP$^{nat}$, r3LCMV-GFP$^{art}$ or r2LCMV was analyzed on day 120 after infection by flow cytometry for the presence of GFP+ cells. Monocytes and Macrophages were identified using the gating strategy outlined in (C). One representative FACS plot for each group and one representative histogram overlay of the GFP expression is shown in (D). (E) Quantification of the GFP+ population within the CD11b+GR1− monocytes/macrophage population. Symbols represent individual mice.

Figure 5:
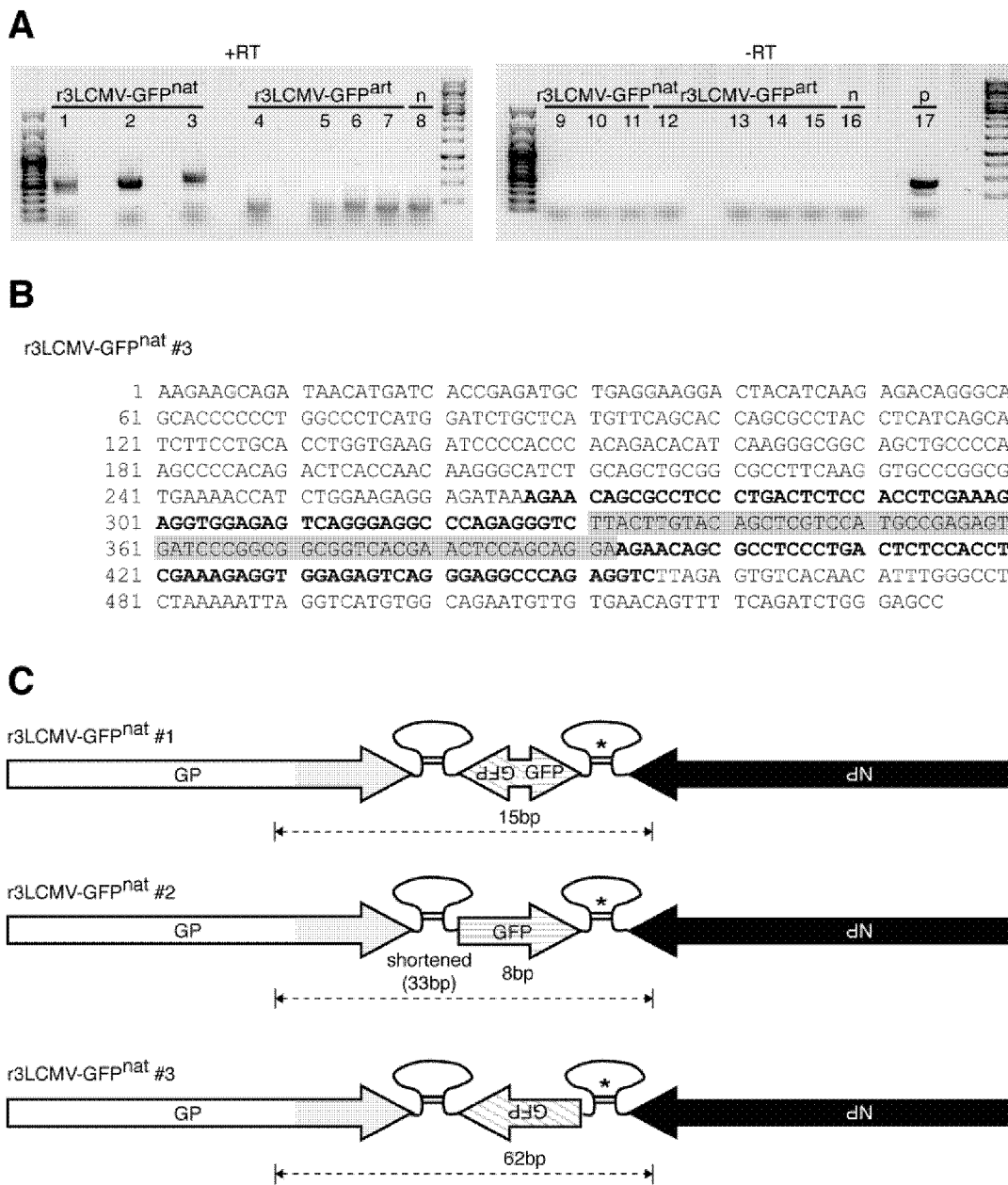

FIG. 5: r3LCMV-GFP$^{nat}$ persistent infection of mice results in S-segment recombination and loss of functional full-length transgenes. Viral RNA was isolated from the serum of AGRAG mice on day 127 after intravenous infection with 1×10$^4$ PFU r3LCMV-GFP$^{nat}$ or r3LCMV-GFP$^{art}$. Viral RNA was reverse transcribed and cDNA carrying both NP as well as GP sequences was PCR-amplified with appropriate gene-specific primers. (A) DNA electrophoresis of PCR products obtained subsequent to (+RT, lanes 1-8) or without prior reverse transcription of RNA template (−RT, negative control, lanes 9-12). Serum of a naive animal was used as a separate negative control (n, lane 8) and a plasmid DNA encoding a wild-type LCMV S segment as positive control (p, lane 17). Amplicons of lanes 1-3 were subject to Sanger sequencing. (B) Representative cDNA sequence obtained from animal #3 (r3LCMV-GFP$^{nat}$ #3) revealing a recombined S segment combining NP and GP sequences, two IGRs (bold) and a C-terminal GFP portion (grey highlight) (SEQ ID NO: 17). (C) Schematic of three recombined viral S segment sequences isolated on day 127 after infection, each of them dominating the viral population in one representative AGRAG mouse. The tagged IGR originating from the NP-carrying S segment is marked with a star (*). The stretch that has been sequenced is indicated by a double-arrow (↔). Base pair (bp) length indications describe the above GFP remnant and truncated (shortened) IGR elements.

Figure 6:
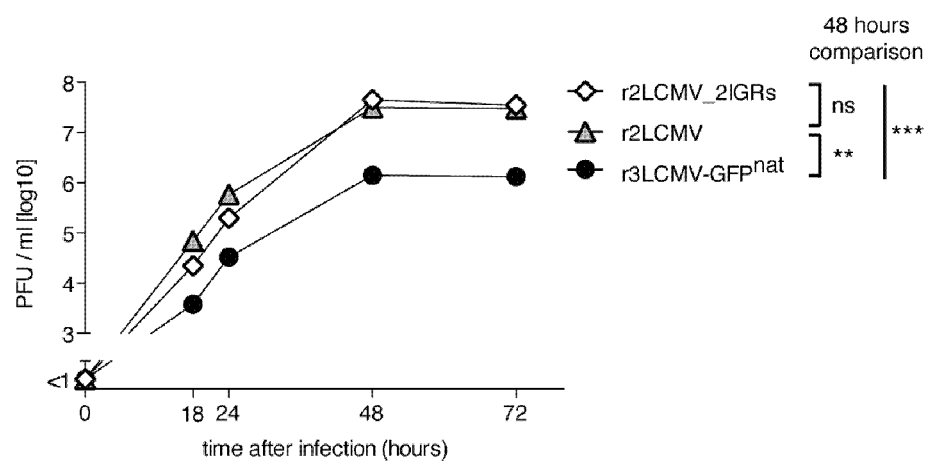

FIG. 6: Growth kinetics of recombined virus with two IGRs on the S segment are similar to bi-segmented virus. BHK-21 cells were infected at moi of 0.01 with either bi-segmented LCMV (grey triangles) carrying a wild type S segment, with tri-segmented r3LCMV-GFP$^{nat}$ (black circles) or with r2LCMV_2IGRs (white diamonds) carrying one S segment corresponding to the recombination product recovered from an infected AGRAG mouse (compare FIG. 5). Supernatant was taken at the indicated time points and viral titers were determined by focus forming assay. Symbols and bars represent the mean±SEM of three replicates per group. Error bars and are hidden in the symbol size. ns.: not statistically significant (p≥0.05); ***: p<0.001 (1-way ANOVA followed by Bonferroni's post-test for multiple comparisons).

Figure 7:
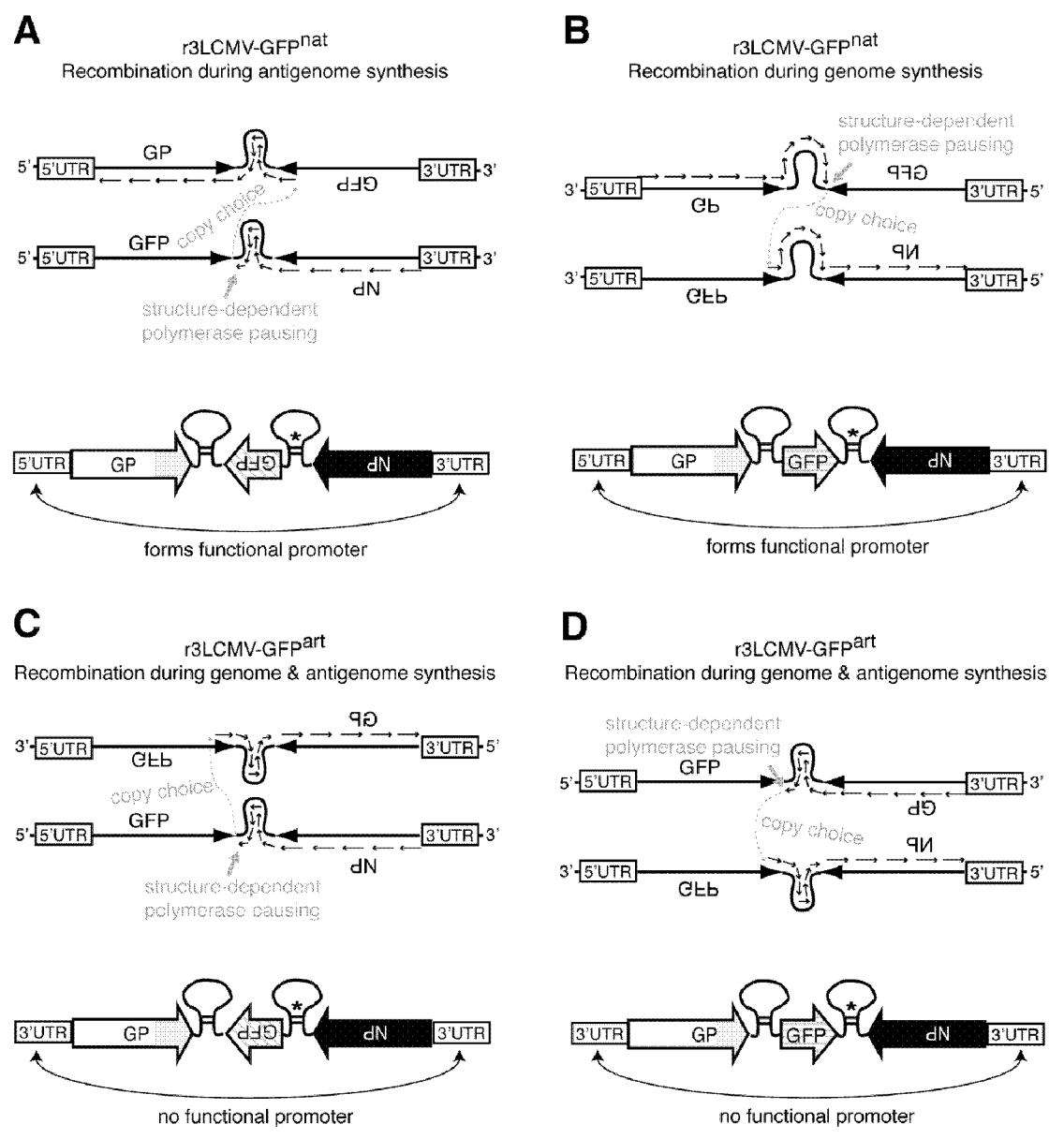

FIG. 7: Model for the recombination events accountable for r3LCMV-GP$^{nat}$ transgene loss and postulated mechanism of r3LCMV-G$^{art}$ genetic stability. This model bases itself upon sequence data of LCMV transcription termination (Meyer and Southern, 1993, J Virol, 67(5):2621-2627) combined with reverse genetic evidence for the IGR as transcription termination signal (Pinschewer et al., 2005, J Virol, 79(7):4519-4526). Together, these findings suggested structure-dependent polymerase pausing when completing the hairpin structure of the IGR. The GFP remnant between the two IGRs in recombined S segments was found to originate from either one or both S segments, fostering the model that polymerase template switch (also referred to as copy-choice) occurred when the polymerase paused, either during genome or antigenome synthesis (below scenarios A and B, respectively). (A) During antigenome synthesis the RNA dependent RNA polymerase (RdRp) initiates at the 3'UTR of a genomic S segment template and then reads through the NP ORF and IGR. At the end of the IGR the polymerase pauses due to the secondary structure ("structure-dependent polymerase pausing"). Stalling of the polymerase facilitates copy choice and continuation of RNA replication on an alternative template (here: GP-encoding S segment genome). Template switch must occur upstream of the GP stop codon, and apparently is most likely to target sequences close to or at the base of the IGR hairpin. Continuing its read through the C-terminus of the second template's GFP, the polymerase then synthesizes a second IGR, the GP ORF and the 5'UTR. (B) During genome synthesis the RdRp initiates RNA synthesis at the 3' end of an antigenomic S segment template containing GP, synthesizes the 5'UTR, GP and most or all of the IGR, followed by structure-dependent polymerase pausing. Copy choice occurs, switching into the C-terminal portion of the GFP ORF near the IGR of an NP-containing S segment. Replication thus adds a fragment of GFP, followed by an IGR in full length, the NP and 3'UTR. (C-D) Template switch analogously to scenarios (A) and (B) can also occur during genome or antigenome synthesis of r3LCMV-GFP$^{art}$. This process also can combine NP and GP ORFs onto one RNA segment. The latter is, however, made up of two 3' UTRs instead of a 3'UTR and a 5'UTR, which only together form a functional viral promoter. Such molecules can therefore not be amplified by the RdRp and thus do not form recombined replication-competent virus.

Figure 8:
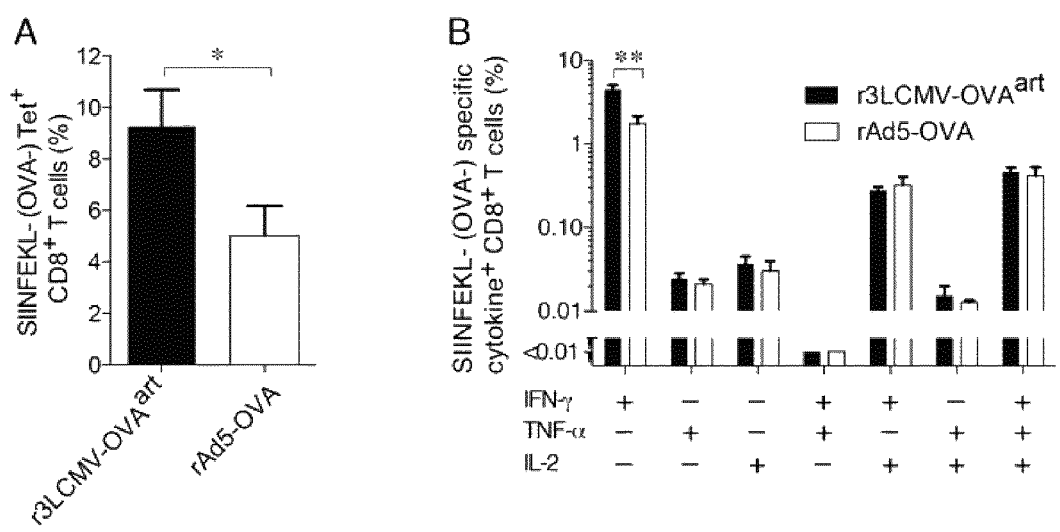

FIG. 8: An r3LCMV-OVA$^{art}$ vaccine vector with a genome organization analogous to r3LCMV-GFP$^{art}$ was generated (see FIG. 1C) but with two ovalbumin (OVA) genes instead of the respective GFP genes in the latter virus. C57BL/6 mice were immunized intramuscularly (i.m.) with either 10$^4$ PFU of r3LCMV-OVA$^{art}$ or with 108 particles of a replication-deficient E1-deleted adenovirus 5-based vector expressing OVA. 8 days later the animals were euthanized and the T cell response elicited in response to the vaccination was analyzed. A: The frequency of OVA-specific CD8+ T cells in spleen was determined using SIINFEKL peptide-loaded MHC class I tetramers. Epitope-specific cell frequencies were determined amongst B220-negative CD8+ lymphocytes. B: The functionality of OVA-specific CD8+ T cells was analyzed by intracellular cytokine assays using SIINFEKL peptide for restimulation. Bars represent the mean+/−SEM of five mice per group. *: p<0.05; **: p>0.01 by unpaired two-tailed student's t test.

Figure 9:
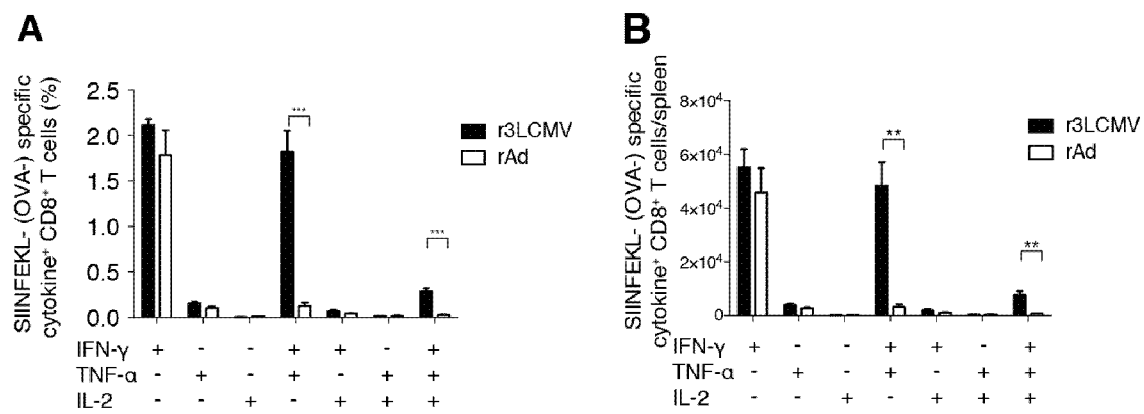

FIG. 9: Trisegmented LCMV induces polyfunctional memory CD8+ T cells. C57BL/6 mice were infected i.v. with 1×10$^5$ PFU r3LCMV-OVA or 1×10$^8$ PFU rAd-OVA. Spleens were taken 25 days after infection and the functionality of OVA-specific CD8+ T cells was analyzed by intracellular cytokine staining. The cytokine profile (IFN-γ, TNF-α and IL-2) of OVA-specific T cells induced by r3LCMV-OVA (black bars) or rAd-OVA (white bars) is shown as percent of CD8+ T cells (A) or as absolute numbers per spleen (B). Symbols and bars represent the mean±SEM of five mice per group. Unpaired two-tailed FIG. 10: Antigen-encoding LCMV induces specific T cell responses to foreign and autoantigens. C57BL/6 mice were infected i.v. with 1×10$^5$ PFU r3LCMV encoding for rat, human or mouse Her2 peptide (A, B and C, respectively). Spleens were taken nine days after infection and the induction of functional antigen-specific CD8+ T cells was analyzed by intracellular cytokine staining and flow cytometry. The cytokine profile (IFN-γ, TNF-α and IL-2) of Her2-specific CD8+ T cells induced by r3LCMV is shown in % of CD8+ T cells. Symbols and bars represent the mean±SEM of three mice per group.

Figure 11:
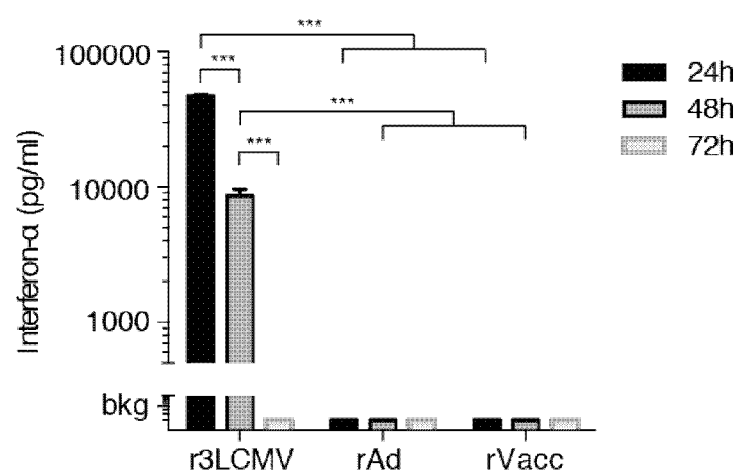

FIG. 11: Interferon-α is induced upon r3LCMV infection but not upon infection with recombinant Adeno- or Vaccini-avirus. C57BL/6 mice were infected i.v. with 1×10$^5$ PFU r3LCMV-OVA, 1×10$^8$ PFU rAd-OVA or 1×10$^6$ PFU rVacc-OVA. Blood was collected on the indicated time points after infection and levels of Interferon-α in the serum were determined by ELISA. Symbols and bars represent the mean±SEM of four mice per group. ***: p<0.001 (2-way ANOVA followed by Bonferroni's post-test for multiple comparisons). Representative data from one out of two independent experiments are shown.

Figure 12:
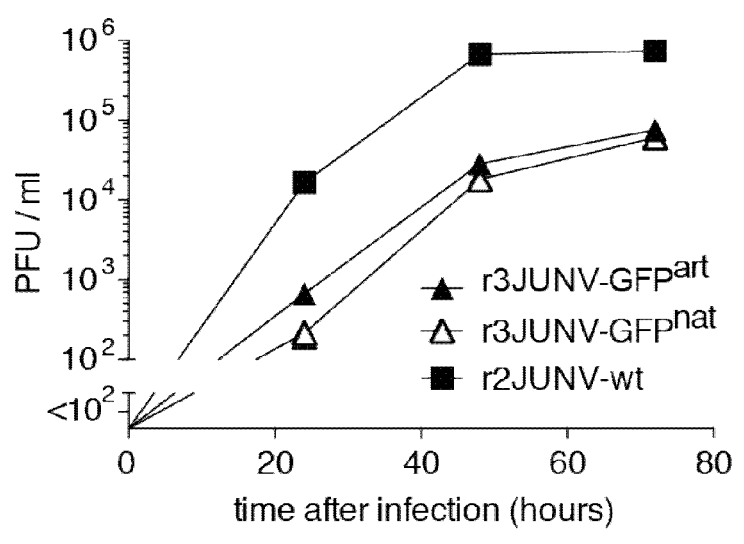

FIG. 12: Cell culture growth of r3JUNV-GFP$^{art}$ in comparison to r3JUNV-GFP$^{nat}$ and r2JUNV-wt. r3JUNV-GFP$^{art}$ and r3JUNV-GFP$^{nat}$ were constructed analogously to the respective r3LCMV vectors schematically outlined in FIG. 1. To compare their cell culture growth properties 293T cells were infected at multiplicity of infection (MOI) of 0.01 with r2LCMV-wt, r3JUNV-GFP$^{art}$, and r3JUNV-GFP$^{nat}$, and supernatant was harvested at the indicated time points. Infectious units (FFU) in supernatant were determined by immunofocus assay. Symbols and bars represent the mean±SEM of three replicates per group and are hidden in the symbol size.

Figure 13:
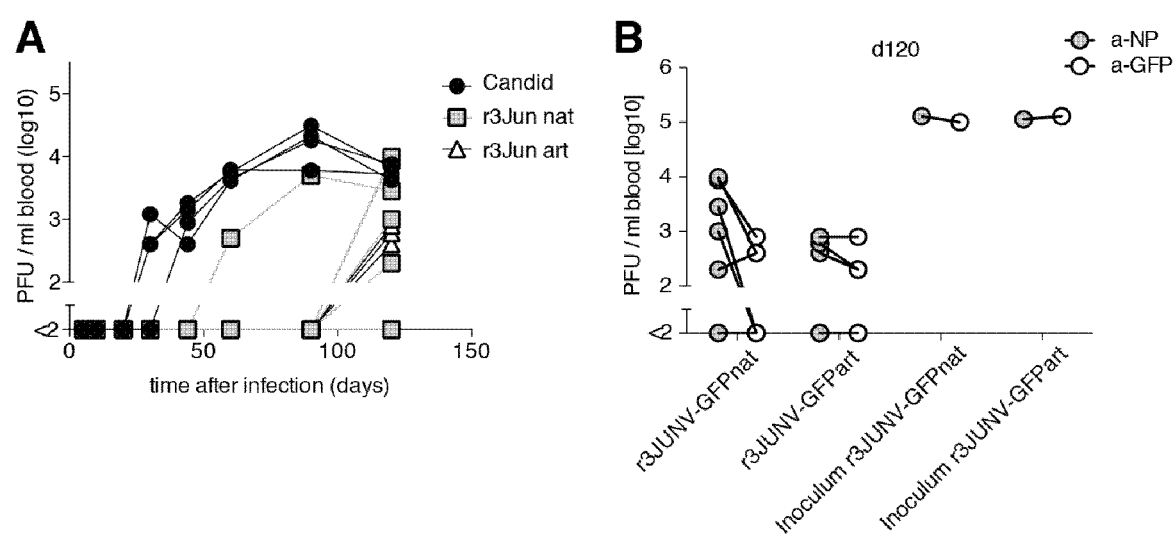

FIG. 13: Trisegmented JUNV are dramatically attenuated in vivo and only lead to detectable viremia upon loss of GFP. (A) AGRAG mice were infected i.v. with 7×10$^4$ PFU of r3JUNV-GFP$^{nat}$ (grey squares), r3JUNV-GFP$^{art}$ (white triangles) or control bi-segmented r2JUNV strain Candid #1 (black circles), and viremia was monitored over time. Symbols represent individual mice (n=3-7 per group). (B) JUNV viremia was determined on day 120 after intravenous infection of AGRAG mice with 7×104 PFU of r3JUNV-GFP$^{nat}$ or r3JUNV-GFP$^{art}$. Immunofocus assays were performed to detect either nucleoprotein NP (grey circles) or GFP (white circles). Viral stocks used to inoculate mice were used as a staining control in the assay. Symbols represent individual mice and inocula, respectively.

Figure 14:
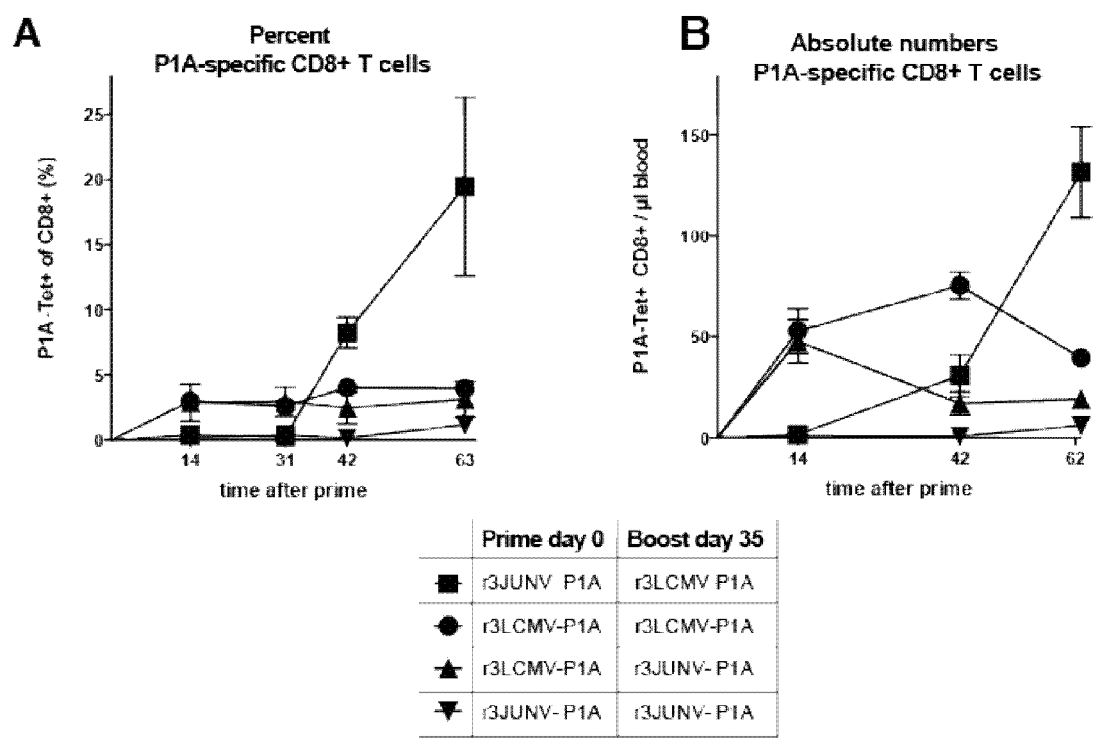

FIG. 14: Homologous and heterologous prime-boost combinations of trisegmented LCMV- and JUNV-based vaccine vectors induce strong PIA autoantigen-specific CD8+ T cells responses. (A) On day 0 and 35 of the experiment BALB/c mice were immunized with 8.5×10$^4$ PFU of r3JUNV-P1A$^{art}$ (r3JUNV-P1A) and r3LCMV-P1A$^{art}$ (r3LCMV-P1A) intravenously in the homologous or heterologous combinations indicated in the chart. Epitope-specific CD8+ T cells were stained using PIA epitope-loaded MHC class I tetramers in combination with anti-CD8a antibody. The frequency of P1A-tetramer-binding cells within the CD8+ T cell compartment in peripheral blood (A) and the absolute number of PIA tetramer-binding CD8+ T cells per microliter of peripheral blood (B) was calculated. Symbols represent the mean+/−SEM of 3-5 mice per group and time point.

DETAILED DESCRIPTION OF THE INVENTION

4.1 Arenaviruses with an Open Reading Frame in a Non-Natural Position

Provided herein are arenaviruses with rearrangements of their ORFs. In certain embodiments, such arenaviruses are replication competent and infectious. Genomic sequences of such arenaviruses are provided herein. In one aspect, provided herein is an arenavirus genomic segment, wherein the arenavirus genomic segment is engineered to carry an arenavirus ORF in a position other than the position in which the respective gene is found in viruses isolated from the wild, such as LCMV-MP (see SEQ ID NOs: 4 and 5) (referred to herein as "wild-type position") of the ORF (i.e., a non-natural position). In one embodiment, the arenavirus particle is an LCMV.

The wild-type arenavirus genomic segments and ORFs are known in the art. In particular, the arenavirus genome consists of an S segment and an L segment. The S segment carries the ORFs encoding the GP and the NP. The L segment encodes the L protein and the Z protein. Both segments are flanked by the respective 5' and 3' UTRs (see FIG. 1A). Illustrative wild-type arenavirus genomic segments are provided in SEQ ID NOs: 1-10.

In certain embodiments, an arenavirus genomic segment can be engineered to carry two or more arenavirus ORFs in a position other than the wild-type position. In other embodiments, the arenavirus genomic segment can be engineered to carry two arenavirus ORFs, or three arenavirus ORFs, or four arenavirus ORFs in a position other than the wild-type position.

In certain embodiments, an arenavirus genomic segment provided herein can be:

(i) an arenavirus S segment, wherein the ORF encoding the NP is under control of an arenavirus 5' UTR;
(ii) an arenavirus S segment, wherein the ORF encoding the Z protein is under control of an arenavirus 5' UTR;
(iii) an arenavirus S segment, wherein the ORF encoding the L protein is under control of an arenavirus 5' UTR;
(iv) an arenavirus S segment, wherein the ORF encoding the GP is under control of an arenavirus 3' UTR;
(v) an arenavirus S segment, wherein the ORF encoding the L protein is under control of an arenavirus 3' UTR;
(vi) an arenavirus S segment, wherein the ORF encoding the Z protein is under control of an arenavirus 3' UTR;
(vii) an arenavirus L segment, wherein the ORF encoding the GP is under control of an arenavirus 5' UTR;
(viii) an arenavirus L segment, wherein the ORF encoding the NP is under control of an arenavirus 5' UTR;
(ix) an arenavirus L segment, wherein the ORF encoding the L protein is under control of an arenavirus 5' UTR;
(x) an arenavirus L segment, wherein the ORF encoding the GP is under control of an arenavirus 3' UTR;
(xi) an arenavirus L segment, wherein the ORF encoding the NP is under control of an arenavirus 3' UTR; and
(xii) an arenavirus L segment, wherein the ORF encoding the Z protein is under control of an arenavirus 3' UTR.

In certain embodiments, the ORF that is in the non-natural position of the arenavirus genomic segment described herein can be under the control of an arenavirus 3' UTR or an arenavirus 5' UTR. In more specific embodiments, the arenavirus 3' UTR is the 3' UTR of the arenavirus S segment. In another specific embodiment, the arenavirus 3' UTR is the 3'UTR of the arenavirus L segment. In more specific embodiments, the arenavirus 5' UTR is the 5' UTR of the arenavirus S segment. In other specific embodiments, the 5' UTR is the 5' UTR of the L segment.

In other embodiments, the ORF that is in the non-natural position of the arenavirus genomic segment described herein can be under the control of the arenavirus conserved terminal sequence element (the 5'- and 3'-terminal 19-20-nt regions) (see e.g., Perez & de la Tone, 2003, J Virol. 77(2): 1184-1194).

In certain embodiments, the ORF that is in the non-natural position of the arenavirus genomic segment can be under the control of the promoter element of the 5' UTR (see e.g., Albarino et al., 2011, J Virol., 85(8):4020-4). In another embodiment, the ORF that is in the non-natural position of the arenavirus genomic segment can be under the control of the promoter element of the 3' UTR (see e.g., Albarino et al., 2011, J Virol., 85(8):4020-4). In more specific embodiments, the promoter element of the 5' UTR is the 5' UTR promoter element of the S segment or the L segment. In another specific embodiment, the promoter element of the 3' UTR is the 3' UTR the promoter element of the S segment or the L segment.

In certain embodiments, the ORF that is in the non-natural position of the arenavirus genomic segment can be under the control of a truncated arenavirus 3' UTR or a truncated arenavirus 5' UTR (see e.g., Perez & de la Torre, 2003, J Virol. 77(2): 1184-1194; Albarino et al., 2011, J Virol., 85(8):4020-4). In more specific embodiments, the truncated 3' UTR is the 3' UTR of the arenavirus S segment or L segment. In more specific embodiments, the truncated 5' UTR is the 5' UTR of the arenavirus S segment or L segment.

Also provided herein, is an arenavirus particle comprising a first genomic segment that has been engineered to carry an ORF in a position other than the wild-type position of the ORF and a second arenavirus genomic segment so that the arenavirus particle comprises an S segment and an L segment. In specific embodiments, the ORF in a position other than the wild-type position of the ORF is one of the arenavirus ORFs.

In certain specific embodiments, the arenavirus particle can comprise a full complement of all four arenavirus ORFs. In specific embodiments, the second arenavirus genomic segment has been engineered to carry an ORF in a position other than the wild-type position of the ORF. In another specific embodiment, the second arenavirus genomic segment can be the wild-type genomic segment (i.e., comprises the ORFs on the segment in the wild-type position).

In certain embodiments, the first arenavirus genomic segment is an L segment and the second arenavirus genomic segment is an S segment. In other embodiments, the first arenavirus genomic segment is an S segment and the second arenavirus genomic segment is an L segment.

Non-limiting examples of the arenavirus particle comprising a genomic segment with an ORF in a position other than the wild-type position of the ORF and a second genomic segment are illustrated in Table 1.

TABLE 1

| Arenavirus particle | | | |
|---|---|---|---|
| Position 1 | Position 2 | Position 3 | Position 4 |
| GP | NP | L | Z |
| GP | Z | L | NP |
| GP | Z | NP | L |
| GP | L | NP | Z |
| GP | L | Z | NP |

TABLE 1-continued

| Arenavirus particle | | | |
|---|---|---|---|
| Position 1 | Position 2 | Position 3 | Position 4 |
| NP | GP | L | Z |
| NP | GP | Z | L |
| NP | L | GP | Z |
| NP | L | Z | GP |
| NP | Z | GP | L |
| NP | Z | L | GP |
| Z | GP | L | NP |
| Z | GP | NP | L |
| Z | NP | GP | L |
| Z | NP | L | GP |
| Z | L | NP | GP |
| Z | L | GP | NP |
| L | NP | GP | Z |
| L | NP | Z | GP |
| L | GP | Z | NP |
| L | GP | NP | Z |
| L | Z | NP | GP |
| L | Z | GP | NP |

*Position 1 is under the control of an arenavirus S segment 5' UTR;
Position 2 is under the control of an arenavirus S segment 3' UTR;
Position 3 is under the control of an arenavirus L segment 5' UTR;
Position 4 is under the control of an arenavirus L segment 3' UTR.

Also provided herein, is a cDNA of the arenavirus genomic segment engineered to carry an ORF in a position other than the wild-type position of the ORF. In more specific embodiments, provided herein is a cDNA or a set of cDNAs of an arenavirus genome as set forth in Table 1.

In certain embodiments, a cDNA of the arenavirus genomic segment that is engineered to carry an ORF in a position other than the wild-type position of the ORF is part of or incorporated into a DNA expression vector. In a specific embodiment, a cDNA of the arenavirus genomic segment that is engineered to carry an ORF in a position other than the wild-type position of the ORF is part of or incorporated into a DNA expression vector that facilitates production of an arenavirus genomic segment as described herein. In another embodiment, a cDNA described herein can be incorporated into a plasmid. More detailed description of the cDNAs or nucleic acids and expression systems are provided is Section 4.5.1. Techniques for the production of a cDNA are routine and conventional techniques of molecular biology and DNA manipulation and production. Any cloning technique known to the skilled artesian can be used. Such as techniques are well known and are available to the skilled artesian in laboratory manuals such as, Sambrook and Russell, Molecular Cloning: A laboratory Manual, 3$^{rd}$ edition, Cold Spring Harbor Laboratory N.Y. (2001).

In certain embodiments, the cDNA of the arenavirus genomic segment that is engineered to carry an ORF in a position other than the wild-type position of the ORF is introduced (e.g., transfected) into a host cell. Thus, in some embodiments provided herein, is a host cell comprising a cDNA of the arenavirus genomic segment that is engineered to carry an ORF in a position other than the wild-type position of the ORF (i.e., a cDNA of the genomic segment). In other embodiments, the cDNA described herein is part of or can be incorporated into a DNA expression vector and introduced into a host cell. Thus, in some embodiments provided herein is a host cell comprising a cDNA described herein that is incorporated into a vector. In other embodiments, the arenavirus genomic segment described herein is introduced into a host cell.

In certain embodiments, described herein is a method of producing the arenavirus genomic segment, wherein the method comprises transcribing the cDNA of the arenavirus genomic segment. In certain embodiments, a viral polymerase protein can be present during transcription of the arenavirus genomic segment in vitro or in vivo.

In certain embodiments transcription of the arenavirus genomic segment is performed using a bi-directional promoter. In other embodiments, transcription of the arenavirus genomic segment is performed using a bi-directional expression cassette (see e.g., Ortiz-Riaño et al., 2013, J Gen Virol., 94(Pt 6): 1175-1188). In more specific embodiments the bi-directional expression cassette comprises both a polymerase I and a polymerase II promoter reading from opposite sides into the two termini of the inserted arenavirus genomic segment, respectively. In yet more specific embodiments the bi-directional expression cassette with pol-I and pol-II promoters read from opposite sides into the L segment and S segment In other embodiments, transcription of the cDNA of the arenavirus genomic segment described herein comprises a promoter. Specific examples of promoters include an RNA polymerase I promoter, an RNA polymerase II promoter, an RNA polymerase III promoter, a T7 promoter, an SP6 promoter or a T3 promoter.

In certain embodiments, the method of producing the arenavirus genomic segment can further comprise introducing into a host cell the cDNA of the arenavirus genomic segment. In certain embodiments, the method of producing the arenavirus genomic segment can further comprise introducing into a host cell the cDNA of the arenavirus genomic segment, wherein the host cell expresses all other components for production of the arenavirus genomic segment; and purifying the arenavirus genomic segment from the supernatant of the host cell. Such methods are well-known to those skilled in the art.

Provided herein are cell lines, cultures and methods of culturing cells infected with nucleic acids, vectors, and compositions provided herein. More detailed description of nucleic acids, vector systems and cell lines described herein is provided in Section 4.5.

In certain embodiments, the arenavirus particle as described herein results in an infectious and replication competent arenavirus particle. In specific embodiments, the arenavirus particle described herein is attenuated. In a particular embodiment, the arenavirus particle is attenuated such that the virus remains, at least partially, able to spread and can replicate in vivo, but can only generate low viral loads resulting in subclinical levels of infection that are non-pathogenic. Such attenuated viruses can be used as an immunogenic composition. Provided herein, are immunogenic compositions that comprise an arenavirus with an ORF in a non-natural position as described in Section 4.7.

4.1.1 Replication-Defective Arenavirus Particle with an Open Reading Frame in a Non-Natural Position In certain embodiments, provided herein is an arenavirus particle in which (i) an ORF is in a position other than the wild-type position of the ORF; and (ii) an ORF encoding GP, NP, Z protein, and L protein has been removed or functionally inactivated such that the resulting virus cannot produce further infectious progeny virus particles. An arenavirus particle comprising a genetically modified genome in which one or more ORFs has been deleted or functionally inactivated can be produced in complementing cells (i.e., cells that express the arenavirus ORF that has been deleted or functionally inactivated). The genetic material of the resulting arenavirus particle can be transferred upon infection of a host cell into the host cell, wherein the genetic material can be expressed and amplified. In addition, the genome of the genetically modified arenavirus particle described herein can encode a heterologous ORF from an organism other than an arenavirus particle.

In certain embodiments, at least one of the four ORFs encoding GP, NP, Z protein, and L protein is removed and replaced with a heterologous ORF from an organism other than an arenavirus. In another embodiment, at least one ORF, at least two ORFs, at least three ORFs, or at least four ORFs encoding GP, NP, Z protein and L protein can be removed and replaced with a heterologous ORF from an organism other than an arenavirus. In specific embodiments, only one of the four ORFs encoding GP, NP, Z protein, and L protein is removed and replaced with a heterologous ORF from an organism other than an arenavirus particle. In more specific embodiments, the ORF that encodes GP of the arenavirus genomic segment is removed. In another specific embodiment, the ORF that encodes the NP of the arenavirus genomic segment is removed. In more specific embodiments, the ORF that encodes the Z protein of the arenavirus genomic segment is removed. In yet another specific embodiment, the ORF encoding the L protein is removed.

Thus, in certain embodiments, the arenavirus particle provided herein comprises a genomic segment that (i) is engineered to carry an ORF in a non-natural position; (ii) an ORF encoding GP, NP, Z protein, or L protein is removed; (iii) the ORF that is removed is replaced with a heterologous ORF from an organism other than an arenavirus.

In certain embodiments, the heterologous ORF is 8 to 100 nucleotides in length, 15 to 100 nucleotides in length, 25 to 100 nucleotides in length, 50 to 200 nucleotide in length, 50 to 400 nucleotide in length, 200 to 500 nucleotide in length, or 400 to 600 nucleotides in length, 500 to 800 nucleotide in length. In other embodiments, the heterologous ORF is 750 to 900 nucleotides in length, 800 to 100 nucleotides in length, 850 to 1000 nucleotides in length, 900 to 1200 nucleotides in length, 1000 to 1200 nucleotides in length, 1000 to 1500 nucleotides or 10 to 1500 nucleotides in length, 1500 to 2000 nucleotides in length, 1700 to 2000 nucleotides in length, 2000 to 2300 nucleotides in length, 2200 to 2500 nucleotides in length, 2500 to 3000 nucleotides in length, 3000 to 3200 nucleotides in length, 3000 to 3500 nucleotides in length, 3200 to 3600 nucleotides in length, 3300 to 3800 nucleotides in length, 4000 nucleotides to 4400 nucleotides in length, 4200 to 4700 nucleotides in length, 4800 to 5000 nucleotides in length, 5000 to 5200 nucleotides in length, 5200 to 5500 nucleotides in length, 5500 to 5800 nucleotides in length, 5800 to 6000 nucleotides in length, 6000 to 6400 nucleotides in length, 6200 to 6800 nucleotides in length, 6600 to 7000 nucleotides in length, 7000 to 7200 nucleotides in lengths, 7200 to 7500 nucleotides in length, or 7500 nucleotides in length. In some embodiments, the heterologous ORF encodes a peptide or polypeptide that is 5 to 10 amino acids in length, 10 to 25 amino acids in length, 25 to 50 amino acids in length, 50 to 100 amino acids in length, 100 to 150 amino acids in length, 150 to 200 amino acids in length, 200 to 250 amino acids in length, 250 to 300 amino acids in length, 300 to 400 amino acids in length, 400 to 500 amino acids in length, 500 to 750 amino acids in length, 750 to 1000 amino acids in length, 1000 to 1250 amino acids in length, 1250 to 1500 amino acids in length, 1500 to 1750 amino acids in length, 1750 to 2000 amino acids in length, 2000 to 2500 amino acids in length, or more than 2500 or more amino acids in length. In some embodiments, the heterologous ORF encodes a polypeptide that does not exceed 2500 amino acids in length. In specific embodiments the heterologous ORF does not contain a stop codon. In certain embodiments, the heterologous ORF is codon-optimized. In certain embodiments the nucleotide composition, nucleotide pair composition or both can be optimized. Techniques for such optimizations are known in the art and can be applied to optimize a heterologous ORF.

Any heterologous ORF from an organism other than an arenavirus may be included in an arenavirus genomic segment. In one embodiment, the heterologous ORF encodes a reporter protein. More detailed description of reporter proteins are described in Section 4.3. In another embodiment, the heterologous ORF encodes an antigen for an infectious pathogen or an antigen associated with any disease that is capable of eliciting an immune response. In specific embodiments the antigen is derived from an infectious organism, a tumor (i.e., cancer), or an allergen. More detailed description on heterologous ORFs is described in Section 4.3.

In certain embodiments, the growth and infectivity of the arenavirus particle is not affected by the heterologous ORF from an organism other than an arenavirus.

Techniques known to one skilled in the art may be used to produce an arenavirus particle comprising an arenavirus genomic segment engineered to carry an arenavirus ORF in a position other than the wild-type position. For example, reverse genetics techniques may be used to generate such arenavirus particle. In other embodiments, the replication-defective arenavirus particle (i.e., the arenavirus genomic segment engineered to carry an arenavirus ORF in a position other than the wild-type position, wherein an ORF encoding GP, NP, Z protein, L protein, has been deleted) can be produced in a complementing cell.

In certain embodiments, the arenavirus genomic segment or the arenavirus particle using according to the present application can be Old World Viruses, for example, LCMV.

In certain embodiments, the present application relates to the arenavirus particle as described herein suitable for use as a vaccine and methods of using such arenavirus particle in a vaccination and treatment or prevention of, for example, infections or cancers. More detailed description of the methods of using the arenavirus particle described herein is provided in Section 4.6

In certain embodiments, provided herein is a kit comprising, in one or more containers, one or more cDNAs described herein. In a specific embodiment, a kit comprises, in one or two or more containers an arenavirus genomic segment or an arenavirus particle as described herein. The kit may further comprise one or more of the following: a host cell suitable for rescue of the arenavirus genomic segment or the arenavirus particle, reagents suitable for transfecting plasmid cDNA into a host cell, a helper virus, plasmids encoding viral proteins and/or one or more primers specific for an modified arenavirus genomic segment or arenavirus particle or cDNAs of the same.

In certain embodiments, the present application relates to the arenavirus particle as described herein suitable for use as a pharmaceutical composition and methods of using such arenavirus particle in a vaccination and treatment or prevention of, for example, infections and cancers. More detailed description of the methods of using the arenavirus particle described herein is provided in Section 4.7.

4.2 Tri-Segmented Arenavirus Particle

Provided herein are tri-segmented arenavirus particles with rearrangements of their ORFs. In one aspect, provided herein is a tri-segmented arenavirus particle comprising one L segment and two S segments or two L segments and one S segment. In certain embodiments, the tri-segmented arenavirus particle does not recombine into a replication competent bi-segmented arenavirus particle. More specifically, in certain embodiments, two of the genomic segments (e.g., the two S segments or the two L segments, respectively) cannot recombine in a way to yield a single viral segment that could replace the two parent segments. In specific embodiments, the tri-segmented arenavirus particle comprises an ORF in a position other than the wild-type position of the ORF. In yet another specific embodiment, the tri-segmented arenavirus particle comprises all four arenavirus ORFs. Thus, in certain embodiments, the tri-segmented arenavirus particle is replication competent and infectious. In other embodiments, the tri-segmented arenavirus particle lacks one of the four arenavirus ORFs. Thus, in certain embodiments, the tri-segmented arenavirus particle is infectious but unable to produce further infectious progeny in non-complementing cells.

In certain embodiments, the ORF encoding GP, NP, Z protein, or the L protein of the tri-segmented arenavirus particle described herein can be under the control of an arenavirus 3' UTR or an arenavirus 5' UTR. In more specific embodiments, the tri-segmented arenavirus 3' UTR is the 3' UTR of an arenavirus S segment(s). In another specific embodiment, the tri-segmented arenavirus 3' UTR is the 3' UTR of a tri-segmented arenavirus L segment(s). In more specific embodiments, the tri-segmented arenavirus 5' UTR is the 5' UTR of an arenavirus S segment(s). In other specific embodiments, the 5' UTR is the 5' UTR of the L segment(s).

In other embodiments, the ORF encoding GP, NP, Z protein, or the L protein of tri-segmented arenavirus particle described herein can be under the control of the arenavirus conserved terminal sequence element (the 5'- and 3'-terminal 19-20-nt regions) (see e.g., Perez & de la Torre, 2003, J Virol. 77(2): 1184-1194).

In certain embodiments, the ORF encoding GP, NP, Z protein or the L protein of the tri-segmented arenavirus particle can be under the control of the promoter element of the 5' UTR (see e.g., Albarino et al., 2011, J Virol., 85(8): 4020-4). In another embodiment, the ORF encoding GP, NP Z protein, L protein of the tri-segmented arenavirus particle can be under the control of the promoter element of the 3' UTR (see e.g., Albarino et al., 2011, J Virol., 85(8):4020-4). In more specific embodiments, the promoter element of the 5' UTR is the 5' UTR promoter element of the S segment(s) or the L segment(s). In another specific embodiment, the promoter element of the 3' UTR is the 3' UTR the promoter element of the S segment(s) or the L segment(s).

In certain embodiments, the ORF that encoding GP, NP, Z protein or the L protein of the tri-segmented arenavirus particle can be under the control of a truncated arenavirus 3' UTR or a truncated arenavirus 5' UTR (see e.g., Perez & de la Torre, 2003, J Virol. 77(2): 1184-1194; Albarino et al., 2011, J Virol., 85(8):4020-4). In more specific embodiments, the truncated 3' UTR is the 3' UTR of the arenavirus S segment or L segment. In more specific embodiments, the truncated 5' UTR is the 5' UTR of the arenavirus S segment(s) or L segment(s).

Also provided herein, is a cDNA of the tri-segmented arenavirus particle. In more specific embodiments, provided herein is a DNA nucleotide sequence or a set of DNA nucleotide sequences encoding a tri-segmented arenavirus particle as set forth in Table 2 or Table 3.

In certain embodiments, the nucleic acids encoding the tri-segmented arenavirus genome are part of or incorporated into one or more DNA expression vectors. In a specific embodiment, nucleic acids encoding the genome of the tri-segmented arenavirus particle is part of or incorporated into one or more DNA expression vectors that facilitate production of a tri-segmented arenavirus particle as described herein. In another embodiment, a cDNA described herein can be incorporated into a plasmid. More detailed description of the cDNAs and expression systems are provided is Section 4.5.1. Techniques for the production of a cDNA routine and conventional techniques of molecular biology and DNA manipulation and production. Any cloning technique known to the skilled artesian can be used. Such techniques are well known and are available to the skilled artesian in laboratory manuals such as, Sambrook and Russell, Molecular Cloning: A laboratory Manual, $3^{rd}$ edition, Cold Spring Harbor Laboratory N.Y. (2001).

In certain embodiments, the cDNA of the tri-segmented arenavirus is introduced (e.g., transfected) into a host cell. Thus, in some embodiments provided herein, is a host cell comprising a cDNA of the tri-segmented arenavirus particle (i.e., a cDNA of the genomic segments of the tri-segmented arenavirus particle). In other embodiments, the cDNA described herein that is part of or can be incorporated into a DNA expression vector and introduced into a host cell. Thus, in some embodiments provided herein is a host cell comprising a cDNA described herein that is incorporated into a vector. In other embodiments, the tri-segmented arenavirus genomic segments (i.e., the L segment and/or S segment or segments) described herein is introduced into a host cell.

In certain embodiments, described herein is a method of producing the tri-segmented arenavirus particle, wherein the method comprises transcribing the cDNA of the tri-segmented arenavirus particle. In certain embodiments, a viral polymerase protein can be present during transcription of the tri-segmented arenavirus particle in vitro or in vivo. In certain embodiments, transcription of the arenavirus genomic segment is performed using a bi-directional promoter.

In other embodiments, transcription of the arenavirus genomic segment is performed using a bi-directional expression cassette (see e.g., Ortiz-Riaño et al., 2013, J Gen Virol., 94(Pt 6): 1175-1188). In more specific embodiments the bi-directional expression cassette comprises both a polymerase I and a polymerase II promoter reading from opposite sides into the two termini of the inserted arenavirus genomic segment, respectively.

In other embodiments, transcription of the cDNA of the arenavirus genomic segment described herein comprises a promoter. Specific examples of promoters include an RNA polymerase I promoter, an RNA polymerase II promoter, an RNA polymerase III promoter, a T7 promoter, an SP6 promoter or a T3 promoter.

In certain embodiments, the method of producing the tri-segmented arenavirus particle can further comprise introducing into a host cell the cDNA of the tri-segmented arenavirus particle. In certain embodiments, the method of producing the tri-segmented arenavirus particle can further comprise introducing into a host cell the cDNA of the tri-segmented arenavirus particle, wherein the host cell expresses all other components for production of the tri-segmented arenavirus particle; and purifying the tri-segmented arenavirus particle from the supernatant of the host cell. Such methods are well-known to those skilled in the art.

Provided herein are cell lines, cultures and methods of culturing cells infected with nucleic acids, vectors, and compositions provided herein. More detailed description of nucleic acids, vector systems and cell lines described herein is provided in Section 4.5.

In certain embodiments, the tri-segmented arenavirus particle as described herein results in an infectious and replication competent arenavirus particle. In specific embodiments, the arenavirus particle described herein is attenuated. In a particular embodiment, the tri-segmented arenavirus particle is attenuated such that the virus remains, at least partially, replication-competent and can replicate in vivo, but can only generate low viral loads resulting in subclinical levels of infection that are non-pathogenic. Such attenuated viruses can be used as an immunogenic composition.

In certain embodiments, the tri-segmented arenavirus particle has the same tropism as the bi-segmented arenavirus particle.

Also provided herein is a kit comprising, in one or more containers, one or more cDNAs described herein. In a specific embodiment, a kit comprises, in one or two or more containers a tri-segmented arenavirus particle as described herein. The kit may further comprise one or more of the following: a host cell suitable for rescue of the tri-segmented arenavirus particle, reagents suitable for transfecting plasmid cDNA into a host cell, a helper virus, plasmids encoding viral proteins and/or one or more oligonucleotide primers specific for a modified arenavirus genomic segment or arenavirus particle or nucleic acids encoding the same.

Also provided herein are immunogenic compositions that comprise the tri-segmented arenavirus particle as described in Section 4.6 and 4.7.

4.2.1 Tri-Segmented Arenavirus Particle Comprising One L Segment and Two S Segments In one aspect, provided herein is a tri-segmented arenavirus particle comprising one L segment and two S segments. In certain embodiments, propagation of the tri-segmented arenavirus particle comprising one L segment and two S segments does not result in a replication-competent bi-segmented viral particle. In specific embodiments, propagation of the tri-segmented arenavirus particle comprising one L segment and two S segments does not result in a replication-competent bi-segmented viral particle after at least 10 days, at least 20 days, at least 30 days, at least 40 days, at least 50 days, at least 60 days, at least 70 days, at least 80 days, at least 90 days, or at least 100 days of persistent infection in mice lacking type I interferon receptor, type II interferon receptor and recombination activating gene (RAG1), and having been infected with $10^4$ PFU of the tri-segmented arenavirus particle (see Section 4.8.13). In other embodiments, propagation of the tri-segmented arenavirus particle comprising one L segment and two S segments does not result in a replication-competent bi-segmented viral particle after at least 10 passages, at least 20 passages, at least 30 passages, at least 40 passages, or at least 50 passages.

The tri-segmented arenavirus particle with all viral genes in their respective wild-type position is known in the art (e.g., Emonet et al., 2011 J. Virol., 85(4):1473; Popkin et al., 2011, J. Virol, 85(15):7928). In particular, the tri-segmented arenavirus genome consists of one L segment and two S segments, in which a heterologous ORF (e.g., a GFP) is inserted into one position on each S segment. More specifically, one S segment encodes GP and GFP, respectively. The other S segment encodes GFP and NP, respectively. The L segment encodes the L protein and Z protein. All segments are flanked by the respective 5' and 3' UTRs.

In certain embodiments, inter-segmental recombination of the two S segments of the tri-segmented arenavirus particle, provided herein, that unities the two arenaviral ORFs on one instead of two separate segments results in a non functional promoter (i.e., a genomic segment of the structure: 5' UTR-5' UTR or a 3' UTR-3' UTR), wherein each UTR forming one end of the genome is an inverted repeat sequence of the other end of the same genome.

In certain embodiments, the tri-segmented arenavirus particle comprising one L segment and two S segments has been engineered to carry an arenavirus ORF in a position other than the wild-type position of the ORF. In other embodiments, the tri-segmented arenavirus particle comprising one L segment and two S segments has been engineered to carry two arenavirus ORFs, or three arenavirus ORFs, or four arenavirus ORFs, or five arenavirus ORFs, or six arenavirus ORFs in a position other than the wild-type position. In specific embodiments, the tri-segmented arenavirus particle comprising one L segment and two S segments comprises a full complement of all four arenavirus ORFs. Thus, in some embodiments, the tri-segmented arenavirus particle is an infectious and replication competent tri-segmented arenavirus particle. In specific embodiments, the two S segments of the tri-segmented arenavirus particle have been engineered to carry one of their ORFs in a position other than the wild-type position. In more specific embodiments, the two S segments comprise a full complement of the S segment ORF's. In certain specific embodiments, the L segment has been engineered to carry an ORF in a position other than the wild-type position or the L segment can be the wild-type genomic segment.

In certain embodiments, one of the two S segments can be:
(i) an arenavirus S segment, wherein the ORF encoding the Z protein is under control of an arenavirus 5' UTR;
(ii) an arenavirus S segment, wherein the ORF encoding the L protein is under control of an arenavirus 5' UTR;
(iii) an arenavirus S segment, wherein the ORF encoding the NP is under control of an arenavirus 5' UTR;
(iv) an arenavirus S segment, wherein the ORF encoding the GP is under control of an arenavirus 3' UTR;
(v) an arenavirus S segment, wherein the ORF encoding the L is under control of an arenavirus 3' UTR; and
(vi) an arenavirus S segment, wherein the ORF encoding the Z protein is under control of an arenavirus 3' UTR.

In certain embodiments, the tri-segmented arenavirus particle comprising one L segment and two S segments can comprise a duplicate ORF (i.e., two wild-type S segment ORFs e.g., GP or NP). In specific embodiments, the tri-segmented arenavirus particle comprising one L segment and two S segments can comprise one duplicate ORF (e.g., (GP, GP)) or two duplicate ORFs (e.g., (GP, GP) and (NP, NP)).

Table 2A, below, is an illustration of the genome organization of a tri-segmented arenavirus particle comprising one L segment and two S segments, wherein intersegmental recombination of the two S segments in the tri-segmented arenavirus genome does not result in a replication-competent bi-segmented viral particle and abrogates arenaviral promoter activity (i.e., the resulting recombined S segment is made up of two 3'UTRs instead of a 3' UTR and a 5' UTR).

TABLE 2A

Tri-segmented arenavirus particle comprising one L segment and two S segments

| Position 1 | Position 2 | Position 3 | Position 4 | Position 5 | Position 6 |
|---|---|---|---|---|---|
| *ORF | GP | *ORF | NP | Z | L |
| *ORF | NP | *ORF | GP | Z | L |
| *ORF | NP | *ORF | GP | L | Z |
| *ORF | NP | *ORF | Z | L | GP |
| *ORF | NP | Z | GP | *ORF | Z |

TABLE 2A-continued

Tri-segmented arenavirus particle comprising one L segment and two S segments

| Position 1 | Position 2 | Position 3 | Position 4 | Position 5 | Position 6 |
|---|---|---|---|---|---|
| *ORF | NP | Z | GP | Z | *ORF |
| *ORF | NP | *ORF | L | Z | GP |
| *ORF | L | *ORF | NP | Z | GP |
| *ORF | L | Z | NP | *ORF | GP |
| *ORF | L | *ORF | GP | Z | NP |
| *ORF | L | Z | GP | *ORF | NP |
| *ORF | Z | L | NP | *ORF | GP |
| *ORF | Z | *ORF | GP | L | NP |
| *ORF | Z | L | GP | *ORF | NP |
| L | GP | *ORF | NP | *ORF | Z |
| L | GP | *ORF | *ORF | Z | NP |
| L | GP | *ORF | Z | *ORF | NP |
| L | *ORF | Z | GP | *ORF | NP |
| L | GP | *ORF | NP | *ORF | Z |
| L | GP | *ORF | Z | *ORF | NP |
| L | GP | Z | NP | *ORF | *ORF |
| L | GP | Z | NP | *ORF | *ORF |
| L | *ORF | Z | NP | *ORF | GP |
| L | NP | *ORF | Z | *ORF | GP |
| L | NP | Z | *ORF | GP | *ORF |
| L | *ORF | Z | *ORF | GP | NP |
| L | NP | Z | GP | *ORF | *ORF |
| L | NP | *ORF | Z | *ORF | GP |
| L | *ORF | Z | NP | *ORF | GP |
| L | Z | *ORF | GP | *ORF | NP |
| L | Z | *ORF | NP | *ORF | GP |
| Z | GP | *ORF | NP | *ORF | L |
| Z | GP | *ORF | *ORF | L | NP |
| Z | GP | *ORF | L | *ORF | NP |
| Z | *ORF | L | GP | *ORF | NP |
| Z | GP | *ORF | NP | *ORF | L |
| Z | GP | *ORF | L | *ORF | NP |
| Z | GP | L | NP | *ORF | *ORF |
| Z | GP | L | NP | *ORF | *ORF |
| Z | *ORF | L | NP | *ORF | GP |
| Z | NP | *ORF | *ORF | L | GP |
| Z | NP | *ORF | GP | *ORF | L |
| Z | NP | *ORF | *ORF | L | GP |
| Z | NP | *ORF | L | *ORF | GP |
| Z | NP | L | GP | *ORF | *ORF |
| Z | *ORF | L | GP | *ORF | NP |
| Z | NP | *ORF | GP | *ORF | L |
| Z | NP | *ORF | L | *ORF | GP |
| Z | *ORF | L | NP | *ORF | GP |
| Z | L | *ORF | GP | *ORF | NP |

Position 1 is under the control of an arenavirus S segment 5' UTR;
Position 2 is under the control of an arenavirus S segment 3' UTR;
Position 3 is under the control of an arenavirus S segment 5' UTR;
Position 4 under the control of an arenavirus S segment 3' UTR;
Position 5 is under the control of an arenavirus L segment 5' UTR;
Position 6 is under the control of an arenavirus L segment 3' UTR.
*ORF indicates that a heterologous ORF has been inserted.

In certain embodiments, the IGR between position one and position two can be an arenavirus S segment or L segment IGR; the IGR between position two and three can be an arenavirus S segment or L segment IGR; and the IGR between the position five and six can be an arenavirus L segment IGR. In a specific embodiment, the IGR between position one and position two can be an arenavirus S segment IGR; the IGR between position two and three can be an arenavirus S segment IGR; and the IGR between the position five and six can be an arenavirus L segment IGR. In certain embodiments, other combinations are also possible. For example, a tri-segmented arenavirus particle comprising one L segment and two S segments, wherein intersegmental recombination of the two S segments in the tri-segmented arenavirus genome does not result in a replication-competent bi-segmented viral particle and abrogates arenaviral promoter activity (i.e., the resulting recombined S segment is made up of two 5'UTRs instead of a 3' UTR and a 5' UTR).

In certain embodiments, intersegmental recombination of an S segment and an L segment in the tri-segmented arenavirus particle comprising one L segment and two S segments, restores a functional segment with two viral genes on only one segment instead of two separate segments. In other embodiments, intersegmental recombination of an S segment and an L segment in the tri-segmented arenavirus particle comprising one L segment and two S segments does not result in a replication-competent bi-segmented viral particle.

Table 2B, below, is an illustration of the genome organization of a tri-segmented arenavirus particle comprising one L segment and two S segments, wherein intersegmental recombination of an S segment and an L segment in the tri-segmented arenavirus genome does not result in a replication-competent bi-segmented viral particle and abrogates arenaviral promoter activity (i.e., the resulting recombined S segment is made up of two 3'UTRs instead of a 3' UTR and a 5' UTR).

TABLE 2B

Tri-segmented arenavirus particle comprising one L segment and two S segments

| Position 1 | Position 2 | Position 3 | Position 4 | Position 5 | Position 6 |
|---|---|---|---|---|---|
| L | GP | *ORF | NP | Z | *ORF |
| L | GP | Z | *ORF | *ORF | NP |
| L | GP | *ORF | NP | Z | *ORF |
| L | GP | Z | *ORF | *ORF | NP |
| L | NP | *ORF | GP | Z | *ORF |
| L | NP | Z | *ORF | *ORF | GP |
| L | NP | *ORF | GP | Z | *ORF |
| L | NP | Z | *ORF | *ORF | GP |
| Z | GP | *ORF | NP | L | *ORF |
| Z | GP | L | *ORF | *ORF | NP |
| Z | GP | *ORF | NP | L | *ORF |
| Z | NP | L | *ORF | *ORF | GP |
| Z | NP | *ORF | GP | L | *ORF |
| Z | NP | L | *ORF | *ORF | GP |

Position 1 is under the control of an arenavirus S segment 5' UTR;
Position 2 is under the control of an arenavirus S segment 3' UTR;
Position 3 is under the control of an arenavirus S segment 5' UTR;
Position 4 under the control of an arenavirus S segment 3' UTR;
Position 5 is under the control of an arenavirus L segment 5' UTR;
Position 6 is under the control of an arenavirus L segment 3' UTR.
*ORF indicates that a heterologous ORF has been inserted.

In certain embodiments, the IGR between position one and position two can be an arenavirus S segment or L segment IGR; the IGR between position two and three can be an arenavirus S segment or L segment IGR; and the IGR between the position five and six can be an arenavirus L segment IGR. In a specific embodiment, the IGR between position one and position two can be an arenavirus S segment IGR; the IGR between position two and three can be an arenavirus S segment IGR; and the IGR between the position five and six can be an arenavirus L segment IGR. In certain embodiments, other combinations are also possible. For example, a tri-segmented arenavirus particle comprising one L segment and two S segments, wherein intersegmental recombination of the two S segments in the tri-segmented arenavirus genome does not result in a replication-competent bi-segmented viral particle and abrogates arenaviral promoter activity (i.e., the resulting recombined S segment is made up of two 5'UTRs instead of a 3' UTR and a 5' UTR).

In certain embodiments, one of skill in the art could construct an arenavirus genome with an organization as illustrated in Table 2A or 2B and as described herein, and then use an assay as described in Section 4.8 to determine whether the tri-segmented arenavirus particle is genetically stable, i.e., does not result in a replication-competent bi-segmented viral particle as discussed herein.

4.2.2 Tri-Segmented Arenavirus Particle Comprising Two L Segments and One S Segment In one aspect, provided herein is a tri-segmented arenavirus particle comprising two L segments and one S segment. In certain embodiments, propagation of the tri-segmented arenavirus particle comprising two L segments and one S segment does not result in a replication-competent bi-segmented viral particle. In specific embodiments, propagation of the tri-segmented arenavirus particle comprising two L segments and one S segment does not result in a replication-competent bi-segmented viral particle after at least 10 days, at least 20 days, at least 30 days, at least 40 days, or at least 50 days, at least 60 days, at least 70 days, at least 80 days, at least 90 days, at least 100 days of persistent in mice lacking type I interferon receptor, type II interferon receptor and recombination activating gene (RAG1), and having been infected with $10^4$ PFU of the tri-segmented arenavirus particle (see Section 4.8.13). In other embodiments, propagation of the tri-segmented arenavirus particle comprising two L segments and one S segment does not result in a replication-competent bi-segmented viral particle after at least 10 passages, 20 passages, 30 passages, 40 passages, or 50 passages.

In certain embodiments, inter-segmental recombination of the two L segments of the tri-segmented arenavirus particle, provided herein, that unities the two arenaviral ORFs on one instead of two separate segments results in a non functional promoter (i.e., a genomic segment of the structure: 5' UTR-5' UTR or a 3' UTR-3' UTR), wherein each UTR forming one end of the genome is an inverted repeat sequence of the other end of the same genome.

In certain embodiments, the tri-segmented arenavirus particle comprising two L segments and one S segment has been engineered to carry an arenavirus ORF in a position other than the wild-type position of the ORF. In other embodiments, the tri-segmented arenavirus particle comprising two L segments and one S segment has been engineered to carry two arenavirus ORFs, or three arenavirus ORFs, or four arenavirus ORFs, or five arenavirus ORFs, or six arenavirus ORFs in a position other than the wild-type position. In specific embodiments, the tri-segmented arenavirus particle comprising two L segments and one S segment comprises a full complement of all four arenavirus ORFs. Thus, in some embodiments, the tri-segmented arenavirus particle is an infectious and replication competent tri-segmented arenavirus particle. In specific embodiments, the two L segments of the tri-segmented arenavirus particle have been engineered to carry one of their ORFs in a position other than the wild-type position. In more specific embodiments, the two L segments comprise a full complement of the L segment ORF's. In certain specific embodiments, the S segment has been engineered to carry one of their ORFs in a position other than the wild-type position or the S segment can be the wild-type genomic segment.

In certain embodiments, one of the two L segments can be:
(i) an L segment, wherein the ORF encoding the GP is under control of an arenavirus 5' UTR;
(ii) an L segment, wherein the ORF encoding NP is under control of an arenavirus 5' UTR;
(iii) an L segment, wherein the ORF encoding the L protein is under control of an arenavirus 5' UTR;
(iv) an L segment, wherein the ORF encoding the GP is under control of an arenavirus 3' UTR;

(v) an L segment, wherein the ORF encoding the NP is under control of an arenavirus 3' UTR; and (vi) an L segment, wherein the ORF encoding the Z protein is under control of an arenavirus 3' UTR.

In certain embodiments, the tri-segmented arenavirus particle comprising one L segment and two S segments can comprise a duplicate ORF (i.e., two wild-type L segment ORFs e.g., Z protein or L protein). In specific embodiments, the tri-segmented arenavirus particle comprising two L segments and one S segment can comprise one duplicate ORF (e.g., (Z protein, Z protein)) or two duplicate ORFs (e.g., (Z protein, Z protein) and (L protein, L protein)).

Table 3, below, is an illustration of the genome organization of a tri-segmented arenavirus particle comprising two L segments and one S segment, wherein intersegmental recombination of the two L segments in the tri-segmented arenavirus genome does not result in a replication-competent bi-segmented viral particle and abrogates arenaviral promoter activity (i.e., the putatively resulting recombinant L segment would be made up of two 3'UTRs or two 5' UTRs instead of a 3' UTR and a 5' UTR). Based on Table 3 similar combinations could be predicted for generating an arenavirus particle made up of two 5' UTRs instead of a 3' UTR and a 5' UTR.

TABLE 3

Tri-segmented arenavirus particle comprising two L segments and one S segment

| Position 1 | Position 2 | Position 3 | Position 4 | Position 5 | Position 6 |
|---|---|---|---|---|---|
| ORF* | Z | ORF* | L | NP | GP |
| ORF* | Z | ORF* | L | GP | NP |
| ORF* | Z | GP | L | ORF* | NP |
| ORF* | Z | ORF* | GP | NP | L |
| ORF* | Z | GP | ORF* | NP | L |
| ORF* | Z | NP | ORF* | GP | L |
| ORF* | ORF* | NP | Z | GP | L |
| ORF* | Z | GP | NP | ORF* | L |
| ORF* | Z | NP | GP | ORF* | L |
| ORF* | L | ORF* | Z | NP | GP |
| ORF* | L | ORF* | Z | GP | NP |
| ORF* | L | ORF* | GP | NP | Z |
| ORF* | L | GP | Z | ORF* | NP |
| ORF* | L | ORF* | GP | NP | Z |
| ORF* | L | NP | Z | ORF* | GP |
| ORF* | L | GP | NP | ORF* | Z |
| ORF* | L | NP | GP | ORF* | Z |
| ORF* | GP | ORF* | L | NP | Z |
| ORF* | GP | NP | L | ORF* | Z |
| ORF* | GP | ORF* | Z | NP | L |
| ORF* | GP | NP | Z | ORF* | L |
| ORF* | NP | ORF* | L | GP | Z |
| ORF* | NP | GP | L | ORF* | Z |
| ORF* | NP | GP | Z | ORF* | L |
| ORF* | NP | ORF* | Z | GP | L |
| ORF* | L | ORF* | Z | NP | GP |
| ORF* | L | ORF* | Z | GP | NP |
| ORF* | L | ORF* | NP | GP | Z |
| ORF* | L | ORF* | GP | NP | Z |
| ORF* | L | NP | Z | ORF* | GP |
| ORF* | Z | ORF* | GP | NP | L |
| ORF* | Z | GP | L | ORF* | NP |
| ORF* | Z | NP | GP | ORF* | L |
| ORF* | Z | GP | NP | ORF* | L |
| ORF* | GP | ORF* | L | NP | Z |
| ORF* | GP | ORF* | L | Z | NP |
| ORF* | GP | ORF* | Z | GP | L |
| ORF* | GP | NP | L | ORF* | Z |
| GP | L | ORF* | Z | ORF* | NP |
| GP | L | ORF* | NP | ORF* | Z |
| GP | Z | ORF* | L | ORF* | NP |
| GP | Z | ORF* | L | ORF* | NP |
| GP | Z | ORF* | NP | ORF* | L |
| GP | NP | ORF* | Z | ORF* | L |

TABLE 3-continued

Tri-segmented arenavirus particle comprising two L segments and one S segment

| Position 1 | Position 2 | Position 3 | Position 4 | Position 5 | Position 6 |
|---|---|---|---|---|---|
| NP | L | ORF* | Z | ORF* | GP |
| NP | L | ORF* | GP | ORF* | Z |
| NP | L | ORF* | Z | ORF* | GP |

*Position 1 is under the control of an arenavirus L segment 5' UTR;
position 2 is under the control of an arenavirus L segment 3' UTR;
position 3 is under the control of an arenavirus L segment 5' UTR;
position 4 is under the control of an arenavirus L segment 3' UTR;
position 5 is under the control of an arenavirus S segment 5' UTR; position 6 is under the control of an arenavirus S segment 3' UTR.
*ORF indicates that a heterologous ORF has been inserted.

In certain embodiments, the IGR between position one and position two can be an arenavirus S segment or L segment IGR; the IGR between position two and three can be an arenavirus S segment or L segment IGR; and the IGR between the position five and six can be an arenavirus S segment or L segment IGR. In a specific embodiment, the IGR between position one and position two can be an arenavirus L segment IGR; the IGR between position two and three can be an arenavirus L segment IGR; and the IGR between the position five and six can be an arenavirus S segment IGR. In certain embodiments, other combinations are also possible.

In certain embodiments intersegmental recombination of an L segment and an S segment from the tri-segmented arenavirus particle comprising two L segments and one S segment restores a functional segment with two viral genes on only one segment instead of two separate segments. In other embodiments, intersegmental recombination of an L segment and an S segment in the tri-segmented arenavirus particle comprising two L segments and one S segment does not result in a replication-competent bi-segmented viral particle.

Table 3B, below, is an illustration of the genome organization of a tri-segmented arenavirus particle comprising two L segments and one S segment, wherein intersegmental recombination of an L segment and an S segment in the tri-segmented arenavirus genome does not result in a replication-competent bi-segmented viral particle and abrogates arenaviral promoter activity (i.e., the resulting recombined S segment is made up of two 3'UTRs instead of a 3' UTR and a 5' UTR).

TABLE 3B

Tri-segmented arenavirus particle comprising two L segments and one S segment

| Position 1 | Position 2 | Position 3 | Position 4 | Position 5 | Position 6 |
|---|---|---|---|---|---|
| NP | Z | *ORF | GP | L | *ORF |
| NP | Z | GP | *ORF | *ORF | L |
| NP | Z | *ORF | GP | L | *ORF |
| NP | Z | GP | *ORF | *ORF | L |
| NP | L | *ORF | GP | Z | *ORF |
| NP | L | GP | *ORF | *ORF | Z |
| NP | L | *ORF | GP | Z | *ORF |
| NP | L | GP | *ORF | *ORF | Z |
| GP | Z | *ORF | NP | L | *ORF |
| GP | Z | NP | *ORF | *ORF | L |
| GP | Z | *ORF | NP | L | *ORF |
| GP | L | NP | *ORF | *ORF | Z |

TABLE 3B-continued

Tri-segmented arenavirus particle comprising
two L segments and one S segment

| Position 1 | Position 2 | Position 3 | Position 4 | Position 5 | Position 6 |
|---|---|---|---|---|---|
| GP | L | *ORF | NP | Z | *ORF |
| GP | L | NP | *ORF | *ORF | Z |

*Position 1 is under the control of an arenavirus L segment 5' UTR;
position 2 is under the control of an arenavirus L segment 3' UTR;
position 3 is under the control of an arenavirus L segment 5' UTR;
position 4 is under the control of an arenavirus L segment 3' UTR;
position 5 is under the control of an arenavirus S segment 5' UTR;
position 6 is under the control of an arenavirus S segment 3' UTR.
*ORF indicates that a heterologous ORF has been inserted.

In certain embodiments, the IGR between position one and position two can be an arenavirus S segment or L segment IGR; the IGR between position two and three can be an arenavirus S segment or L segment IGR; and the IGR between the position five and six can be an arenavirus S segment or L segment IGR. In a specific embodiment, the IGR between position one and position two can be an arenavirus L segment IGR; the IGR between position two and three can be an arenavirus L segment IGR; and the IGR between the position five and six can be an arenavirus S segment IGR. In certain embodiments, other combinations are also possible.

In certain embodiments, one of skill in the art could construct an arenavirus genome with an organization as illustrated in Table 3A or 3B and as described herein, and then use an assay as described in Section 4.8 to determine whether the tri-segmented arenavirus particle is genetically stable, i.e., does not result in a replication-competent bi-segmented viral particle as discussed herein.

4.2.3 Replication-Defective Tri-Segmented Arenavirus Particle

In certain embodiments, provided herein is a tri-segmented arenavirus particle in which (i) an ORF is in a position other than the wild-type position of the ORF; and (ii) an ORF encoding GP, NP, Z protein, or L protein has been removed or functionally inactivated such that the resulting virus cannot produce further infectious progeny virus particles (i.e., is replication defective). In certain embodiments, the third arenavirus segment can be an S segment. In other embodiments, the third arenavirus segment can be an L segment. In more specific embodiments, the third arenavirus segment can be engineered to carry an ORF in a position other than the wild-type position of the ORF or the third arenavirus segment can be the wild-type arenavirus genomic segment. In yet more specific embodiments, the third arenavirus segment lacks an arenavirus ORF encoding GP, NP, Z protein, or the L protein.

In certain embodiments, a tri-segmented genomic segment could be a S or a L segment hybrid (i.e., a genomic segment that can be a combination of the S segment and the L segment). In other embodiments, the hybrid segment is an S segment comprising an L segment IGR. In another embodiment, the hybrid segment is an L segment comprising an S segment IGR. In other embodiments, the hybrid segment is an S segment UTR with and L segment IGR. In another embodiment, the hybrid segment is an L segment UTR with an S segment IGR. In specific embodiments, the hybrid segment is an S segment 5' UTR with an L segment IGR or an S segment 3' UTR with an L segment IGR. In other specific embodiments, the hybrid segment is an L segment 5' UTR with an S segment IGR or an L segment 3' UTR with an S segment IGR.

A tri-segmented arenavirus particle comprising a genetically modified genome in which one or more ORFs has been deleted or functionally inactivated can be produced in complementing cells (i.e., cells that express the arenavirus ORF that has been deleted or functionally inactivated). The genetic material of the resulting arenavirus particle can be transferred upon infection of a host cell into the host cell, wherein the genetic material can be expressed and amplified. In addition, the genome of the genetically modified arenavirus particle described herein can encode a heterologous ORF from an organism other than an arenavirus particle.

In certain embodiments, at least one of the four ORFs encoding GP, NP, Z protein, and L protein is removed and replaced with a heterologous ORF from an organism other than an arenavirus. In another embodiment, at least one ORF, at least two ORFs, at least three ORFs, or at least four ORFs encoding GP, NP, Z protein and L protein can be removed and replaced with a heterologous ORF from an organism other than an arenavirus. In specific embodiments, only one of the four ORFs encoding GP, NP, Z protein, and L protein is removed and replaced with a heterologous ORF from an organism other than an arenavirus particle. In more specific embodiments, the ORF that encodes GP of the arenavirus genomic segment is removed. In another specific embodiment, the ORF that encodes the NP of the arenavirus genomic segment is removed. In more specific embodiments, the ORF that encodes the Z protein of the arenavirus genomic segment is removed. In yet another specific embodiment, the ORF encoding the L protein is removed.

In certain embodiments, provided herein is a tri-segmented arenavirus particle comprising one L segment and two S segments in which (i) an ORF is in a position other than the wild-type position of the ORF; and (ii) an ORF encoding GP or NP has been removed or functionally inactivated, such that the resulting virus is replication-defective and not infectious. In a specific embodiment, one ORF is removed and replaced with a heterologous ORF from an organism other than an arenavirus. In another specific embodiment, two ORFs are removed and replaced with a heterologous ORF from an organism other than an arenavirus. In other specific embodiments, three ORFs are removed and replaced with a heterologous ORF from an organism other than an arenavirus. In specific embodiments, the ORF encoding GP is removed and replaced with a heterologous ORF from an organism other than an arenavirus. In other specific embodiments, the ORF encoding NP is removed and replaced with a heterologous ORF from an organism other than an arenavirus. In yet more specific embodiments, the ORF encoding NP and the ORF encoding GP are removed and replaced with one or two heterologous ORFs from an organism other than an arenavirus particle. Thus, in certain embodiments the tri-segmented arenavirus particle comprises (i) one L segment and two S segments; (ii) an ORF in a position other than the wild-type position of the ORF; (iii) one or more heterologous ORFs from an organism other than an arenavirus.

In certain embodiments, provided herein is a tri-segmented arenavirus particle comprising two L segments and one S segment in which (i) an ORF is in a position other than the wild-type position of the ORF; and (ii) an ORF encoding the Z protein, and/or the L protein has been removed or functionally inactivated, such that the resulting virus replication-defective and not infectious. In a specific embodiment, one ORF is removed and replaced with a heterologous ORF from an organism other than an arenavirus. In another specific embodiment, two ORFs are removed and replaced with a heterologous ORF from an organism other than an arenavirus. In specific embodiments, the ORF encoding the Z protein is removed and replaced with a heterologous ORF from an organism other than an arenavirus. In other specific embodiments, the ORF encoding the L protein is removed and replaced with a heterologous ORF from an organism other than an arenavirus. In yet more specific embodiments, the ORF encoding the Z protein and the ORF encoding the L protein is removed and replaced with a heterologous ORF from an organism other than an arenavirus particle. Thus, in certain embodiments the tri-segmented arenavirus particle comprises (i) two L segments and one S segment; (ii) an ORF in a position other than the wild-type position of the ORF; (iii) a heterologous ORF from an organism other than an arenavirus.

Thus, in certain embodiments, the tri-segmented arenavirus particle provided herein comprises a tri-segmented arenavirus particle (i.e., one L segment and two S segments or two L segments and one S segment) that i) is engineered to carry an ORF in a non-natural position; ii) an ORF encoding GP, NP, Z protein, or L protein is removed); iii) the ORF that is removed is replaced with one or more heterologous ORFs from an organism other than an arenavirus.

In certain embodiments, the heterologous ORF is 8 to 100 nucleotides in length, 15 to 100 nucleotides in length, 25 to 100 nucleotides in length, 50 to 200 nucleotide in length, 50 to 400 nucleotide in length, 200 to 500 nucleotide in length, or 400 to 600 nucleotides in length, 500 to 800 nucleotide in length. In other embodiments, the heterologous ORF is 750 to 900 nucleotides in length, 800 to 100 nucleotides in length, 850 to 1000 nucleotides in length, 900 to 1200 nucleotides in length, 1000 to 1200 nucleotides in length, 1000 to 1500 nucleotides or 10 to 1500 nucleotides in length, 1500 to 2000 nucleotides in length, 1700 to 2000 nucleotides in length, 2000 to 2300 nucleotides in length, 2200 to 2500 nucleotides in length, 2500 to 3000 nucleotides in length, 3000 to 3200 nucleotides in length, 3000 to 3500 nucleotides in length, 3200 to 3600 nucleotides in length, 3300 to 3800 nucleotides in length, 4000 nucleotides to 4400 nucleotides in length, 4200 to 4700 nucleotides in length, 4800 to 5000 nucleotides in length, 5000 to 5200 nucleotides in length, 5200 to 5500 nucleotides in length, 5500 to 5800 nucleotides in length, 5800 to 6000 nucleotides in length, 6000 to 6400 nucleotides in length, 6200 to 6800 nucleotides in length, 6600 to 7000 nucleotides in length, 7000 to 7200 nucleotides in lengths, 7200 to 7500 nucleotides in length, or 7500 nucleotides in length. In some embodiments, the heterologous ORF encodes a peptide or polypeptide that is 5 to 10 amino acids in length, 10 to 25 amino acids in length, 25 to 50 amino acids in length, 50 to 100 amino acids in length, 100 to 150 amino acids in length, 150 to 200 amino acids in length, 200 to 250 amino acids in length, 250 to 300 amino acids in length, 300 to 400 amino acids in length, 400 to 500 amino acids in length, 500 to 750 amino acids in length, 750 to 1000 amino acids in length, 1000 to 1250 amino acids in length, 1250 to 1500 amino acids in length, 1500 to 1750 amino acids in length, 1750 to 2000 amino acids in length, 2000 to 2500 amino acids in length, or more than 2500 or more amino acids in length. In some embodiments, the heterologous ORF encodes a polypeptide that does not exceed 2500 amino acids in length. In specific embodiments the heterologous ORF does not contain a stop codon. In certain embodiments, the heterologous ORF is codon-optimized. In certain embodiments the nucleotide composition, nucleotide pair composition or both can be optimized. Techniques for such optimizations are known in the art and can be applied to optimize a heterologous ORF.

Any heterologous ORF from an organism other than an arenavirus may be included in the tri-segmented arenavirus particle. In one embodiment, the heterologous ORF encodes a reporter protein. More detailed description of reporter proteins are described in Section 4.3. In another embodiment, the heterologous ORF encodes an antigen for an infectious pathogen or an antigen associated with any disease and where the antigen is capable of eliciting an immune response. In specific embodiments the antigen is derived from an infectious organism, a tumor (i.e., cancer), or an allergen. More detailed description on heterologous ORFs is described in Section 4.3

In certain embodiments, the growth and infectivity of the arenavirus particle is not affected by the heterologous ORF from an organism other than an arenavirus.

Techniques known to one skilled in the art may be used to produce an arenavirus particle comprising an arenavirus genomic segment engineered to carry an arenavirus ORF in a position other than the wild-type position. For example, reverse genetics techniques may be used to generate such arenavirus particle. In other embodiments, the replication-defective arenavirus particle (i.e., the arenavirus genomic segment engineered to carry an arenavirus ORF in a position other than the wild-type position, wherein an ORF encoding GP, NP, Z protein, L protein, has been deleted) can be produced in a complementing cell.

In certain embodiments, the tri-segmented arenavirus particle using according to the present application can be Old World viruses, for example, LCMV.

In certain embodiments, the present application relates to the arenavirus particle as described herein suitable for use as a vaccine and methods of using such arenavirus particle in a vaccination and treatment or prevention of, for example, infections and cancers. More detailed description of the methods of using the arenavirus particle described herein is provided in Section 4.6.

In certain embodiments, the present application relates to the arenavirus particle as described herein suitable for use as a pharmaceutical composition and methods of using such arenavirus particle in a vaccination and treatment or prevention of, for example, infections or cancers. More detailed description of the methods of using the arenavirus particle described herein is provided in Section 4.6.

4.3 Arenavirus Particle or Tri-Segmented Arenavirus Particle Expressing a Heterologous ORF In certain embodiments, the arenavirus genomic segment, and the respective arenavirus particle or tri-segmented arenavirus particle can comprise a heterologous ORF. In other embodiments, the arenavirus genomic segment and the respective arenavirus particle or tri-segmented arenavirus particle can comprise a gene of interest. In more specific embodiments, the heterologous ORF or the gene of interest encodes an antigen. In more specific embodiments, the heterologous ORF or the gene or interest encodes a reporter protein or a fluorescent protein.

In certain embodiments, the arenavirus genomic segment, the arenavirus particle or the tri-segmented arenavirus particle can comprise one or more heterologous ORFs or one or more genes of interest. In other embodiments, the arenavirus genomic segment, the arenavirus particle or the tri-segmented arenavirus particle can comprise at least one heterologous ORF, at least two heterologous ORFs, at least three heterologous ORFs, or more heterologous ORFs. In other embodiments, the arenavirus particle or the tri-segmented arenavirus particle comprises at least one gene of interest, at least two genes of interest, at least three genes of interest, or more genes of interest.

A wide variety of antigens may be expressed by the arenavirus genomic segment, arenavirus particle or the trisegmented arenavirus particle of the present application. In one embodiment, the heterologous ORF encodes an antigen of an infectious pathogen or an antigen associated with any disease that is capable of eliciting an immune response. In certain embodiments, the heterologous ORF can encode an antigen derived from a virus, a bacterium, a fungus, a parasite, or can be expressed in a tumor or tumor associated disease (i.e., cancer), an autoimmune disease, a degenerative disease, an inherited disease, substance dependency, obesity, or an allergic disease.

In some embodiments, the heterologous ORF encodes a viral antigen. Non-limiting examples of viral antigens include antigens from adenoviridae (e.g., mastadenovirus and aviadenovirus), herpesviridae (e.g., herpes simplex virus 1, herpes simplex virus 2, herpes simplex virus 5, herpes simplex virus 6, Epstein-Barr virus, HHV6-HHV8 and cytomegalovirus), leviviridae (e.g., levivirus, enterobacteria phase MS2, allolevirus), poxyiridae (e.g., chordopoxyirinae, parapoxvirus, avipoxvirus, capripoxvirus, leporiipoxvirus, suipoxvirus, molluscipoxvirus, and entomopoxyirinae), papovaviridae (e.g., polyomavirus and papillomavirus), paramyxoviridae (e.g., paramyxovirus, parainfluenza virus 1, mobillivirus (e.g., measles virus), rubulavirus (e.g., mumps virus), pneumonovirinae (e.g., pneumovirus, human respiratory syncytial virus), human respiratory syncytial virus and metapneumovirus (e.g., avian pneumovirus and human metapneumovirus), picornaviridae (e.g., enterovirus, rhinovirus, hepatovirus (e.g., human hepatitis A virus), cardiovirus, and apthovirus), reoviridae (e.g., orthoreovirus, orbivirus, rotavirus, cypovirus, fijivirus, phytoreovirus, and oryzavirus), retroviridae (e.g., mammalian type B retroviruses, mammalian type C retroviruses, avian type C retroviruses, type D retrovirus group, BLV-HTLV retroviruses, lentivirus (e.g. human immunodeficiency virus (HIV) 1 and HIV-2 (e.g., HIV gp160), spumavirus), flaviviridae (e.g., hepatitis C virus, dengue virus, West Nile virus), hepadnaviridae (e.g., hepatitis B virus), togaviridae (e.g., alphavirus (e.g., sindbis virus) and rubivirus (e.g., rubella virus)), rhabdoviridae (e.g., vesiculovirus, lyssavirus, ephemerovirus, cytorhabdovirus, and necleorhabdovirus), arenaviridae (e.g., arenavirus, lymphocytic choriomeningitis virus, Ippy virus, and lassa virus), and coronaviridae (e.g., coronavirus and torovirus). In a specific embodiment the viral antigen, is HIV gp120, gp41, HIV Nef, RSV F glycoprotein, RSV G glycoprotein, HTLV tax, herpes simplex virus glycoprotein (e.g., gB, gC, gD, and gE) or hepatitis B surface antigen, hepatitis C virus E protein or coronavirus spike protein. In one embodiment, the viral antigen is not an HIV antigen.

In other embodiments, the heterologous ORF encodes a bacterial antigen (e.g., bacterial coat protein). In other embodiments, the heterologous ORF encodes parasitic antigen (e.g., a protozoan antigen). In yet other embodiments, a heterologous nucleotide sequence encodes a fungal antigen.

Non-limiting examples of bacterial antigens include antigens from bacteria of the Aquaspirillum family, Azospirillum family, Azotobacteraceae family, Bacteroidaceae family, *Bartonella* species, Bdellovibrio family, *Campylobacter* species, *Chlamydia* species (e.g., *Chlamydia pneumoniae*), *clostridium*, Enterobacteriaceae family (e.g., *Citrobacter* species, *Edwardsiella, Enterobacter aerogenes, Envinia species, Escherichia coli, Hafnia species, Klebsiella species, Morganella species, Proteus vulgaris, Providencia, Salmonella* species, *Serratia marcescens*, and *Shigella flexneri*), Gardinella family, *Haemophilus influenzae*, Halobacteriaceae family, Helicobacter family, Legionallaceae family, *Listeria* species, Methylococcaceae family, mycobacteria (e.g., *Mycobacterium tuberculosis*), Neisseriaceae family, Oceanospirillum family, Pasteurellaceae family, *Pneumococcus* species, *Pseudomonas* species, Rhizobiaceae family, Spirillum family, Spirosomaceae family, *Staphylococcus* (e.g., methicillin resistant *Staphylococcus aureus* and *Staphylococcus* pyrogenes), *Streptococcus* (e.g., *Streptococcus enteritidis, Streptococcus fasciae*, and *Streptococcus pneumoniae*), Vampirovibr Helicobacter family, *Yersinia* family, *Bacillus antracis* and Vampirovibrio family.

Non-limiting examples of parasite antigens include antigens from a parasite such as an amoeba, a malarial parasite, *Plasmodium, Trypanosoma cruzi*. Non-limiting examples of fungal antigens include antigens from fungus of *Absidia* species (e.g., *Absidia corymbifera* and *Absidia ramosa*), *Aspergillus* species, (e.g., *Aspergillus flavus, Aspergillus fumigatus, Aspergillus nidulans, Aspergillus niger*, and *Aspergillus terreus*), *Basidiobolus ranarum, Blastomyces dermatitidis, Candida* species (e.g., *Candida albicans, Candida glabrata, Candida kern, Candida krusei, Candida parapsilosis, Candida pseudotropicalis, Candida quillermondii, Candida rugosa, Candida stellatoidea*, and *Candida tropicalis*), *Coccidioides immitis, Conidiobolus species, Cryptococcus neoforms, Cunninghamella* species, *dermatophytes, Histoplasma capsulatum, Microsporum gypseum, Mucor pusillus, Paracoccidioides brasiliensis, Pseudallescheria boydii, Rhinosporidium seeberi, Pneumocystis carinii, Rhizopus* species (e.g., *Rhizopus arrhizus, Rhizopus oryzae*, and *Rhizopus microsporus*), *Saccharomyces* species, *Sporothrix schenckii, zygomycetes*, and classes such as Zygomycetes, Ascomycetes, the Basidiomycetes, Deuteromycetes, and Oomycetes.

In some embodiments, a heterologous ORF encodes a tumor antigen or tumor associated antigen. In some embodiments, the tumor antigen or tumor associated antigen includes antigens from tumor associated diseases including acute lymphoblastic leukemia, acute myeloid leukemia, adrenocortical carcinoma, childhood adrenocortical carcinoma, AIDS-Related Cancers, Kaposi Sarcoma, anal cancer, appendix cancer, astrocytomas, atypical teratoid/rhabdoid tumor, basal-cell carcinoma, bile duct cancer, extrahepatic (see cholangiocarcinoma), bladder cancer, bone osteosarcoma/malignant fibrous histiocytoma, brainstem glioma, brain cancer, brain tumor, cerebellar astrocytoma, cerebral astrocytoma/malignant glioma brain tumor, ependymoma, medulloblastoma, supratentorial primitive neuroectodermal tumors, visual pathway and hypothalamic glioma, breast cancer, bronchial adenomas/carcinoids, burkitt's lymphoma, carcinoid tumor, carcinoid gastrointestinal tumor, carcinoma of unknown primary, central nervous system lymphoma, primary, cerebellar astrocytoma, cerebral astrocytoma/malignant glioma, cervical cancer, childhood cancers, chronic bronchitis, chronic lymphocytic leukemia, chronic myelogenous leukemia, chronic myeloproliferative disorders, colon cancer, cutaneous T-cell lymphoma, desmoplastic small round cell tumor, emphysema, endometrial cancer, ependymoma, esophageal cancer, ewing's sarcoma in the Ewing family of tumors, extracranial germ cell tumor, extragonadal germ cell tumor, extrahepatic bile duct cancer, intraocular melanoma, retinoblastoma, gallbladder cancer, gastric (stomach) cancer, gastrointestinal carcinoid tumor, gastrointestinal stromal tumor, germ cell tumor: extracranial, extragonadal, or ovarian gestational trophoblastic tumor, glioma of the brain stem, glioma, childhood cerebral astrocytoma, childhood visual pathway and hypothalamic, gastric carcinoid, hairy cell leukemia, head and neck cancer, heart cancer, hepatocellular (liver) cancer, hodgkin lymphoma, hypopharyngeal cancer, hypothalamic and visual pathway glioma, intraocular melanoma, islet cell carcinoma (endocrine pancreas), kaposi sarcoma, kidney cancer (renal cell cancer), laryngeal cancer, acute lymphoblastic lymphoma, acute lymphocytic leukemia, acute myelogenous leukemia, chronic lymphocytic leukemia, chronic myeloid leukemia, lip and oral cavity cancer, liposarcoma, liver cancer (primary), lung cancer, non-small cell, small cell, AIDS-related lymphoma, Burkitt lymphoma, cutaneous T-cell lymphoma, hodgkin lymphoma, non-hodgkin lymphoma, lymphoma, primary central nervous system, macroglobulinemia, Waldenström, male breast cancer, malignant fibrous histicoytoma of bone/osteosarcoma, medulloblastoma, melanoma, intraocular (eye), merkel cell cancer, mesothelioma, adult malignant, mesothelioma, metastatic squamous neck cancer with occult primary, mouth cancer, multiple endocrine neoplasia syndrome, multiple myeloma/plasma cell neoplasm, mycosis fungoides, myelodysplastic syndromes, myelodysplastic/myeloproliferative diseases, myelogenous leukemia, chronic, myeloid leukemia, adult acute, myeloid leukemia, childhood acute, myeloma, multiple (cancer of the bone-marrow), myeloproliferative disorders, chronic, nasal cavity and paranasal sinus cancer, nasopharyngeal carcinoma, neuroblastoma, non-small cell lung cancer, oligodendroglioma, oral cancer, oropharyngeal cancer, osteosarcoma/malignant fibrous histicoytoma of bone, ovarian cancer, ovarian epithelial cancer (surface epithelial-stromal tumor), ovarian germ cell tumor, ovarian low malignant potential tumor, pancreatic cancer, islet cell, paranasal sinus and nasal cavity cancer, parathyroid cancer, penile cancer, pharyngeal cancer, pheochromocytoma, pineal astrocytoma, pineal germinoma, pineoblastoma and supratentorial primitive neuroectodermal tumors, pituitary adenoma, plasma cell neoplasia/multiple myeloma, pleuropulmonary blastoma, primary central nervous system lymphoma, prostate cancer, rectal cancer, renal cell carcinoma (kidney cancer), renal pelvis and ureter, transitional cell cancer, retinoblastoma, rhabdomyosarcoma, childhood, salivary gland cancer, sarcoma, Ewing family of tumors, Kaposi sarcoma, soft tissue sarcoma, uterine sarcoma, sézary syndrome, skin cancer (non-melanoma), skin cancer (melanoma), merkel cell skin carcinoma, small cell lung cancer, small intestine cancer, soft tissue sarcoma, squamous cell carcinoma—see skin cancer (non-melanoma), squamous neck cancer with occult primary, metastatic, stomach cancer, supratentorial primitive neuroectodermal tumor, T-Cell lymphoma, cutaneous—see Mycosis Fungoides and Sézary syndrome, testicular cancer, throat cancer, thymoma and thymic carcinoma, thyroid cancer, childhood transitional cell cancer of the renal pelvis and ureter, gestational trophoblastic tumor, unknown primary site, carcinoma of, adult unknown primary site, cancer of childhood, ureter and renal pelvis, transitional cell cancer, rethral cancer, uterine cancer, endometrial uterine sarcoma, bronchial tumor, central nervous system embryonal tumor; childhood chordoma, colorectal cancer, craniopharyngioma, ependymoblastoma, langerhans cell histiocytosis, acute lymphoblastic leukemia, acute myeloid leukemia (adult/childhood), small cell lung cancer, medulloepithelioma, oral cavity cancer, papillomatosis, pineal parenchymal tumors of intermediate differentiation, pituary tumor, respiratory tract carcinoma involving the NUT gene on chromosome 15, spinal cord tumor, thymoma, thyroid cancer, vaginal Cancer; vulvar Cancer, and Wilms Tumor.

Non-limiting examples of tumor or tumor associated antigens include Adipophilin, AIM-2, ALDH1A1, BCLX (L), BING-4, CALCA, CD45, CPSF, cyclin Dl, DKK1, ENAH (hMena), EpCAM, EphA3, EZH2, FGF5, glypican-3, G250/MN/CAIX, HER-2/neu, IDO1, IGF2B3, IL13Ralpha2, Intestinal carboxyl esterase, alpha-fetoprotein, Kallikrein 4, KIF20A, Lengsin, M-CSF, MCSP, mdm-2, Meloe, MMP-2, MMP-7, MUC1, MUC5AC, p53, PAXS, PBF, PRAME, PSMA, RAGE-1, RGSS, RhoC, RNF43, RU2AS, secernin 1, SOX10, STEAP1, survivinn, Telomerase, VEGF, or WT1, EGF-R, CEA, CD52, gp 100 protein, MELANA/MART1, NY-ESO-1, p53 MAGE1, MAGE3 and CDK4, alpha-actinin-4, ARTC1, BCR-ABL fusion protein (b3a2), B-RAF, CASP-5, CASP-8, beta-catenin, Cdc27, CDK4, CDKN2A, CLPP, COA-1, dek-can fusion protein, EFTUD2, Elongation factor 2, ETV6-AML1 fusion protein, FLT3-ITD, FN1, GPNMB, LDLR-fucosyltransferaseAS fusion protein, NFYC, OGT, OS-9, pml-RARalpha fusion protein, PRDXS, PTPRK, K-ras, N-ras, RBAF600, SIRT2, SNRPD1, SYT-SSX1 or -SSX2 fusion protein, TGF-betaRII, Triosephosphate isomerase, Lengsin, M-CSF, MCSP, or mdm-2.

In some embodiments, the heterologous ORF encodes a respiratory pathogen antigen. In a specific embodiment, the respiratory pathogen is a virus such as RSV, coronavirus, human metapneumovirus, parainfluenza virus, hendra virus, nipah virus, adenovirus, rhinovirus, or PRRSV. Non-limiting examples of respiratory viral antigens include Respiratory Syncytial virus F, G and M2 proteins, Coronavirus (SARS, HuCoV) spike proteins (S), human metapneumovirus fusion proteins, Parainfluenza virus fusion and hemagglutinin proteins (F, HN), Hendra virus (HeV) and Nipah virus (NiV) attachment glycoproteins (G and F), Adenovirus capsid proteins, Rhinovirus proteins, and PRRSV wild type or modified GP5 and M proteins.

In a specific embodiment, the respiratory pathogen is a bacteria such as *Bacillus anthracis, Mycobacterium tuberculosis, Bordetella pertussis, Streptococcus pneumoniae, Yersinia pestis, Staphylococcus aureus, Francisella tularensis, Legionella pneumophila, Chlamydia pneumoniae, Pseudomonas aeruginosa, Neisseria meningitides,* and *Haemophilus influenzae*. Non-limiting examples of respiratory bacterial antigens include *Bacillus anthracis* Protective antigen PA, *Mycobacterium tuberculosis* mycobacterial antigen 85A and heat shock protein (Hsp65), *Bordetella pertussis* pertussis toxoid (PT) and filamentous hemagglutinin (FHA), *Streptococcus pneumoniae* sortase A and surface adhesin A (PsaA), *Yersinia pestis* F1 and V subunits, and proteins from *Staphylococcus aureus, Francisella tularensis, Legionella pneumophila, Chlamydia pneumoniae, Pseudomonas aeruginosa, Neisseria meningitides,* and *Haemophilus influenzae*.

In some embodiments, the heterologous ORF encodes a T-cell epitope. In other embodiments, the heterologous ORF encodes a cytokine or growth factor.

In other embodiments, the heterologous ORF encodes an antigen expressed in an autoimmune disease. In more specific embodiments, the autoimmune disease can be type I diabetes, multiple sclerosis, rheumatoid arthritis, lupus erythmatosus, and psoriasis. Non-limiting examples of autoimmune disease antigens include Ro60, dsDNA, or RNP.

In other embodiments, ORF encodes an antigen expressed in an allergic disease. In more specific embodiments, the allergic disease can include but is not limited to seasonal and perennial rhinoconjunctivitis, asthma, and eczema. Non-limiting examples of allergy antigens include Bet v 1 and Fel d 1.

In other embodiments, the arenavirus genomic segment, the arenavirus particle or the ticle further comprises a reporter protein. The reporter protein is capable of expression at the same time as the antigen described herein. Ideally, expression is visible in normal light or other wavelengths of light. In certain embodiments, the intensity of the effect created by the reporter protein can be used to directly measure and monitor the arenavirus particle or tri-segmented arenavirus particle.

Reporter genes would be readily recognized by one of skill in the art. In certain embodiments, the arenavirus particle is a fluorescent protein. In other embodiments, the reporter gene is GFP. GFP emits bright green light when exposed to UV or blue like.

Non-limiting examples of reporter proteins include various enzymes, such as, but not to β-galactosidase, chloramphenicol acetyltransferase, neomycin phosphotransferase, luciferase or RFP.

In certain embodiments, the arenavirus genomic segment, the arenavirus particle or the tri-segmented arenavirus particle expressing a heterologous ORF has desirable properties for use as a vector for vaccination (see e.g., Section 4.6). In another embodiment, the arenavirus genomic segment, the arenavirus particle or the tri-segmented arenavirus particle expressing a heterologous ORF is capable of inducing an immune response in a host (e.g., mouse rabbit, goat, donkey, human). In other embodiments, the arenavirus genomic segment, the arenavirus particle or the tri-segmented arenavirus particle expressing a heterologous ORF described herein induces an innate immune response. In other embodiments, the arenavirus genomic segment, the arenavirus particle or the tri-segmented arenavirus particle expressing a heterologous ORF induces an adaptive immune response. In more specific embodiments, the arenavirus genomic segment, the arenavirus particle or the tri-segmented arenavirus particle expressing a heterologous ORF both an innate and adaptive immune response.

In another embodiment, the arenavirus genomic segment, the arenavirus particle or the tri-segmented arenavirus particle expressing a heterologous ORF induces a T cell response. In yet more specific embodiments, the arenavirus genomic segment, the arenavirus particle or tri-segmented arenavirus particle expressing a heterologous ORF induces a CD8+ T cell response. In other embodiments, the arenavirus particle carrying a foreign gene of interest induces a potent CD8+ T cell response of high frequency and functionality. In other embodiments, the arenavirus genomic segment, the arenavirus particle or the tri-segmented arenavirus particle expressing an antigen derived from an infectious organism, a cancer, or an allergen induces CD8+ T cells specific to one or multiple epitopes of the corresponding foreign gene of interest.

In certain embodiments, the arenavirus genomic segment, the arenavirus particle or the tri-segmented arenavirus particle expressing a heterologous ORF can induce T helper 1 differentiation, memory formation of CD4+ T cells and/or elicit durable antibody responses. These antibodies can be neutralizing, opsonizing, toxic to tumor cells or have other favorable biological features. In other embodiments, the arenavirus genomic segment, the arenavirus particle or tri-segmented arenavirus particle expressing a heterologous ORF has a strong tropism for dendritic cells and activates them upon infection. This potentiates presentation of the antigen by antigen presenting cells.

In certain embodiments, the arenavirus genomic segment, the arenavirus particle or the tri-segmented arenavirus particle expressing an antigen derived from an infectious organism, a cancer, or an allergen induces low or undetectable neutralizing antibody titers against LCMV and high protective neutralizing antibody responses to the respective foreign transgene. In some embodiments, the arenavirus backbone forming the particle or tri-segmented arenavirus particle expressing an antigen derived from an infectious organism, a cancer, or an allergen has low capacity for inducing immunity to the arenaviral backbone components.

4.4 Generation of an Arenavirus Particle and a Tri-Segmented Arenavirus Particle Generally, arenavirus particles can be recombinantly produced by standard reverse genetic techniques as described for LCMV (see Flatz et al., 2006, Proc Natl Acad Sci USA 103:4663-4668; Sanchez et al., 2006, Virology 350:370; Ortiz-Riano et al., 2013, J Gen Virol. 94:1175-88, which are incorporated by reference herein). To generate the arenavirus particles provided herein, these techniques can be applied as described below. The genome of the viruses can be modified as described in Section 4.1 and Section 4.2, respectively.

4.4.1 Non-Natural Position Open Reading Frame

The generation of an arenavirus particle comprising a genomic segment that has been engineered to carry a viral ORF in a position other than the wild-type position of the ORF can be recombinantly produced by any reverse genetic techniques known to one skilled in the art.

(i) Infectious and Replication Competent Arenavirus Particle

In certain embodiments, the method of generating the arenavirus particle comprises (i) transfecting into a host cell the cDNA of the first arenavirus genomic segment; (ii) transfecting into a host cell the cDNA of the second arenavirus genomic segment; (iii) transfecting into a host cell plasmids expressing the arenavirus' minimal trans-acting factors NP and L; (iv) maintaining the host cell under conditions suitable for virus formation; and (v) harvesting the arenavirus particle. In certain more specific embodiments, the cDNA is comprised in a plasmid.

Once generated from cDNA, arenavirus particles (i.e., infectious and replication competent) can be propagated. In certain embodiments, the arenavirus particle can be propagated in any host cell that allows the virus to grow to titers that permit the uses of the virus as described herein. In one embodiment, the host cell allows the arenavirus particle to grow to titers comparable to those determined for the corresponding wild-type.

In certain embodiments, the arenavirus particle may be propagated in host cells. Specific examples of host cells that can be used include BHK-21, HEK 293, VERO or other. In a specific embodiment, the arenavirus particle may be propagated in a cell line.

In certain embodiments, the host cells are kept in culture and are transfected with one or more plasmid(s). The plasmid(s) express the arenavirus genomic segment(s) to be generated under control of one or more expression cassettes suitable for expression in mammalian cells, e.g., consisting of a polymerase I promoter and terminator.

Plasmids that can be used for the generation of the arenavirus particle can include: i) a plasmid encoding the S genomic segment e.g., pol-I S, ii) a plasmid encoding the L genomic segment e.g., pol-I L. In certain embodiments, the plasmid encoding an arenavirus polymerase that direct intracellular synthesis of the viral L and S segments can be incorporated into the transfection mixture. For example, a plasmid encoding the L protein and/or a plasmid encoding NP (pC-L and pC-NP, respectively) can be present. The L protein and NP are the minimal trans-acting factors necessary for viral RNA transcription and replication. Alternatively, intracellular synthesis of viral L and S segments, together with NP and L protein can be performed using an expression cassette with pol-I and pol-II promoters reading from opposite sides into the L and S segment cDNAs of two separate plasmids, respectively.

In certain embodiments, the arenavirus genomic segments are under the control of a promoter. Typically, RNA polymerase I-driven expression cassettes, RNA polymerase II-driven cassettes or T7 bacteriophage RNA polymerase driven cassettes can be used. In certain embodiments, the plasmid(s) encoding the arenavirus genomic segments can be the same, i.e., the genome sequence and transacting factors can be transcribed by a promoter from one plasmid. Specific examples of promoters include an RNA polymerase I promoter, an RNA polymerase II promoter, an RNA polymerase III promoter, a T7 promoter, an SP6 promoter or a T3 promoter.

In addition, the plasmid(s) can feature a mammalian selection marker, e.g., puromycin resistance, under control of an expression cassette suitable for gene expression in mammalian cells, e.g., polymerase II expression cassette as above, or the viral gene transcript(s) are followed by an internal ribosome entry site, such as the one of encephalomyocarditis virus, followed by the mammalian resistance marker. For production in E. coli, the plasmid additionally features a bacterial selection marker, such as an ampicillin resistance cassette.

Transfection of a host cell with a plasmid(s) can be performed using any of the commonly used strategies such as calcium-phosphate, liposome-based protocols or electroporation. A few days later the suitable selection agent, e.g., puromycin, is added in titrated concentrations. Surviving clones are isolated and subcloned following standard procedures, and high-expressing clones are identified using Western blot or flow cytometry procedures with antibodies directed against the viral protein(s) of interest.

For recovering the arenavirus particle described herein, the following procedures are envisaged. First day: cells, typically 80% confluent in M6-well plates, are transfected with a mixture of the plasmids, as described above. For this one can exploit any commonly used strategies such as calcium-phosphate, liposome-based protocols or electroporation.

3-5 days later: The cultured supernatant (arenavirus vector preparation) is harvested, aliquoted and stored at 4° C., −20° C., or −80° C., depending on how long the arenavirus vector should be stored prior use. The arenavirus vector preparation's infectious titer is assessed by an immunofocus assay. Alternatively, the transfected cells and supernatant may be passaged to a larger vessel (e.g., a T75 tissue culture flask) on day 3-5 after transfection, and culture supernatant is harvested up to five days after passage.

The present application furthermore relates to expression of a heterologous ORF, wherein a plasmid encoding the genomic segment is modified to incorporated a heterologous ORF. The heterologous ORF can be incorporated into the plasmid using restriction enzymes.

(ii) Infectious, Replication-Defective Arenavirus Particle

Infectious, replication-defective arenavirus particles can be rescued as described above. However, once generated from cDNA, the infectious, replication-deficient arenaviruses provided herein can be propagated in complementing cells. Complementing cells are cells that provide the functionality that has been eliminated from the replication-deficient arenavirus by modification of its genome (e.g., if the ORF encoding the GP protein is deleted or functionally inactivated, a complementing cell does provide the GP protein).

Owing to the removal or functional inactivation of one or more of the ORFs in arenavirus vectors (here deletion of the glycoprotein, GP, will be taken as an example), arenavirus vectors can be generated and expanded in cells providing in trans the deleted viral gene(s), e.g., the GP in the present example. Such a complementing cell line, henceforth referred to as C-cells, is generated by transfecting a cell line such as BHK-21, HEK 293, VERO or other with one or more plasmid(s) for expression of the viral gene(s) of interest (complementation plasmid, referred to as C-plasmid). The C-plasmid(s) express the viral gene(s) deleted in the arenavirus vector to be generated under control of one or more expression cassettes suitable for expression in mammalian cells, e.g., a mammalian polymerase II promoter such as the EFlalpha promoter with a polyadenylation signal. In addition, the complementation plasmid features a mammalian selection marker, e.g., puromycin resistance, under control of an expression cassette suitable for gene expression in mammalian cells, e.g., polymerase II expression cassette as above, or the viral gene transcript(s) are followed by an internal ribosome entry site, such as the one of encephalomyocarditis virus, followed by the mammalian resistance marker. For production in E. coli, the plasmid additionally features a bacterial selection marker, such as an ampicillin resistance cassette.

Cells that can be used, e.g., BHK-21, HEK 293, MC57G or other, are kept in culture and are transfected with the complementation plasmid(s) using any of the commonly used strategies such as calcium-phosphate, liposome-based protocols or electroporation. A few days later the suitable selection agent, e.g., puromycin, is added in titrated concentrations. Surviving clones are isolated and subcloned following standard procedures, and high-expressing C-cell clones are identified using Western blot or flow cytometry procedures with antibodies directed against the viral protein (s) of interest. As an alternative to the use of stably transfected C-cells transient transfection of normal cells can complement the missing viral gene(s) in each of the steps where C-cells will be used below. In addition, a helper virus can be used to provide the missing functionality in trans.

Plasmids can be of two types: i) two plasmids, referred to as TF-plasmids for expressing intracellularly in C-cells the minimal transacting factors of the arenavirus, is derived from e.g., NP and L proteins of LCMV in the present example; and ii) plasmids, referred to as GS-plasmids, for expressing intracellularly in C-cells the arenavirus vector genome segments, e.g., the segments with designed modifications. TF-plasmids express the NP and L proteins of the respective arenavirus vector under control of an expression cassette suitable for protein expression in mammalian cells, typically e.g., a mammalian polymerase II promoter such as the CMV or EFlalpha promoter, either one of them preferentially in combination with a polyadenylation signal. GS-plasmids express the small (S) and the large (L) genome segments of the vector. Typically, polymerase I-driven expression cassettes or T7 bacteriophage RNA polymerase (T7-) driven expression cassettes can be used, the latter preferentially with a 3'-terminal ribozyme for processing of the primary transcript to yield the correct end. In the case of using a T7-based system, expression of T7 in C-cells must be provided by either including in the recovery process an additional expression plasmid, constructed analogously to TF-plasmids, providing T7, or C-cells are constructed to additionally express T7 in a stable manner. In certain embodiments, TF and GS plasmids can be the same, i.e., the genome sequence and transacting factors can be transcribed by T7, polI and polII promoters from one plasmid.

For recovering of the arenavirus vector, the following procedures can be used. First day: C-cells, typically 80% confluent in M6-well plates, are transfected with a mixture of the two TF-plasmids plus the two GS-plasmids. In certain embodiments, the TF and GS plasmids can be the same, i.e., the genome sequence and transacting factors can be transcribed by T7, polI and polII promoters from one plasmid. For this one can exploit any of the commonly used strategies such as calcium-phosphate, liposome-based protocols or electroporation.

3-5 days later: The culture supernatant (arenavirus vector preparation) is harvested, aliquoted and stored at 4° C., −20° C. or −80° C. depending on how long the arenavirus vector should be stored prior to use. Then the arenavirus vector preparation's infectious titer is assessed by an immunofocus assay on C-cells. Alternatively, the transfected cells and supernatant may be passaged to a larger vessel (e.g., a T75 tissue culture flask) on day 3-5 after transfection, and culture supernatant is harvested up to five days after passage.

The invention furthermore relates to expression of a antigen in a cell culture wherein the cell culture is infected with an infectious, replication-deficient arenavirus expressing a antigen. When used for expression of a antigen in cultured cells, the following two procedures can be used:

i) The cell type of interest is infected with the arenavirus vector preparation described herein at a multiplicity of infection (MOI) of one or more, e.g., two, three or four, resulting in production of the antigen in all cells already shortly after infection.

ii) Alternatively, a lower MOI can be used and individual cell clones can be selected for their level of virally driven antigen expression. Subsequently individual clones can be expanded infinitely owing to the non-cytolytic nature of arenavirus vectors. Irrespective of the approach, the antigen can subsequently be collected (and purified) either from the culture supernatant or from the cells themselves, depending on the properties of the antigen produced. However, the invention is not limited to these two strategies, and other ways of driving expression of antigen using infectious, replication-deficient arenaviruses as vectors may be considered.

4.4.2 Generation of a Tri-Segmented Arenavirus Particle

A tri-segmented arenavirus particle can be recombinantly produced by reverse genetic techniques known in the art, for example as described by Emonet et al., 2008, PNAS, 106 (9):3473-3478; Popkin et al., 2011, J. Virol., 85 (15):7928-7932, which are incorporated by reference herein. The generation of the tri-segmented arenavirus particle provided herein can be modified as described in Section 4.2.

(i) Infectious and Replication Competent Tri-Segmented Arenavirus Particle

In certain embodiments, the method of generating the tri-segmented arenavirus particle comprises (i) transfecting into a host cell the cDNAs of the one L segment and two S segments or two L segments and one S segment; (ii) transfecting into a host cell plasmids expressing the arenavirus' minimal trans-acting factors NP and L; (iii) maintaining the host cell under conditions suitable for virus formation; and (iv) harvesting the arenavirus particle.

Once generated from cDNA, the tri-segmented arenavirus particle (i.e., infectious and replication competent) can be propagated. In certain embodiments tri-segmented arenavirus particle can be propagated in any host cell that allows the virus to grow to titers that permit the uses of the virus as described herein. In one embodiment, the host cell allows the tri-segmented arenavirus particle to grow to titers comparable to those determined for the corresponding wild-type.

In certain embodiments, the tri-segmented arenavirus particle may be propagated in host cells. Specific examples of host cells that can be used include BHK-21, HEK 293, VERO or other. In a specific embodiment, the tri-segmented arenavirus particle may be propagated in a cell line.

In certain embodiments, the host cells are kept in culture and are transfected with one or more plasmid(s). The plasmid(s) express the arenavirus genomic segment(s) to be generated under control of one or more expression cassettes suitable for expression in mammalian cells, e.g., consisting of a polymerase I promoter and terminator.

In specific embodiments, the host cells are kept in culture and are transfected with one or more plasmid(s). The plasmid(s) express the viral gene(s) to be generated under control of one or more expression cassettes suitable for expression in mammalian cells, e.g., consisting of a polymerase I promoter and terminator.

Plasmids that can be used for generating the tri-segmented arenavirus comprising one L segment and two S segments can include: i) two plasmids each encoding the S genome segment e.g., pol-I S, ii) a plasmid encoding the L genome segment e.g., pol-I L. Plasmids needed for the tri-segmented arenavirus comprising two L segments and one S segments are: i) two plasmids each encoding the L genome segment e.g., pol-L, ii) a plasmid encoding the S genome segment e.g., pol-I S.

In certain embodiments, plasmids encoding an arenavirus polymerase that direct intracellular synthesis of the viral L and S segments can be incorporated into the transfection mixture. For example, a plasmid encoding the L protein and a plasmid encoding NP (pC-L and pC-NP, respectively). The L protein and NP are the minimal trans-acting factors necessary for viral RNA transcription and replication. Alternatively, intracellular synthesis of viral L and S segments, together with NP and L protein can be performed using an expression cassette with pol-I and pol-II promoters reading from opposite sides into the L and S segment cDNAs of two separate plasmids, respectively.

In addition, the plasmid(s) features a mammalian selection marker, e.g., puromycin resistance, under control of an expression cassette suitable for gene expression in mammalian cells, e.g., polymerase II expression cassette as above, or the viral gene transcript(s) are followed by an internal ribosome entry site, such as the one of encephalomyocarditis virus, followed by the mammalian resistance marker. For production in *E. coli*, the plasmid additionally features a bacterial selection marker, such as an ampicillin resistance cassette.

Transfection of BHK-21 cells with a plasmid(s) can be performed using any of the commonly used strategies such as calcium-phosphate, liposome-based protocols or electroporation. A few days later the suitable selection agent, e.g., puromycin, is added in titrated concentrations. Surviving clones are isolated and subcloned following standard procedures, and high-expressing clones are identified using Western blot or flow cytometry procedures with antibodies directed against the viral protein(s) of interest.

Typically, RNA polymerase I-driven expression cassettes, RNA polymerase II-driven cassettes or T7 bacteriophage RNA polymerase driven cassettes can be used, the latter preferentially with a 3'-terminal ribozyme for processing of the primary transcript to yield the correct end. In certain embodiments, the plasmids encoding the arenavirus genomic segments can be the same, i.e., the genome sequence and transacting factors can be transcribed by T7, polI and polII promoters from one plasmid.

For recovering the arenavirus the tri-segmented arenavirus vector, the following procedures are envisaged. First day: cells, typically 80% confluent in M6-well plates, are transfected with a mixture of the plasmids, as described above. For this one can exploit any commonly used strategies such as calcium-phosphate, liposome-based protocols or electroporation.

3-5 days later: The cultured supernatant (arenavirus vector preparation) is harvested, aliquoted and stored at 4° C., −20° C., or −80° C., depending on how long the arenavirus vector should be stored prior use. The arenavirus vector preparation's infectious titer is assessed by an immunofocus assay. Alternatively, the transfected cells and supernatant may be passaged to a larger vessel (e.g., a T75 tissue culture flask) on day 3-5 after transfection, and culture supernatant is harvested up to five days after passage.

The present application furthermore relates to expression of a heterologous ORF and/or a gene of interest, wherein a plasmid encoding the genomic segment is modified to incorporated a heterologous ORF and/or a gene of interest. The heterologous ORF and/or gene of interest can be incorporated into the plasmid using restriction enzymes.

(ii) Infectious, Replication-Defective Tri-Segmented Arenavirus Particle

Infectious, replication-defective tri-segmented arenavirus particles can be rescued as described above. However, once generated from cDNA, the infectious, replication-deficient arenaviruses provided herein can be propagated in complementing cells. Complementing cells are cells that provide the functionality that has been eliminated from the replication-deficient arenavirus by modification of its genome (e.g., if the ORF encoding the GP protein is deleted or functionally inactivated, a complementing cell does provide the GP protein).

Owing to the removal or functional inactivation of one or more of the ORFs in arenavirus vectors (here deletion of the glycoprotein, GP, will be taken as an example), arenavirus vectors can be generated and expanded in cells providing in trans the deleted viral gene(s), e.g., the GP in the present example. Such a complementing cell line, henceforth referred to as C-cells, is generated by transfecting a mammalian cell line such as BHK-21, HEK 293, VERO or other (here BHK-21 will be taken as an example) with one or more plasmid(s) for expression of the viral gene(s) of interest (complementation plasmid, referred to as C-plasmid). The C-plasmid(s) express the viral gene(s) deleted in the arenavirus vector to be generated under control of one or more expression cassettes suitable for expression in mammalian cells, e.g., a mammalian polymerase II promoter such as the CMV or EF1alpha promoter with a polyadenylation signal. In addition, the complementation plasmid features a mammalian selection marker, e.g., puromycin resistance, under control of an expression cassette suitable for gene expression in mammalian cells, e.g., polymerase II expression cassette as above, or the viral gene transcript(s) are followed by an internal ribosome entry site, such as the one of encephalomyocarditis virus, followed by the mammalian resistance marker. For production in *E. coli*, the plasmid additionally features a bacterial selection marker, such as an ampicillin resistance cassette.

Cells that can be used, e.g., BHK-21, HEK 293, MC57G or other, are kept in culture and are transfected with the complementation plasmid(s) using any of the commonly used strategies such as calcium-phosphate, liposome-based protocols or electroporation. A few days later the suitable selection agent, e.g., puromycin, is added in titrated concentrations. Surviving clones are isolated and subcloned following standard procedures, and high-expressing C-cell clones are identified using Western blot or flow cytometry procedures with antibodies directed against the viral protein(s) of interest. As an alternative to the use of stably transfected C-cells transient transfection of normal cells can complement the missing viral gene(s) in each of the steps where C-cells will be used below. In addition, a helper virus can be used to provide the missing functionality in trans.

Plasmids of two types can be used: i) two plasmids, referred to as TF-plasmids for expressing intracellularly in C-cells the minimal transacting factors of the arenavirus, is derived from e.g., NP and L proteins of LCMV in the present example; and ii) plasmids, referred to as GS-plasmids, for expressing intracellularly in C-cells the arenavirus vector genome segments, e.g., the segments with designed modifications. TF-plasmids express the NP and L proteins of the respective arenavirus vector under control of an expression cassette suitable for protein expression in mammalian cells, typically e.g., a mammalian polymerase II promoter such as the CMV or EF1 alpha promoter, either one of them preferentially in combination with a polyadenylation signal. GS-plasmids express the small (S) and the large (L) genome segments of the vector. Typically, polymerase I-driven expression cassettes or T7 bacteriophage RNA polymerase (T7-) driven expression cassettes can be used, the latter preferentially with a 3'-terminal ribozyme for processing of the primary transcript to yield the correct end. In the case of using a T7-based system, expression of T7 in C-cells must be provided by either including in the recovery process an additional expression plasmid, constructed analogously to TF-plasmids, providing T7, or C-cells are constructed to additionally express T7 in a stable manner. In certain embodiments, TF and GS plasmids can be the same, i.e., the genome sequence and transacting factors can be transcribed by T7, polI and polII promoters from one plasmid.

For recovering of the arenavirus vector, the following procedures can be used. First day: C-cells, typically 80% confluent in M6-well plates, are transfected with a mixture of the two TF-plasmids plus the two GS-plasmids. In certain embodiments, the TF and GS plasmids can be the same, i.e., the genome sequence and transacting factors can be transcribed by T7, polI and polII promoters from one plasmid. For this one can exploit any of the commonly used strategies such as calcium-phosphate, liposome-based protocols or electroporation.

3-5 days later: The culture supernatant (arenavirus vector preparation) is harvested, aliquoted and stored at 4° C., −20° C. or −80° C. depending on how long the arenavirus vector should be stored prior to use. Then the arenavirus vector preparation's infectious titer is assessed by an immunofocus assay on C-cells. Alternatively, the transfected cells and supernatant may be passaged to a larger vessel (e.g., a T75 tissue culture flask) on day 3-5 after transfection, and culture supernatant is harvested up to five days after passage.

The invention furthermore relates to expression of an antigen in a cell culture wherein the cell culture is infected with an infectious, replication-deficient tri-segmented arenavirus expressing a antigen. When used for expression of a CMV antigen in cultured cells, the following two procedures can be used:

i) The cell type of interest is infected with the arenavirus vector preparation described herein at a multiplicity of infection (MOI) of one or more, e.g., two, three or four, resulting in production of the antigen in all cells already shortly after infection.

ii) Alternatively, a lower MOI can be used and individual cell clones can be selected for their level of virally driven antigen expression. Subsequently individual clones can be expanded infinitely owing to the non-cytolytic nature of arenavirus vectors. Irrespective of the approach, the antigen can subsequently be collected (and purified) either from the culture supernatant or from the cells themselves, depending on the properties of the antigen produced. However, the invention is not limited to these two strategies, and other ways of driving expression of CMV antigen using infectious, replication-deficient arenaviruses as vectors may be considered.

4.5 Nucleic Acids, Vector Systems and Cell Lines

In certain embodiments, provided herein are cDNAs comprising or consisting of the arenavirus genomic segment or the tri-segmented arenavirus particle as described in Section 4.1 and Section 4.2, respectively.

4.5.1 Non-Natural Position Open Reading Frame

In one embodiment, provided herein are nucleic acids that encode an arenavirus genomic segment as described in Section 4.1. In more specific embodiments, provided herein is a DNA nucleotide sequence or a set of DNA nucleotide sequences as set forth in Table 1. Host cells that comprise such nucleic acids are also provided Section 4.1.

In specific embodiments, provided herein is a cDNA of the arenavirus genomic segment engineered to carry an ORF in a position other than the wild-type position of the ORF, wherein the arenavirus genomic segment encodes a heterologous ORF as described in Section 4.1.

In one embodiment, provided herein is a DNA expression vector system that encodes the arenavirus genomic segment engineered to carry an ORF in a position other than the wild-type position of the ORF. Specifically, provided herein is a DNA expression vector system wherein one or more vectors encodes two arenavirus genomic segments, namely, an L segment and an S segment, of an arenavirus particle described herein. Such a vector system can encode (one or more separate DNA molecules).

In another embodiment, provided herein is a cDNA of the arenavirus S segment that has been engineered to carry an ORF in a position other than the wild-type position is part of or incorporated into a DNA expression system. In other embodiments, a cDNA of the arenavirus L segment that has been engineered to carry an ORF in a position other than the wild-type position is part of or incorporated into a DNA expression system. In certain embodiments, is a cDNA of the arenavirus genomic segment that has been engineered to carry (i) an ORF in a position other than the wild-type position of the ORF; and (ii) and ORF encoding GP, NP, Z protein, or L protein has been removed and replaced with a heterologous ORF from an organism other than an arenavirus.

In certain embodiments, the cDNA provided herein can be derived from a particular strain of LCMV. Strains of LCMV include Clone 13, MP strain, Arm CA 1371, Arm E-250, WE, UBC, Traub, Pasteur, 810885, CH-5692, Marseille #12, HP65-2009, 200501927, 810362, 811316, 810316, 810366, 20112714, Douglas, GR01, SN05, CABN and their derivatives. In specific embodiments, the cDNA is derived from LCMV Clone 13. In other specific embodiments, the cDNA is derived from LCMV MP strain.

In certain embodiments, the vector generated to encode an arenavirus particle or a tri-segmented arenavirus particle as described herein may be based on a specific strain of LCMV. Strains of LCMV include Clone 13, MP strain, Arm CA 1371, Arm E-250, WE, UBC, Traub, Pasteur, 810885, CH-5692, Marseille #12, HP65-2009, 200501927, 810362, 811316, 810316, 810366, 20112714, Douglas, GR01, SN05, CABN and their derivatives. In certain embodiments, an arenavirus particle or a tri-segmented arenavirus particle as described herein may be based on LCMV Clone 13. In other embodiments, the vector generated to encode an arenavirus particle or a tri-segmented arenavirus particle as described herein LCMV MP strain. The sequence of the S segment of LCMV Clone 13 is listed as SEQ ID NO: 2. In certain embodiments, the sequence of the S segment of LCMV Clone 13 is the sequence set forth in SEQ ID NO: 1. The sequence of the L segment of LCMV Clone 13 is listed as SEQ ID NO: 5. The sequence of the S segment of LCMV strain MP is listed as SEQ ID NO: 53. The sequence of the L segment of LCMV strain MP is listed as SEQ ID NO: 4.

In another embodiment, provided herein is a cell, wherein the cell comprises a cDNA or a vector system described above in this section. Cell lines derived from such cells, cultures comprising such cells, methods of culturing such cells infected are also provided herein. In certain embodiments, provided herein is a cell, wherein the cell comprises a cDNA of the arenavirus genomic segment that has been engineered to carry an ORF in a position other than the wild-type position of the ORF. In some embodiments, the cell comprises the S segment and/or the L segment.

4.5.2 Tri-Segmented Arenavirus Particle

In one embodiment, provided herein are nucleic acids that encode a tri-segmented arenavirus particle as described in Section 4.2. In more specific embodiments, provided herein is a DNA nucleotide sequence or a set of DNA nucleotide sequences, for example, as set forth in Table 2 or Table 3. Host cells that comprise such nucleic acids are also provided Section 4.2.

In specific embodiments, provided herein is a cDNA consisting of a cDNA of the tri-segmented arenavirus particle that has been engineered to carry an ORF in a position other than the wild-type position of the ORF. In other embodiments, is a cDNA of the tri-segmented arenavirus particle that has been engineered to (i) carry an arenavirus ORF in a position other than the wild-type position of the ORF; and (ii) wherein the tri-segmented arenavirus particle encodes a heterologous ORF as described in Section 4.2.

In one embodiment, provided herein is a DNA expression vector system that together encode the tri-segmented arenavirus particle as described herein. Specifically, provided herein is a DNA expression vector system wherein one or more vectors encode three arenavirus genomic segments, namely, one L segment and two S segments or two L segments and one S segment of a tri-segmented arenavirus particle described herein. Such a vector system can encode (one or more separate DNA molecules).

In another embodiment, provided herein is a cDNA of the arenavirus S segment(s) that has been engineered to carry an ORF in a position other than the wild-type position, and is part of or incorporated into a DNA expression system. In other embodiments, a cDNA of the arenavirus L segment(s) that has been engineered to carry an ORF in a position other than the wild-type position is part of or incorporated into a DNA expression system. In certain embodiments, is a cDNA of the tri-segmented arenavirus particle that has been engineered to carry (i) an ORF in a position other than the wild-type position of the ORF; and (ii) an ORF encoding GP, NP, Z protein, or L protein has been removed and replaced with a heterologous ORF from an organism other than an arenavirus.

In certain embodiments, the cDNA provided herein can be derived from a particular strain of LCMV. Strains of LCMV include Clone 13, MP strain, Arm CA 1371, Arm E-250, WE, UBC, Traub, Pasteur, 810885, CH-5692, Marseille #12, HP65-2009, 200501927, 810362, 811316, 810316, 810366, 20112714, Douglas, GR01, SN05, CABN and their derivatives. In specific embodiments, the cDNA is derived from LCMV Clone 13. In other specific embodiments, the cDNA is derived from LCMV MP strain.

In certain embodiments, the vector generated to encode an arenavirus particle or a tri-segmented arenavirus particle as described herein may be based on a specific strain of LCMV. Strains of LCMV include Clone 13, MP strain, Arm CA 1371, Arm E-250, WE, UBC, Traub, Pasteur, 810885, CH-5692, Marseille #12, HP65-2009, 200501927, 810362, 811316, 810316, 810366, 20112714, Douglas, GR01, SN05, CABN and their derivatives. In certain embodiments, an arenavirus particle or a tri-segmented arenavirus particle as described herein may be based on LCMV Clone 13. In other embodiments, the vector generated to encode an arenavirus particle or a tri-segmented arenavirus particle as described herein LCMV MP strain. The sequence of the S segment of LCMV Clone 13 is listed as SEQ ID NO: 2. In certain embodiments, the sequence of the S segment of LCMV Clone 13 is the sequence set forth in SEQ ID NO: 1. The sequence of the L segment of LCMV Clone 13 is listed as SEQ ID NO: 5. The sequence of the S segment of LCMV strain MP is listed as SEQ ID NO: 53. The sequence of the L segment of LCMV strain MP is listed as SEQ ID NO: 4.

In another embodiment, provided herein is a cell, wherein the cell comprises a cDNA or a vector system described above in this section. Cell lines derived from such cells, cultures comprising such cells, methods of culturing such cells infected are also provided herein. In certain embodiments, provided herein is a cell, wherein the cell comprises a cDNA of the tri-segmented arenavirus particle. In some embodiments, the cell comprises the S segment and/or the L segment.

4.6 Methods of Use

Vaccines have been successful for preventing and/or treating infectious diseases, such as those for polio virus and measles. However, therapeutic immunization in the setting of established, chronic disease, including both chronic infections and cancer has been less successful. The ability to generate an arenavirus particle and/or a tri-segmented arenavirus particle represents a new novel vaccine strategy.

In one embodiment, provided herein are methods of treating an infection and/or cancer in a subject comprising administering to the subject one or more types of arenavirus particles or tri-segmented arenavirus particles, as described herein or a composition thereof. In a specific embodiment, a method for treating an infection and/or cancer described herein comprises administering to a subject in need thereof an effective amount of one or more arenavirus particles or tri-segmented arenavirus particles, described herein or a composition thereof. The subject can be a mammal, such as but not limited to a human being, a mouse, a rat, a guinea pig, a domesticated animal, such as, but not limited to, a cow, a horse, a sheep, a pig, a goat, a cat, a dog, a hamster, a donkey. In a specific embodiment, the subject is a human. The human subject might be male, female, adults, children, seniors (65 and older), and those with multiple diseases (i.e., a polymorbid subject). In certain embodiments, subjects are those whose disease has progressed after treatment with chemotherapy, radiotherapy, surgery, and/or biologic agents.

In another embodiment, provided herein are methods for inducing an immune response against an antigen derived from an infectious organism, tumor, or allergen in a subject comprising administering to the subject an arenavirus particle or a tri-segmented arenavirus particle expressing an antigen derived from an infectious organism, tumor, or allergen or a composition thereof In another embodiment, the subjects to whom an arenavirus particle or tri-segmented arenavirus particle expressing an antigen derived from an infectious organism, tumor, or allergen described herein or a composition thereof is administered have, are susceptible to, or are at risk for a infection, development of cancer or a allergy, or exhibit a pre-cancerous tissue lesion. In another specific embodiment, the subjects to whom a arenavirus particle or tri-segmented arenavirus particle expressing an antigen derived from an infectious organism, tumor, or allergen described herein or a composition thereof is administered are infected with, are susceptible to, are at risk for, or diagnosed with an infection, cancer, pre-cancerous tissue lesion, or allergy.

In another embodiment, the subjects to whom an arenavirus particle or tri-segmented arenavirus particle expressing an antigen derived from an infectious organism, tumor, or allergen described herein or a composition thereof is administered are suffering from, are susceptible to, or are at risk for, an infection, a cancer, a pre-cancerous lesion, or an allergy in the pulmonary system, central nervous system, lymphatic system, gastrointestinal system, or circulatory system among others. In a specific embodiment, the subjects to whom an arenavirus particle or tri-segmented arenavirus particle expressing an antigen derive from an infectious organism, tumor, or allergen described herein or a composition thereof is administered are suffering from, are susceptible to, or are at risk for, an infection, a cancer, or an allergy in one or more organs of the body, including but not limited to the brain, liver, lungs, eyes, ears, intestines, esophagus, uterus, nasopharynx or salivary glands.

In another embodiment, the subjects to whom an arenavirus particle or tri-segmented arenavirus particle expressing an antigen derived from an infectious organism, a cancer, or an allergen described herein or a composition thereof is administered to a subject suffering from symptoms including but not limited to fever, night sweats, tiredness, malaise, uneasiness, sore throat, swollen glands, joint pain, muscle pain, loss of appetite, weight loss, diarrhea, gastrointestinal ulcerations, gastrointestinal bleeding, shortness of breath, pneumonia, mouth ulcers, vision problems, hepatitis, jaundice, encephalitis, seizures, coma, pruritis, erythema, hyperpigmentation, changes in lymph node, or hearing loss.

In another embodiment, an arenavirus or tri-segmented arenavirus particle expressing an antigen derived from an infectious organism, a cancer, or an allergen as described herein or a composition thereof is administered to a subject of any age group suffering from, are susceptible to, or are at risk for, an infection, a cancer, or an allergy. In a specific embodiment, an arenavirus particle or a tri-segmented arenavirus particle expressing an antigen derived from an infectious organism, a cancer, or an allergen as described herein or a composition thereof is administered to a subject with a compromised immune system, a pregnant subject, a subject undergoing an organ or bone marrow transplant, a subject taking immunosuppressive drugs, a subject undergoing hemodialysis, a subject who has cancer, or a subject who is suffering from, are susceptible to, or are at risk for, an infection, a cancer, or an allergy. In a more specific embodiment, an arenavirus particle or a tri-segmented arenavirus particle expressing an antigen derived from an infectious organism, a cancer, or an allergen as described herein or a composition thereof is administered to a subject who is a child of 0, 1, 2, 3, 4, 5, 6, 7, 8, 9, 10, 11, 12, 13, 14, 15, 16, or 17 years of age suffering from, are susceptible to, or are at risk for, an infection, a cancer, or an allergy. In yet another specific embodiment, an arenavirus particle or a tri-segmented arenavirus particle expressing an antigen derived from an infectious organism, a cancer, or an allergen described herein or a composition thereof is administered to a subject who is an infant suffering from, is susceptible to, or is at risk for, an infection, cancer or an allergy. In yet another specific embodiment, an arenavirus particle or tri-segmented arenavirus particle expressing an antigen derived from an infectious organism, a cancer, or an allergen described herein or a composition thereof is administered to a subject who is an infant of 0, 1, 2, 3, 4, 5, 6, 7, 8, 9, 10, 11, or 12 months of age suffering from, is susceptible to, or is at risk for, an infection, cancer, or an allergy. In yet another specific embodiment, an arenavirus particle or tri-segmented arenavirus particle expressing an antigen derived from an infectious organism, a cancer, or an allergen described herein or a composition thereof is administered to an elderly subject who is suffering from, is susceptible to, or is at risk for, an infection, cancer, or an allergy. In a more specific embodiment, an arenavirus particle or a tri-segmented arenavirus particle expressing an antigen derived from an infectious organism, a cancer, or an allergen described herein or a composition thereof is administered to a subject who is a senior subject of 65, 66, 67, 68, 69, 70, 71, 72, 73, 74, 75, 76, 77, 78, 79, 80, 81, 82, 83, 84, 85, 86, 87, 88, 89, or 90 years of age.

In another embodiment, an arenavirus particle or tri-segmented arenavirus particle expressing an antigen derived from an infectious organism, a cancer, or an allergen described herein or a composition thereof is administered to subjects with a heightened risk of disseminated infection, a cancer, or an allergy. In a specific embodiment, arenavirus particle or a tri-segmented arenavirus particle expressing an antigen derived from an infectious organism, a cancer, or an allergen described herein or a composition thereof is administered to subjects in the neonatal period with a neonatal and therefore immature immune system.

In another embodiment, an arenavirus particle or tri-segmented arenavirus particle expressing an antigen derived from an infectious organism, a cancer, or an allergen as described herein or a composition thereof is administered to a subject having a dormant infection, cancer, or allergy. In a specific embodiment, an arenavirus particle or a tri-segmented arenavirus expressing an antigen derived from an infectious organism, a cancer, or an allergen described herein or a composition thereof is administered to a subject having a dormant infection, a dormant cancer, or a dormant allergy which can reactivate upon immune system compromise. Thus, provided herein is a method for preventing reactivation of an infection, a cancer, or an allergy.

In another embodiment, an arenavirus particle or tri-segmented arenavirus particle expressing an antigen derived from an infectious organism, a cancer, or an allergen as described herein or a composition thereof is administered to a subject having a recurrent infection, a cancer, or an allergy.

In another embodiment, an arenavirus particle or a tri-segmented arenavirus particle expressing an antigen derived from an infectious organism, a cancer, or an allergen as described herein or a composition thereof is administered to a subject with a genetic predisposition for an infection, a cancer, or an allergy. In another embodiment, an arenavirus particle or tri-segmented arenavirus particle expressing an antigen derived from an infectious organism, a cancer, or an allergen as described herein or a composition thereof is administered to a subject. In another embodiment, an arenavirus particle or a tri-segmented arenavirus particle expressing an antigen derived from an infectious organism, a cancer, or an allergen is administered to a subject with risk factors. Exemplary risk factors include, aging, tobacco, sun exposure, radiation exposure, chemical exposure, family history, alcohol, poor diet, lack of physical activity, or being overweight.

In another embodiment, administering an arenavirus particle or a tri-segmented arenavirus particle expressing an antigen derived from an infectious organism, a cancer, or an allergen reduces a symptomatic infection, cancer, or allergy. In another embodiment, administering an arenavirus particle or tri-segmented arenavirus particle expressing an antigen derived from an infectious organism, a cancer, or an allergen reduces an asymptomatic infection, cancer, or allergy.

In another embodiment, an arenavirus particle or a tri-segmented arenavirus particle expressing an antigen derived from an infectious organism described herein or a composition thereof is administered to subjects or animals infected with one or more strains of influenza virus, infectious bursal disease virus, rotavirus, infectious bronchitis virus, infectious laryngotracheitis virus, chicken anemia virus, Marek's disease virus, avian leukosis virus, avian adenovirus, or avian pneumovirus, SARS-causing virus, human respiratory syncytial virus, human immunodeficiency virus, hepatitis A virus, hepatitis B virus, hepatitis C virus, poliovirus, rabies virus, Hendra virus, Nipah virus, human parainfluenza 3 virus, measles virus, mumps virus, Ebola virus, Marburg virus, West Nile disease virus, Japanese encephalitis virus, Dengue virus, Hantavirus, Rift Valley fever virus, Lassa fever virus, herpes simplex virus and yellow fever virus.

In another embodiment, an arenavirus particle or a tri-segmented arenavirus particle expressing an antigen derived from a cancer described herein or a composition thereof is administered to subjects who suffer from one or more types of cancers. In other embodiments, any type of a cancer susceptible to treatment with the vaccines described herein might be targeted. In a more specific embodiment, an arenavirus particle or a tri-segmented arenavirus particle expressing an antigen derived from a cancer described herein or a composition thereof is administered to subjects suffering from, for example, melanoma, prostate carcinoma, breast carcinoma, lung carcinoma, neuroblastoma, hepatocellular carcinoma, cervical carcinoma, and stomach carcinoma, burkitt lymphoma; non-Hodgkin lymphoma; Hodgkin lymphoma; nasopharyngeal carcinoma (cancer of the upper part of the throat behind the nose), leukemia, mucosa-associated lymphoid tissue lymphoma.

In another embodiment, an arenavirus particle or a tri-segmented arenavirus particle expressing an antigen derived from an allergen described herein or a composition thereof is administered to subjects who suffer from one or more allergies. In a more specific embodiment, an arenavirus particle or a tri-segmented arenavirus particle expressing an antigen derived from an allergen described herein or a composition thereof is administered to subjects suffering from, for example, a seasonal allergy, a perennial allergy, rhinoconjunctivitis, asthma, eczema, a food allergy.

In another embodiment, administering an arenavirus particle or a tri-segmented arenavirus particle expressing an antigen derived from an infectious organism, a cancer, or an allergen as described herein or a composition thereof to subjects confer cell-mediated immunity (CMI) against an infection, a cancer, or an allergen. Without being bound by theory, in another embodiment, an arenavirus particle or a tri-segmented arenavirus particle expressing an antigen derived from an infectious organism, a cancer, an allergen as described herein or a composition thereof infects and expresses antigens of interest in antigen presenting cells (APC) of the host (e.g., macrophages, dendritic cells, or B cells) for direct presentation of antigens on Major Histocompatibility Complex (MHC) class I and II. In another embodiment, administering an arenavirus particle or a tri-segmented arenavirus particle expressing an antigen derived from an infectious organism, a cancer, an allergen as described herein or a composition thereof to subjects induces plurifunctional cytolytic as well as IFN-γ and TNF-α co-producing CMV-specific CD4+ and CD8+ T cell responses of high magnitude to treat or prevent an infection, a cancer, or an allergy.

In another embodiment, administering an arenavirus particle or a tri-segmented arenavirus particle expressing an antigen derived from an infectious organism, a cancer, or an allergen or a composition thereof reduces the risk that an individual will develop an infection, a cancer, an allergy by at least about 10%, at least about 20%, at least about 25%, at least about 30%, at least about 35%, at least about 40%, at least about 50%, at least about 60%, at least about 70%, at least about 80%, at least about 90%, or more, compared to the risk of developing an infection, a cancer, or an allergy in the absence of such treatment.

In another embodiment, administering an arenavirus particle or a tri-segmented arenavirus particle expressing an antigen derived from an infectious organism, a cancer, or an allergen or a composition thereof reduces the symptoms of an infection, a cancer, or an allergy by at least about 10%, at least about 20%, at least about 25%, at least about 30%, at least about 35%, at least about 40%, at least about 50%, at least about 60%, at least about 70%, at least about 80%, at least about 90%, or more, compared to the manifestation of the symptoms of an infection, a cancer, an allergy in the absence of such treatment.

In certain embodiments, the arenavirus particle or tri-segmented arenavirus particle expressing an antigen derived from an infectious organism, a cancer, or an allergen is preferably administered in multiple injections (e.g., at least 2, 3, 4, 5, 6, 7, 8, 9, 10, 12, 14, 16, 18, 20, 25, 30, 40, 45, or 50 injections) or by continuous infusion (e.g., using a pump) at multiple sites (e.g., at least 2, 3, 4, 5, 6, 7, 8, 9, 10, 12, or 14 sites). In certain embodiments, the arenavirus particle or tri-segmented arenavirus particle expressing an antigen derived from an infectious organism, a cancer, or an allergen is administered in two or more separate injections over a 6-month period, a 12-month period, a 24-month period, or a 48-month period. In certain embodiments, the arenavirus particle or tri-segmented arenavirus particle expressing an antigen derived from a infectious organism, a cancer, or an allergen is administered with a first dose at an elected date, a second dose at least 2 months after the first dose, and a third does 6 months after the first dose.

In one example, cutaneous injections are performed at multiple body sites to reduce extent of local skin reactions. On a given vaccination day, the patient receives the assigned total dose of cells administered from one syringe in 3 to 5 separate intradermal injections of the dose (e.g., at least 0.4 ml, 0.2 ml, or 0.1 ml) each in an extremity spaced at least about 5 cm (e.g., at least 4.5, 5, 6, 7, 8, 9, or cm) at needle entry from the nearest neighboring injection. On subsequent vaccination days, the injection sites are rotated to different limbs in a clockwise or counter-clockwise manner.

In another embodiment, administering an infectious, replication-deficient arenavirus expressing a CMV antigen or a composition thereof in subjects with a neonatal and therefore immune system induces a cell-mediated immune (CMI) response against an infection, a cancer, or an allergy, exceeding by at least about 10%, at least about 20%, at least about 25%, at least about 30%, at least about 35%, at least about 40%, at least about 50%, at least about 60%, at least about 70%, at least about 80%, at least about 90%, or more, the CMI response against an infection, a cancer, or a allergy in the absence of such a treatment.

In certain embodiments, administrating to a subject an arenavirus particle or a tri-segmented arenavirus particle expressing an antigen derived from an infectious organism, a cancer, or an allergen, as described herein induces a detectable antibody titer for a minimum of at least four weeks. In another embodiment, administering to a subject an arenavirus particle or a tri-segmented arenavirus particle expressing an antigen derived from an infectious organism, a cancer, or an allergen, as describe herein increases the antibody titer by at least 100%, at least 200%, at least 300%, at least 400%, at least 500%, or at least 1000%.

In certain embodiments, primary antigen exposure elicits a functional, (neutralizing) and minimum antibody titer of at least 50%, at least 100%, at least 200%, at least 300%, at least 400%, at least 500%, or at least 1000% of mean control sera from infection-immune human subjects. In more specific embodiments, the primary neutralizing geometric mean antibody titer increases up to a peak value of at least 1:50, at least 1:100, at least 1:200, or at least 1:1000 within at least 4 weeks post-immunization. In another embodiment, immunization with an arenavirus particle or a tri-segmented arenavirus particle expressing an antigen derived from an infectious organism, a cancer, or an allergy, as described herein produces high titers of antibodies that last for at least 4 weeks, at least 8 weeks, at least 12 weeks, at least 6 months, at least 12 months, at least 2 years, at least 3 years, at least 4 years, or at least 5 years post-immunization following a single administration of the vaccine, or following two or more sequential immunizations.

In yet another embodiment, secondary antigen exposure increases the antibody titer by at least 100%, at least 200%, at least 300%, at least 400%, at least 500%, or at least 1000%. In another embodiment, secondary antigen exposure elicits a functional, (neutralizing) and minimum antibody titer of at least 50%, at least 100%, at least 200%, at least 300%, at least 400%, at least 500%, or at least 1000% of mean control sera from infection-immune human subjects. In more specific embodiments, the secondary neutralizing geometric mean antibody titer increases up to a peak value of at least 1:50, at least 1:100, at least 1:200, or at least 1:1000 within at least 4 weeks post-immunization. In another embodiment, a second immunization with an arenavirus particle or a tri-segmented arenavirus particle expressing an antigen derived from an infectious organism, a cancer, or an allergy, as described herein produces high titers of antibodies that last for at least 4 weeks, at least 8 weeks, at least 12 weeks, at least 6 months, at least 12 months, at least 2 years, at least 3 years, at least 4 years, or at least 5 years post-immunization.

In yet another embodiment, a third boosting immunization increases the antibody titer by at least 100%, at least 200%, at least 300%, at least 400%, at least 500%, or at least 1000%. In another embodiment, the boosting immunization elicits a functional, (neutralizing) and minimum antibody titer of at least 50%, at least 100%, at least 200%, at least 300%, at least 400%, at least 500%, or at least 1000% of mean control sera from infection-immune human subjects. In more specific embodiments, the third boosting immunization elicits a functional, (neutralizing), and minimum antibody titer of at least 50%, at least 100%, at least 200%, at least 300%, at least 400%, at least 500%, or at least 1000% of mean control sera from infection-immune human subjects. In another embodiment, a third boosting immunization prolongs the antibody titer by at least 4 weeks, at least 8 weeks, at least 12 weeks, at least 6 months, at least 12 months, at least 2 years, at least 3 years, at least 4 years, or at least 5 years post-immunization In certain embodiments, the arenavirus particle or a tri-segmented arenavirus particle expressing an antigen derived from an infectious organism, a cancer, or an allergy, elicits a T cell independent or T cell dependent response. In other embodiments, arenavirus particle or a tri-segmented arenavirus particle expressing an antigen derived from an infectious organism, a cancer, or an allergy, elicits a T cell response. In other embodiments, an arenavirus particle or a tri-segmented arenavirus particle expressing an antigen derived from an infectious organism, a cancer, or an allergy, as described herein elicits a T helper response. In another embodiment, arenavirus particle or a tri-segmented arenavirus particle expressing an antigen derived from an infectious organism, a cancer, or an allergy, as described herein elicits a Th1-orientated response or a Th2-orientated response.

In more specific embodiments, the Th1-orientated response is indicated by a predominance of IgG1 antibodies versus IgG2. In other embodiments the ratio of IgG1:IgG2 is greater than 1:1, greater than 2:1, greater than 3:1, or greater than 4:1. In another embodiment the infectious, arenavirus particle or a tri-segmented arenavirus particle expressing an antigen derived from an infectious organism, a cancer, or an allergy, as described herein is indicated by a predominance of IgG1, IgG2, IgG3, IgG4, IgM, IgA, IgD or IgE antibodies.

In some embodiments, the infectious, replication-deficient arenavirus expressing a CMV antigen or a fragment thereof elicits a CD8+ T cell response. In another embodiment, the arenavirus particle or a tri-segmented arenavirus particle expressing an antigen derived from an infectious organism, a cancer, or an allergy elicits both CD4+ and CD8+ T cell responses, in combination with antibodies or not.

In certain embodiments, the arenavirus particle or a tri-segmented arenavirus particle expressing an antigen derived from an infectious organism, a cancer, or an allergy, as described herein elicits high titers of neutralizing antibodies. In another embodiment, the arenavirus particle or a tri-segmented arenavirus particle expressing an antigen derived from an infectious organism, a cancer, or an allergy, as described herein elicits higher titers of neutralizing antibodies than expression of the protein complex components individually.

In another embodiment, the arenavirus particle or a tri-segmented arenavirus particle expressing one, two, three, four, five, or more antigen derived from an infectious organism, a cancer, or an allergy elicits higher titers of neutralizing antibodies than an arenavirus particle or a tri-segmented arenavirus particle expressing one expressing one antigen derived from an infectious organism, a cancer, or an allergen.

In certain embodiments, the methods further comprise co-administration of the arenavirus particle or tri-segmented arenavirus particle and at least one additional therapy. In certain embodiments, the co-administration is simultaneous. In another embodiment, the arenavirus particle or tri-segmented arenavirus particle is administered prior to administration of the additional therapy. In other embodiments, the arenavirus particle or tri-segmented arenavirus particle is administered after administration of the additional therapy. In certain embodiments, the administration of the arenavirus particle or tri-segmented arenavirus particle and the additional therapy is about 1 hour, about 2 hours, about 3 hours, about 4 hours, about 5 hours, about 6 hours, about 7 hours, about 8 hours, about 9 hours, about 10 hours, about 11 hours, or about 12 hours. In certain embodiments, the interval between administration of the arenavirus particle or tri-segmented arenavirus particle and said additional therapy is about 1 day, 1 week, about 2 weeks, about 3 weeks, about 4 weeks, about 5 weeks, about 6 weeks, about 7 weeks, about 8 weeks, about 9 weeks, about 10 weeks, about 11 weeks, about 12 weeks. In certain embodiments, the interval between administration of the arenavirus particle or tri-segmented arenavirus particle and the additional therapy is about 1 month, about 2 months, about 3 months, about 4 months, about 5 months, or about 6 months.

In certain embodiments, administering an arenavirus particle expressing an antigen derived from an infectious organism, a cancer, or an allergen or a composition thereof reduces the number of antibodies detected in a patient blood sample, or serum sample. In certain embodiments, administering an arenavirus particle expressing an antigen derived from an infectious organism, a cancer, or an allergen composition thereof reduces the amount of the infectious organism, cancer, or allergy detected in urine, saliva, blood, tears, semen, exfoliated cell sample, or breast milk.

In another embodiment, the arenavirus particle or the tri-segmented arenavirus particle expressing an antigen derived from an infection organism, a cancer, or an allergen as described herein or a composition may further comprise a reporter protein. In a more specific embodiment, the arenavirus particle or a tri-segmented arenavirus particle expressing an antigen derived from an infection organism, a cancer, or an allergen and reporter protein as described herein or a composition is administered to subjects for treating and/or preventing an infection, a cancer, or an allergy. In yet another specific embodiment, the reporter protein can be used for monitoring gene expression, protein localization, and vaccine delivery, in vivo, in situ and in real time.

In another embodiment, the arenavirus particle or a tri-segmented arenavirus particle expressing an antigen derived from an infection organism, a cancer, or an allergen as described herein or a composition may further comprise a fluorescent protein. In a more specific embodiment, the arenavirus particle or a tri-segmented arenavirus particle expressing an antigen derived from an infection organism, a cancer, or an allergen and reporter protein as described herein or a composition is administered to subjects for treating and/or preventing an infection, a cancer, or an allergy. In yet another specific embodiment, the fluorescent protein can be the reporter protein can be used for monitoring gene expression, protein localization, and vaccine delivery, in vivo, in situ and in real time.

Changes in the CMI response function against an infection, a cancer, or an allergy induced by administering an arenavirus particle or a tri-segmented arenavirus particle expressing an antigen derived from an infectious organism, a cancer, an allergen or a composition thereof in subjects can be measured by any assay known to the skilled artisan including, but not limited to flow cytometry (see, e.g., Perfetto S. P. et al., 2004, Nat Rev Immun., 4(8):648-55), lymphocyte proliferation assays (see, e.g., Bonilla F. A. et al., 2008, Ann Allergy Asthma Immunol, 101:101-4; and Hicks M. J. et al., 1983, Am J Clin Pathol., 80:159-63), assays to measure lymphocyte activation including determining changes in surface marker expression following activation of measurement of cytokines of T lymphocytes (see, e.g., Caruso A. et al., Cytometry. 1997; 27:71-6), ELISPOT assays (see, e.g., Czerkinsky C. C. et al., 1983, J Immunol Methods, 65:109-121; and Hutchings P. R. et al., 1989, J Immunol Methods, 120:1-8), or Natural killer cell cytotoxicity assays (see, e.g., Bonilla F. A. et al., 2006, Ann Allergy Asthma Immunol., 94(5 Suppl 1):S1-63).

Successful treatment of a cancer patient can be assessed as prolongation of expected survival, induction of an anti-tumor immune response, or improvement of a particular characteristic of a cancer. Examples of characteristics of a cancer that might be improved include tumor size (e.g., T0, T is, or T1-4), state of metastasis (e.g., M0, M1), number of observable tumors, node involvement (e.g., N0, N1-4, Nx), grade (i.e., grades 1, 2, 3, or 4), stage (e.g., 0, I, II, III, or IV), presence or concentration of certain markers on the cells or in bodily fluids (e.g., AFP, B2M, beta-HCG, BTA, CA 15-3, CA 27.29, CA 125, CA 72.4, CA 19-9, calcitonin, CEA, chromgrainin A, EGFR, hormone receptors, HER2, HCG, immunoglobulins, NSE, NMP22, PSA, PAP, PSMA, S-100, TA-90, and thyroglobulin), and/or associated pathologies (e.g., ascites or edema) or symptoms (e.g., cachexia, fever, anorexia, or pain). The improvement, if measureable by percent, can be at least 5, 10, 15, 20, 25, 30, 40, 50, 60, 70, 80, or 90% (e.g., survival, or volume or linear dimensions of a tumor).

In another embodiment, described herein, is a method of use with an arenavirus particle (e.g., LCMV) expressing an antigen derived from an infectious organism, a cancer, or an allergen as described herein in which the at least one of the ORF encoding the GP, NP, Z protein, and L protein is substituted with a nucleotide sequence encoding an infectious a nucleotide sequence encoding an antigen derived from an infectious organism, a cancer, an allergen, or an antigenic fragment thereof.

4.7 Compositions, Administration, and Dosage

The present application furthermore relates to vaccines, immunogenic compositions (e.g., vaccine formulations), and pharmaceutical compositions comprising an arenavirus particle or a tri-segmented arenavirus particle as described herein. Such vaccines, immunogenic compositions and pharmaceutical compositions can be formulated according to standard procedures in the art.

It will be readily apparent to one of ordinary skill in the relevant arts that suitable modifications and adaptations to the methods and applications described herein can be obvious and can be made without departing from the scope of the scope or any embodiment thereof In another embodiment, provided herein are compositions comprising an arenavirus particle or a tri-segmented arenavirus particle described herein. Such compositions can be used in methods of treatment and prevention of disease. In a specific embodiment, the compositions described herein are used in the treatment of subjects infected with, or susceptible to, an infection. In other embodiments, the compositions described herein are used in the treatment of subjects susceptible to or exhibiting symptoms characteristic of cancer or tumorigenesis or are diagnosed with cancer. In another specific embodiment, the immunogenic compositions provided herein can be used to induce an immune response in a host to whom the composition is administered. The immunogenic compositions described herein can be used as vaccines and can accordingly be formulated as pharmaceutical compositions. In a specific embodiment, the immunogenic compositions described herein are used in the prevention of infection or cancer of subjects (e.g., human subjects). In other embodiments, the vaccine, immunogenic composition or pharmaceutical composition are suitable for veterinary and/or human administration.

In certain embodiments, provided herein are immunogenic compositions comprising an arenavirus vector as described herein. In certain embodiments, such an immunogenic composition further comprises a pharmaceutically acceptable excipient. In certain embodiments, such an immunogenic composition further comprises an adjuvant. The adjuvant for administration in combination with a composition described herein may be administered before, concomitantly with, or after administration of said composition. In some embodiments, the term "adjuvant" refers to a compound that when administered in conjunction with or as part of a composition described herein augments, enhances and/or boosts the immune response to a arenavirus particle or tri-segmented arenavirus particle and, most importantly, the gene products it vectorises, but when the compound is administered alone does not generate an immune response to the arenavirus particle or tri-segmented arenavirus particle and the gene products vectorised by the latter. In some embodiments, the adjuvant generates an immune response to the arenavirus particle or tri-segmented arenavirus particle and the gene products vectorised by the latter and does not produce an allergy or other adverse reaction. Adjuvants can enhance an immune response by several mechanisms including, e.g., lymphocyte recruitment, stimulation of B and/or T cells, and stimulation of macrophages or dendritic cells. When a vaccine or immunogenic composition of the invention comprises adjuvants or is administered together with one or more adjuvants, the adjuvants that can be used include, but are not limited to, mineral salt adjuvants or mineral salt gel adjuvants, particulate adjuvants, microparticulate adjuvants, mucosal adjuvants, and immunostimulatory adjuvants. Examples of adjuvants include, but are not limited to, aluminum salts (alum) (such as aluminum hydroxide, aluminum phosphate, and aluminum sulfate), 3 De-O-acylated monophosphoryl lipid A (MPL) (see GB 2220211), MF59 (Novartis), AS03 (GlaxoSmithKline), AS04 (GlaxoSmithKline), polysorbate 80 (Tween 80; ICL Americas, Inc.), imidazopyridine compounds (see International Application No. PCT/US2007/064857, published as International Publication No. WO2007/109812), imidazoquinoxaline compounds (see International Application No. PCT/US2007/064858, published as International Publication No. WO2007/109813) and saponins, such as QS21 (see Kensil et al., 1995, in Vaccine Design: The Subunit and Adjuvant Approach (eds. Powell & Newman, Plenum Press, NY); U.S. Pat. No. 5,057,540). In some embodiments, the adjuvant is Freund's adjuvant (complete or incomplete). Other adjuvants are oil in water emulsions (such as squalene or peanut oil), optionally in combination with immune stimulants, such as monophosphoryl lipid A (see Stoute et al., 1997, N. Engl. J. Med. 336, 86-91).

The compositions comprise the arenaviruses particle or tri-segmented arenavirus particle described herein alone or together with a pharmaceutically acceptable carrier. Suspensions or dispersions of the arenavirus particle or tri-segmented arenavirus particle, especially isotonic aqueous suspensions or dispersions, can be used. The pharmaceutical compositions may be sterilized and/or may comprise excipients, e.g., preservatives, stabilizers, wetting agents and/or emulsifiers, solubilizers, salts for regulating osmotic pressure and/or buffers and are prepared in a manner known per se, for example by means of conventional dispersing and suspending processes. In certain embodiments, such dispersions or suspensions may comprise viscosity-regulating agents. The suspensions or dispersions are kept at temperatures around 2° C. to 8° C., or preferentially for longer storage may be frozen and then thawed shortly before use, or alternatively may be lyophilized for storage. For injection, the vaccine or immunogenic preparations may be formulated in aqueous solutions, preferably in physiologically compatible buffers such as Hanks's solution, Ringer's solution, or physiological saline buffer. The solution may contain formulatory agents such as suspending, stabilizing and/or dispersing agents.

In certain embodiments, the compositions described herein additionally comprise a preservative, e.g., the mercury derivative thimerosal. In a specific embodiment, the pharmaceutical compositions described herein comprise 0.001% to 0.01% thimerosal. In other embodiments, the pharmaceutical compositions described herein do not comprise a preservative.

The pharmaceutical compositions comprise from about $10^3$ to about $10^{11}$ focus forming units of the arenavirus particle or tri-segmented arenavirus particle.

In one embodiment, administration of the pharmaceutical composition is parenteral administration. Parenteral administration can be intravenous or subcutaneous administration. Accordingly, unit dose forms for parenteral administration are, for example, ampoules or vials, e.g., vials containing from about $10^3$ to $10^{10}$ focus forming units or $10^5$ to $10^{15}$ physical particles of the arenavirus particle or tri-segmented arenavirus particle.

In another embodiment, a vaccine or immunogenic composition provided herein is administered to a subject by, including but not limited to, oral, intradermal, intramuscular, intraperitoneal, intravenous, topical, subcutaneous, percutaneous, intranasal and inhalation routes, and via scarification (scratching through the top layers of skin, e.g., using a bifurcated needle). Specifically, subcutaneous or intravenous routes can be used.

For administration intranasally or by inhalation, the preparation for use according to the present invention can be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin for use in an inhaler or insufflators may be formulated containing a powder mix of the compound and as a suitable powder base such as lactose or starch.

The dosage of the active ingredient depends upon the type of vaccination and upon the subject, and their age, weight, individual condition, the individual pharmacokinetic data, and the mode of administration. In certain embodiments, an in vitro assay is employed to help identify optimal dosage ranges. Effective doses may be extrapolated from dose response curves derived from in vitro or animal model test systems.

In certain embodiments, the vaccine, immunogenic composition, or pharmaceutical composition comprising an arenavirus particle or the tri-segmented arenavirus particle can be used as a live vaccination. Exemplary doses for a live arenavirus particle may vary from 10-100, or more, PFU of live virus per dose. In some embodiments, suitable dosages of an arenavirus particle or the tri-segmented arenavirus particle are $10^2$, $5\times10^2$, $10^3$, $5\times10^3$, $10^4$, $5\times10^4$, $10^5$, $5\times10^5$, $10^6$, $5\times10^6$, $10^7$, $5\times10^7$, $10^8$, $5\times10^8$, $1\times10^9$, $5\times10^9$, $1\times10^{10}$, $5\times10^{10}$, $1\times10^{11}$, $5\times10"$ or $10^{12}$ pfu, and can be administered to a subject once, twice, three or more times with intervals as often as needed. In another embodiment, a live arenavirus is formulated such that a 0.2-mL dose contains $10^{6.5}$-$10^{7.5}$ fluorescent focal units of live arenavirus particle. In another embodiment, an inactivated vaccine is formulated such that it contains about 15 μg to about 100 μg, about 15 μg to about 75 μg, about 15 μg to about 50 μg, or about 15 μg to about 30 μg of an arenavirus In certain embodiments, for administration to children, two doses of an arenavirus particle or a tri-segmented arenavirus particle described herein or a composition thereof, given at least one month apart, are administered to a child. In specific embodiments for administration to adults, a single dose of the arenavirus particle or tri-segmented arenavirus particle described herein or a composition thereof is given. In another embodiment, two doses of an arenavirus particle or a tri-segmented arenavirus particle described herein or a composition thereof, given at least one month apart, are administered to an adult. In another embodiment, a young child (six months to nine years old) may be administered an arenavirus particle or a tri-segmented arenavirus particle described herein or a composition thereof for the first time in two doses given one month apart. In a particular embodiment, a child who received only one dose in their first year of vaccination should receive two doses in the following year. In some embodiments, two doses administered 4 weeks apart are preferred for children 2-8 years of age who are administered an immunogenic composition described herein, for the first time. In certain embodiments, for children 6-35 months of age, a half dose (0.25 ml) may be preferred, in contrast to 0.5 ml which may be preferred for subjects over three years of age.

In certain embodiments, the compositions can be administered to the patient in a single dosage comprising a therapeutically effective amount of the arenavirus particle or the tri-segmented arenavirus particle. In some embodiments, the arenavirus particle or tri-segmented arenavirus particle can be administered to the patient in a single dose comprising a therapeutically effective amount of an arenavirus particle or tri-segmented arenavirus particle and, one or more pharmaceutical compositions, each in a therapeutically effective amount.

In certain embodiments, the composition is administered to the patient as a single dose followed by a second dose three to six weeks later. In accordance with these embodiments, the booster inoculations may be administered to the subjects at six to twelve month intervals following the second inoculation. In certain embodiments, the booster inoculations may utilize a different arenavirus or composition thereof. In some embodiments, the administration of the same composition as described herein may be repeated and separated by at least 1 day, 2 days, 3 days, 4 days, 5 days, 10 days, 15 days, 30 days, 45 days, 2 months, 75 days, 3 months, or at least 6 months.

Also provided herein, are processes and to the use the arenavirus particle or the tri-segmented arenavirus particle for the manufacture of vaccines in the form of pharmaceutical preparations, which comprise the arenavirus particle or tri-segmented arenavirus particle as an active ingredient. The pharmaceutical compositions of the present application are prepared in a manner known per se, for example by means of conventional mixing and/or dispersing processes.

4.8 Assays 4.8.1 Arenavirus Detection Assays

The skilled artesian could detect an arenavirus genomic segment or tri-segmented arenavirus particle, as described herein using techniques known in the art. For example, RT-PCR can be used with primers that are specific to an arenavirus to detect and quantify an arenavirus genomic segment that has been engineered to carry an ORF in a position other than the wild-type position of the ORF or a tri-segmented arenavirus particle. Western blot, ELISA, radioimmunoassay, immuneprecipitation, immunecytochemistry, or immunocytochemistry in conjunction with FACS can be used to quantify the gene products of the arenavirus genomic segment or tri-segmented arenavirus particle.

4.8.2 Assay to Measure Infectivity

Any assay known to the skilled artisan can be used for measuring the infectivity of an arenavirus vector preparation. For example, determination of the virus/vector titer can be done by a "focus forming unit assay" (FFU assay). In brief, complementing cells, e.g., MC57 cells are plated and inoculated with different dilutions of a virus/vector sample. After an incubation period, to allow cells to form a monolayer and virus to attach to cells, the monolayer is covered with Methylcellulose. When the plates are further incubated, the original infected cells release viral progeny. Due to the Methylcellulose overlay the spread of the new viruses is restricted to neighboring cells. Consequently, each infectious particle produces a circular zone of infected cells called a Focus. Such Foci can be made visible and by that countable using antibodies against LCMV-NP or another protein expressed by the arenavirus particle or the tri-segmented arenavirus particle and a HRP-based color reaction. The titer of a virus/vector can be calculated in focus-forming units per milliliter (FFU/mL).

4.8.3 Growth of an Arenavirus Particle

Growth of an arenavirus particle described herein can be assessed by any method known in the art or described herein (e.g., cell culture). Viral growth may be determined by inoculating serial dilutions of an arenavirus particle described herein into cell cultures (e.g., Vero cells or BHK-21 cells). After incubation of the virus for a specified time, the virus is isolated using standard methods.

4.8.4 Serum ELISA

Determination of the humoral immune response upon vaccination of animals (e.g., mice, guinea pigs) can be done by antigen-specific serum ELISA's (enzyme-linked immunosorbent assays). In brief, plates are coated with antigen (e.g., recombinant protein), blocked to avoid unspecific binding of antibodies and incubated with serial dilutions of sera. After incubation, bound serum-antibodies can be detected, e.g., using an enzyme-coupled anti-species (e.g., mouse, guinea pig)-specific antibody (detecting total IgG or IgG subclasses) and subsequent color reaction. Antibody titers can be determined as, e.g., endpoint geometric mean titer.

4.8.5 Assay to Measure the Neutralizing Activity of Induced Antibodies

Determination of the neutralizing antibodies in sera is performed with the following cell assay using ARPE-19 cells from ATCC and a GFP-tagged virus. In addition supplemental guinea pig serum as a source of exogenous complement is used. The assay is started with seeding of $6.5 \times 10^3$ cells/well (50 μl/well) in a 384 well plate one or two days before using for neutralization. The neutralization is done in 96-well sterile tissue culture plates without cells for 1 h at 37° C. After the neutralization incubation step the mixture is added to the cells and incubated for additional 4 days for GFP-detection with a plate reader. A positive neutralizing human sera is used as assay positive control on each plate to check the reliability of all results. Titers (EC50) are determined using a 4 parameter logistic curve fitting. As additional testing the wells are checked with a fluorescence microscope.

4.8.6 Plaque Reduction Assay

In brief, plaque reduction (neutralization) assays for LCMV can be performed by use of a replication-competent or -deficient LCMV that is tagged with green fluorescent protein, 5% rabbit serum may be used as a source of exogenous complement, and plaques can be enumerated by fluorescence microscopy. Neutralization titers may be defined as the highest dilution of serum that results in a 50%, 75%, 90% or 95% reduction in plaques, compared with that in control (pre-immune) serum samples.

qPCR LCMV RNA genomes are isolated using QlAamp Viral RNA mini Kit (QIAGEN), according to the protocol provided by the manufacturer. LCMV RNA genome equivalents are detected by quantitative PCR carried out on an StepOnePlus Real Time PCR System (Applied Biosystems) with SuperScript® III Platinum® One-Step qRT-PCR Kit (Invitrogen) and primers and probes (FAM reporter and NFQ-MGB Quencher) specific for part of the LCMV NP coding region or another genomic stretch of the arenavirus particle or the tri-segmented arenavirus particle. The temperature profile of the reaction may be: 30 min at 60° C., 2 min at 95° C., followed by 45 cycles of 15 s at 95° C., 30 s at 56° C. RNA can be quantified by comparison of the sample results to a standard curve prepared from a log 10 dilution series of a spectrophotometrically quantified, in vitro-transcribed RNA fragment, corresponding to a fragment of the LCMV NP coding sequence or another genomic stretch of the arenavirus particle or the tri-segmented arenavirus particle containing the primer and probe binding sites.

4.8.7 Western Blotting

Infected cells grown in tissue culture flasks or in suspension are lysed at indicated timepoints post infection using RIPA buffer (Thermo Scientific) or used directly without cell-lysis. Samples are heated to 99° C. for 10 minutes with reducing agent and NuPage LDS Sample buffer (NOVEX) and chilled to room temperature before loading on 4-12% SDS-gels for electrophoresis. Proteins are blotted onto membranes using Invitrogens iBlot Gel transfer Device and visualized by Ponceau staining. Finally, the preparations are probed with a primary antibodies directed against proteins of interest and alkaline phosphatase conjugated secondary antibodies followed by staining with 1-Step NBT/BCIP solution (INVITROGEN).

4.8.8 MHC-Peptide Multimer Staining Assay for Detection of Antigen-Specific CD8+ T-Cell Proliferation Any assay known to the skilled artisan can be used to test antigen-specific CD8+ T-cell responses. For example, the MHC-peptide tetramer staining assay can be used (see, e.g., Altman J. D. et al., Science. 1996; 274:94-96; and Murali-Krishna K. et al., Immunity. 1998; 8:177-187). Briefly, the assay comprises the following steps, a tetramer assay is used to detect the presence of antigen specific T-cells. In order for a T-cell to detect the peptide to which it is specific, it must both recognize the peptide and the tetramer of MHC molecules custom made for a defined antigen specificity and MHC haplotype of T-cells (typically fluorescently labeled). The tetramer is then detected by flow cytometry via the fluorescent label.

4.8.9 ELISPOT Assay for Detection of Antigen-Specific CD4+ T-cell Proliferation.

Any assay known to the skilled artisan can be used to test antigen-specific CD4+ T-cell responses. For example, the ELISPOT assay can be used (see, e.g., Czerkinsky C. C. et al., J Immunol Methods. 1983; 65:109-121; and Hutchings P. R. et al., J Immunol Methods. 1989; 120:1-8). Briefly, the assay comprises the following steps: An immunospot plate is coated with an anti-cytokine antibody. Cells are incubated in the immunospot plate. Cells secrete cytokines and are then washed off. Plates are then coated with a second biotyinlated-anticytokine antibody and visualized with an avidin-HRP system. 4.8.10 Intracellular Cytokine Assay for Detection of Functionality of CD8+ and CD4+ T-cell Responses.

Any assay known to the skilled artisan can be used to test the functionality of CD8+ and CD4+ T cell responses. For example, the intracellular cytokine assay combined with flow cytometry can be used (see, e.g., Suni M. A. et al., J Immunol Methods. 1998; 212:89-98; Nomura L. E. et al., Cytometry. 2000; 40:60-68; and Ghanekar S. A. et al., Clinical and Diagnostic Laboratory Immunology. 2001; 8:628-63). Briefly, the assay comprises the following steps: activation of cells via specific peptides or protein, an inhibition of protein transport (e.g., brefeldin A) is added to retain the cytokines within the cell. After a defined period of incubation, typically 5 hours, a washing steps follows, and antibodies to other cellular markers can be added to the cells. Cells are then fixed and permeabilized. The flurochrome-conjugated anti-cytokine antibodies are added and the cells can be analyzed by flow cytometry.

4.8.11 Assay for Confirming Replication-Deficiency of Viral Vectors

Any assay known to the skilled artisan that determines concentration of infectious and replication-competent virus particles can also be used as a to measure replication-deficient viral particles in a sample. For example, FFU assays with non-complementing cells can be used for this purpose.

Furthermore, plaque-based assays are the standard method used to determine virus concentration in terms of plaque forming units (PFU) in a virus sample. Specifically, a confluent monolayer of non-complementing host cells is infected with the virus at varying dilutions and covered with a semi-solid medium, such as agar to prevent the virus infection from spreading indiscriminately. A viral plaque is formed when a virus successfully infects and replicates itself in a cell within the fixed cell monolayer, and spreads to surrounding cells (see, e.g., Kaufmann, S. H.; Kabelitz, D. (2002). Methods in Microbiology Vol. 32: Immunology of Infection. Academic Press. ISBN 0-12-521532-0). Plaque formation can take 2-14 days, depending on the virus being analyzed. Plaques are generally counted manually and the results, in combination with the dilution factor used to prepare the plate, are used to calculate the number of plaque forming units per sample unit volume (PFU/mL). The PFU/mL result represents the number of infective replication-competent particles within the sample. When C-cells are used, the same assay can be used to titrate replication-deficient arenavirus particles or tri-segmented arenavirus particles.

4.8.12 Assay for Expression of Viral Antigen

Any assay known to the skilled artisan can be used for measuring expression of viral antigens. For example, FFU assays can be performed. For detection, mono- or polyclonal antibody preparation(s) against the respective viral antigens are used (transgene-specific FFU).

4.8.13 Animal Models

To investigate recombination and infectivity of an arenavirus particle described herein in vivo animal models can be used. In certain embodiments, the animal models that can be used to investigate recombination and infectivity of a tri-segmented arenavirus particle include mouse, guinea pig, rabbit, and monkeys. In a preferred embodiment, the animal models that can be used to investigate recombination and infectivity of an arenavirus include mouse. In a more specific embodiment, the mice can be used to investigate recombination and infectivity of an arenavirus particle are triple-deficient for type I interferon receptor, type II interferon receptor and recombination activating gene 1 (RAG1).

In certain embodiments, the animal models can be used to determine arenavirus infectivity and transgene stability. In some embodiments, viral RNA can be isolated from the serum of the animal model. Techniques are readily known by those skilled in the art. The viral RNA can be reverse transcribed and the cDNA carrying the arenavirus ORFs can be PCR-amplified with gene-specific primers. Flow cytometry can also be used to investigate arenavirus infectivity and transgene stability.

5. Examples

These examples demonstrate that LCMV virus-based vector technology can be used to successfully develop (1) an arenavirus genomic segment with a viral ORF in a position other than the wild-type position of the ORF, and (2) a tri-segmented arenavirus particle that does not result in a replication competent bi-segmented viral particle.

5.1 Materials and Methods 5.1.1 Cells

BHK-21 cells were cultured in high-glucose Dulbecco's Eagle medium (DMEM; Sigma) supplemented with 10% heat-inactivated fetal calf serum (FCS; Biochrom), 10 mM HEPES (Gibco), 1 mM sodium pyruvate (Gibco) and 1× tryptose phosphate broth. MC57 cells were maintained in Minimum Essential Medium (MEM; Sigma) complemented with 5% heat-inactivated FCS, 2 mM L-glutamine (Gibco) and penicillin-streptomycin (100'000 U/ml penicillin and 50 mg/l streptomycin; Gibco). Both cell lines were cultured at 37° C. in a humidified 5% CO2 incubator.

NP-expressing BHK-21 cells were generated by transfecting BHK-21 cells with a plasmid expressing NP under the control of the eukaryotic EF1-alpha promoter and encoding the puromycin resistance gene according to the manufacturer's protocol. 48 hours after transfection, 4 μg/ml puromycin was added to the medium. Another 48 hours later, cells were passaged into T150 flasks. Once separate clones became visible, cells were harvested and serially diluted into a 96-well plate to obtain single clones. Wells were checked optically for the growth of cell populations from single clones and respective cells were passaged into 6-well plates once they formed a confluent monolayer. NP-expressing BHK-21 cells were cultured in BHK-21 medium in the presence of 4 μg/ml puromycin.

GP-expressing BHK-21 cells have previously been described. Briefly, BHK-21 cells were stably transfected with a plasmid that expresses a codon-optimized LCMV-GP cDNA and the puromycin resistance cassette. GP-expressing clones were selected by the addition of 4 μg/ml puromycin to the medium and single clones were obtained by serial dilutions as described for the NP-expressing BHK-21 cells.

5.1.2 Plasmids

The pol-I L, pC-NP and pC-L plasmids have previously been described. For the generation of pol-I S plasmids encoding for GFP or RFP as reporter genes and either NP or GP, we used a pol-I Bbs/Bsm cloning plasmid as a basis (pol-I 5'-BsmBI_IGR_BbsI_3'). This plasmid encodes for the 5' untranslated region (5' UTR) of the viral S segment followed by two BsmBI restriction sites, the intergenic region (IGR), an NP rest and CAT open reading frame (ORF) flanked by BbsI restriction sites and the 3' UTR of the S segment. The pol-I S plasmids encoding for GP in its natural 5' and GFP in antisense orientation at the 3' position (pol-I 5'-GP_IGR_GfP-3') were cloned by inserting GP by BsmBI site-specific restriction and ligation into the pol-I Bbs/Bsm plasmid. In a second step GFP was inserted by BbsI digestion and ligation. In order to obtain pol-I S plasmids encoding for GP in the artificial 3' orientation (pol-I 5'-GFP_IGR_GP-3'), GP was inserted by BbsI digest at the 3' position into the pol-I Bbs/Bsm plasmid and GFP with BsmBI restriction/ligation at the 5' position. pol-I S encoding for GFP or RFP and NP (pol-I 5'-GFP_IGR_NP-3' or pol-I 5'RFP_IGR_NP-3') were cloned by inserting NP by BbsI digestion and ligation into the pol-I Bbs/Bsm cloning plasmid and GFP or RFP by BsmBI cloning. The pol-I plasmid with GP of LCMV strain WE and NP of LCMV strain Clone 13 (Cl13) were cloned by inserting the respective genes by Bbs and Bsm site-specific restriction/ligation at the respective sites in the pol-I Bbs/Bsm cloning plasmid.

The S segment encoding for the WE/WET fusion GP was obtained by replacing the last 255 base pairs of the WE ORF with a codon-optimized sequence named "WET". This was achieved by PCR amplifying in a first step a fragment of WE GP with one WE specific primer (SEQ ID NO: 11) and a WE specific fusion-primer carrying an overhang complementary to the WET sequence (SEQ ID NO: 12). In parallel the WET sequence was amplified by PCR using a WET-specific primer (SEQ ID NO: 13) and a WET-specific fusion-primer complementary to the WE sequence (SEQ ID NO: 14). In a third PCR reaction the two PCR products were fused by PCR fusion using the two mentioned fusion-primers. The resulting WE/WET fusion fragment was digested with BsmBI and ligated into a pol-I BsmBI_IGR_GFP-3' plasmid that had been digested with the same restriction enzyme.

The pol-I plasmid encoding for the recombined S segment of the in vivo recombined virus r3LCMV-GFP$^{nat}$ #3 was cloned by inserting the synthesized DNA fragment (gene synthesis by GenScript) by site-specific restriction/ligation with SacI and XmaI into a plasmid encoding a wild-type S-segment under the control of a pol-I promoter (pol-I GP_IGR_NP) resulting in pol-I GP_IGR_GFPrest_I-GR_NP.

5.1.3 DNA Transfection of Cells and Rescue of Recombinant Viruses

BHK-21 cells were seeded into 6-well plates at a density of 4×105 cells/well and transfected 24 hours later with different amounts of DNA using either lipofectamine (3 µl/µg DNA; Invitrogen) or jetPRIME (2 µl/µg DNA; Polyplus) according to the manufacturer's instructions. For rescue of recombinant bi-segmented viruses entirely from plasmid DNA, the two minimal viral trans-acting factors NP and L were delivered from pol-II driven plasmids (0.8 µg pC-NP, 1 µg pC-L) and were co-transfected with 1.4 µg of pol-I L and 0.8 µg of pol-I S. In case of rescue of tri-segmented r3LCMV consisting of one L and two S segments, 0.8 µg of both pol-I driven S segments were included in the transfection mix. 72 hours after transfection the supernatant was harvested and passaged on BHK-21 cells for further amplification of the virus. Viral titers in the supernatant were determined by focus forming assay.

5.1.4 Viruses and Growth Kinetics of Viruses

Wild-type Cl13 LCMV, originally derived from wild-type LCMV Armstrong, has previously been described. Stocks of wild-type and recombinant viruses were produced by infecting BHK-21 cells at a multiplicity of infection (moi) of 0.01 and supernatant was harvested 48 hours after infection. Growth curves of viruses were done in vitro in a 6-well format. BHK-21 cells were seeded at a density of 6×105 cells/well and infected 24 hours later by incubating the cells together with 500 µl of the virus inoculum at a moi of 0.01 for 90 minutes on a rocker plate at 37° C. and 5% CO2. Fresh medium was added and cells incubated at 37° C./5% CO2 for 72 to 96 hours. Supernatant was taken at given time points (normally 18, 24, 48, 72 hours) and viral titers analyzed by focus forming assay.

5.1.5 Focus Forming Assay

Next, titers of LCMV are determined by focus forming assay. LCMV is a non-cytolytic virus that does not lyse its host cells and as such does not create plaques. Nevertheless, units in this work will be expressed in the more commonly used term plaque forming units (PFU) instead of the correct term focus forming units (FFU). MC57 cells were used for focus forming assay if not stated otherwise. Cells were seeded at a density of 1.6×105 cells per well in a 24-well plate and mixed with 200 µl of 10-fold serial dilutions of virus prepared in MEM/2% FCS. After 2-4 hours of incubation at 37° C., 200 µl of a viscous medium (2% Methylcellulose in 2× supplemented DMEM) were added per well to ensure spreading of viral particles only to neighboring cells. After 48 hours at 37° C. the supernatant was flicked off and cells were fixed by adding 200 µl of 4% paraformaldehyde (PFA) in PBS for 30 minutes at room temperature (all following steps are performed at room temperature). Cells were permeabilised with 200 µl per well of BSS/1% Triton X-100 (Merck Millipore) for 20 minutes and subsequently blocked for 60 minutes with PBS/5% FCS. For anti-NP staining a rat anti-LCMV-NP monoclonal antibody was used as a primary staining antibody at a dilution of 1:30 in PBS/2.5% FCS for 60 minutes. For anti-GFP staining purified rat-anti-GFP antibody (Biolegend 338002) was used at a dilution of 1:2000 in PBS/2.5% FCS. Plates were washed three times with tap water and the secondary HRP-goat-anti-rat-IgG was added at a dilution of 1:100 in PBS/2.5% FCS and incubated for 1 hour. The plate was again washed three times with tap water. The color reaction (0.5 g/l DAB (Sigma D-5637), 0.5 g/l Ammonium Nickel sulfate in PBS/ 0.015% H2O2) was added and the reaction was stopped after 10 minutes with tap water. Stained foci were counted manually and the final titer calculated according to the dilution.

For anti-GP staining of cells, plates were fixed with 50% MeOH/50% Acetone for 5 minutes and washed with PBS. Blocking was done as described. As primary antibody anti-GP GP83.4 (produced from hybridomas) was diluted 1:10 in PBS/2.5% FCS and incubated for 60 minutes. After three washes with tap water, the secondary HRP-rabbit-anti-mouse IgG antibody was added at a dilution of 1:50 in PBS/2.5% FCS and incubated for 60 minutes. After another three washes with tap water the color reaction was added as described above.

In order to determine the viremia of mice in blood, one drop of blood (corresponding to 50 µl volume) was collected in 950 µl of BSS-heparin (Na-heparin, Braun, 1 IE/ml final), mixed by inverting and stored at −80° C. until further use.

5.1.6 Mice

AGRAG mice (IFNα/βR−/−, IFNγR−/−, RAG−/−) have previously been described and were bred and housed under specific pathogen-free (SPF) conditions. They were bred at the Institut für Labortierkunde of the University of Zurich, Switzerland. All animal experiments were performed at the Universities of Geneva and Basel in accordance with the Swiss law for animal protection and the permission of the respective responsible cantonal authorities of Geneva and Basel. Infection of the mice was done intravenously at a dose of 1×104 PFU per mouse.

5.1.7 Preparation of Viral RNA and Sequencing

Viral RNA was extracted from cell culture supernatant or from the serum of infected mice using the QIAamp Viral RNA Mini Kit (QIAGEN) according to the manufacturer's instructions. The reverse-transcription reaction was done with ThermoScript RT-PCR System (Invitrogen) and a primer specific for LCMV NP (SEQ ID NO: 15) following the manufacturer's protocol. Amplification by PCR was done by using 2 µl of the cDNA from the RT step and NP- and GP-specific primers (SEQ ID NO: 16). The PCR reaction was done using Phusion High-Fidelity DNA Polymerase (NEB). Amplified products were analyzed on and excised from a 2% agarose gel, purified using QIAquick Gel Extraction Kit (QIAGEN) and sent for DNA Sanger Sequencing (Microsynth) using the NP- and GP-specific primers.

5.1.8 Flow Cytometry

Blood was stained with antibodies against CD11c (N418), CD11b (M1/70), CD19 (6D5), NK1.1 (PK136), CD90.2 (30-H12) and GR-1 (RB6-8C5). The expression of surface molecules stained with specific antibodies as well as GFP and RFP expression was analyzed on a BD LSR Fortessa flow cytometer using FlowJo software (Tree Star, Ashland, Oreg.).

5.1.9 Statistical Analysis

Statistical significance was determined by two-tailed unpaired t test or 1-way ANOVA followed by Dunnett's or Bonferroni's post-test for multiple comparisons using Graphpad Prism software (version 6.0d). p values of p>0.5 were considered not significant (ns), whereas p values of p<0.5 were considered significant (*) with gradations of p<0.01 () and p<0.001 (*) being highly significant.

5.2 Results

5.2.1 Recombinant Tri-Segmented Viruses Grow to Lower Titers than Wild-Type LCMV The genome of wild-type LCMV consists of two single-stranded RNA segments of negative polarity (one L, one S segment) (FIG. 1A). In recent years it has been shown that it is possible to introduce additional foreign genes into the normally bi-segmented genome found in LCMV particles. The NP and GP genes are segregated onto two S segment analogues, and genes of interest are inserted into each resulting S segment of LCMV resulting in replication-competent viral particles with three RNA segments (two S+one L). The only currently published strategy keeps both NP and GP in their natural position in the S segment, thus placing GFP or other transgenes in the respective free sites (r3LCMV-GFP$^{nat}$) (FIG. 1B). This was the intuitive approach aimed at minimizing the likely risk that genetic reshuffling of the S segment abrogates the resulting genome's viability. However, this study hypothesized that it should also be possible to juxtapose the GP to the 3'UTR, expressing it from the promoter element that normally drives the NP (r3LCMV-GFP$^{art}$; FIG. 1C). Respective expression plasmids were generated by recombinant cDNA cloning and all three viral constructs were rescued entirely from plasmid DNA. Comparative growth curves were performed with the three viruses (FIG. 1D). All three viruses showed highest titers 48 hours after infection, with peak titers of tri-segmented viruses 10-100 fold lower than wild-type virus. Wild-type LCMV reached $3.4 \times 10^6$ PFU/ml, r3LCMV-GF-P$^{nat}$ peaked at $2.7 \times 10^4$ PFU/ml and r3LCMV-GFP$^{art}$ at $2.2 \times 10^5$ PFU/ml. Irrespective of its similarly reduced peak titers, r3LCMV-GFP$^{nat}$ exhibited somewhat higher cell-free infectivity during early time points than r3LCMV-GFP$^{art}$.

5.2.2 Packaging of Tri-Segmented Viral Particles is Less Efficient than of Bi-Segmented Virus These observations suggested that the addition of a second S segment impaired and delayed viral growth. It was hypothesized that this reduction in viral fitness might be due to inefficient packaging of all three RNA segments into viral particles, and that an excess of bi-segmented particles were formed, which failed to productively replicate when infecting fresh cells. For these experiments r3LCMVs with two different reporter genes i.e., GFP together with GP on one S segment, and NP next to RFP on the second S segment were used. This resulted in two viruses named r3LCMV-GFP/RFP$^{nat}$ and r3LCMV-GFP/RFP$^{art}$, which differed only in the arrangement of GFP and GP on the respective S segment. BHK-21 cells were infected with r3LCMV-GFP-RFP$^{nat}$ or bi-segmented r2LCMV and focus forming assays were performed on normal BHK-21 cells or, in parallel, with stably transfected BHK-21 cells expressing either GP (BHK-GP) or NP (BHK-NP) as cell substrate to trans-complement viral genomes lacking the respective genes. Wild-type and GP-complementing cells were stained for nucleoprotein-expressing viral foci, whereas NP-complementing cells were stained for GP-positive foci. Thereby, immunofocus formation on wild-type BHK-21 cells detected only tri-segmented virions. Without being limited by theory, BHK-GP cells should replicate tri-segmented virions as well as bi-segmented ones containing the L segment in combination with the NP-expressing S segment (but devoid of the GP-expressing S). Conversely, BHK-NP cells should replicate tri-segmented LCMV and additionally NP-deficient virions consisting of the L and the GP-expressing S segment (but devoid of the NP-expressing S segment). Infectious titers of both r3LCMV-GFP/RFP$^{nat}$ and r3LCMV-GFP/RFP$^{art}$, were consistently higher when assessed on BHK-GP or BHK-NP cells than when infectivity was tested on wt BHK-21 cells. Conversely, titers of r2LCMV were similar, irrespective of the cell substrate used to assess its infectivity. In order to correct for potential intrinsic differences in permissiveness of each cell line to LCMV, each virus' titer on BHK-21 cells was normalized to one, for display and BHK-GP as well as BHK-NP titers were expressed as a multiple thereof. Thus reflecting cell clone-related titer differences relating to potential clone-intrinsic differences in viral permissiveness (FIG. 2A). On either one of the complementing cells, an approximately five to ten-fold titer difference was observed for r3LCMV-GFP/RFP$^{nat}$ and r3LCMV-GFP/RFP$^{art}$, which was significantly higher than for r2LCMV. This suggested that a majority of the viral particles, which were formed by the two tri-segmented viruses, contained only one of the two S-segments, encoding either only the NP-(NP-only particles) or the GP-expressing S segment (GP-only particles), respectively. The 5-fold or greater difference in titer suggested that both, NP-only and also GP-only particles outnumbered tri-segmented particles approximately five-fold each, and that tri-segmented particles made up for less than 10 percent of virions only, which was compatible with delayed growth and a reduction in viral peak titers when grown on non-complementing cells (FIG. 1D). These findings were further validated by flow cytometry. Non-complementing BHK-21 cells or BHK-NP cells were infected with r3LCMV-GFP/RFP$^{art}$ or r2LCMV as gating control and fluorescence intensities of GFP and RFP were assessed with a flow cytometer (FIG. 2B). Since the minimal transacting factors are not provided by wild-type BHK-21 cells, only virions containing at least an L segment together with the NP-expressing S segment can initiate an infectious cycle after cell entry, resulting in fluorescence signal (RFP). Accordingly, a population of RFP+GFP− cells was observed upon infection of BHK-21 cells, reflecting NP-only particles. RFP+GFP+ double-positive cells were evidence of bona fide tri-segmented particles. According to the gating RFP−GFP+ cells were also observed, yet had a higher RFP MFI than RFP−GFP− cells, suggesting that they represented early stages of infection by trisegmented particles, an interpretation that is also supported by the continuity of this population and the RFP+GFP+ double positive one. However, when growing tri-segmented r3LCMV-GFP/RFP$^{art}$ on BHK-NP cells, thus substituting for this minimal transacting factor, we observed a more than 10-fold higher number of RFP−GFP+ cells as compared to infection of non-complementing BHK-21 cells. Conversely, RFP+GFP− (evidence of NP-only particles) and GFP+RFP+ double-positive cells (tri-segmented particles) were detected in comparable abundance (FIG. 2C). These results confirmed at the single-cell level the findings obtained by focus forming assay, thus corroborating that tri-segmented virus preparations contain a majority of bi-segmented replication-deficient particles. These findings offered a likely explanation for attenuated growth of r3LCMV-GFP/RFP$^{nat}$ and r3LCMV-GFP/RFP$^{art}$ providing insight into an apparently quite inefficient random packaging of tri-segmented viruses.

5.2.3 Cloning and Rescue of Recombinant Viruses to Track Recombination In Vivo

Since tri-segmented viruses show impaired growth kinetics as seen in FIG. 1, it was hypothesized that there should be high selection pressure on the viruses to recombine their genetic information for NP and GP on only one S segment. Inter-segmental recombination of arenaviruses is postulated to have led to the phylogenetic evolution of the North American Glade, and thus seemed a potential mechanism whereby tri-segmented viruses could re-establish a functional bi-segmented genome. Without being limited by theory, looking at the genomic organization of the two tri-segmented viruses it was postulated that the selection pressure on r3LCMV-GFP$^{nat}$ might favor recombination events in the area of the IGR, to bring GP and NP together on the same segment, while getting rid of GFP. In the population of r3LCMV-GFP$^{art}$ selection pressure should be equally high, however, the reshuffling of GP and its positioning next to the 3'UTR should render it very difficult if not impossible for this virus to combine its two S segments into one functional segment (see FIG. 7 below). In account of the caveats for the identification of RNA recombination and to firmly discriminate it from potential cDNA contamination, we cloned an S segment carrying GFP together with a recombinant GP ORF in which the terminal 255 nucleotides were codon-optimized. The resulting GP had a different nucleotide sequence but identical translation product as the wild-type WE strain GP (WE/WET-GP, FIG. 3A). This recombinant WE/WET GP ORF did not, however, exist as an infectious bi-segmented virus nor did the laboratory possess a cDNA construct where it was associated with NP. Any potential bi-segmented virus containing WE/WET on the same segment as NP was therefore deemed clear evidence of intersegmental recombination, differentiating such viruses from potentially contaminating cDNA or RNA in the respective assays. To test whether the chimeric GP had an effect on viral fitness, cell culture growth curves of the recombinant tri-segmented virus carrying the WE/WET fusion GP (r3LCMV-WEWET/GFP$^{nat}$) were performed in comparison with a tri-segmented virus carrying the wild-type WE GP (r3LCMV-WE/GFP$^{nat}$) (FIG. 3B). Growth kinetics and peak titers of the two viruses were comparable (r3LCMV-WE/GFP$^{nat}$: $1.7\times10^6$ PFU/ml, r3LCMV-WEWET/GFP$^{nat}$: $2.3\times10^6$ PFU/ml). Thus the chimeric WEWET glycoprotein did not detectably impact viral growth.

To test whether potential recombination events could happen between the NP and GP genes of the S segment that would involve the IGR. Hence a single nucleotide deletion was introduced in the intergenic region of the NP-encoding S segment, to serve as a genetic tag. The choice of this nucleotide deletion was made because it is situated in a stretch that unlike most of the S segment IGR is not conserved between strains, neither in sequence nor in length. In case of a recombination event this "tagged" (marked as * throughout, both in figures and text) intergenic region should allow the identification of the genetic origin of the S segment IGR sequences. The position of the deleted cytosine (marked with an arrow) and a schematic of the resulting NP carrying S segment is depicted in FIG. 3C. In order to test whether the introduced deletion in the IGR had an impact on viral growth, recombinant r3LCMV-GFP$^{nat}$ with or without the single nucleotide deletion was rescued. Growth curve experiments were performed on BHK-21 cells (moi=0.01). A tri-segmented virus with a wild-type IGR (r3LCMV-GFP$^{nat}$) and its comparator with the mutated IGR (r3LCMV-GFP$^{nat}$ IGR*) grew at a similar rate and reached indistinguishable peak titers (FIG. 3D). Consequently the tag of the IGR on the NP-carrying S segment did not have a detectable impact on viral fitness, thus validating its use for subsequent experimentation in vivo.

5.2.4 r3LCMV-GFP$^{nat}$ but not r3LCMV-GFP$^{art}$ Persistent Infection in Mice Reaches Viremia Levels Equivalent to Bi-Segmented Wt Virus and Results in Loss of GFP Expression Upon rescue of the recombinant r3LCMV-GFP$^{nat}$ an aim was to investigate whether tri-segmented viruses recombined in vivo. For this purpose AGRAG mice were infected with r3LCMV-GFP$^{nat}$, r3LCMV-GFP$^{nat}$ or a bi-segmented r2LCMV as control. AGRAG mice carry targeted deletions in the genes encoding for the Interferon-α/β receptor, the Interferon-γ receptor and RAG1, leading to an immunodeficient phenotype and establishment of chronic viremia after infection with tri-segmented LCMV. Blood samples were taken over time and viral titers were assessed by focus forming assay (FIG. 4A). Carriers of bi-segmented LCMV showed high titer viremia in the range of $5\times10^5$ PFU/ml blood within 5 days after infection, with subsequently stable viremia in the $10^4$-$10^5$ PFU/ml range until at least day 50 post infection. Mice infected with tri-segmented LCMV showed viral loads of about $5\times10^3$ PFU/ml blood until day 20, in line with attenuated growth in cell culture (compared to FIG. 1D). From day 30 onwards, carriers of r3LCMV-GFP$^{nat}$ displayed a rise in viral loads, which was not observed in animals infected with r3LCMV-GFP$^{art}$, resulting in more than a 10-fold difference in viremia on day 50. To determine whether the dominating virus population still carried the GFP reporter gene, thus resulting in GFP expression in infected cells, viral focus formation assays with blood samples of r3LCMV-GFP$^{nat}$ and r3LCMV-GFP$^{art}$ carriers taken on day 127 after infection were performed and stained for the nucleoprotein or the reporter gene GFP (FIG. 4B). Whereas staining of blood isolated from r3LCMV-GFP$^{art}$ carriers resulted in equal amounts of foci with anti-NP and anti-GFP antibody detection (both assessments independently indicating viral titers in the $10^3$ PFU/ml range) at least 100-fold higher numbers of total (NP+) r3LCMV-GFP$^{nat}$ foci were evident than foci expressing GFP. Viral titers of at least $10^4$ PFU/ml were measured based on anti-NP detection, whereas two out of three mice failed to show any detectable GFP-positive infectivity and one mouse had a residual fraction of GFP-positive foci in the 100 PFU/ml range, corresponding to the lower limit of detection of our assays. GFP expression of infected cells was also assessed by fluorescence microscopy (data not shown). GFP-fluorescent foci were virtually undetectable when assaying blood from r3LCMV-GFP$^{nat}$ carriers whereas manual counts of GFP-positive foci from r3LCMV-GFP$^{art}$ carrier blood matched the titer results obtained with anti-NP focus forming assay. Reporter gene expression was further verified by flow cytometric analysis of PBMCs of infected mice on day 120 after infection. We found that more than 10% of CD11b+GR1-monocytes/macrophages were positive for GFP in r3LCMV-GFP$^{art}$ infected animals whereas blood from r3LCMV-GFP$^{nat}$ evidenced only background levels of GFP, which was comparable to animals infected with non-fluorescent r2LCMV (FIG. 4C-E). This finding further supported the hypothesis that tri-segmented viruses with GP in their natural position lose reporter gene expression over time whereas transposition of the GP in the artificial 3'UTR juxtaposition prevented transgene loss.

5.2.5 Tri-Segmented Viruses with GP in the Natural Position can Recombine their Two S Segments Resulting in a Single S Segment with Partial or Complete IGR Duplications Flanking a Transgene Sequence Rudiment FIG. 4 showed elevated viremia and loss of reporter gene expression in mice infected with r3LCMV-GFP$^{nat}$. Therefore, it was hypothesized that a recombination event could account for this experimental outcome. Intersegmental recombination should combine GP and NP on the same S segment, obviating the need for a second S segment in the viral replication cycle. Such an event could then have explained viremia at the level of wild-type virus, in combination with loss of reporter gene expression. To test this possibility viral RNA from the serum of infected mice was isolated and a pair of primers binding to NP and GP sequences, respectively, were used to selectively amplify by RT-PCR only the putatively recombined RNA molecules, carrying both NP and GP ORFs in ambisense orientation on one RNA segment. The resulting PCR fragments were analyzed by gel electrophoresis (FIG. 5A). The sera of all r3LCMV-GFP$^{nat}$ carriers gave rise to RT-dependent PCR products, whereas r3LCMV-GFP$^{art}$ carriers and naïve controls did not show specific bands. Control PCR reactions were performed on mock-RT-treated RNA samples to rule out cDNA contaminations as a source of PCR product. Sequencing results of three individual r3LCMV-GFP$^{nat}$ carriers are schematically represented in FIG. 5C. The three mice contained viral RNA segments of distinct sequences yet with a similar pattern: C-terminal portions of GP and NP were found in ambisense orientation on one RNA segment. Between them, both intergenic regions, i.e., the one of the NP-expressing and the one of the original GP-expressing segment were at least partially retained, separated by a fragment from either one or both GFP reporter genes in the parental S segments of the trisegmented virus. The direction and length of the GFP fragment varied between the three RNA species recovered from individual mice, which was indicative of independent recombination events. In further support of this notion, the exact same recombined RNA sequence was recovered from two consecutive samples taken from the same mouse with more than three weeks interval between sampling. Based on the recombined S segment sequences obtained, we proposed a molecular mechanism, as schematically outlined in FIG. 7 and described in the figure's legend, whereby r3LCMV-GFP$^{nat}$ recombines its two S segments, resulting in transgene loss and phenotypic reversion to wild-type virus. The schematics in FIG. 7 also explain why, according to the proposed mechanism of S segment recombination, r3LCMV-GFP$^{art}$ cannot recombine and bring together its NP and GP ORFs on one functional S segment.

5.2.6 Recombinant r2LCMV with Two IGRs on the S Segment is Viable and Grows to Similar Titers as Bi-Segmented LCMV with Only One IGR in the S Segment.

The above sequencing data revealed a consistent pattern of viral genetic elements in recombined S segments amongst which the (at least partial) duplication of the IGR was particularly noteworthy and characteristic. However, arenaviruses with repeats of intergenic regions on one S segment were not known. A dual stem loop is, however, naturally found in the Old World arenavirus Mopeia. Hence, we cloned the rearranged S segment of r3LCMV-GFP$^{nat}$ carrier #3 with the two IGRs and the remnant of GFP into a pol-I driven S segment expression plasmid and rescued the respective virus. Growth kinetics of this virus (r2LCMV_2IGRs) on BHK-21 cells were compared to tri-segmented r3LCMV-GFP$^{nat}$ and bi-segmented r2LCMV (FIG. 6). Infectious cell-free titers of r2LCMV_2IGRs exceeded those of r3LCMV-GFP$^{nat}$ already at early time points and reached identical peak titers as r2LCMV (1.7×10$^7$ PFU/ml vs. 1.6×10$^7$ PFU/ml, respectively). Importantly, r2LCMV_2IGRs grew to considerably higher peak titers than its parental tri-segmented r3LCMV-GFP$^{nat}$ attesting to the selective advantage of intersegmental recombination despite duplication of the IGR during this process.

5.2.7 Recombinant r3LCMV Expressing Ovalbumin (OVA) Induces a Rapid, Strong and Polyfunctional OVA-Specific CD8+ T Cell Response.

To test the utility of the r3LCMV$^{art}$ vector delivery technology for vaccination purposes we generated the r3LCMV-OVA$^{art}$ vaccine vector with a genome organization analogous to r3LCMV-GFP$^{art}$ (FIG. 1C) but with two ovalbumin (OVA) genes instead of the respective GFP genes in the latter virus. We immunized C57BL/6 mice intramuscularly (i.m.) with 10$^4$ PFU of r3LCMV-OVA$^{art}$ and eight days later we analyzed the T cell response in spleen. For comparison to a widely used vector platform we immunized a second group of C57BL/6 mice with 10$^8$ particles of a replication-deficient E1-deleted adenovirus 5-based vector also expressing OVA (rAd5-OVA). The frequency of OVA-specific CD8+ T cells recognizing the immunodominant OVA-derived SIINFEKL epitope was in the 10% range of CD8+ T cells in the r3LCMV-OVA$^{art}$ vaccine group, which was significantly higher than in the rAd5-OVA group (FIG. 8A). r3LCMV-OVA$^{art}$ induced CD8+ T cell responses were not only of high magnitude but also highly functional as determined by intracellular cytokine assays, revealing that most SIINFEKL-reactive r3LCMV-OVA$^{art}$ induced CD8+ T cells produced IFN-γ in response to peptide stimulation, and that a fair proportion co-produced TNF-α and/or IL-2. This demonstrated the utility of the r3LCMV-OVA$^{art}$ vector technology for vaccine delivery.

5.2.8 Trisegmented LCMV Induces Polyfunctional Memory CD8+ T Cells.

To address the question whether r3LCMV vectors induce functional CD8+ T cell memory we immunized C57BL/6 mice with 10e5 PFU of r3LCMV-OVA$^{art}$ i.v. and analyzed OVA-specific (SIINFEKL-specific) CD8+ T cell responses in spleen on day 25. A reference control group of mice was vaccinated with 10e8 viral particles (vp) of recombinant E1-deleted adenoviral vector (rAd) expressing OVA by the same route. OVA-specific CD8+ T cells producing IFN-γ, TNF-α and/or IL-2 upon peptide stimulation were assessed in standard intracellular cytokine assays upon SIINFEKL peptide stimulation. The frequency (FIG. 9A) and absolute number (FIG. 9B) of cytokine producing cells as indicated in the chart was determined. r3LCMV-OVA$^{art}$-immune mice exhibited significantly higher frequencies and numbers of polyfunctional IFN-γ/TNF-α and IFN-γ/TNF-α/IL-2 co-producing OVA-specific CD8+ T cells than rAd-OVA-immune mice.

5.2.9 Antigen-Encoding LCMV Induces Specific T Cell Responses to Foreign and Self Antigens.

Figure 10:
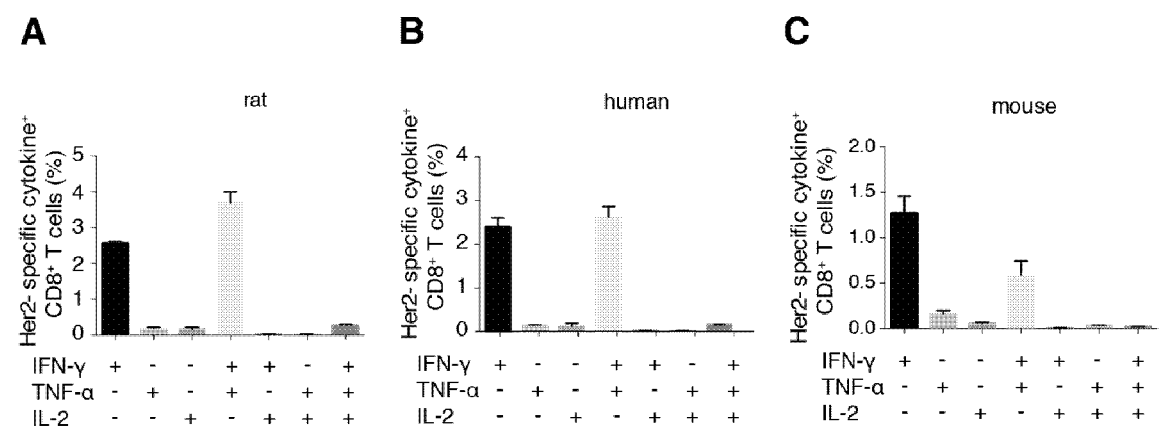

To investigate whether r3LCMV$^{art}$ vectors can be exploited to induce CD8+ T cell responses against tumor-expressed self antigens, we immunized BALB/c mice with r3LCMV$^{art}$ vectors expressing either rat (TYVPANASL), human (TYLPTNASL) or mouse (TYLPANASL) Her2-derived CD8+ T cell epitopes (FIG. 10). Nine days later we measured specific CD8+ T cells producing IFN-γ, TNF-α and/or IL-2 upon stimulation with the respective peptides in intracellular cytokine assays. FIG. 10 displays the frequencies of epitope-specific CD8+ T cells as the percentage of CD8+ T cells producing the indicated cytokine combination upon stimulation with the cognate peptide. Frequencies of cytokine-producing CD8+ T cells upon restimulation with medium only were insignificant. The results document that r3LCMV$^{art}$ vectors have the capacity to induce substantial frequencies of tumor self-antigen-reactive CD8+ T cell responses.

5.2.10 Interferon-α is Induced Upon r3LCMV$^{art}$ Infection but not Upon Infection with Recombinant Adeno- or Vaccinia Virus Vectors.

Type I interferons can have multiple immunostimulatory and anti-tumoral effects. Hence, type I interferon induction can represent a favorable feature of a virally vectored vaccine. We performed ELISA measurements to determine interferon-alpha concentrations in the serum of mice immunized with r3LCMV-OVA$^{art}$, rAd-OVA or recombinant vaccinia virus expressing OVA (rVacc) 24, 48 or 72 hours previously (FIG. 11). r3LCMV$^{art}$ but neither rAd nor rVacc induced a detectable and sustained (at least 48 hours) systemic interferon-alpha response. This attested to the capacity of r3LCMV$^{art}$ vectors to induce strong innate immune responses.

5.2.11 Cell culture growth of r3JUNV-GFP$^{art}$ in comparison to r3JUNV-GFP$^{nat}$ and parental Junin strain Candid #1.

By analogy to the r3LCMV-GFP$^{nat}$ and r3LCMV-GFP$^{art}$ vectors, carrying a genome as outlined in FIG. 1B we engineered r3JUNV-GFP$^{nat}$ and r3JUNV-GFP$^{art}$, consisting of trisegmented Junin vaccine strain Candid #1-based vectors carrying GFP genes in each one of their respective two S segments (r3JUNV-GFP$^{nat}$ and r3JUNV-GFP$^{art}$). We tested their growth properties in 293T cells, which we infected at multiplicity of infection of 0.01 and collected supernatant over time (FIG. 12). We found that r3JUNV-GFP$^{art}$ grew more slowly than its parental bisegmented Junin vaccine strain Candid #1 (FIG. 12). However, it grew more quickly than r3JUNV-GFP$^{nat}$, (FIG. 12). This differential growth behavior of trisegmented Junin virus-based vectors paralleled the growth rates of r3LCMV-GFP$^{nat}$ and r3LCMV-GFP$^{art}$ vectors (FIG. 1D).

5.2.12 Trisegmented JUNV are Dramatically Attenuated In Vivo, and r3JUNV-GFr$^{nat}$ but not r3JUNV-GFP$^{art}$ Loses GFP Expression Upon Prolonged In Vivo Replication.

To investigate the genetic stability of r3JUNV-GFP$^{nat}$ and r3JUNV-GFP$^{art}$ we infected AGRAG mice (IFNα/βR−/−, IFNγR−/−, RAG−/−) with 7×10e4 PFU of either of these GFP-expressing vectors. For the purpose of comparison, a third group was infected with the wild type bisegmented Candid #1 virus. The latter virus was readily detected in the blood of all infected mice by day 20 after infection (FIG. 13A), whereas the trisegmented viruses remained undetectable for at least 40 days. This finding documented attenuated in vivo growth as a result of genome reorganization, extending our findings with r3LCMV-GFP vectors in FIG. 4A to Junin-based vectors. After day 40, also r3JUNV-GFP$^{nat}$ and r3JUNV-GFP$^{art}$ became detectable in several animals in each group (FIG. 13A). Importantly, however, some of the r3JUNV-GFP$^{nat}$-infected mice reached viral loads in the range of wild type Candid #1-infected mice whereas viremic r3JUNV-GFP$^{art}$-infected mice retained lower viral load than Candid #1-infected controls.

To determine whether the dominating virus population in these viremic animals still carried the GFP reporter gene, thus resulting in GFP expression in infected cells, we performed viral focus formation assays with blood samples of r3JUNV-GFP$^{nat}$ and r3JUNV-GFP$^{art}$ carriers taken on day 120 after infection. We compared infectious titers of viruses retaining GFP expression (anti-GFP, FIG. 13B) and total Junin virus infectivity (anti-NP, FIG. 13B). r3JUNV-GFP$^{art}$ titers were in similar ranges when determined by either anti-GFP or anti-NP Immunofocus assay documenting that the majority of the virus population retained GFP expression. Conversely, in the blood of the four r3JUNV-GFP$^{nat}$ infected animals with highest viremia (comparable to wildtype Candid #1) the anti-GFP infectious titer was at least 10 fold lower than the total infectious titer as determined by NP staining. This documented that r3JUNV-GFP$^{art}$ but not r3JUNV-GFP$^{nat}$ stably retained the GFP transgene in vivo.

5.2.13 Homologous and Heterologous Prime-Boost Combinations of Trisegmented LCMV- and JUNV-Based Vaccine Vectors Induce Strong P1A Autoantigen-Specific CD8+ T Cells Responses.

Next we investigated whether r3LCMV$^{art}$- and r3JUNV$^{art}$-based vectors can be used in homologous and heterologous prime-boost combinations for inducing tumor autoantigen-specific CD8+ T cell responses. We constructed r3LCMV$^{art}$ and r3JUNV$^{art}$-based vectors expressing the P815 mouse mastocytoma-derived self antigen PIA (SEQ ID NO: 24) (r3LCMV-P1A$^{art}$ (SEQ ID NOs: 18, 19, 20) and r3JUNV-P1A$^{art}$ (SEQ ID NOs: 21, 22, 23)). These vaccine constructs were used to immunize BALB/c mice i.v. in homologous and heterologous prime-boost combinations as outlined in FIG. 14. Both, r3LCMV-P1A$^{art}$ and r3JUNV-P1A$^{art}$ induced PIA epitope-specific CD8+ T cells when administered in homologous prime-boost vaccination, as determined from blood using H-2L$^{d}$-tetramers loaded with the LPYLGWLVF peptide (PIA epitope 35-43). Mean frequencies of epitope-specific CD8+ T cells on day 63 of the experiment were 1.2% (r3JUNV-P1A$^{art}$) and 3.9% (r3LCMV-P1A$^{art}$), respectively. Additionally, animals primed with r3JUNV-P1A$^{art}$ and boosted with r3LCMV-P1A$^{art}$ in a heterologous fashion mounted even higher responses with average epitope-specific CD8+ T cell frequencies of 19.5% on day 63. Frequencies of r3LCMV-P1A$^{art}$-primed and r3JUNV-P1A$^{art}$-boosted animals (3.1%) were comparable to those undergoing r3LCMV-P1A$^{art}$ homologous prime-boost vaccination.

6. Equivalents

The viruses, nucleic acids, methods, host cells, and compositions disclosed herein are not to be limited in scope by the specific embodiments described herein. Indeed, various modifications of the viruses, nucleic acids, methods, host cells, and compositions in addition to those described will become apparent to those skilled in the art from the foregoing description and accompanying figures. Such modifications are intended to fall within the scope of the appended claims.

Various publications, patents and patent applications are cited herein, the disclosures of which are incorporated by reference in their entireties.

Various publications, patents and patent applications are cited herein, the disclosures of which are incorporated by reference in their entireties.

7. Sequence Listing

| SEQ ID NO. | Description | Sequence | |
|---|---|---|---|
| 1 | LCMV segment S, complete sequence. The genomic segment is RNA, the sequence in SEQ ID NO: 1 is shown for DNA; however, exchanging all thymidines ("T") in SEQ ID NO: 1 for uridines ("U") provides the RNA sequence. | cgcaccgggg atcctaggct ttttggattg cgctttcctc tagatcaact gggtgtcagg ccctatccta cagaaggatg ggtcagattg tgacaatgtt tgaggctctg cctcacatca tcgatgaggt gatcaacatt gtcattattg tgcttatcgt gatcacgggt atcaaggctg tctacaattt tgccacctgt gggatattcg cattgatcag tttcctactt ctggctggca ggtcctgtgg catgtacggt cttaagggac ccgacattta caaaggagtt taccaattta agtcagtgga gtttgatatg tcacatctga acctgaccat gcccaacgca tgttcagcca acaactccca ccattacatc agtatgggga cttctggact agaattgacc ttcaccaatg attccatcat cagtcacaac ttttgcaatc tgacctctgc cttcaacaaa aagacctttg accacacact catgagtata gtttcgagcc tacacctcag tatcagaggg aactccaact ataaggcagt atcctgcgac ttcaacaatg gcataaccat ccaatacaac ttgacattct cagatcgaca aagtgctcag agccagtgta gaaccttcag aggtagagtc ctagatatgt ttagaactgc cttcgggggg aaatacatga ggagtggctg gggctggaca ggctcagatg gcaagaccac ctggtgtagc cagacgagtt accaatacct gattatacaa aatagaacct gggaaaacca ctgcacatat gcaggtcctt ttgggatgtc caggattctc ctttcccaag agaagactaa gttcttcact aggagactag cgggcacatt cacctggact ttgtcagact cttcaggggt ggagaatcca ggtggttatt gcctgaccaa atggatgatt cttgctgcag agcttaagtg tttcgggaac acagcagttg cgaaatgcaa tgtaaatcat gatgccgaat tctgtgacat gctgcgacta attgactaca acaaggctgc tttgagtaag ttcaaagagg acgtagaatc tgccttgcac ttattcaaaa caacagtgaa ttctttgatt tcagatcaac tactgatgag gaaccacttg agagatctga tggggtgcc atattgcaat tactcaaagt tttggtacct agaacatgca aagaccggcg aaactagtgt ccccaagtgc tggcttgtca ccaatggttc ttacttaaat gagacccact tcagtgatca aatcgaacag gaagccgata acatgattac agagatgttg aggaaggatt acataaagag gcaggggagt acccccctag cattgatgga ccttctgatg ttttccacat ctgcatatct agtcagcatc ttcctgcacc ttgtcaaaat accaacacac aggcacataa aaggtggctc atgtccaaag ccacaccgat taccaacaa aggaatttgt agttgtggtg catttaaggt gcctggtgta aaaaccgtct ggaaaagacg ctgaagaaca gcgcctccct gactctccac ctcgaaagag gtggagagtc agggaggccc agagggtctt agagtgtcac aacatttggg cctctaaaaa ttaggtcatg tggcagaatg ttgtgaacag ttttcagatc tgggagcctt gctttggagg cgctttcaaa aatgatgcag tccatgagtg cacagtgcgg ggtgatctct ttcttctttt tgtcccttac tattccagta tgcatcttac acaaccagcc atatttgtcc cacactttgt cttcatactc cctcgaagct tccctggtca tttcaacatc gataagctta atgtccttcc tattctgtga | 60 120 180 240 300 360 420 480 540 600 660 720 780 840 900 960 1020 1080 1140 1200 1260 1320 1380 1440 1500 1560 1620 1680 1740 1800 1860 1920 |

| SEQ ID NO. | Description | Sequence | |
|---|---|---|---|
| | | gtccagaagc tttctgatgt catcggagcc | |
| | | ttgacagctt agaaccatcc cctgcggaag | 1980 |
| | | agcacctata actgacgagg tcaacccggg | |
| | | ttgcgcattg aagaggtcgg caagatccat | 2040 |
| | | gccgtgtgag tacttggaat cttgcttgaa | |
| | | ttgttttga tcaacgggtt ccctgtaaaa | 2100 |
| | | gtgtatgaac tgcccgttct gtggttggaa | |
| | | aattgctatt tccactggat cattaaatct | 2160 |
| | | accctcaatg tcaatccatg taggagcgtt | |
| | | ggggtcaatt cctcccatga ggtcttttaa | 2220 |
| | | aagcattgtc tggctgtagc ttaagcccac | |
| | | ctgaggtgga cctgctgctc caggcgctgg | 2280 |
| | | cctgggtgaa ttgactgcag gtttctcgct | |
| | | tgtgagatca attgttgtgt tttcccatgc | 2340 |
| | | tctccccaca atcgatgttc tacaagctat | |
| | | gtatggccat ccttcacctg aaaggcaaac | 2400 |
| | | tttatagagg atgttttcat aagggttcct | |
| | | gtccccaact tggtctgaaa caaacatgtt | 2460 |
| | | gagttttctc ttggccccga gaactgcctt | |
| | | caagaggtcc tcgctgttgc ttggcttgat | 2520 |
| | | caaaattgac tctaacatgt taccccatc | |
| | | caacagggct gcccctgcct tcacggcagc | 2580 |
| | | accaagacta aagttatagc cagaaatgtt | |
| | | gatgctggac tgctgttcag tgatgacccc | 2640 |
| | | cagaactggg tgcttgtctt tcagcctttc | |
| | | aagatcatta agatttggat acttgactgt | 2700 |
| | | gtaaagcaag ccaaggtctg tgagcgcttg | |
| | | tacaacgtca ttgagcggag tctgtgactg | 2760 |
| | | tttggccata caagccatag ttagacttgg | |
| | | cattgtgcca aattgattgt tcaaaagtga | 2820 |
| | | tgagtctttc acatcccaaa ctcttaccac | |
| | | accacttgca ccctgctgag gctttctcat | 2880 |
| | | cccaactatc tgtaggatct gagatctttg | |
| | | gtctagttgc tgtgttgtta agttccccat | 2940 |
| | | atatacccct gaagcctggg gccttttcaga | |
| | | cctcatgatc ttggccttca gcttctcaag | 3000 |
| | | gtcagccgca agagacatca gttcttctgc | |
| | | actgagcctc cccactttca aaacattctt | 3060 |
| | | ctttgatgtt gactttaaat ccacaagaga | |
| | | atgtacagtc tggttgagac ttctgagtct | 3120 |
| | | ctgtaggtct ttgtcatctc tcttttcctt | |
| | | cctcatgatc ctctgaacat tgctgacctc | 3180 |
| | | agagaagtcc aacccattca gaaggttggt | |
| | | tgcatcctta atgacagcag ccttcacatc | 3240 |
| | | tgatgtgaag ctctgcaatt ctcttctcaa | |
| | | tgcttgcgtc cattggaagc tcttaacttc | 3300 |
| | | cttagacaag gacatcttgt tgctcaatgg | |
| | | tttctcaaga caaatgcgca atcaaatgcc | 3360 |
| | | taggatccac tgtgcg | |
| 2 | LCMV clone 13 segment S, complete sequence (GenBank: DQ361065.2). The genomic segment is RNA, the sequence in SEQ ID NO: 2 is shown for DNA; however, exchanging all thymidines ("T") in SEQ ID NO: 2 for uridines ("U") provides the RNA sequence. | gcgcaccggg gatcctaggc tttttggatt | |
| | | gcgctttcct ctagatcaac tgggtgtcag | 60 |
| | | gccctatcct acagaaggat gggtcagatt | |
| | | gtgacaatgt ttgaggctct gcctcacatc | 120 |
| | | atcgatgagg tgatcaacat tgtcattatt | |
| | | gtgcttatcg tgatcacggg tcatcaaggct | 180 |
| | | gtctacaatt ttgccacctg tgggatattc | |
| | | gcattgatca gtttcctact tctggctggc | 240 |
| | | aggtcctgtg gcatgtacgg tcttaaggga | |
| | | cccgacattt acaaaggagt ttaccaattt | 300 |
| | | aagtcagtgg agtttgatat gtcacatctg | |
| | | aacctgacca tgcccaacgc atgttcagcc | 360 |
| | | aacaactccc accattacat cagtatgggg | |
| | | acttctggac tagaattgac cttcaccaat | 420 |
| | | gattccatca tcagtcacaa cttttgcaat | |
| | | ctgacctctg ccttcaacaa aaagaccttt | 480 |
| | | gaccacacac tcatgagtat agtttcgagc | |
| | | ctacacctca gtatcagagg gaactccaac | 540 |
| | | tataaggcag tatcctgcga cttcaacaat | |
| | | ggcataacca tccaatacaa cttgacattc | 600 |
| | | tcagatgcac aaagtgctca gagccagtgt | |
| | | agaaccttca gaggtagagt cctagatatg | 660 |
| | | tttagaactg ccttcggggg gaaatacatg | |
| | | aggagtggct ggggctggac aggctcagat | 720 |
| | | ggcaagacca cctggtgtag ccagacgagt | |
| | | taccaatacc tgattataca aaatagaacc | 780 |

| SEQ ID NO. | Description | Sequence | |
|---|---|---|---|
| | | tgggaaaacc actgcacata tgcaggtcct tttgggatgt ccaggattct cctttcccaa | 840 |
| | | gagaagacta agttcctcac taggagacta gcgggcacat tcacctggac tttgtcagac | 900 |
| | | tcttcagggg tggagaatcc aggtggttat tgcctgacca aatggatgat tcttgctgca | 960 |
| | | gagcttaagt gtttcgggaa cacagcagtt gcgaaatgca atgtaaatca tgatgaagaa | 1020 |
| | | ttctgtgaca tgctgcgact aattgactac aacaaggctg ctttgagtaa gttcaaagag | 1080 |
| | | gacgtagaat ctgccttgca cttattcaaa acaacagtga attctttgat ttcagatcaa | 1140 |
| | | ctactgatga ggaaccactt gagagatctg atgggggtgc catattgcaa ttactcaaag | 1200 |
| | | ttttggtacc tagaacatgc aaagaccggc gaaactagtg tccccaagtg ctggcttgtc | 1260 |
| | | accaatggtt cttacttaaa tgagacccac ttcagtgacc aaatcgaaca ggaagccgat | 1320 |
| | | aacatgatta cagagatgtt gaggaaggat tacataaaga ggcaggggag tacccccta | 1380 |
| | | gcattgatgg accttctgat gttttccaca tctgcatatc tagtcagcat cttcctgcac | 1440 |
| | | cttgtcaaaa taccaacaca caggcacata aaaggtggct catgtccaaa gccacaccga | 1500 |
| | | ttaaccaaca aaggaatttg tagttgtggt gcatttaagg tgcctggtgt aaaaaccgtc | 1560 |
| | | tggaaaagac gctgaagaac agcgcctccc tgactctcca cctcgaaaga ggtggagagt | 1620 |
| | | cagggaggcc cagagggtct tagagtgtca caacatttgg gcctctaaaa attaggtcat | 1680 |
| | | gtggcagaat gttgtgaaca gttttcagat ctgggagcct tgctttggag gcgctttcaa | 1740 |
| | | aaatgatgca gtccatgagt gcacagtgcg gggtgatctc tttcttcttt ttgtcccta | 1800 |
| | | ctattccagt atgcatctta cacaaccagc catatttgtc ccacactttg tcttcatact | 1860 |
| | | ccctcgaagc ttccctggtc atttcaacat cgataagctt aatgtccttc ctattctgtg | 1920 |
| | | agtccagaag ctttctgatg tcatcggagc cttgacagct tagaaccatc ccctgcggaa | 1980 |
| | | gagcacctat aactgacgag gtcaacccgg gttgcgcatt gaagaggtcg gcaagatcca | 2040 |
| | | tgccgtgtga gtacttggaa tcttgcttga attgtttttg atcaacgggt tccctgtaaa | 2100 |
| | | agtgtatgaa ctgcccgttc tgtggttgga aaattgctat ttccactgga tcattaaatc | 2160 |
| | | taccctcaat gtcaatccat gtaggagcgt tggggtcaat tcctcccatg aggtctttta | 2220 |
| | | aaagcattgt ctggctgtag cttaagccca cctgaggtgg acctgctgct ccaggcgctg | 2280 |
| | | gcctgggtga attgactgca ggtttctcgc ttgtgagatc aattgttgtg ttttcccatg | 2340 |
| | | ctctccccac aatcgatgtt ctacaagcta tgtatggcca tccttcacct gaaaggcaaa | 2400 |
| | | ctttatagag gatgttttca taagggttcc tgtccccaac ttggtctgaa acaaacatgt | 2460 |
| | | tgagttttct cttggccccg agaactgcct tcaagaggtc ctcgctgttg cttggcttga | 2520 |
| | | tcaaaattga ctctaacatg ttaccccat ccaacagggc tgcccctgcc ttcacggcag | 2580 |
| | | caccaagact aaagttatag ccagaaatgt tgatgctgga ctgctgttca gtgatgaccc | 2640 |
| | | ccagaactgg gtgcttgtct ttcagccttt caagatcatt aagatttgga tacttgactg | 2700 |
| | | tgtaaagcaa gccaaggtct gtgagcgctt gtacaacgtc attgagcgga gtctgtgact | 2760 |
| | | gtttggccat acaagccata gttagacttg gcattgtgcc aaattgattg ttcaaaagtg | 2820 |
| | | atgagtcttt cacatcccaa actcttacca caccacttgc accctgctga ggctttctca | 2880 |
| | | tcccaactat ctgtaggatc tgagatcttt ggtctagttg ctgtgttgtt aagttcccca | 2940 |
| | | tatatacccc tgaagcctgg ggcctttcag acctcatgat cttggccttc agcttctcaa | 3000 |
| | | ggtcagccgc aagagacatc agttcttctg cactgagcct ccccactttc aaaacattct | 3060 |

| SEQ ID NO. | Description | Sequence | |
|---|---|---|---|
| | | tctttgatgt tgactttaaa tccacaagag | |
| | | aatgtacagt ctggttgaga cttctgagtc | 3120 |
| | | tctgtaggtc tttgtcatct ctcttttcct | |
| | | tcctcatgat cctctgaaca ttgctgacct | 3180 |
| | | cagagaagtc caacccattc agaaggttgg | |
| | | ttgcatcctt aatgacagca gccttcacat | 3240 |
| | | ctgatgtgaa gctctgcaat tctcttctca | |
| | | atgcttgcgt ccattggaag ctcttaactt | 3300 |
| | | ccttagacaa ggacatcttg ttgctcaatg | |
| | | gtttctcaag acaaatgcgc aatcaaatgc | 3360 |
| | | ctaggatcca ctgtgcg | |
| 3 | LCMV clone 13 segment L, complete sequence (GenBank: DQ361066.1). The genomic segment is RNA, the sequence in SEQ ID NO: 3 is shown for DNA; however, exchanging all thymidines ("T") in SEQ ID NO: 3 for uridines ("U") provides the RNA sequence. | gcgcaccggg gatcctaggc gtttagttgc | |
| | | gctgtttggt tgcacaactt tcttcgtgag | 60 |
| | | gctgtcagaa gtggacctgg ctgatagcga | |
| | | tgggtcaagg caagtccaga gaggagaaag | 120 |
| | | gcaccaatag tacaaacagg gccgaaatcc | |
| | | taccagatac cacctatctt ggccctttaa | 180 |
| | | gctgcaaatc ttgctggcag aaatttgaca | |
| | | gcttggtaag atgccatgac cactaccttt | 240 |
| | | gcaggcactg tttaaacctt ctgctgtcag | |
| | | tatccgacag gtgtcctctt tgtaaatatc | 300 |
| | | cattaccaac cagattgaag atatcaacag | |
| | | ccccaagctc tccacctccc tacgaagagt | 360 |
| | | aacaccgtcc ggccccggcc ccgacaaaca | |
| | | gcccagcaca agggaaccgc acgtcaccca | 420 |
| | | acgcacacag acacagcacc caacacagaa | |
| | | cacgcacaca cacacacaca cacacccaca | 480 |
| | | cgcacgcgcc cccaccaccg gggggcgccc | |
| | | ccccccgggg ggcggccccc cgggagcccg | 540 |
| | | ggcggagccc cacggagatg cccatcagtc | |
| | | gatgtcctcg gccaccgacc cgcccagcca | 600 |
| | | atcgtcgcag gacctcccct tgagtctaaa | |
| | | cctgccccccc actgtttcat acatcaaagt | 660 |
| | | gctcctagat ttgctaaaac aaagtctgca | |
| | | atccttaaag gcgaaccagt ctggcaaaag | 720 |
| | | cgacagtgga atcagcagaa tagatctgtc | |
| | | tatacatagt tcctggagga ttacacttat | 780 |
| | | ctctgaaccc aacaaatgtt caccagttct | |
| | | gaatcgatgc aggaagaggt tcccaaggac | 840 |
| | | atcactaatc ttttcatagc cctcaagtcc | |
| | | tgctagaaag actttcatgt ccttggtctc | 900 |
| | | cagcttcaca atgatatttt ggacaaggtt | |
| | | tcttccttca aaaagggcac ccatctttac | 960 |
| | | agtcagtggc acaggctccc actcaggtcc | |
| | | aactctctca aagtcaatag atctaatccc | 1020 |
| | | atccagtatt cttttggagc ccaacaactc | |
| | | aagctcaaga gaatcaccaa gtatcaaggg | 1080 |
| | | atcttccatg taatcctcaa actcttcaga | |
| | | tctgatatca aagcaccat cgttcacctt | 1140 |
| | | gaagacagag tctgtcctca gtaagtggag | |
| | | gcattcatcc aacattcttc tatctatctc | 1200 |
| | | acccttaaag aggtgagagc atgataaaag | |
| | | ttcagccaca cctggattct gtaattggca | 1260 |
| | | cctaaccaag aatatcaatg aaaatttcct | |
| | | taaacagtca gtattattct gattgtgcgt | 1320 |
| | | aaagtccact gaaattgaaa actccaatac | |
| | | ccctttgtg tagttgagca tgtagtccca | 1380 |
| | | cagatccttt aaggatttaa atgcctttgg | |
| | | gtttgtcagg ccctgcctaa tcaacatggc | 1440 |
| | | agcattacac acaacatctc ccattcggta | |
| | | agagaaccac ccaaaaccaa actgcaaatc | 1500 |
| | | attcctaaac ataggcctct ccacattttt | |
| | | gttcaccacc tttgagacaa atgattgaaa | 1560 |
| | | ggggcccagt gcctcagcac catcttcaga | |
| | | tggcatcatt tctttatgag ggaaccatga | 1620 |
| | | aaaattgcct aatgtcctgg ttgttgcaac | |
| | | aaattctcga acaaatgatt caaaatacac | 1680 |
| | | ctgttttaag aagttcttgc agacatccct | |
| | | cgtgctaaca acaaattcat caaccagact | 1740 |
| | | ggagtcagat cgctgatgag aattggcaag | |
| | | gtcagaaaac agaacagtgt aatgttcatc | 1800 |
| | | cctttccac ttaacaacat gagaaatgag | |
| | | tgacaaggat tctgagttaa tatcaattaa | 1860 |
| | | aacacagagg tcaaggaatt taattctggg | |
| | | actccacctc atgtttttg agctcatgtc | 1920 |

| SEQ ID NO. | Description | Sequence | |
|---|---|---|---|
| | | agacataaat ggaagaagct gatcctcaaa | |
| | | gatcttggga tatagccgcc tcacagattg | 1980 |
| | | aatcacttgg ttcaaattca ctttgtcctc | |
| | | cagtagcctt gagctctcag gctttcttgc | 2040 |
| | | tacataatca catgggttta agtgcttaag | |
| | | agttaggttc tcactgttat tcttcccttt | 2100 |
| | | ggtcggttct gctaggaccc aaacacccaa | |
| | | ctcaaaagag ttgctcaatg aaatacaaat | 2160 |
| | | gtagtcccaa agaagaggcc ttaaaaggca | |
| | | tatatgatca cggtgggctt ctggatgaga | 2220 |
| | | ctgtttgtca caaatgtaca gcgttatacc | |
| | | atcccgattg caaactcttg tcacatgatc | 2280 |
| | | atctgtggtt agatcctcaa gcagcttttt | |
| | | gatatacaga ttttccctat ttttgtttct | 2340 |
| | | cacacacctg cttcctagag ttttgcaaag | |
| | | gcctataaag ccagatgaga tacaactctg | 2400 |
| | | gaaagctgac ttgttgattg cttctgacag | |
| | | cagcttctgt gcaccccttg tgaatttact | 2460 |
| | | acaaagtttg ttctggagtg tcttgatcaa | |
| | | tgatgggatt ctttcctctt ggaaagtcat | 2520 |
| | | cactgatgga taaaccacct tttgtcttaa | |
| | | aaccatcctt aatgggaaca tttcattcaa | 2580 |
| | | attcaaccag ttaacatctg ctaactgatt | |
| | | cagatcttct tcaagaccga ggaggtctcc | 2640 |
| | | caattgaaga atggcctcct ttttatctct | |
| | | gttaaatagg tctaagaaaa attcttcatt | 2700 |
| | | aaattcacca ttttgagct tatgatgcag | |
| | | tttccttaca agctttctta caacctttgt | 2760 |
| | | ttcattagga cacagttcct caatgagtct | |
| | | ttgtattctg taacctctag aaccatccag | 2820 |
| | | ccaatctttc acatcagtgt tggtattcag | |
| | | tagaaatgga tccaagggga aattggcata | 2880 |
| | | ctttaggagg tccagtgttc tcctttggat | |
| | | actattaact agggagactg ggacgccatt | 2940 |
| | | tgcgatggct tgatctgcaa ttgtatctat | |
| | | tgtttcacaa agttgatgtg gctctttaca | 3000 |
| | | cttgacattg tgtagcgctg cagatacaaa | |
| | | ctttgtgaga agagggactt cctccccccca | 3060 |
| | | tacatagaat ctagattaa attctgcagc | |
| | | gaacctccca gccacacttt tgggctgat | 3120 |
| | | aaatttgttt aacaagccgc tcagatgaga | |
| | | ttggaattcc aacaggacaa ggactttcctc | 3180 |
| | | cggatcactt acaaccaggt cactcagcct | |
| | | cctatcaaat aaagtgatct gatcatcact | 3240 |
| | | tgatgtgtaa gcctctggtc tttcgccaaa | |
| | | gataacacca atgcagtagt tgatgaacct | 3300 |
| | | ctcgctaagc aaaccataga agtcagaagc | |
| | | attatgcaag attccctgcc ccatatcaat | 3360 |
| | | aaggctggat atatgggatg gcactatccc | |
| | | catttcaaaa tattgtctga aaattctctc | 3420 |
| | | agtaacagtt gtttctgaac ccctgagaag | |
| | | ttttagcttc gacttgacat atgatttcat | 3480 |
| | | cattgcattc acaacaggaa aggggacctc | |
| | | gacaagctta tgcatgtgcc aagttaacaa | 3540 |
| | | agtgctaaca tgatctttcc cggaacgcac | |
| | | atactggtca tcacctagtt tgagattttg | 3600 |
| | | tagaaacatt aagaacaaaa atgggcacat | |
| | | cattggtccc catttgctgt gatccatact | 3660 |
| | | atagtttaag aacccttccc gcacattgat | |
| | | agtcattgac aagattgcat tttcaaattc | 3720 |
| | | cttatcattg tttaaacagg agcctgaaaa | |
| | | gaaacttgaa aaagactcaa aataatcttc | 3780 |
| | | tattaacctt gtgaacattt ttgtcctcaa | |
| | | atctccaata tagagttctc tatttccccc | 3840 |
| | | aacctgctct ttataagata gtgcaaattt | |
| | | cagccttcca gagtcaggac ctactgaggt | 3900 |
| | | gtatgatgtt ggtgattctt ctgagtagaa | |
| | | gcacagattt ttcaaagcag cactcataca | 3960 |
| | | ttgtgtcaac gacagagctt tactaaggga | |
| | | ctcagaatta cttttccctct cactgattct | 4020 |
| | | cacgtcttct tccagtttgt cccagtcaaa | |
| | | tttgaaattc aagccttgcc tttgcatatg | 4080 |
| | | cctgtatttc cctgagtacg catttgcatt | |
| | | catttgcaac agaatcatct tcatgcaaga | 4140 |
| | | aaaccaatca ttctcagaaa agaactttct | |
| | | acaaaggttt tttgccatct catcgaggcc | 4200 |

| SEQ ID NO. | Description | Sequence | |
|---|---|---|---|
| | | acactgatct ttaatgactg aggtgaaata | |
| | | caaaggtgac agctctgtgg aaccctcaac | 4260 |
| | | agcctcacag ataaatttca tgtcatcatt | |
| | | ggttagacat gatgggtcaa agtcttctac | 4320 |
| | | taaatggaaa gatatttctg acaagataac | |
| | | ttttcttaag tgagccatct tccctgttag | 4380 |
| | | aataagctgt aaatgatgta gtccttttgt | |
| | | atttgtaagt ttttctccat ctccttttgtc | 4440 |
| | | attggccctc ctacctcttc tgtaccgtgc | |
| | | tattgtggtg ttgacctttt cttcgagact | 4500 |
| | | tttgaagaag cttgtctctt cttctccatc | |
| | | aaaacatatt tctgccaggt tgtcttccga | 4560 |
| | | tctccctgtc tcttctccct tggaaccgat | |
| | | gaccaatcta gagactaact tggaaacttt | 4620 |
| | | atattcatag tctgagtggc tcaacttata | |
| | | cttttgtttt cttacgaaac tctccgtaat | 4680 |
| | | ttgactcaca gcactaacaa gcaatttgtt | |
| | | aaagtcatat tccagaagtc gttctccatt | 4740 |
| | | tagatgctta ttaaccacca cactttttgtt | |
| | | actagcaaga tctaatgctg tcgcacatcc | 4800 |
| | | agagttagtc atgggatcta ggctgtttag | |
| | | cttcttctct cctttgaaaa ttaaagtgcc | 4860 |
| | | gttgttaaat gaagacacca ttaggctaaa | |
| | | ggcttccaga ttaacacctg gagttgtatg | 4920 |
| | | ctgacagtca atttctttac tagtgaatct | |
| | | cttcatttgc tcatagaaca cacattcttc | 4980 |
| | | ctcaggagtg attgcttcct tggggttgac | |
| | | aaaaaaacca aattgacttt tgggctcaaa | 5040 |
| | | gaacttttca aaacatttta tctgatctgt | |
| | | tagcctgtca ggggtctcct ttgtgatcaa | 5100 |
| | | atgacacagg tatgacacat tcaacataaa | |
| | | tttaaatttt gcactcaaca caccttctc | 5160 |
| | | accagtacca aaaatagttt ttattaggaa | |
| | | tctaagcagc ttatacacca ccttctcagc | 5220 |
| | | aggtgtgatc agatcctccc tcaacttatc | |
| | | cattaatgat gtagatgaaa aatctgacac | 5280 |
| | | tattgccatc accaaatatc tgacactctg | |
| | | tacctgcttt tgatttctct ttgttgggtt | 5340 |
| | | ggtgagcatt agcaacaata gggtcctcag | |
| | | tgcaacctca atgtcggtga gacagtcttt | 5400 |
| | | caaatcagga catgatctaa tccatgaaat | |
| | | catgatgtct atcatattgt ataagacctc | 5460 |
| | | atctgaaaaa attggtaaaa agaacctttt | |
| | | aggatctgca tagaaggaaa ttaaatgacc | 5520 |
| | | atccgggcct tgtatggagt agcaccttga | |
| | | agattctcca gtcttctggt ataataggtg | 5580 |
| | | gtattcttca gagtccagtt ttattacttg | |
| | | gcaaaacact tctttgcatt ctaccacttg | 5640 |
| | | atatctcaca gaccctattt gattttgcct | |
| | | tagtctagca actgagctag ttttcatact | 5700 |
| | | gtttgttaag gccagacaaa cagatgataa | |
| | | tcttctcagg ctctgtatgt tcttcagctg | 5760 |
| | | ctctgtgctg ggttggaaat tgtaatcttc | |
| | | aaacttcgta taatacatta tcgggtgagc | 5820 |
| | | tccaattttc ataaagttct caaattcagt | |
| | | gaatggtatg tggcattctt gctcaaggtg | 5880 |
| | | ttcagacagt ccgtaatgct cgaaactcag | |
| | | tcccaccact aacaggcatt tttgaatttt | 5940 |
| | | tgcaatgaac tcactaatag atgccctaaa | |
| | | caattcctca aaagacacct ttctaaacac | 6000 |
| | | cttttgacttt tttctattcc tcaaaagtct | |
| | | aatgaactcc tctttagtgc tgtgaaagct | 6060 |
| | | taccagccta tcattcacac tactatagca | |
| | | acaacccacc cagtgtttat cattttttaa | 6120 |
| | | cccttttgaat ttcgactgtt ttatcaatga | |
| | | ggaaagacac aaaacatcca gatttaacaa | 6180 |
| | | ctgtctcctt ctagtattca acagtttcaa | |
| | | actcttgact ttgtttaaca tagagaggag | 6240 |
| | | cctctcatat tcagtgctag tctcacttcc | |
| | | cctttcgtgc ccatgggtct ctgcagttat | 6300 |
| | | gaatctcatc aaaggacagg attcgactgc | |
| | | ctccctgctt aatgttaaga tatcatcact | 6360 |
| | | atcagcaagg ttttcataga gctcagagaa | |
| | | ttccttgatc aagccttcag ggtttacttt | 6420 |
| | | ctgaaagttt ctctttaatt tcccactttc | |
| | | taaatctctt ctaaacctgc tgaaaagaga | 6480 |

| SEQ ID NO. | Description | Sequence | |
|---|---|---|---|
| | | gtttattcca aaaaccacat catcacagct | |
| | | catgttgggg ttgatgcctt cgtggcacat | 6540 |
| | | cctcataatt tcatcattgt gagttgacct | |
| | | cgcatctttc agaattttca tagagtccat | 6600 |
| | | accggagcgc ttgtcgatag tagtcttcag | |
| | | ggactcacag agtctaaaat attcagactc | 6660 |
| | | ttcaaagact ttctcatttt ggttagaata | |
| | | ctccaaaagt ttgaataaaa ggtctctaaa | 6720 |
| | | tttgaagttt gcccactctg gcataaaact | |
| | | attatcataa tcacaacgac catctactat | 6780 |
| | | tggaactaat gtgacacccg caacagcaag | |
| | | gtcttccctg atgcatgcca atttgttagt | 6840 |
| | | gtcctctata aatttcttct caaaactggc | |
| | | tggagtgctc ctaacaaaac actcaagaag | 6900 |
| | | aatgagagaa ttgtctatca gcttgtaacc | |
| | | atcaggaatg ataagtggta gtcctgggca | 6960 |
| | | tacaattcca gactccacca aaattgtttc | |
| | | cacagactta tcgtcgtggt tgtgtgtgca | 7020 |
| | | gccactcttg tctgcactgt ctatttcaat | |
| | | gcagcgtgac agcaacttga gtccctcaat | 7080 |
| | | cagaaccatt ctgggttccc tttgtcccag | |
| | | aaagttgagt ttctgccttg acaacctctc | 7140 |
| | | atcctgttct atatagttta aacataactc | |
| | | tctcaattct gagatgattt catccattgc | 7200 |
| | | gcatcaaaaa gcctaggatc ctcggtgcg | |
| | | | 7229 |
| 4 | LCMV strain MP segment L, complete sequence. The genomic segment is RNA, the sequence in SEQ ID NO: 4 is shown for DNA; however, exchanging all thymidines ("T") in SEQ ID NO: 4 for uridines ("U") provides the RNA sequence. | gcgcaccggg gatcctaggc attttttgttg | |
| | | cgcattttgt tgtgttattt gttgcacagc | 60 |
| | | ccttcatcgt gggaccttca caaacaaacc | |
| | | aaaccaccag ccatgggcca aggcaagtcc | 120 |
| | | aaagagggaa gggatgccag caatacgagc | |
| | | agagctgaaa ttctgccaga caccacctat | 180 |
| | | ctcggacctc tgaactgcaa gtcatgctgg | |
| | | cagagatttg acagtttagt cagatgccat | 240 |
| | | gaccactatc tgcagaca ctgcctgaac | |
| | | ctcctgctgt cagtctccga caggtgccct | 300 |
| | | ctctgcaaac atccattgcc aaccaaactg | |
| | | aaaatatcca cggcccaag ctctccaccc | 360 |
| | | ccttacgagg agtgacgccc cgagcccaa | |
| | | caccgacaca aggaggccac caacacaacg | 420 |
| | | cccaacacgg aacacacaca cacacaccca | |
| | | cacacacatc cacacacacg cgcccccaca | 480 |
| | | acggggcgc cccccgggg gtggcccccc | |
| | | gggtgctcgg gcggagcccc acggagaggc | 540 |
| | | caattagtcg atctcctcga ccaccgactt | |
| | | ggtcagccag tcatcacagg acttgccctt | 600 |
| | | aagtctgtac ttgcccacaa ctgtttcata | |
| | | catcaccgtg ttctttgact tactgaaaca | 660 |
| | | tagcctacag tctttgaaag tgaaccagtc | |
| | | aggcacaagt gacagcggta ccagtagaat | 720 |
| | | ggatctatct atacacaact cttggagaat | |
| | | tgtgctaatt tccgacccct gtagatgctc | 780 |
| | | accagttctg aatcgatgta gaagaaggct | |
| | | cccaaggacg tcatcaaaat ttccataacc | 840 |
| | | ctcgagctct gccaagaaaa ctctcatatc | |
| | | cttggtctcc agtttcacaa cgatgttctg | 900 |
| | | aacaaggctt cttccctcaa aaagagcacc | |
| | | cattctcaca gtcaagggca caggctccca | 960 |
| | | ttcaggccca atcctctcaa aatcaaggga | |
| | | tctgatcccg tccagtattt tccttgagcc | 1020 |
| | | tatcagctca agctcaagag agtcaccgag | |
| | | tatcagggg tcctccatat agtcctcaaa | 1080 |
| | | ctcttcagac ctaatgtcaa aaacaccatc | |
| | | gttcaccttg aagatagagt ctgatctcaa | 1140 |
| | | caggtggagg cattcgtcca agaaccttct | |
| | | gtccacctca cctttaaaga ggtgagagca | 1200 |
| | | tgataggaac tcagctacac ctggaccttg | |
| | | taactggcac ttcactaaaa agatcaatga | 1260 |
| | | aaacttcctc aaacaatcag tgttattctg | |
| | | gttgtgagtg aaatctactg taattgagaa | 1320 |
| | | ctctagcact ccctctgtat tatttatcat | |
| | | gtaatcccac aagtttctca aagacttgaa | 1380 |
| | | tgcctttgga tttgtcaagc cttgtttgat | |
| | | tagcatggca gcattgcaca caatatctcc | 1440 |

| SEQ ID NO. | Description | Sequence | |
|---|---|---|---|
| | | caatcggtaa gagaaccatc caaatccaaa | |
| | | ttgcaagtca ttcctaaaca tgggcctctc | 1500 |
| | | catattttg ttcactactt ttaagatgaa | |
| | | tgattggaaa ggccccaatg cttcagcgcc | 1560 |
| | | atcttcagat ggcatcatgt ctttatgagg | |
| | | gaaccatgaa aaacttccta gagttctgct | 1620 |
| | | tgttgctaca aattctcgta caaatgactc | |
| | | aaaatacact tgttttaaaa agttttgca | 1680 |
| | | gacatccctt gtactaacga caaattcatc | |
| | | aacaaggctt gagtcagagc gctgatggga | 1740 |
| | | atttacaaga tcagaaaata gaacagtgta | |
| | | gtgttcgtcc ctcttccact taactacatg | 1800 |
| | | agaaatgagc gataaagatt ctgaattgat | |
| | | atcgatcaat acgcaaaggt caaggaattt | 1860 |
| | | gattctggga ctccatctca tgtttttga | |
| | | gctcatatca gacatgaagg gaagcagctg | 1920 |
| | | atcttcatag attttagggt acaatcgcct | |
| | | cacagattgg attacatggt ttaaacttat | 1980 |
| | | cttgtcctcc agtagccttg aactctcagg | |
| | | cttccttgct acataatcac atgggttcaa | 2040 |
| | | gtgcttgagg cttgagcttc cctcattctt | |
| | | cccttcaca ggttcagcta agacccaaac | 2100 |
| | | acccaactca aaggaattac tcagtgagat | |
| | | gcaaatatag tcccaaagga ggggcctcaa | 2160 |
| | | gagactgatg tggtcgcagt gagcttctgg | |
| | | atgactttgc ctgtcacaaa tgtacaacat | 2220 |
| | | tatgccatca tgtctgtgga ttgctgtcac | |
| | | atgcgcatcc atagctagat cctcaagcac | 2280 |
| | | ttttctaatg tatagattgt ccctattttt | |
| | | atttctcaca catctacttc ccaaagtttt | 2340 |
| | | gcaaagacct ataaagcctg atgagatgca | |
| | | actttgaaag gctgacttat tgattgcttc | 2400 |
| | | tgacagcaac ttctgtgcac ctcttgtgaa | |
| | | cttactgcag agcttgttct ggagtgtctt | 2460 |
| | | gattaatgat gggattcttt cctcttggaa | |
| | | agtcattact gatggataaa ccactttctg | 2520 |
| | | cctcaagacc attcttaatg ggaacaactc | |
| | | attcaaattc agccaattta tgtttgccaa | 2580 |
| | | ttgacttaga tcctcttcga ggccaaggat | |
| | | gtttcccaac tgaagaatgg cttcctttt | 2640 |
| | | atccctattg aagaggtcta agaagaattc | |
| | | ttcattgaac tcaccattct tgagcttatg | 2700 |
| | | atgtagtctc cttacaagcc ttctcatgac | |
| | | cttcgtttca ctaggacaca attcttcaat | 2760 |
| | | aagcctttgg attctgtaac ctctagagcc | |
| | | atccaaccaa tccttgacat cagtattagt | 2820 |
| | | gttaagcaaa aatgggtcca agggaaagtt | |
| | | ggcatatttt aagaggtcta atgttctctt | 2880 |
| | | ctggatgcag tttaccaatg aaactggaac | |
| | | accatttgca acagcttgat cggcaattgt | 2940 |
| | | atctattgtt tcacagagtt ggtgtggctc | |
| | | tttacactta acgttgtgta atgctgctga | 3000 |
| | | cacaaatttt gttaaaagtg ggacctcttc | |
| | | cccccacaca taaaatctgg atttaaattc | 3060 |
| | | tgcagcaaat cgccccacca cactttcgg | |
| | | actgatgaac ttgttaagca agccactcaa | 3120 |
| | | atgagaatga aattccagca atacaaggac | |
| | | ttcctcaggg tcactatcaa ccagttcact | 3180 |
| | | caatctccta tcaaataagg tgatctgatc | |
| | | atcacttgat gtgtaagatt ctggtctctc | 3240 |
| | | accaaaaatg acaccgatac aataattaat | |
| | | gaatctctca ctgattaagc cgtaaaagtc | 3300 |
| | | agaggcatta tgtaagattc cctgtcccat | |
| | | gtcaatgaga ctgcttatat gggaaggcac | 3360 |
| | | tattcctaat tcaaaatatt ctcgaaagat | |
| | | tctttcagtc acagttgtct ctgaaccct | 3420 |
| | | aagaagtttc agctttgatt tgatatatga | |
| | | tttcatcatt gcattcacaa caggaaaagg | 3480 |
| | | gacctcaaca agtttgtgca tgtgccaagt | |
| | | taataaggtg ctgatatgat cctttccgga | 3540 |
| | | acgcacatac tggtcatcac ccagtttgag | |
| | | attttgaagg agcattaaaa acaaaaatgg | 3600 |
| | | gcacatcatt ggcccccatt tgctatgatc | |
| | | catactgtag ttcaacaacc cctctcgcac | 3660 |
| | | attgatggtc attgatagaa ttgcattttc | |
| | | aaattcttg tcattgttta agcatgaacc | 3720 |

| SEQ ID NO. | Description | Sequence | |
|---|---|---|---|
| | | tgagaagaag ctagaaaaag actcaaaata | |
| | | atcctctatc aatcttgtaa acattttgt | 3780 |
| | | tctcaaatcc ccaatataaa gttctctgtt | |
| | | tcctccaacc tgctctttgt atgataacgc | 3840 |
| | | aaacttcaac cttccggaat caggaccaac | |
| | | tgaagtgtat gacgttggtg actcctctga | 3900 |
| | | gtaaaaacat aaattcttta aagcagcact | |
| | | catgcatttt gtcaatgata gagccttact | 3960 |
| | | tagagactca gaattacttt ccctttcact | |
| | | aattctaaca tcttcttcta gtttgtccca | 4020 |
| | | gtcaaacttg aaattcagac cttgtctttg | |
| | | catgtgcctg tatttccctg agtatgcatt | 4080 |
| | | tgcattcatt tgcagtagaa tcattttcat | |
| | | acacgaaaac caatcaccct ctgaaaaaaa | 4140 |
| | | cttcctgcag aggtttttg ccatttcatc | |
| | | cagaccacat tgttctttga cagctgaagt | 4200 |
| | | gaaatacaat ggtgacagtt ctgtagaagt | |
| | | ttcaatagcc tcacagataa atttcatgtc | 4260 |
| | | atcattggtg agacaagatg ggtcaaaatc | |
| | | ttccacaaga tgaaaagaaa tttctgataa | 4320 |
| | | gatgaccttc cttaaatatg ccattttacc | |
| | | tgacaatata gtctgaaggt gatgcaatcc | 4380 |
| | | ttttgtattt tcaaacccca cctcatttc | |
| | | cccttcattg gtcttcttgc ttctttcata | 4440 |
| | | ccgctttatt gtggagttga ccttatcttc | |
| | | taaattcttg aagaaacttg tctcttcttc | 4500 |
| | | cccatcaaag catatgtctg ctgagtcacc | |
| | | ttctagtttc ccagcttctg tttctttaga | 4560 |
| | | gccgataacc aatctagaga ccaactttga | |
| | | aaccttgtac tcgtaatctg agtggttcaa | 4620 |
| | | tttgtacttc tgctttctca tgaagctctc | |
| | | tgtgatctga ctcacagcac taacaagcaa | 4680 |
| | | tttgttaaaa tcatactcta ggagccgttc | |
| | | cccatttaaa tgtttgttaa caaccacact | 4740 |
| | | tttgttgctg gcaaggtcta atgctgttgc | |
| | | acacccagag ttagtcatgg gatccaagct | 4800 |
| | | attgagcctc ttctcccctt tgaaaatcaa | |
| | | agtgccattg ttgaatgagg acaccatcat | 4860 |
| | | gctaaaggcc tccagattga cacctggggt | |
| | | tgtgcgctga cagtcaactt cttccccagt | 4920 |
| | | gaacttcttc atttggtcat aaaaaacaca | |
| | | ctcttcctca ggggtgattg actcttagg | 4980 |
| | | gttaacaaag aagccaaact cacttttagg | |
| | | ctcaaagaat ttctcaaagc atttaatttg | 5040 |
| | | atctgtcagc ctatcagggg tttcctttgt | |
| | | gattaaatga cacaggtatg acacattcaa | 5100 |
| | | catgaacttg aactttgcgc tcaacagtac | |
| | | cttttcacca gtcccaaaaa cagttttgat | 5160 |
| | | caaaaatctg agcaatttgt acactacttt | |
| | | ctcagcaggt gtgatcaaat cctccttcaa | 5220 |
| | | cttgtccatc aatgatgtgg atgagaagtc | |
| | | tgagacaatg gccatcacta aatacctaat | 5280 |
| | | gttttgaacc tgttttttgat tcctctttgt | |
| | | tgggttggtg agcatgagta ataataggg | 5340 |
| | | tctcaatgca atctcaacat catcaatgct | |
| | | gtccttcaag tcaggacatg atctgatcca | 5400 |
| | | tgagatcatg gtgtcaatca tgttgtgcaa | |
| | | cacttcatct gagaagattg gtaaaaagaa | 5460 |
| | | cctttttggg tctgcataaa aagagattag | |
| | | atggccattg ggaccttgta tagaataaca | 5520 |
| | | ccttgaggat tctccagtct tttgatacag | |
| | | caggtgatat tcctcagagt ccaattttat | 5580 |
| | | cacttggcaa aatacctctt tacattccac | |
| | | cacttgatac cttacagagc ccaattggtt | 5640 |
| | | ttgtcttaat ctagcaactg aacttgtttt | |
| | | catactgttt gtcaaagcta gacagacaga | 5700 |
| | | tgacaatctt ttcaaactat gcatgttcct | |
| | | taattgttcc gtattaggct ggaaatcata | 5760 |
| | | atcttcaaac tttgtataat acattatagg | |
| | | atgagttccg gacctcatga aattctcaaa | 5820 |
| | | ctcaataaat ggtatgtggc actcatgctc | |
| | | aagatgttca gacagaccat agtgcccaaa | 5880 |
| | | actaagtccc accactgaca agcacctttg | |
| | | aacttttaaa atgaactcat ttatggatgt | 5940 |
| | | tctaaacaaa tcctcaagag atacctttct | |
| | | atacgccttt gactttctcc tgttccttag | 6000 |

| SEQ ID NO. | Description | Sequence | |
|---|---|---|---|
| | | aagtctgatg aactcttcct tggtgctatg | |
| | | aaagctcacc aacctatcat tcacactccc | 6060 |
| | | atagcaacaa ccaacccagt gcttatcatt | |
| | | ttttgacccct ttgagtttag actgtttgat | 6120 |
| | | caacgaagag agacacaaga catccaaatt | |
| | | cagtaactgt ctccttctgg tgttcaataa | 6180 |
| | | ttttaaactt ttaactttgt tcaacataga | |
| | | gaggagcctc tcatactcag tgctagtctc | 6240 |
| | | acttcctctc tcataaccat gggtatctgc | |
| | | tgtgataaat ctcatcaaag gacaggattc | 6300 |
| | | aactgcctcc ttgcttagtg ctgaaatgtc | |
| | | atcactgtca gcaagagtct cataaagctc | 6360 |
| | | agagaattcc ttaattaaat ttccggggtt | |
| | | gattttctga aaactcctct tgagcttccc | 6420 |
| | | agtttccaag tctcttctaa acctgctgta | |
| | | aagggagttt atgccaagaa ccacatcatc | 6480 |
| | | gcagttcatg tttgggttga caccatcatg | |
| | | gcacattttc ataatttcat cattgtgaaa | 6540 |
| | | tgatcttgca tctttcaaga ttttcataga | |
| | | gtctataccg gaacgcttat caacagtggt | 6600 |
| | | cttgagagat tcgcaaagtc tgaagtactc | |
| | | agattcctca aagactttct catcttggct | 6660 |
| | | agaatactct aaaagtttaa acagaaggtc | |
| | | tctgaacttg aaattcaccc actctggcat | 6720 |
| | | aaagctgtta tcataatcac accgaccatc | |
| | | cactattggg accaatgtga tacccgcaat | 6780 |
| | | ggcaaggtct tctttgatac aggctagttt | |
| | | attggtgtcc tctataaatt tcttctcaaa | 6840 |
| | | actagctggt gtgcttctaa cgaagcactc | |
| | | aagaagaatg agggaattgt caatcagttt | 6900 |
| | | ataaccatca ggaatgatca aaggcagtcc | |
| | | cgggcacaca atcccagact ctattagaat | 6960 |
| | | tgcctcaaca gatttatcat catggttgtg | |
| | | tatgcagccg ctcttgtcag cactgtctat | 7020 |
| | | ctctatacaa cgcgacaaaa gtttgagtcc | |
| | | ctctatcaat accattctgg gttctcttg | 7080 |
| | | ccctaaaaag ttgagcttct gccttgacaa | |
| | | cctctcatct tgttctatgt ggtttaagca | 7140 |
| | | caactctctc aactccgaaa tagcctcatc | |
| | | cattgcgcat caaaaagcct aggatcctcg | 7200 |
| | | gtgcg | 7205 |
| 5 | LCMV strain MP segment S, complete sequence. The genomic segment is RNA, the sequence in SEQ ID NO: 5 is shown for DNA; however, exchanging all thymidines ("T") in SEQ ID NO: 5 for uridines ("U") provides the RNA sequence. | cgcaccgggg atcctaggct ttttggattg cgctttcctc agctccgtct tgtgggagaa | 60 |
| | | tgggtcaaat tgtgacgatg tttgaggctc tgcctcacat cattgatgag gtcattaaca | 120 |
| | | ttgtcattat cgtgctatt atcatcacga gcatcaaagc tgtgtacaat ttcgccacct | 180 |
| | | gcgggatact tgcattgatc agcttttctt ttctggctgg caggtcctgt ggaatgtatg | 240 |
| | | gtcttgatgg gcctgacatt tacaaagggg tttaccgatt caagtcagtg gagtttgaca | 300 |
| | | tgtcttacct taacctgacg atgcccaatg catgttcggc aaacaactcc catcattata | 360 |
| | | taagtatggg gacttctgga ttggagttaa ccttcacaaa tgactccatc atcacccaca | 420 |
| | | actttttgtaa tctgacttcc gccctcaaca agaggacttt tgaccacaca cttatgagta | 480 |
| | | tagtctcaag tctgcacctc agcattagag gggtccccag ctacaaagca gtgtcctgtg | 540 |
| | | attttaacaa tggcatcact attcaataca acctgtcatt ttctaatgca cagagcgctc | 600 |
| | | tgagtcaatg taagaccttc aggggagag tcctggatat gttcagaact gcttttggag | 660 |
| | | gaaagtacat gaggagtggc tggggctgga caggttcaga tggcaagact acttggtgca | 720 |
| | | gccagacaaa ctaccaatat ctgattatac aaaacaggac ttgggaaaac cactgcaggt | 780 |
| | | acgcaggccc tttcggaatg tctagaattc tcttcgctca agaaaagaca aggtttctaa | 840 |
| | | ctagaaggct tgcaggcaca ttcacttgga ctttatcaga ctcatcagga gtggagaatc | 900 |
| | | caggtggtta ctgcttgacc aagtggatga tcctcgctgc agagctcaag tgtttggga | 960 |
| | | acacagctgt tgcaaagtgc aatgtaaatc atgatgaaga gttctgtgat atgctacgac | 1020 |

| SEQ ID NO. | Description | Sequence | |
|---|---|---|---|
| | | tgattgatta caacaaggct gctttgagta | |
| | | aattcaaaga agatgtagaa tccgctctac | 1080 |
| | | atctgttcaa gacaacagtg aattctttga | |
| | | tttctgatca gcttttgatg agaaatcacc | 1140 |
| | | taagagactt gatgggagtg ccatactgca | |
| | | attactcgaa attctggtat ctagagcatg | 1200 |
| | | caaagactgg tgagactagt gtccccaagt | |
| | | gctggcttgt cagcaatggt tcttatttga | 1260 |
| | | atgaaaccca tttcagcgac caaattgagc | |
| | | aggaagcaga taatatgatc acagaaatgc | 1320 |
| | | tgagaaagga ctacataaaa aggcaaggga | |
| | | gtacccctct agccttgatg gatctattga | 1380 |
| | | tgttttctac atcagcatat ttgatcagca | |
| | | tctttctgca tcttgtgagg ataccaacac | 1440 |
| | | acagacacat aaagggcggc tcatgcccaa | |
| | | aaccacatcg gttaaccagc aagggaatct | 1500 |
| | | gtagttgtgg tgcatttaaa gtaccaggtg | |
| | | tggaaaccac ctggaaaaga cgctgaacag | 1560 |
| | | cagcgcctcc ctgactcacc acctcgaaag | |
| | | aggtggtgag tcagggaggc ccagagggtc | 1620 |
| | | ttagagtgtt acgacatttg gacctctgaa | |
| | | gattaggtca tgtggtagga tattgtggac | 1680 |
| | | agttttcagg tcggggagcc ttgccttgaa | |
| | | ggcgcttca aagatgatac agtccatgag | 1740 |
| | | tgcacagtgt ggggtgacct cttttctttt | |
| | | cttgtccctc actattccag tgtgcatctt | 1800 |
| | | gcatagccag ccatatttgt cccagacttt | |
| | | gtcctcatat tctcttgaag cttctttagt | 1860 |
| | | catctcaaca tcgatgagct taatgtctct | |
| | | tctgttttgt gaatctagga gtttcctgat | 1920 |
| | | gtcatcagat ccctgacaac ttaggaccat | |
| | | tccctgtgga agagcaccta ttactgaaga | 1980 |
| | | tgtcagccca ggttgtgcat tgaagaggtc | |
| | | agcaaggtcc atgccatgtg agtatttgga | 2040 |
| | | gtcctgcttg aattgttttt gatcagtggg | |
| | | ttctctatag aaatgtatgt actgcccatt | 2100 |
| | | ctgtggctga aatattgcta tttctaccgg | |
| | | gtcattaaat ctgccctcaa tgtcaatcca | 2160 |
| | | tgtaggagcg ttagggtcaa tacctcccat | |
| | | gaggtccttc agcaacattg tttggctgta | 2220 |
| | | gcttaagccc acctgaggtg ggcccgctgc | |
| | | cccaggcgct ggtttgggtg agttggccat | 2280 |
| | | aggcctctca tttgtcagat caattgttgt | |
| | | gttctcccat gctctcccta caactgatgt | 2340 |
| | | tctacaagct atgtatggcc acccctcccc | |
| | | tgaaagacag actttgtaga ggatgttctc | 2400 |
| | | gtaaggattc ctgtctccaa cctgatcaga | |
| | | aacaaacatg ttgagtttct tcttggcccc | 2460 |
| | | aagaactgct ttcaggagat cctcactgtt | |
| | | gcttggctta attaagatgg attccaacat | 2520 |
| | | gttaccccca tctaacaagg ctgcccctgc | |
| | | tttcacagca gcaccgagac tgaaattgta | 2580 |
| | | gccagatatg ttgatgctag actgctgctc | |
| | | agtgatgact cccaagactg ggtgcttgtc | 2640 |
| | | tttcagcctt tcaaggtcac ttaggttcgg | |
| | | gtacttgact gtgtaaagca gcccaaggtc | 2700 |
| | | tgtgagtgct tgcacaacgt cattgagtga | |
| | | ggtttgtgat tgtttggcca tacaagccat | 2760 |
| | | tgttaagctt ggcattgtgc cgaattgatt | |
| | | gttcagaagt gatgagtcct tcacatccca | 2820 |
| | | gaccctcacc acaccatttg cactctgctg | |
| | | aggtctcctc attccaacca tttgcagaat | 2880 |
| | | ctgagatctt tggtcaagtc gttgtgctgt | |
| | | taagttcccc atgtagactc cagaagttag | 2940 |
| | | aggcctttca gacctcatga ttttagcctt | |
| | | cagttttca aggtcagctg caagggacat | 3000 |
| | | cagttcttct gcactaagcc tccctacttt | |
| | | tagaacattc ttttttgatg ttgactttag | 3060 |
| | | gtccacaagg gaatacacag tttggttgag | |
| | | gcttctgagt ctctgtaaat ctttgtcatc | 3120 |
| | | cctcttctct ttcctcatga tcctctgaac | |
| | | attgctcacc tcagagaagt ctaatccatt | 3180 |
| | | cagaaggctg gtggcatcct tgatcacagc | |
| | | agctttcaca tctgatgtga agccttgaag | 3240 |
| | | ctctctcctc aatgcctggg tccattgaaa | |
| | | gcttttaact tctttggaca gagacatttt | 3300 |

| SEQ ID NO. | Description | Sequence | |
|---|---|---|---|
| | | gtcactcagt ggatttccaa gtcaaatgcg<br>caatcaaaat gcctaggatc cactgtgcg | 3359 |
| 6 | Amino acid sequence of the NP protein of the MP strain of LCMV. | Met Ser Leu Ser Lys Glu Val Lys Ser Phe<br>Gln Trp Thr Gln Ala Leu Arg Arg Glu Leu<br>Gln Gly Phe Thr Ser Asp Val Lys Ala Ala<br>Val Ile Lys Asp Ala Thr Ser Leu Leu Asn<br>Gly Leu Asp Phe Ser Glu Val Ser Asn Val<br>Gln Arg Ile Met Arg Lys Glu Lys Arg Asp<br>Asp Lys Asp Leu Gln Arg Leu Arg Ser Leu<br>Asn Gln Thr Val Tyr Ser Leu Val Asp Leu<br>Lys Ser Thr Ser Lys Lys Asn Val Leu Lys<br>Val Gly Arg Leu Ser Ala Glu Glu Leu Met<br>Ser Leu Ala Ala Asp Leu Glu Lys Leu Lys<br>Ala Lys Ile Met Arg Ser Glu Arg Pro Leu<br>Thr Ser Gly Val Tyr Met Gly Asn Leu Thr<br>Ala Gln Gln Leu Asp Gln Arg Ser Gln Ile<br>Leu Gln Met Val Gly Met Arg Arg Pro Gln<br>Gln Ser Ala Asn Gly Val Val Arg Val Trp<br>Asp Val Lys Asp Ser Ser Leu Leu Asn Asn<br>Gln Phe Gly Thr Met Pro Ser Leu Thr Met<br>Ala Cys Met Ala Lys Gln Ser Gln Thr Ser<br>Leu Asn Asp Val Val Gln Ala Leu Thr Asp<br>Leu Gly Leu Leu Tyr Thr Val Lys Tyr Pro<br>Asn Leu Ser Asp Leu Glu Arg Leu Lys Asp<br>Lys His Pro Val Leu Gly Val Ile Thr Glu<br>Gln Gln Ser Ser Ile Asn Ile Ser Gly Tyr<br>Asn Phe Ser Leu Gly Ala Ala Val Lys Ala<br>Gly Ala Ala Leu Leu Asp Gly Gly Asn Met<br>Leu Glu Ser Ile Leu Ile Lys Pro Ser Asn<br>Ser Glu Asp Leu Lys Ala Val Leu Gly<br>Ala Lys Lys Lys Leu Asn Met Phe Asp Arg<br>Asn Pro Tyr Glu Asn Ile Leu Tyr Lys Val<br>Cys Leu Ser Gly Glu Gly Trp Pro Tyr Ile<br>Ala Cys Arg Thr Ser Val Val Gly Arg Ala<br>Trp Glu Asn Thr Thr Ile Asp Leu Thr Asn<br>Glu Arg Pro Met Ala Asn Ser Pro Lys Pro<br>Ala Pro Gly Ala Ala Gly Pro Pro Gln Val<br>Gly Leu Ser Tyr Ser Gln Thr Met Leu Leu<br>Lys Asp Leu Met Gly Gly Ile Asp Pro Asn<br>Ala Pro Thr Trp Ile Asp Ile Glu Gly Arg<br>Phe Asn Asp Pro Val Glu Ile Ala Ile Phe<br>Gln Pro Gln Asn Gly Gln Tyr Ile His Phe<br>Tyr Arg Glu Pro Thr Asp Gln Lys Gln Phe<br>Lys Gln Asp Ser Lys Tyr Ser His Gly Met<br>Asp Leu Ala Asp Leu Phe Asn Ala Gln Pro<br>Gly Leu Thr Ser Ser Val Ile Gly Ala Leu<br>Pro Gln Gly Met Val Leu Ser Cys Gln Gly<br>Ser Asp Asp Ile Arg Lys Leu Leu Asp Ser<br>Gln Asn Arg Arg Asp Ile Lys Leu Ile Asp<br>Val Glu Met Thr Lys Glu Ala Ser Arg Glu<br>Tyr Glu Asp Lys Val Trp Asp Lys Tyr Gly<br>Trp Leu Cys Lys Met His Thr Gly Ile Val<br>Arg Asp Lys Lys Lys Glu Val Thr Pro<br>His Cys Ala Leu Met Asp Cys Ile Ile Phe<br>Glu Ser Ala Ser Lys Ala Arg Leu Pro Asp<br>Leu Lys Thr Val His Asn Ile Leu Pro His<br>Asp Leu Ile Phe Arg Gly Pro Asn Val Val<br>Thr Leu | |
| 7 | Amino acid sequence of the GP protein of the MP strain of LCMV. | Met Gly Gln Ile Val Thr Met Phe Glu Ala<br>Leu Pro His Ile Ile Asp Glu Val Ile Asn<br>Ile Val Ile Ile Val Leu Ile Ile Ile Thr<br>Ser Ile Lys Ala Val Tyr Asn Phe Ala Thr<br>Cys Gly Ile Leu Ala Leu Ile Ser Phe Leu<br>Phe Leu Ala Gly Arg Ser Cys Gly Met Tyr<br>Gly Leu Asp Gly Pro Asp Ile Tyr Lys Gly<br>Val Tyr Arg Phe Lys Ser Val Glu Phe Asp<br>Met Ser Tyr Leu Asn Leu Thr Met Pro Asn<br>Ala Cys Ser Ala Asn Asn Ser His His<br>Ile Ser Met Gly Thr Ser Gly Leu Glu<br>Thr Phe Thr Asn Asp Ser Ile Ile Thr<br>Asn Phe Cys Asn Leu Thr Ser Ala Leu<br>Lys Arg Thr Phe Asp His Thr Leu Met<br>Ile Val Ser Ser Leu His Leu Ser Ile<br>Gly Val Pro Ser Tyr Lys Ala Val Ser | |

| SEQ ID NO. | Description | Sequence |
|---|---|---|
| | | Asp Phe Asn Asn Gly Ile Thr Ile Gln |
| | | Asn Leu Ser Phe Ser Asn Ala Gln Ser |
| | | Leu Ser Gln Cys Lys Thr Phe Arg Gly |
| | | Val Leu Asp Met Phe Arg Thr Ala Phe |
| | | Gly Lys Tyr Met Arg Ser Gly Trp Gly |
| | | Thr Gly Ser Asp Gly Lys Thr Thr Trp |
| | | Ser Gln Thr Asn Tyr Gln Tyr Leu Ile |
| | | Gln Asn Arg Thr Trp Glu Asn His Cys |
| | | Tyr Ala Gly Pro Phe Gly Met Ser Arg |
| | | Leu Phe Ala Gln Glu Lys Thr Arg Phe |
| | | Thr Arg Arg Leu Ala Gly Thr Phe Thr |
| | | Thr Leu Ser Asp Ser Ser Gly Val Glu |
| | | Pro Gly Gly Tyr Cys Leu Thr Lys Trp |
| | | Ile Leu Ala Ala Glu Leu Lys Cys Phe |
| | | Asn Thr Ala Val Ala Lys Cys Asn Val |
| | | His Asp Glu Glu Phe Cys Asp Met Leu |
| | | Leu Ile Asp Tyr Asn Lys Ala Ala Leu |
| | | Lys Phe Lys Glu Asp Val Glu Ser Ala |
| | | His Leu Phe Lys Thr Thr Val Asn Ser |
| | | Ile Ser Asp Gln Leu Leu Met Arg Asn |
| | | Leu Arg Asp Leu Met Gly Val Pro Tyr |
| | | Asn Tyr Ser Lys Phe Trp Tyr Leu Glu |
| | | Ala Lys Thr Gly Glu Thr Ser Val Pro |
| | | Cys Trp Leu Val Ser Asn Gly Ser Tyr Leu |
| | | Asn Glu Thr His Phe Ser Asp Gln Ile Glu |
| | | Gln Glu Ala Asp Asn Met Ile Thr Glu Met |
| | | Leu Arg Lys Asp Tyr Ile Lys Arg Gln Gly |
| | | Ser Thr Pro Leu Ala Leu Met Asp Leu Leu |
| | | Met Phe Ser Thr Ser Ala Tyr Leu Ile Ser |
| | | Ile Phe Leu His Leu Val Arg Ile Pro Thr |
| | | His Arg His Ile Lys Gly Gly Ser Cys Pro |
| | | Lys Pro His Arg Leu Thr Ser Lys Gly Ile |
| | | Cys Ser Cys Gly Ala Phe Lys Val Pro Gly |
| | | Val Glu Thr Thr Trp Lys Arg Arg |
| 8 | Amino acid sequence of the L protein of the MP strain of LCMV. | Met Asp Glu Ala Ile Ser Glu Leu Arg Glu |
| | | Leu Cys Leu Asn His Ile Glu Gln Asp Glu |
| | | Arg Leu Ser Arg Gln Lys Leu Asn Phe Leu |
| | | Gly Gln Arg Glu Pro Arg Met Val Leu Ile |
| | | Glu Gly Leu Lys Leu Leu Ser Arg Cys Ile |
| | | Glu Ile Asp Ser Ala Asp Lys Ser Gly Cys |
| | | Ile His Asn His Asp Asp Lys Ser Val Glu |
| | | Ala Ile Leu Ile Glu Ser Gly Ile Val Cys |
| | | Pro Gly Leu Pro Leu Ile Ile Pro Asp Gly |
| | | Tyr Lys Leu Ile Asp Asn Ser Leu Ile Leu |
| | | Leu Glu Cys Phe Val Arg Ser Thr Pro Ala |
| | | Ser Phe Glu Lys Lys Phe Ile Glu Asp Thr |
| | | Asn Lys Leu Ala Cys Ile Lys Glu Asp Leu |
| | | Ala Ile Ala Gly Ile Thr Leu Val Pro |
| | | Val Asp Gly Arg Cys Asp Tyr Asp Asn |
| | | Phe Met Pro Glu Trp Val Asn Phe Lys |
| | | Arg Asp Leu Leu Phe Lys Leu Leu Glu |
| | | Ser Ser Gln Asp Glu Lys Val Phe Glu |
| | | Ser Glu Tyr Phe Arg Leu Cys Glu Ser |
| | | Lys Thr Thr Val Asp Lys Arg Ser Gly |
| | | Asp Ser Met Lys Ile Leu Lys Asp Ala |
| | | Ser Phe His Asn Asp Glu Ile Met Lys |
| | | Cys His Asp Gly Val Asn Pro Asn Met |
| | | Cys Asp Asp Val Val Leu Gly Ile Asn |
| | | Leu Tyr Ser Arg Phe Arg Arg Asp Leu |
| | | Thr Gly Lys Leu Lys Arg Ser Phe Gln |
| | | Ile Asn Pro Gly Asn Leu Ile Lys Glu |
| | | Ser Glu Leu Tyr Glu Thr Leu Ala Asp |
| | | Asp Asp Ile Ser Ala Leu Ser Lys Glu |
| | | Val Glu Ser Cys Pro Leu Met Arg Phe |
| | | Thr Ala Asp Thr His Gly Tyr Glu Arg |
| | | Ser Glu Thr Ser Thr Glu Tyr Glu Arg |
| | | Leu Ser Met Leu Asn Lys Val Lys Ser |
| | | Lys Leu Leu Asn Thr Arg Arg Arg Gln |
| | | Leu Asn Leu Asp Val Leu Cys Leu Ser |
| | | Leu Ile Lys Gln Ser Lys Leu Lys Ser |
| | | Lys Asn Asp Lys His Trp Val Gly Cys |
| | | Tyr Gly Ser Val Asn Asp Arg Leu Val |
| | | Phe His Ser Thr Lys Glu Glu Phe Ile |
| | | Leu Leu Arg Asn Arg Arg Lys Ser Lys |
| | | Tyr Arg Lys Val Ser Leu Glu Asp Leu |

| SEQ ID NO. | Description | Sequence |
|---|---|---|
| | | Arg Thr Ser Ile Asn Glu Phe Ile Leu |
| | | Val Gln Arg Cys Leu Ser Val Val Gly |
| | | Ser Phe Gly His Tyr Gly Leu Ser Glu |
| | | Leu Glu His Glu Cys His Ile Pro Phe |
| | | Glu Phe Glu Asn Phe Met Arg Ser Gly |
| | | His Pro Ile Met Tyr Tyr Thr Lys Phe |
| | | Asp Tyr Asp Phe Gln Pro Asn Thr Glu |
| | | Leu Arg Asn Met His Ser Leu Lys Arg |
| | | Ser Ser Val Cys Leu Ala Leu Thr Asn Ser |
| | | Met Lys Thr Ser Ser Val Ala Arg Leu Arg |
| | | Gln Asn Gln Leu Gly Ser Val Arg Tyr Gln |
| | | Val Val Glu Cys Lys Glu Val Phe Cys Gln |
| | | Val Ile Lys Leu Asp Ser Glu Glu Tyr His |
| | | Leu Leu Tyr Gln Lys Thr Gly Glu Ser Ser |
| | | Arg Cys Tyr Ser Ile Gln Gly Pro Asn Gly |
| | | His Leu Ile Ser Phe Tyr Ala Asp Pro Lys |
| | | Arg Phe Phe Leu Pro Ile Phe Ser Asp Glu |
| | | Val Leu His Asn Met Ile Asp Thr Met Ile |
| | | Ser Trp Ile Arg Ser Cys Pro Asp Leu Lys |
| | | Asp Ser Ile Asp Asp Val Glu Ile Ala Leu |
| | | Arg Thr Leu Leu Leu Met Leu Thr Asn |
| | | Pro Thr Lys Arg Asn Gln Lys Gln Val Gln |
| | | Asn Ile Arg Tyr Leu Val Met Ala Ile Val |
| | | Ser Asp Phe Ser Ser Thr Ser Leu Met Asp |
| | | Lys Leu Lys Glu Asp Leu Ile Thr Pro Ala |
| | | Glu Lys Val Val Tyr Lys Leu Leu Arg Phe |
| | | Leu Ile Lys Thr Val Phe Gly Thr Gly Glu |
| | | Lys Val Leu Leu Ser Ala Lys Phe Lys |
| | | Met Leu Asn Val Ser Tyr Leu Cys His |
| | | Ile Thr Lys Glu Thr Pro Asp Arg Leu |
| | | Asp Gln Ile Lys Cys Phe Glu Lys Phe |
| | | Glu Pro Lys Ser Glu Phe Gly Phe Phe |
| | | Asn Pro Lys Glu Ser Ile Thr Pro Glu |
| | | Glu Cys Val Phe Tyr Asp Gln Met Lys |
| | | Phe Thr Gly Lys Glu Val Asp Cys Gln |
| | | Thr Thr Pro Gly Val Asn Leu Glu Met |
| | | Val Ser Ser Phe Asn Asn Gly Thr Leu |
| | | Phe Lys Arg Leu Asn Ser Leu Asp Pro |
| | | Thr Asn Ser Gly Cys Ala Thr Ala Leu |
| | | Leu Ala Ser Asn Lys Ser Val Val Val |
| | | Lys His Leu Asn Gly Glu Arg Leu Leu |
| | | Tyr Asp Phe Asn Lys Leu Leu Val Ser |
| | | Val Ser Gln Ile Thr Glu Ser Phe Met |
| | | Lys Gln Lys Tyr Lys Leu Asn His Ser |
| | | Tyr Glu Tyr Lys Val Ser Lys Leu Val |
| | | Arg Leu Val Ile Gly Ser Lys Glu Thr |
| | | Ala Gly Lys Leu Glu Gly Asp Ser Ala |
| | | Ile Cys Phe Asp Gly Glu Glu Thr |
| | | Phe Phe Lys Asn Leu Glu Asp Lys Val |
| | | Ser Thr Ile Lys Arg Tyr Glu Arg Ser |
| | | Lys Thr Asn Glu Gly Glu Asn Glu Val |
| | | Phe Glu Asn Thr Lys Gly Leu His His |
| | | Gln Thr Ile Leu Ser Gly Lys Met Ala |
| | | Leu Arg Lys Val Ile Leu Ser Glu Ile |
| | | Phe His Leu Val Glu Asp Phe Asp Pro |
| | | Cys Leu Thr Asn Asp Asp Met Lys Phe |
| | | Cys Glu Ala Ile Glu Thr Ser Thr Glu |
| | | Ser Pro Leu Tyr Phe Thr Ser Ala Val |
| | | Glu Gln Cys Gly Leu Asp Glu Met Ala |
| | | Asn Leu Cys Arg Lys Phe Phe Ser Glu |
| | | Asp Trp Phe Ser Cys Met Lys Met Ile |
| | | Leu Gln Met Asn Ala Asn Ala Tyr Ser |
| | | Lys Tyr Arg His Met Gln Arg Gln Gly |
| | | Asn Phe Lys Phe Asp Trp Asp Lys Leu |
| | | Glu Asp Val Arg Ile Ser Glu Arg Glu |
| | | Asn Ser Glu Ser Leu Ser Lys Ala Leu |
| | | Leu Thr Lys Cys Met Ser Ala Ala Leu |
| | | Asn Leu Cys Phe Tyr Ser Glu Glu Ser |
| | | Thr Ser Tyr Thr Ser Val Gly Pro Asp |
| | | Gly Arg Leu Lys Phe Ala Leu Ser Tyr Lys |
| | | Glu Gln Val Gly Gly Asn Arg Glu Leu Tyr |
| | | Ile Gly Asp Leu Arg Thr Lys Met Phe Thr |
| | | Arg Leu Ile Glu Asp Tyr Phe Glu Ser Phe |
| | | Ser Ser Phe Phe Ser Gly Ser Cys Leu Asn |
| | | Asn Asp Lys Glu Phe Glu Asn Ala Ile Leu |
| | | Ser Met Thr Ile Asn Val Arg Glu Gly Leu |

| SEQ ID NO. | Description | Sequence |
|---|---|---|
| | | Leu Asn Tyr Ser Met Asp His Ser Lys Trp |
| | | Gly Pro Met Met Cys Pro Phe Leu Phe Leu |
| | | Met Leu Leu Gln Asn Leu Lys Asp Asp Gln |
| | | Tyr Val Arg Ser Gly Lys Asp His Ile Ser |
| | | Thr Leu Leu Thr Trp His Met His Lys Leu |
| | | Val Glu Val Pro Phe Pro Val Val Asn Ala |
| | | Met Met Lys Ser Tyr Ile Lys Ser Lys Leu |
| | | Lys Leu Leu Arg Gly Ser Glu Thr Thr Val |
| | | Thr Glu Arg Ile Phe Arg Glu Tyr Phe Glu |
| | | Leu Gly Ile Val Pro Ser His Ile Ser Ser |
| | | Leu Ile Asp Met Gly Gln Gly Ile Leu His |
| | | Asn Ala Ser Asp Phe Tyr Gly Leu Ile Ser |
| | | Glu Arg Phe Ile Asn Tyr Cys Ile Gly |
| | | Ile Phe Gly Glu Arg Pro Glu Ser Tyr |
| | | Ser Ser Asp Asp Gln Ile Thr Leu Phe |
| | | Arg Arg Leu Ser Glu Leu Val Asp Ser |
| | | Pro Glu Glu Val Leu Val Leu Leu Glu |
| | | His Ser His Leu Ser Gly Leu Leu Asn |
| | | Phe Ile Ser Pro Lys Ser Val Val Gly |
| | | Phe Ala Ala Glu Phe Lys Ser Arg Phe |
| | | Val Trp Gly Glu Glu Val Pro Leu Leu |
| | | Lys Phe Val Ser Ala Ala Leu His Asn |
| | | Lys Cys Lys Glu Pro His Gln Leu Cys |
| | | Thr Ile Asp Thr Ile Ala Asp Gln Ala |
| | | Ala Asn Gly Val Pro Val Ser Leu Val |
| | | Cys Ile Gln Lys Arg Thr Leu Asp Leu |
| | | Lys Tyr Ala Asn Phe Pro Leu Asp Pro |
| | | Leu Leu Asn Thr Asn Thr Asp Val Lys |
| | | Trp Leu Asp Gly Ser Arg Gly Tyr Arg |
| | | Gln Arg Leu Ile Glu Glu Leu Cys Pro |
| | | Glu Thr Lys Val Met Arg Arg Leu Val |
| | | Arg Leu His His Lys Leu Lys Asn Gly |
| | | Phe Asn Glu Glu Phe Phe Leu Asp Leu |
| | | Asn Arg Asp Lys Lys Glu Ala Ile Leu |
| | | Leu Gly Asn Ile Leu Gly Leu Glu Glu |
| | | Leu Ser Gln Leu Ala Asn Ile Asn Trp |
| | | Asn Leu Asn Glu Leu Phe Pro Leu Arg |
| | | Val Leu Arg Gln Lys Val Val Tyr Pro |
| | | Val Met Thr Phe Gln Glu Glu Arg Ile |
| | | Ser Leu Ile Lys Thr Leu Gln Asn Lys |
| | | Cys Ser Lys Phe Thr Arg Gly Ala Gln |
| | | Leu Leu Ser Glu Ala Ile Asn Lys Ser |
| | | Phe Gln Ser Cys Ile Ser Ser Gly Phe |
| | | Gly Leu Cys Lys Thr Leu Gly Ser Arg |
| | | Val Arg Asn Lys Asn Arg Asp Asn Leu |
| | | Ile Arg Lys Val Leu Glu Asp Leu Ala |
| | | Asp Ala His Val Thr Ala Ile His Arg |
| | | Asp Gly Ile Met Leu Tyr Ile Cys Asp |
| | | Gln Ser His Pro Glu Ala His Cys Asp |
| | | Ile Ser Leu Leu Arg Pro Leu Leu Trp |
| | | Tyr Ile Cys Ile Ser Leu Ser Asn Ser |
| | | Glu Leu Gly Val Trp Val Leu Ala Glu |
| | | Val Lys Gly Lys Asn Glu Gly Ser Ser |
| | | Leu Lys His Leu Asn Pro Cys Asp Tyr |
| | | Ala Arg Lys Pro Glu Ser Ser Arg Leu Leu |
| | | Glu Asp Lys Ile Ser Leu Asn His Val Ile |
| | | Gln Ser Val Arg Arg Leu Tyr Pro Lys Ile |
| | | Tyr Glu Asp Gln Leu Leu Pro Phe Met Ser |
| | | Asp Met Ser Ser Lys Asn Met Arg Trp Ser |
| | | Pro Arg Ile Lys Phe Leu Asp Leu Cys Val |
| | | Leu Ile Asp Ile Asn Ser Gly Ser Leu Ser |
| | | Leu Ile Ser His Val Val Lys Trp Lys Arg |
| | | Asp Glu His Tyr Thr Val Leu Phe Ser Asp |
| | | Leu Val Asn Ser His Gln Arg Ser Asp Ser |
| | | Ser Leu Val Asp Glu Phe Val Val Ser Thr |
| | | Arg Asp Val Cys Lys Asn Phe Leu Lys Gln |
| | | Val Tyr Phe Glu Ser Phe Val Arg Glu Phe |
| | | Val Ala Thr Ser Arg Thr Leu Gly Ser Phe |
| | | Ser Trp Phe Pro His Lys Asp Met Met Pro |
| | | Ser Glu Asp Gly Ala Glu Ala Leu Gly Pro |
| | | Phe Gln Ser Phe Ile Leu Lys Val Val Asn |
| | | Lys Asn Met Glu Arg Pro Met Phe Arg Asn |
| | | Asp Leu Gln Phe Gly Phe Gly Trp Phe Ser |
| | | Tyr Arg Leu Gly Asp Ile Val Cys Asn Ala |
| | | Ala Met Leu Ile Lys Gln Gly Leu Thr Asn |
| | | Pro Lys Ala Phe Lys Ser Leu Arg Asn Leu |

| SEQ ID NO. | Description | Sequence | |
|---|---|---|---|
| | | Trp Asp Tyr Met Ile Asn Asn Thr Glu Gly | |
| | | Val Leu Glu Phe Ser Ile Thr Val Asp Phe | |
| | | Thr His Asn Gln Asn Asn Thr Asp Cys Leu | |
| | | Arg Lys Phe Ser Leu Ile Phe Leu Val Lys | |
| | | Cys Gln Leu Gln Gly Pro Gly Val Ala Glu | |
| | | Phe Leu Ser Cys Ser His Leu Phe Lys Gly | |
| | | Glu Val Asp Arg Arg Phe Leu Asp Glu Cys | |
| | | Leu His Leu Leu Arg Ser Asp Ser Ile Phe | |
| | | Lys Val Asn Asp Gly Val Phe Asp Ile Arg | |
| | | Ser Glu Glu Phe Glu Asp Tyr Met Glu Asp | |
| | | Pro Leu Ile Leu Gly Asp Ser Leu Glu Leu | |
| | | Glu Leu Ile Gly Ser Arg Lys Ile Leu Asp | |
| | | Gly Ile Arg Ser Leu Asp Phe Glu Arg Ile | |
| | | Gly Pro Glu Trp Glu Pro Val Pro Leu Thr | |
| | | Val Arg Met Gly Ala Leu Phe Glu Gly Arg | |
| | | Ser Leu Val Gln Asn Ile Val Val Lys Leu | |
| | | Glu Thr Lys Asp Met Arg Val Phe Leu Ala | |
| | | Glu Leu Glu Gly Tyr Gly Asn Phe Asp Asp | |
| | | Val Leu Gly Ser Leu Leu Leu His Arg Phe | |
| | | Arg Thr Gly Glu His Leu Gln Gly Ser Glu | |
| | | Ile Ser Thr Ile Leu Gln Glu Leu Cys Ile | |
| | | Asp Arg Ser Ile Leu Leu Val Pro Leu Ser | |
| | | Leu Val Pro Asp Trp Phe Thr Phe Lys Asp | |
| | | Cys Arg Leu Cys Phe Ser Lys Ser Lys Asn | |
| | | Thr Val Met Tyr Glu Thr Val Val Gly Lys | |
| | | Tyr Arg Leu Lys Gly Lys Ser Cys Asp Asp | |
| | | Trp Leu Thr Lys Ser Val Val Glu Glu Ile | |
| | | Asp | |
| 9 | amino acid sequence of the Z protein of the MP strain of LCMV. | Met Gly Gln Gly Lys Ser Lys Glu Asp Ala Ser Asn Thr Ser Arg Ala Leu Pro Asp Thr Thr Tyr Leu Gly Asn Cys Lys Ser Cys Trp Gln Arg Ser Leu Val Arg Cys His Asp His Cys Arg His Cys Leu Asn Leu Leu Val Ser Asp Arg Cys Pro Leu Pro Leu Pro Thr Lys Leu Lys Ala Pro Ser Ser Pro Pro Pro | |
| 10 | LCMV clone 13 S-Segment encoding HCMV strain Merlin gB; full-length wildtype. The genomic segment is RNA, the sequence in SEQ ID No. 10 is shown for DNA; however, exchanging all thymidines ("T") in SEQ ID NO: 10 for uridines ("U") provides the RNA sequence. | gcgcaccggg gatcctaggc ttttggatt gcgctttcct ctagatcaac tgggtgtcag gccctatcct acagaaggat ggaatccagg atctggtgcc tggtagtctg cgttaacttg tgtatcgtct gtctgggtgc tgcggtttcc tcatcttcta ctcgtggaac ttctgctact cacagtcacc attcctctca tacgacgtct gctgctcact ctcgatccgg ttcagtctct caacgcgtaa cttcttccca aacggtcagc catggtgtta acgagaccat ctacaacact accctcaagt acggagatgt ggtgggggtc aataccacca agtacccta tcgcgtgtgt tctatggccc agggtacgga tcttattcgc tttgaacgta atatcgtctg cacctcgatg aagcccatca atgaagacct ggacgagggc atcatggtgg tctacaaacg caacatcgtc gcgcacacct ttaaggtacg agtctaccag aaggtttga cgtttcgtcg tagctacgct tacatccaca ccacttatct gctgggcagc aacacggaat acgtggcgcc tcctatgtgg gagattcatc atatcaacag ccacagtcag tgctacagtt cctacagccg cgttatagca ggcacggttt tcgtggctta tcatagggac agctatgaaa acaaaaccat gcaattaatg cccgacgatt attccaacac ccacagtacc cgttacgtga cggtcaagga tcaatggcac agccgcggca gcacctggct ctatcgtgag acctgtaatc tgaattgtat ggtgaccatc actactgcgc gctccaaata tccttatcat ttttcgcca cttccacggg tgacgtggtt gacatttctc ctttctacaa cggaaccaat cgcaatgcca gctactttgg agaaaacgcc gacaagtttt tcatttttcc gaactacact attgtctccg actttggaag accgaattct gcgttagaga cccacaggtt ggtggctttt cttgaacgtg cggactcggt gatctcctgg | 60 120 180 240 300 360 420 480 540 600 660 720 780 840 900 960 1020 1080 |

-continued

| SEQ ID NO. | Description | Sequence | |
|---|---|---|---|
| | | gatatacagg acgaaaagaa tgtcacttgt | |
| | | caactcactt tctgggaagc ctcggaacgc | 1140 |
| | | accattcgtt ccgaagccga ggactcgtat | |
| | | cacttttctt ctgccaaaat gaccgccact | 1200 |
| | | ttcttatcta agaagcaaga ggtgaacatg | |
| | | tccgactctg cgctggactg cgtacgtgat | 1260 |
| | | gaggctataa ataagttaca gcagattttc | |
| | | aatacttcat acaatcaaac atatgaaaaa | 1320 |
| | | tatggaaacg tgtccgtctt tgaaaccact | |
| | | ggtggtttgg tagtgttctg gcaaggtatc | 1380 |
| | | aagcaaaaat ctctggtgga actcgaacgt | |
| | | ttggccaacc gctccagtct gaatcttact | 1440 |
| | | cataatagaa ccaaaagaag tacagatggc | |
| | | aacaatgcaa ctcatttatc caacatggaa | 1500 |
| | | tcggtgcaca atctggtcta cgcccagctg | |
| | | cagttcacct atgacacgtt gcgcggttac | 1560 |
| | | atcaaccggg cgctggcgca aatcgcagaa | |
| | | gcctggtgtg tggatcaacg gcgcaccta | 1620 |
| | | gaggtcttca aggaactcag caagatcaac | |
| | | ccgtcagcca ttctctcggc catttacaac | 1680 |
| | | aaaccgattg ccgcgcgttt catgggtgat | |
| | | gtcttgggcc tggccagctg cgtgaccatc | 1740 |
| | | aaccaaacca gcgtcaaggt gctgcgtgat | |
| | | atgaacgtga aggagtcgcc aggacgctgc | 1800 |
| | | tactcacgac ccgtggtcat ctttaatttc | |
| | | gccaacagct cgtacgtgca gtacggtcaa | 1860 |
| | | ctgggcgagg acaacgaaat cctgttgggc | |
| | | aaccaccgca ctgaggaatg tcagcttccc | 1920 |
| | | agcctcaaga tcttcatcgc cgggaactcg | |
| | | gcctacgagt acgtggacta cctcttcaaa | 1980 |
| | | cgcatgattg acctcagcag tatctccacc | |
| | | gtcgacagca tgatcgccct ggatatcgac | 2040 |
| | | ccgctggaaa ataccgactt cagggtactg | |
| | | gaactttact cgcagaaaga gctgcgttcc | 2100 |
| | | agcaacgttt ttgacctcga agagatcatg | |
| | | cgcgaattca actcgtacaa gcagcgggta | 2160 |
| | | aagtacgtgg aggacaaggt agtcgacccg | |
| | | ctaccgccct acctcaaggg tctggacgac | 2220 |
| | | ctcatgagcg gcctgggcgc cgcgggaaag | |
| | | gccgttggcg tagccattgg ggccgtgggt | 2280 |
| | | ggcgcggtgg cctccgtggt cgaaggcgtt | |
| | | gccaccttcc tcaaaaaccc cttcggagcg | 2340 |
| | | ttcaccatca tcctcgtggc catagctgta | |
| | | gtcattatca cttatttgat ctatactcga | 2400 |
| | | cagcggcgtt tgtgcacgca gccgctgcag | |
| | | aacctctttc cctatctggt gtccgccgac | 2460 |
| | | gggaccaccg tgacgtcggg cagcaccaaa | |
| | | gacacgtcgt tacaggctcc gccttcctac | 2520 |
| | | gaggaaagtg tttataattc tggtcgcaaa | |
| | | ggaccgggac caccgtcgtc tgatgcatcc | 2580 |
| | | acggcggctc cgccttacac caacgagcag | |
| | | gcttaccaga tgcttctggc cctggcccgt | 2640 |
| | | ctggacgcag agcagcgagc gcagcagaac | |
| | | ggtacagatt ctttggacgg acggactggc | 2700 |
| | | acgcaggaca agggacagaa gcccaaccta | |
| | | ctagaccgac tgcgacatcg caaaaacggc | 2760 |
| | | taccgacact tgaaagactc tgacgaagaa | |
| | | gagaacgtct gaagaacagc gcctccctga | 2820 |
| | | ctctccacct cgaaagaggt ggagagtcag | |
| | | ggaggcccag agggtcttag agtgtcacaa | 2880 |
| | | catttgggcc tctaaaaatt aggtcatgtg | |
| | | gcagaatgtt gtgaacagtt ttcagatctg | 2940 |
| | | ggagccttgc tttggaggcg ctttcaaaaa | |
| | | tgatgcagtc catgagtgca cagtgcgggg | 3000 |
| | | tgatctcttt cttcttttg tcccttacta | |
| | | ttccagtatg catcttacac aaccagccat | 3060 |
| | | atttgtccca cactttatct tcatactccc | |
| | | tcgaagcttc cctggtcatt tcaacatcga | 3120 |
| | | taagcttaat gtccttccta ttttgtgagt | |
| | | ccagaagctt tctgatgtca tcggagcctt | 3180 |
| | | gacagcttag aaccatcccc tgcggaagag | |
| | | cacctataac tgacgaggtc aacccgggtt | 3240 |
| | | gcgcattgaa gaggtcggca agatccatgc | |
| | | cgtgtgagta cttggaatct tgcttgaatt | 3300 |
| | | gttttgatc aacgggttcc ctgtaaaagt | |
| | | gtatgaactg cccgttctgt ggttggaaaa | 3360 |

-continued

| SEQ ID NO. | Description | Sequence | |
|---|---|---|---|
| | | ttgctatttc cactggatca ttaaatctac | |
| | | cctcaatgtc aatccatgta ggagcgttgg | |
| | | ggtcaattcc tcccatgagg tcttttaaaa | |
| | | gcattgtctg gctgtagctt aagcccacct | 3480 |
| | | gaggtggacc tgctgctcca ggcgctggcc | |
| | | tgggtgagtt gactgcaggt ttctcgcttg | 3540 |
| | | tgagatcaat tgttgtgttt tcccatgctc | |
| | | tccccacaat cgatgttcta caagctatgt | 3600 |
| | | atggccatcc ttcacctgaa aggcaaactt | |
| | | tatagaggat gttttcataa gggttcctgt | 3660 |
| | | ccccaacttg gtctgaaaca aacatgttga | |
| | | gttttctctt ggccccgaga actgccttca | 3720 |
| | | agagatcctc gctgttgctt ggcttgatca | |
| | | aaattgactc taacatgtta cccccatcca | 3780 |
| | | acagggctgc ccctgccttc acggcagcac | |
| | | caagactaaa gttatagcca gaaatgttga | 3840 |
| | | tgctggactg ctgttcagtg atgacccca | |
| | | gaactgggtg cttgtctttc agccttttcaa | 3900 |
| | | gatcattaag atttggatac ttgactgtgt | |
| | | aaagcaagcc aaggtctgtg agcgcttgta | 3960 |
| | | caacgtcatt gagcggagtc tgtgactgtt | |
| | | tggccataca agccatagtt agacttggca | 4020 |
| | | ttgtgccaaa ttgattgttc aaaagtgatg | |
| | | agtctttcac atcccaaact cttaccacac | 4080 |
| | | cacttgcacc ctgctgaggc tttctcatcc | |
| | | caactatctg taggatctga gatctttggt | 4140 |
| | | ctagttgctg tgttgttaag ttccccatat | |
| | | ataccctga agcctggggc ctttcagacc | 4200 |
| | | tcatgatctt ggccttcagc ttctcaaggt | |
| | | cagccgcaag agacatcagt tcttctgcac | 4260 |
| | | tgagcctccc cactttcaaa acattcttct | |
| | | ttgatgttga ctttaaatcc acaagagaat | 4320 |
| | | gtacagtctg gttgagactt ctgagtctct | |
| | | gtaggtcttt gtcatctctc ttttccttcc | 4380 |
| | | tcatgatcct ctgaacattg ctgacctcag | |
| | | agaagtccaa cccattcaga aggttggttg | 4440 |
| | | catccttaat gacagcagcc ttcacatctg | |
| | | atgtgaagct ctgcaattct cttctcaatg | 4500 |
| | | cttgcgtcca ttggaagctc ttaacttcct | |
| | | tagacaagga catcttgttg ctcaatggtt | 4560 |
| | | tctcaagaca aatgcgcaat caaatgccta | |
| | | ggatccactg tgcg | 4604 |
| 11 | WE-specific primer | 5'AATCGTCTCTAAGGATGGGTCAGATTGTGACAATG-3' | |
| 12 | WE specific fusion-primer carrying an overhang complementary to the WET-specific primer | 5'AATCGTCTCTAAGGATGGGTCAGATTGTGACAATG-3' | |
| 13 | WET-specific primer | 5'CTCGGTGATCATGTTATCTGCTTCTTGTTCGATTTGA-3' | |
| 14 | WET-specific fusion-primer complementary to the WE-sequence | 5'AATCGTCTCTTTCTTTATCTCCTCTTCCAGATGG-3' | |
| 15 | Primer specific for LCMV NP | 5'-GGCTCCCAGATCTGAAAACTGTT-3' | |
| 16 | NP- and GP-specific primers; NP-specific: same as in RT reaction, GP-specific: 5' | 5'-GCTGGCTTGTCACTAATGGCTC-3' | |
| 17 | Representative cDNA sequence obtained from animal #3 (r3LCMV-GFPnat #3) revealing a recombed S segment combining NP and GP sequences | aagaagcaga taacatgatc accgagatgc tgaggaagga ctacatcaag agacagggca gcaccccct ggccctcatg gatctgctca tgttcagcac cagcgcctac ctcatcagca tcttcctgca cctggtgaag atccccaccc acagacacat caagggcggc agctgcccca agcccacag actcaccaac aagggcatct gcagctgcgg cgccttcaag gtgcccggcg taaaaccat ctggaagagg agataaagaa cagcgcctcc ctgactctcc acctcgaaag | 60 120 180 240 300 |

| SEQ ID NO. | Description | Sequence | |
|---|---|---|---|
| | | aggtggagag tcagggaggc ccagagggtc | |
| | | ttacttgtac agctcgtcca tgccgagagt | 360 |
| | | gatcccggcg gcggtcacga actccagcag | |
| | | gaagaacagc gcctccctga ctctccacct | 420 |
| | | cgaaagaggt ggagagtcag ggaggcccag | |
| | | aggtcttaga gtgtcacaac atttgggcct | 480 |
| | | ctaaaaatta ggtcatgtgg cagaatgttg | |
| | | tgaacagttt tcagatctgg gagcc | 535 |
| 18 | S segment 1 of r3LCMV-P1A (containing NP) | gcgcaccggg gatcctaggc tttttggatt | |
| | | gcgctttcct ctagatcaac tgggtgtcag | 60 |
| | | gccctatcct acagaaggat gagcgacaac | |
| | | aagaagcccg acaaggccca ctctggcagc | 120 |
| | | ggcggagatg gcgacggcaa cagatgtaac | |
| | | ctgctgcaca gatacagcct ggaagagatc | 180 |
| | | ctgccctacc tgggctggct ggtgttcgcc | |
| | | gtcgtgacaa caagcttcct ggccctgcag | 240 |
| | | atgttcatcg acgccctgta cgaggaacag | |
| | | tacgagaggg acgtggcctg gatcgccaga | 300 |
| | | cagagcaaga gaatgagcag cgtggacgag | |
| | | gacgaggatg atgaggacga cgaagatgac | 360 |
| | | tactacgacg atgaggatga cgacgacgac | |
| | | gccttctacg atgacgagga cgatgaagag | 420 |
| | | gaagaactgg aaaacctgat ggacgacgag | |
| | | tccgaggatg aggccgagga agagatgagc | 480 |
| | | gtggaaatgg gcgctggcgc cgaagagatg | |
| | | ggagccggcg ctaactgtgc ttgcgtgcca | 540 |
| | | ggacaccacc tgagaaagaa cgaagtgaag | |
| | | tgccggatga tctacttctt ccacgacccc | 600 |
| | | aactttctgg tgtccatccc cgtgaacccc | |
| | | aaagaacaga tggaatgcag atgcgagaac | 660 |
| | | gccgacgaag aggtggccat ggaagaagaa | |
| | | gaggaagagg aagaagaaga agaagaggaa | 720 |
| | | gaaatgggca accccgacgg cttcagcccc | |
| | | tgaagaacag cgcctccctg actctccacc | 780 |
| | | tcgaaagagg tggagagtca gggaggccca | |
| | | gagggtctta gagtgtcaca catttgggc | 840 |
| | | ctctaaaaat taggtcatgt ggcagaatgt | |
| | | tgtgaacagt tttcagatct gggagccttg | 900 |
| | | ctttggaggc gctttcaaaa atgatgcagt | |
| | | ccatgagtgc acagtgcggg gtgatctctt | 960 |
| | | tcttctttt gtcccttact attccagtat | |
| | | gcatcttaca caaccagcca tatttgtccc | 1020 |
| | | acactttatc ttcatactcc ctcgaagctt | |
| | | ccctggtcat ttcaacatcg ataagcttaa | 1080 |
| | | tgtccttcct attttgtgag tccagaagct | |
| | | ttctgatgtc atcggagcct tgacagctta | 1140 |
| | | gaaccatccc ctgcggaaga gcacctataa | |
| | | ctgacgaggt caacccgggt tgcgcattga | 1200 |
| | | agaggtcggc aagatccatg ccgtgtgagt | |
| | | acttggaatc ttgcttgaat tgttttttgat | 1260 |
| | | caacgggttc cctgtaaaag tgtatgaact | |
| | | gcccgttctg tggttggaaa attgctattt | 1320 |
| | | ccactggatc attaaatcta ccctcaatgt | |
| | | caatccatgt aggagcgttg gggtcaattc | 1380 |
| | | ctcccatgag gtcttttaaa agcattgtct | |
| | | ggctgtagct taagcccacc tgaggtggac | 1440 |
| | | ctgctgctcc aggcgctggc ctgggtgagt | |
| | | tgactgcagg tttctcgctt gtgagatcaa | 1500 |
| | | ttgttgtgtt ttcccatgct ctccccacaa | |
| | | tcgatgttct acaagctatg tatggccatc | 1560 |
| | | cttcacctga aaggcaaact ttatagagga | |
| | | tgttttcata agggttcctg tccccaactt | 1620 |
| | | ggtctgaaac aaacatgttg agttttctct | |
| | | tggccccgag aactgccttc aagagatcct | 1680 |
| | | cgctgttgct tggcttgatc aaaattgact | |
| | | ctaacatgtt accccatcc aacagggctg | 1740 |
| | | cccctgcctt cacggcagca ccaagactaa | |
| | | agttatagcc agaaatgttg atgctggact | 1800 |
| | | gctgttcagt gatgacccc agaactgggt | |
| | | gcttgtcttt cagccttttca agatcattaa | 1860 |
| | | gatttggata cttgactgtg taaagcaagc | |
| | | caaggtctgt gagcgcttgt acaacgtcat | 1920 |
| | | tgagcggagt ctgtgactgt ttggccatac | |
| | | aagccatagt tagacttggc attgtgccaa | 1980 |

| SEQ ID NO. | Description | Sequence | |
|---|---|---|---|
| | | attgattgtt caaaagtgat gagtctttca | |
| | | catcccaaac tcttaccaca ccacttgcac | 2040 |
| | | cctgctgagg ctttctcatc ccaactatct | |
| | | gtaggatctg agatctttgg tctagttgct | 2100 |
| | | gtgttgttaa gttccccata tatacccctg | |
| | | aagcctgggg cctttcagac ctcatgatct | 2160 |
| | | tggccttcag cttctcaagg tcagccgcaa | |
| | | gagacatcag ttcttctgca ctgagcctcc | 2220 |
| | | ccactttcaa aacattcttc tttgatgttg | |
| | | actttaaatc cacaagagaa tgtacagtct | 2280 |
| | | ggttgagact tctgagtctc tgtaggtctt | |
| | | tgtcatctct cttttccttc ctcatgatcc | 2340 |
| | | tctgaacatt gctgacctca gagaagtcca | |
| | | acccattcag aaggttggtt gcatccttaa | 2400 |
| | | tgacagcagc cttcacatct gatgtgaagc | |
| | | tctgcaattc tcttctcaat gcttgcgtcc | 2460 |
| | | attggaagct cttaacttcc ttagacaagg | |
| | | acatcttgtt gctcaatggt ttctcaagac | 2520 |
| | | aaatgcgcaa tcaaatgcct aggatccact gtgcg | |
| | | | 2555 |
| 19 | S segment 2 of r3LCMV-P1A (containing GP) | gcgcaccggg gatcctaggc tttttggatt | |
| | | gcgctttcct ctagatcaac tgggtgtcag | 60 |
| | | gccctatcct acagaaggat gagcgacaac | |
| | | aagaagcccg acaaggccca ctctggcagc | 120 |
| | | ggcggagatg gcgacggcaa cagatgtaac | |
| | | ctgctgcaca gatacagcct ggaagagatc | 180 |
| | | ctgccctacc tgggctggct ggtgttcgcc | |
| | | gtcgtgacaa caagcttcct ggccctgcag | 240 |
| | | atgttcatcg acgcccgtga cgaggaacag | |
| | | tacgagaggg acgtggcctg gatcgccaga | 300 |
| | | cagagcaaga gaatgagcag cgtggacgag | |
| | | gacgaggatg atgaggacga cgaagatgac | 360 |
| | | tactacgacg atgaggatga cgacgacgac | |
| | | gccttctacg atgacgagga cgatgaagag | 420 |
| | | gaagaactgg aaaacctgat ggacgacgag | |
| | | tccgaggatg aggccgagga agagatgagc | 480 |
| | | gtggaaatgg gcgctggcgc cgaagagatg | |
| | | ggagccggcg ctaactgtgc ttgcgtgcca | 540 |
| | | ggacaccacc tgagaaagaa cgaagtgaag | |
| | | tgccggatga tctacttctt ccacgacccc | 600 |
| | | aactttctgg tgtccatccc cgtgaacccc | |
| | | aaagaacaga tggaatgcag atgcgagaac | 660 |
| | | gccgacgaag aggtggccat ggaagaagaa | |
| | | gaggaagagg aagaagaaga agaagaggaa | 720 |
| | | gaaatgggca accccgacgg cttcagcccc | |
| | | tgaagaacag cgcctccctg actctccacc | 780 |
| | | tcgaaagagg tggagagtca gggaggccca | |
| | | gagggtctca gcgtcttttc cagacggttt | 840 |
| | | ttacaccagg caccttaaat gcaccacaac | |
| | | tacaaattcc tttgttggtt aatcggtgtg | 900 |
| | | gctttggaca tgagccacct tttatgtgcc | |
| | | tgtgtgttgg tattttgaca aggtgcagga | 960 |
| | | agatgctgac tagatatgca gatgtggaaa | |
| | | acatcagaag gtccatcaat gctagggggg | 1020 |
| | | tactcccctg cctctttatg taatccttcc | |
| | | tcaacatctc tgtaatcatg ttatcggctt | 1080 |
| | | cctgttcgat ttggtcactg aagtgggtct | |
| | | catttaagta agaaccattg gtgacaagcc | 1140 |
| | | agcacttggg gacactagtt tcgccggtct | |
| | | ttgcatgttc taggtaccaa aactttgagt | 1200 |
| | | aattgcaata tggcacccc atcagatctc | |
| | | tcaagtggtt cctcatcagt agttgatctg | 1260 |
| | | aaatcaaaga attcactgtt gttttgaata | |
| | | agtgcaaggc agattctacg tcctctttga | 1320 |
| | | acttactcaa agcagccttg ttgtagtcaa | |
| | | ttagtcgcag catgtcacag aattcttcat | 1380 |
| | | catgatttac attgcatttc gcaactgctg | |
| | | tgttcccgaa acacttaagc tctgcagcaa | 1440 |
| | | gaatcatcca tttggtcagg caataaccac | |
| | | ctggattctc caccccctgaa gagtctgaca | 1500 |
| | | aagtccaggt gaatgtgccc gctagtctcc | |
| | | tagtggagaa cttagttttc tcttgggaaa | 1560 |
| | | ggagaatcct ggacatccca aaaggacctg | |
| | | catatgtgca gtggttttcc caggttctat | 1620 |

| SEQ ID NO. | Description | Sequence | |
|---|---|---|---|
| | | tttgtataat caggtattgg taactcgtct | |
| | | ggctacacca ggtggtcttg ccatctgagc | 1680 |
| | | ctgtccagcc ccagccactc ctcatgtatt | |
| | | tcccccgaa ggcagttcta aacatatcta | 1740 |
| | | ggactctacc tctgaaggtt ctacactggc | |
| | | tctgagcact ttgtgcatct gagaatgtca | 1800 |
| | | agttgtattg gatggttatg ccattgttga | |
| | | agtcgcagga tactgcctta tagttggagt | 1860 |
| | | tccctctgat actgaggtgt aggctcgaaa | |
| | | ctatactcat gagtgtgtgg tcaaaggtct | 1920 |
| | | ttttgttgaa ggcagaggtc agattgcaaa | |
| | | agttgtgact gatgatggaa tcattggtga | 1980 |
| | | aggtcaattc tagtccagaa gtccccatac | |
| | | tgatgtaatg gtgggagttg ttggctgaac | 2040 |
| | | atgcgttggg catggtcagg ttcagatgtg | |
| | | acatatcaaa ctccactgac ttaaattggt | 2100 |
| | | aaactccttt gtaaatgtcg ggtcccttaa | |
| | | gaccgtacat gccacaggac ctgccagcca | 2160 |
| | | gaagtaggaa actgatcaat gcgaatatcc | |
| | | cacaggtggc aaaattgtag acagccttga | 2220 |
| | | tacccgtgat cacgataagc acaataatga | |
| | | caatgttgat cacctcatcg atgatgtgag | 2280 |
| | | gcagagcctc aaacattgtc acaatctgac | |
| | | ccatcttgtt gctcaatggt ttctcaagac | 2340 |
| | | aaatgcgcaa tcaaatgcct aggatccact gtgcg | |
| | | | 2375 |
| 20 | L segment of r3LCMV-P1A | gcgcaccggg gatcctaggc gtttagttgc | |
| | | gctgtttggt tgcacaactt tcttcgtgag | 60 |
| | | gctgtcagaa gtggacctgg ctgatagcga | |
| | | tgggtcaagg caagtccaga gaggagaaag | 120 |
| | | gcaccaatag tacaaacagg gccgaaatcc | |
| | | taccagatac cacctatctt ggccctttaa | 180 |
| | | gctgcaaatc ttgctggcag aaatttgaca | |
| | | gcttggtaag atgccatgac cactaccttt | 240 |
| | | gcaggcactg tttaaacctt ctgctgtcag | |
| | | tatccgacag gtgtcctctt tgtaaatatc | 300 |
| | | cattaccaac cagattgaag atatcaacag | |
| | | ccccaagctc tccacctccc tacgaagagt | 360 |
| | | aacaccgtcc ggccccggcc ccgacaaaca | |
| | | gcccagcaca agggaaccgc acgtcaccca | 420 |
| | | acgcacacag acacagcacc caacacagaa | |
| | | cacgcacaca cacacacaca cacacccaca | 480 |
| | | cgcacgcgcc cccaccaccg gggggcgccc | |
| | | cccccgggg ggcggccccc cgggagcccg | 540 |
| | | ggcggagccc cacggagatg cccatcagtc | |
| | | gatgtcctcg gccaccgacc cgcccagcca | 600 |
| | | atcgtcgcag gacctcccct tgagtctaaa | |
| | | cctgcccccc actgtttcat acatcaaagt | 660 |
| | | gctcctagat ttgctaaaac aaagtctgca | |
| | | atccttaaag gcgaaccagt ctggcaaaag | 720 |
| | | cgacagtgga atcagcagaa tagatctgtc | |
| | | tatacatagt tcctggagga ttacacttat | 780 |
| | | ctctgaaccc aacaaatgtt caccagttct | |
| | | gaatcgatgc aggaagaggt tcccaaggac | 840 |
| | | atcactaatc ttttcatagc cctcaagtcc | |
| | | tgctagaaag actttcatgt ccttggtctc | 900 |
| | | cagcttcaca atgatatttt ggacaaggtt | |
| | | tcttccttca aaaagggcac ccatctttac | 960 |
| | | agtcagtggc acaggctccc actcaggtcc | |
| | | aactctctca aagtcaatag atctaatccc | 1020 |
| | | atccagtatt cttttggagc ccaacaactc | |
| | | aagctcaaga gaatcaccaa gtatcaaggg | 1080 |
| | | atcttccatg taatcctcaa actcttcaga | |
| | | tctgatatca aagacaccat cgttcacctt | 1140 |
| | | gaagacagag tctgtcctca gtaagtggag | |
| | | gcattcatcc aacattcttc tatctatctc | 1200 |
| | | acccttaaag aggtgagagc atgataaaag | |
| | | ttcagccaca cctggattct gtaattggca | 1260 |
| | | cctaaccaag aatatcaatg aaaatttcct | |
| | | taaacagtca gtattattct gattgtgcgt | 1320 |
| | | aaagtccact gaaattgaaa actccaatac | |
| | | ccctttgtg tagttgagca tgtagtccca | 1380 |
| | | cagatccttt aaggatttaa atgcctttgg | |
| | | gtttgtcagg ccctgcctaa tcaacatggc | 1440 |

| SEQ ID NO. | Description | Sequence | |
|---|---|---|---|
| | | agcattacac acaacatctc ccattcggta | |
| | | agagaaccac ccaaaaccaa actgcaaatc | 1500 |
| | | attcctaaac ataggcctct ccacattttt | |
| | | gttcaccacc tttgagacaa atgattgaaa | 1560 |
| | | ggggcccagt gcctcagcac catcttcaga | |
| | | tggcatcatt tctttatgag ggaaccatga | 1620 |
| | | aaaattgcct aatgtcctgg ttgttgcaac | |
| | | aaattctcga acaaatgatt caaaatacac | 1680 |
| | | ctgttttaag aagttcttgc agacatccct | |
| | | cgtgctaaca acaaattcat caaccagact | 1740 |
| | | ggagtcagat cgctgatgag aattggcaag | |
| | | gtcagaaaac agaacagtgt aatgttcatc | 1800 |
| | | cctttccac ttaacaacat gagaaatgag | |
| | | tgacaaggat tctgagttaa tatcaattaa | 1860 |
| | | aacacagagg tcaaggaatt taattctggg | |
| | | actccacctc atgtttttg agctcatgtc | 1920 |
| | | agacataaat ggaagaagct gatcctcaaa | |
| | | gatcttggga tatagccgcc tcacagattg | 1980 |
| | | aatcacttgg ttcaaattca ctttgtcctc | |
| | | cagtagcctt gagctctcag gctttcttgc | 2040 |
| | | agttaggttc tcactgttat tcttcccttt | 2100 |
| | | ggtcggttct gctaggaccc aaacacccaa | |
| | | ctcaaaagag ttgctcaatg aaatacaaat | 2160 |
| | | gtagtcccaa agaagaggcc ttaaaaggca | |
| | | tatatgatca cggtgggctt ctggatgaga | 2220 |
| | | ctgtttgtca caaatgtaca gcgttatacc | |
| | | atcccgattg caaactcttg tcacatgatc | 2280 |
| | | atctgtggtt agatcctcaa gcagcttttt | |
| | | gatatacaga ttttccctat ttttgtttct | 2340 |
| | | cacacacctg cttcctagag ttttgcaaag | |
| | | gcctataaag ccagatgaga tacaactctg | 2400 |
| | | gaaagctgac ttgttgattg cttctgacag | |
| | | cagcttctgt gcacccttg tgaatttact | 2460 |
| | | acaaagtttg ttctggagtg tcttgatcaa | |
| | | tgatgggatt ctttcctctt ggaaagtcat | 2520 |
| | | cactgatgga taaaccacct tttgtcttaa | |
| | | aaccatcctt aatgggaaca tttcattcaa | 2580 |
| | | attcaaccag ttaacatctg ctaactgatt | |
| | | cagatcttct tcaagaccga ggaggtctcc | 2640 |
| | | caattgaaga atggcctcct ttttatctct | |
| | | gttaaatagg tctaagaaaa attcttcatt | 2700 |
| | | aaattcacca tttttgagct tatgatgcag | |
| | | tttccttaca agctttctta caacctttgt | 2760 |
| | | ttcattagga cacagttcct caatgagtct | |
| | | ttgtattctg taacctctag aaccatccag | 2820 |
| | | ccaatctttc acatcagtgt tggtattcag | |
| | | tagaaatgga tccaaaggga aattggcata | 2880 |
| | | ctttaggagg tccagtgttc tcctttggat | |
| | | actattaact agggagactg ggacgccatt | 2940 |
| | | tgcgatggct tgatctgcaa ttgtatctat | |
| | | tgtttcacaa agttgatgtg gctctttaca | 3000 |
| | | cttgacattg tgtagcgctg cagatacaaa | |
| | | ctttgtgaga agagggactt cctcccccca | 3060 |
| | | tacatagaat ctagatttaa attctgcagc | |
| | | gaacctccca gccacacttt ttgggctgat | 3120 |
| | | aaatttgttt aacaagccgc tcagatgaga | |
| | | ttggaattcc aacaggacaa ggacttcctc | 3180 |
| | | cggatcactt acaaccaggt cactcagcct | |
| | | cctatcaaat aaagtgatct gatcatcact | 3240 |
| | | tgatgtgtaa gcctctggtc tttcgccaaa | |
| | | gataacacca atgcagtagt tgatgaacct | 3300 |
| | | ctcgctaagc aaaccataga agtcagaagc | |
| | | attatgcaag attccctgcc ccatatcaat | 3360 |
| | | aaggctggat atatgggatg gcactatccc | |
| | | catttcaaaa tattgtctga aaattctctc | 3420 |
| | | agtaacagtt gtttctgaac ccctgagaag | |
| | | ttttagcttc gacttgacat atgatttcat | 3480 |
| | | cattgcattc acaacaggaa aggggacctc | |
| | | gacaagctta tgcatgtgcc aagttaacaa | 3540 |
| | | agtgctaaca tgatcttcc cggaacgcac | |
| | | atactggtca tcacctagtt tgagattttg | 3600 |
| | | tagaaacatt aagaacaaaa atgggcacat | |
| | | cattggtccc catttgctgt gatccatact | 3660 |

| SEQ ID NO. | Description | Sequence | |
|---|---|---|---|
| | | atagtttaag aacccttccc gcacattgat | |
| | | agtcattgac aagattgcat tttcaaattc | 3720 |
| | | cttatcattg tttaaacagg agcctgaaaa | |
| | | gaaacttgaa aaagactcaa aataatcttc | 3780 |
| | | tattaacctt gtgaacattt ttgtcctcaa | |
| | | atctccaata tagagttctc tatttcccc | 3840 |
| | | aacctgctct ttataagata gtgcaaattt | |
| | | cagccttcca gagtcaggac ctactgaggt | 3900 |
| | | gtatgatgtt ggtgattctt ctgagtagaa | |
| | | gcacagattt ttcaaagcag cactcataca | 3960 |
| | | ttgtgtcaac gacagagctt tactaaggga | |
| | | ctcagaatta cttccctct cactgattct | 4020 |
| | | cacgtcttct tccagtttgt cccagtcaaa | |
| | | tttgaaattc aagccttgcc tttgcatatg | 4080 |
| | | cctgtatttc cctgagtacg catttgcatt | |
| | | catttgcaac agaatcatct tcatgcaaga | 4140 |
| | | aaaccaatca ttctcagaaa agaactttct | |
| | | acaaaggttt tttgccatct catcgaggcc | 4200 |
| | | acactgatct ttaatgactg aggtgaaata | |
| | | caaaggtgac agctctgtgg aaccctcaac | 4260 |
| | | agcctcacag ataaatttca tgtcatcatt | |
| | | ggttagacat gatgggtcaa agtcttctac | 4320 |
| | | taaatggaaa gatatttctg acaagataac | |
| | | ttttcttaag tgagccatct tccctgttag | 4380 |
| | | aataagctgt aaatgatgta gtcctttgt | |
| | | atttgtaagt ttttctccat ctcctttgtc | 4440 |
| | | attggccctc ctacctcttc tgtaccgtgc | |
| | | tattgtggtg ttgacctttt cttcgagact | 4500 |
| | | tttgaagaag cttgtctctt cttctccatc | |
| | | aaaacatatt tctgccaggt tgtcttccga | 4560 |
| | | tctccctgtc tcttctccct tggaaccgat | |
| | | gaccaatcta gagactaact tggaaacttt | 4620 |
| | | atattcatag tctgagtggc tcaacttata | |
| | | cttttgtttt cttacgaaac tctccgtaat | 4680 |
| | | ttgactcaca gcactaacaa gcaatttgtt | |
| | | aaagtcatat tccagaagtc gttctccatt | 4740 |
| | | tagatgctta ttaaccacca cacttttgtt | |
| | | actagcaaga tctaatgctg tcgcacatcc | 4800 |
| | | agagttagtc atgggatcta ggctgtttag | |
| | | cttcttctct cctttgaaaa ttaaagtgcc | 4860 |
| | | gttgttaaat gaagacacca ttaggctaaa | |
| | | ggcttccaga ttaacacctg gagttgtatg | 4920 |
| | | ctgacagtca atttctttac tagtgaatct | |
| | | cttcatttgc tcatagaaca cacattcttc | 4980 |
| | | ctcaggagtg attgcttcct tggggttgac | |
| | | aaaaaaacca aattgacttt tgggctcaaa | 5040 |
| | | gaactttca aaacatttta tctgatctgt | |
| | | tagcctgtca ggggtctcct ttgtgatcaa | 5100 |
| | | atgacacagg tatgacacat tcaacataaa | |
| | | tttaaatttt gcactcaaca acaccttctc | 5160 |
| | | accagtacca aaaatagttt ttattaggaa | |
| | | tctaagcagc ttatacacca ccttctcagc | 5220 |
| | | aggtgtgatc agatcctccc tcaacttatc | |
| | | cattaatgat gtagatgaaa aatctgacac | 5280 |
| | | tattgccatc accaaatatc tgacactctg | |
| | | tacctgcttt tgatttctct ttgttgggtt | 5340 |
| | | ggtgagcatt agcaacaata gggtcctcag | |
| | | tgcaacctca atgtcggtga gacagtcttt | 5400 |
| | | caaatcagga catgatctaa tccatgaaat | |
| | | catgatgtct atcatattgt ataagacctc | 5460 |
| | | atctgaaaaa attggtaaaa agaacctttt | |
| | | aggatctgca tagaaggaaa ttaaatgacc | 5520 |
| | | atccgggcct tgtatggagt agcaccttga | |
| | | agattctcca gtcttctggt ataataggtg | 5580 |
| | | gtattcttca gagtccagtt ttattacttg | |
| | | gcaaaacact tctttgcatt ctaccacttg | 5640 |
| | | atatctcaca gaccctattt gattttgcct | |
| | | tagtctagca actgagctag ttttcatact | 5700 |
| | | gtttgttaag gccagacaaa cagatgataa | |
| | | tcttctcagg ctctgtatgt tcttcagctg | 5760 |
| | | ctctgtgctg ggttggaaat tgtaatcttc | |
| | | aaacttcgta taatacatta tcgggtgagc | 5820 |
| | | tccaattttc ataaagttct caaattcagt | |
| | | gaatggtatg tggcattctt gctcaaggtg | 5880 |
| | | ttcagacagt ccgtaatgct cgaaactcag | |
| | | tcccaccact aacaggcatt tttgaatttt | 5940 |

| SEQ ID NO. | Description | Sequence | |
|---|---|---|---|
| | | tgcaatgaac tcactaatag atgccctaaa | |
| | | caattcctca aaagacacct ttctaaacac | 6000 |
| | | ctttgacttt tttctattcc tcaaaagtct | |
| | | aatgaactcc tctttagtgc tgtgaaagct | 6060 |
| | | taccagccta tcattcacac tactatagca | |
| | | acaacccacc cagtgtttat cattttttaa | 6120 |
| | | cccttttgaat ttcgactgtt ttatcaatga | |
| | | ggaaagacac aaaacatcca gatttaacaa | 6180 |
| | | ctgtctcctt ctagtattca acagtttcaa | |
| | | actcttgact ttgtttaaca tagagaggag | 6240 |
| | | cctctcatat tcagtgctag tctcacttcc | |
| | | cctttcgtgc ccatgggtct ctgcagttat | 6300 |
| | | gaatctcatc aaaggacagg attcgactgc | |
| | | ctccctgctt aatgttaaga tatcatcact | 6360 |
| | | atcagcaagg ttttcataga gctcagagaa | |
| | | ttccttgatc aagccttcag ggtttacttt | 6420 |
| | | ctgaaagttt ctctttaatt tcccactttc | |
| | | taaatctctt ctaaacctgc tgaaaagaga | 6480 |
| | | gtttattcca aaaaccacat catcacagct | |
| | | catgttgggg ttgatgcctt cgtggcacat | 6540 |
| | | cctcataatt tcatcattgt gagttgacct | |
| | | cgcatctttc agaattttca tagagtccat | 6600 |
| | | accggagcgc ttgtcgatag tagtcttcag | |
| | | ggactcacag agtctaaaat attcagactc | 6660 |
| | | ttcaaagact ttctcatttt ggttagaata | |
| | | ctccaaaagt ttgaataaaa ggtctctaaa | 6720 |
| | | tttgaagttt gcccactctg gcataaaact | |
| | | attatcataa tcacaacgac catctactat | 6780 |
| | | tggaactaat gtgacacccg caacagcaag | |
| | | gtcttccctg atgcatgcca atttgttagt | 6840 |
| | | gtcctctata aatttcttct caaaactggc | |
| | | tggagtgctc ctaacaaaac actcaagaag | 6900 |
| | | aatgagagaa ttgtctatca gcttgtaacc | |
| | | atcaggaatg ataagtggta gtcctgggca | 6960 |
| | | tacaattcca gactccacca aaattgtttc | |
| | | cacagactta tcgtcgtggt tgtgtgtgca | 7020 |
| | | gccactcttg tctgcactgt ctatttcaat | |
| | | gcagcgtgac agcaacttga gtccctcaat | 7080 |
| | | cagaaccatt ctgggttccc tttgtcccag | |
| | | aaagttgagt ttctgccttg acaacctctc | 7140 |
| | | atcctgttct atatagttta aacataactc | |
| | | tctcaattct gagatgattt catccattgc | 7200 |
| | | gcatcaaaaa gcctaggatc ctcggtgcg | |
| | | | 7229 |
| 21 | S segment 1 of r3JUNV-P1A (containing NP) | gcgcaccggg gatcctaggc gattttggtt | |
| | | acgctataat tgtaactgtt ttctgtttgg | 60 |
| | | acaacatcaa aaacatccat tgcacaatga | |
| | | gcgacaacaa gaagcccgac aaggcccact | 120 |
| | | ctggcagcgg cggagatggc gacggcaaca | |
| | | gatgtaacct gctgcacaga tacagcctgg | 180 |
| | | aagagatcct gccctacctg ggctggctgg | |
| | | tgttcgccgt cgtgacaaca agcttcctgg | 240 |
| | | ccctgcagat gttcatcgac gccctgtacg | |
| | | aggaacagta cgagagggac gtggcctgga | 300 |
| | | tcgccagaca gagcaagaga atgagcagcg | |
| | | tggacgagga cgaggatgat gaggacgacg | 360 |
| | | aagatgacta ctacgacgat gaggatgacg | |
| | | acgacgacgc cttctacgat gacgaggacg | 420 |
| | | atgaagagga agaactggaa aacctgatgg | |
| | | acgacgagtc cgaggatgag gccgaggaag | 480 |
| | | agatgagcgt ggaaatgggc gctggcgccg | |
| | | aagagatggg agccggcgct aactgtgctt | 540 |
| | | gcgtgccagg acaccacctg agaaagaacg | |
| | | aagtgaagtg ccggatgatc tacttcttcc | 600 |
| | | acgaccccaa cttttctggtg tccatccccg | |
| | | tgaaccccaa agaacagatg gaatgcagat | 660 |
| | | gcgagaacgc cgacgaagag gtggccatgg | |
| | | aagaagaaga ggaagaggaa gaagaagaag | 720 |
| | | aagaggaaga aatgggcaac cccgacggct | |
| | | tcagcccctg agacctcctg agggtcccca | 780 |
| | | ccagcccggg cactgcccgg gctggtgtgg | |
| | | cccccagtc cgcggcctgg ccgcggactg | 840 |

| SEQ ID NO. | Description | Sequence | |
|---|---|---|---|
| | | gggaggcact gcttacagtg cataggctgc | |
| | | cttcgggagg aacagcaagc tcggtggtaa | 900 |
| | | tagaggtgta ggttcctcct catagagctt | |
| | | cccatctagc actgactgaa acattatgca | 960 |
| | | gtctagcaga gcacagtgtg gttcactgga | |
| | | ggccaacttg aagggagtat cctttcccct | 1020 |
| | | cttttcttta ttgacaacca ctccattgtg | |
| | | atatttgcat aagtgaccat atttctccca | 1080 |
| | | gacctgttga tcaaactgcc tggcttgttc | |
| | | agatgtgagc ttaacatcaa ccagtttaag | 1140 |
| | | atctcttctt ccatggaggt caaacaactt | |
| | | cctgatgtca tcggatcctt gagtagtcac | 1200 |
| | | aaccatgtct ggaggcagca agccgatcac | |
| | | gtaactaaga actcctggca ttgcatcttc | 1260 |
| | | tatgtccttc attaagatgc cgtgagagtg | |
| | | tctgctacca ttttaaacc ctttctcatc | 1320 |
| | | atgtggtttt ctgaagcagt gaatgtactg | |
| | | cttacctgca ggttggaata atgccatctc | 1380 |
| | | aacagggtca gtggctggtc cttcaatgtc | |
| | | gagccaaagg gtgttggtgg ggtcgagttt | 1440 |
| | | ccccactgcc tctctgatga cagcttcttg | |
| | | tatctctgtc aagttagcca atctcaaatt | 1500 |
| | | ctgaccgttt ttttccggct gtctaggacc | |
| | | agcaactggt ttccttgtca gatcaatact | 1560 |
| | | tgtgttgtcc catgacctgc ctgtgatttg | |
| | | tgatctagaa ccaatataag gccaaccatc | 1620 |
| | | gccagaaaga caaagtttgt acaaaaggtt | |
| | | ttcataagga tttctattgc ctggtttctc | 1680 |
| | | atcaataaac atgccttctc ttcgtttaac | |
| | | ctgaatggtt gattttatga gggaagagaa | 1740 |
| | | gttttctggg gtgactctga ttgtttccaa | |
| | | catgtttcca ccatcaagaa tagatgctcc | 1800 |
| | | agcctttact gcagctgaaa gactgaagtt | |
| | | gtaaccagaa atattgatgg agctttcatc | 1860 |
| | | tttagtcaca atctgaaggc agtcatgttc | |
| | | ctgagtcagt ctgtcaaggt cacttaagtt | 1920 |
| | | tggatacttc acagtgtata gaagcccaag | |
| | | tgaggttaaa gcttgtatga cactgttcat | 1980 |
| | | tgtctcacct ccttgaacag tcatgcatgc | |
| | | aattgtcaat gcaggaacag agccaaactg | 2040 |
| | | attgtttagc tttgaagggt ctttaacatc | |
| | | ccatatcctc accacaccat ttcccccagt | 2100 |
| | | cccttgctgt tgaaatccca gtgttctcaa | |
| | | tatctctgat cttttagcaa gttgtgactg | 2160 |
| | | ggacaagtta cccatgtaaa cccctgaga | |
| | | gcctgtctct gctcttctta tcttgttttt | 2220 |
| | | taatttctca aggtcagacg ccaactccat | |
| | | cagttcatcc ctccccagat ctcccacctt | 2280 |
| | | gaaaactgtg tttcgttgaa cactcctcat | |
| | | ggacatgagt ctgtcaacct ctttattcag | 2340 |
| | | gtccctcaac ttgttgagat cttcttcccc | |
| | | cttttagtc tttctgagtg cccgctgcac | 2400 |
| | | ctgtgccact tggttgaagt cgatgctgtc | |
| | | agcaattagc ttggcgtcct tcaaaacatc | 2460 |
| | | tgacttgaca gtctgagtga attggctcaa | |
| | | acctctcctt aaggactgag tccatctaaa | 2520 |
| | | gcttggaacc tccttggagt gtgccatgcc | |
| | | agaagttctg gtgattttga tctagaatag | 2580 |
| | | agttgctcag tgaaagtgtt agacactatg | |
| | | cctaggatcc actgtgcg | 2628 |
| 22 | S segment 2 of r3JUNV-P1A (containing GP) | gcgcaccggg gatcctaggc gattttggtt acgctataat tgtaactgtt ttctgtttgg | 60 |
| | | acaacatcaa aaacatccat tgcacaatga | |
| | | gcgacaacaa gaagcccgac aaggcccact | 120 |
| | | ctggcagcgg cggagatggc gacggcaaca | |
| | | gatgtaacct gctgcacaga tacagcctgg | 180 |
| | | aagagatcct gccctacctg ggctgctgg | |
| | | tgttcgccgt cgtgacaaca agcttcctgg | 240 |
| | | ccctgcagat gttcatcgac gccctgtacg | |
| | | aggaacagta cgagagggac gtggcctgga | 300 |
| | | tcgccagaca gagcaagaga atgagcagcg | |
| | | tggacgagga cgaggatgat gaggacgacg | 360 |
| | | aagatgacta ctacgacgat gaggatgacg | |
| | | acgacgacgc cttctacgat gacgaggacg | 420 |
| | | atgaagagga agaactggaa aacctgatgg | |

| SEQ ID NO. | Description | Sequence | |
|---|---|---|---|
| | | acgacgagtc cgaggatgag gccgaggaag agatgagcgt ggaaatgggc gctggcgccg | 480 |
| | | aagagatggg agccggcgct aactgtgctt gcgtgccagg acaccacctg agaagaacg | 540 |
| | | aagtgaagtg ccggatgatc tacttcttcc acgaccccaa ctttctggtg tccatccccg | 600 |
| | | tgaaccccaa agaacagatg gaatgcagat gcgagaacgc cgacgaagag gtggccatgg | 660 |
| | | aagaagaaga ggaagaggaa gaagaagaag aagaggaaga aatgggcaac cccgacggct | 720 |
| | | tcagcccctg agacctcctg agggtcccca ccagcccggg cactgcccgg gctggtgtgg | 780 |
| | | cccccagtc cgcggcctgg ccgcggactg gggaggcact gcatgggca gttcattagc | 840 |
| | | ttcatgcaag aaataccaac cttttttgcag gaggctctga acattgctct tgttgcagtc | 900 |
| | | agtctcattg ccatcattaa gggtatagtg aacttgtaca aaagtggttt attccaattc | 960 |
| | | tttgtattcc tagcgcttgc aggaagatcc tgcacagaag aagctttcaa aatcggactg | 1020 |
| | | cacactgagt tccagactgt gtccttctca atggtgggtc tcttttccaa caatccacat | 1080 |
| | | gacctacctt tgttgtgtac cttaaacaag agccatcttt acattaaggg gggcaatgct | 1140 |
| | | tcatttcaga tcagctttga tgatattgca gtattgttgc cacagtatga tgttataata | 1200 |
| | | caacatccag cagatatgag ctggtgttcc aaaagtgatg atcaaatttg gttgtctcag | 1260 |
| | | tggttcatga atgctgtggg acatgattgg catctagacc caccatttct gtgtaggaac | 1320 |
| | | cgtgcaaaga cagaaggctt catctttcaa gtcaacacct ccaagactgg tgtcaatgga | 1380 |
| | | aattatgcta agaagtttaa gactggcatg catcatttat atagagaata cctgacccct | 1440 |
| | | tgcttgaatg gcaaactgtg cttaatgaag gcacaaccta ccagttggcc tctccaatgt | 1500 |
| | | ccactcgacc acgttaacac attcacttc cttacaagag gtaaaaacat tcaacttcca | 1560 |
| | | aggaggtcct tgaaagcatt cttctcctgg tctttgacag actcatccgg caaggatacc | 1620 |
| | | cctggaggct attgtctaga agagtggatg ctcgtagcag ccaaaatgaa gtgttttggc | 1680 |
| | | aatactgctg tagcaaaatg caatttgaat catgactctg aattctgtga catgttgagg | 1740 |
| | | ctcttttgatt acaacaaaaa tgctatcaaa accctaaatg atgaaactaa gaaacaagta | 1800 |
| | | aatctgatgg ggcagacaat caatgccctg atatctgaca atttattgat gaaaaacaaa | 1860 |
| | | attagggaac tgatgagtgt cccttactgc aattacacaa aatttttggta tgtcaaccac | 1920 |
| | | acactttcag gacaacactc attaccaagg tgctggttaa taaaaaacaa cagctatttg | 1980 |
| | | aacatctctg acttccgtaa tgactggata ttagaaagtg acttcttaat ttctgaaatg | 2040 |
| | | ctaagcaaag agtattcgga caggcagggt aaaaactcctt tgactttagt tgacatctgt | 2100 |
| | | atttggagca cagtattctt cacagcgtca ctcttccttc acttggtggg tataccctcc | 2160 |
| | | cacagacaca tcaggggcga agcatgccct ttgccacaca ggttgaacag cttgggtggt | 2220 |
| | | tgcagatgtg gtaagtaccc caatctaaag aaaccaacag tttggcgtag aggacactaa | 2280 |
| | | gccagaagtt ctggtgattt tgatctagaa tagagttgct cagtgaaagt gttagacact | 2340 |
| | | atgcctagga tccactgtgc g | 2391 |
| 23 | L segment of r3JUNV-P1A | gcgcaccggg gatcctaggc gtaac

| SEQ ID NO. | Description | Sequence | |
|---|---|---|---|
| | | aatatctgct ggaagcccct gcccaccaca | |
| | | atcacagtac cggtggagcc aacagcacca | 360 |
| | | ccaccatagg cagactgcac agggtcagac | |
| | | ccgacccccc gggggggcccc catggggacc | 420 |
| | | ccccgtgggg gaacccgggg ggtgatgcgc | |
| | | cattagtcaa tgtctttgat ctcgactttg | 480 |
| | | tgcttcagtg gcctgcatgt cacccctttc | |
| | | aatctgaact gcccttgggg atctgatatc | 540 |
| | | agcaggtcat ttaaagatct gctgaatgcc | |
| | | accttgaaat ttgagaattc caaccagtca | 600 |
| | | ccaaatttat caagtgaacg gatcaactgc | |
| | | tctttgtgta gatcataaac gaggacaaag | 660 |
| | | tcctcttgct gaaataatat tgtttgtgat | |
| | | gttgttttta gataaggcca tagttggctt | 720 |
| | | aataaggttt ccacactatc aatgtcctct | |
| | | agtgctccaa ttgccttgac tatgacatcc | 780 |
| | | ccagacaact caactctata tgttgacaac | |
| | | ctttcattac ctctgtaaaa gatacctct | 840 |
| | | ttcaagacaa gaggttctcc tgggttatct | |
| | | ggcccaatga ggtcatatgc atacttgtta | 900 |
| | | cttagttcag aataaaagtc accaaagttg | |
| | | aacttaacat ggctcagaat attgtcatca | 960 |
| | | tttgtcgcag cgtagcctgc atcaataaac | |
| | | aagccagcta ggtcaaagct ctcatggcct | 1020 |
| | | gtgaacaatg gtaggctagc gataaccagt | |
| | | gcaccatcca acaatgagtg gcttccctca | 1080 |
| | | gacccagaaa cacattgact cattgcatcc | |
| | | acattcagct ctaattcagg ggtaccgaca | 1140 |
| | | tcatccactc ctagtgaact gacaatggtg | |
| | | taactgtaca ccatctttct tctaagttta | 1200 |
| | | aattttgtcg aaactcgtgt gtgttctact | |
| | | tgaatgatca attttagttt cacagcttct | 1260 |
| | | tggcaagcaa cattgcgcaa cacagtgtgc | |
| | | aggtccatca tgtcttcctg aggcaacaag | 1320 |
| | | gagatgttgt caacagagac accctcaagg | |
| | | aaaaccttga tattatcaaa gctagaaact | 1380 |
| | | acataaccca ttgcaatgtc ttcaacaaac | |
| | | attgctcttg atactttatt attcctaact | 1440 |
| | | gacaaggtaa aatctgtgag ttcagctaga | |
| | | tctacttgac tgtcatcttc tagatctaga | 1500 |
| | | acttcattga accaaaagaa ggatttgaga | |
| | | cacgatgttg acatgactag tgggtttatc | 1560 |
| | | atcgaagata agacaacttg caccatgaag | |
| | | ttcctgcaaa cttgctgtgg gctgatgcca | 1620 |
| | | acttcccaat ttgtatactc tgactgtcta | |
| | | acatgggctg aagcgcaatc actctgtttc | 1680 |
| | | acaatataaa cattattatc tcttactttc | |
| | | aataagtgac ttataatccc taagttttca | 1740 |
| | | ttcatcatgt ctagagccac acagacatct | |
| | | agaaacttga gtcttccact atccaaagat | 1800 |
| | | ctgttcactt gaagatcatt cataaagggt | |
| | | gccaaatgtt cttcaaatag tttggggtaa | 1860 |
| | | tttcttcgta tagaatgcaa tacatggttc | |
| | | atgcctaatt ggtcttctat ctgtcgtact | 1920 |
| | | gctttgggtt taacagccca gaagaaattc | |
| | | ttattacata agaccagagg ggcctgtgga | 1980 |
| | | ctcttaatag cagaaaacac ccactcccct | |
| | | aactcacagg catttgtcag caccaaagag | 2040 |
| | | aagtaatccc acaaaattgg tttagaaaat | |
| | | tggttaactt ctttaagtga ttttgacag | 2100 |
| | | taaataactt taggctttct ctcacaaatt | |
| | | ccacaaagac atggcattat tcgagtaaat | 2160 |
| | | atgtccttta tatacagaaa tccgcctta | |
| | | ccatccctaa cacacttact ccccatactc | 2220 |
| | | ttacaaaacc caatgaagcc tgaggcaaca | |
| | | gaagactgaa atgcagattt gttgattgac | 2280 |
| | | tctgccaaga tcttcttcac gccttttgtg | |
| | | aaatttcttg acagcctgga ctgtattgtc | 2340 |
| | | cttatcaatg ttggcatctc ttcttctct | |
| | | aacactcttc gacttgtcat gagtttggtc | 2400 |
| | | ctcaagacca acctcaagtc cccaaagctc | |
| | | gctaaattga cccatctgta gtctagagtt | 2460 |
| | | tgtctgattt catcttcact acacccggca | |
| | | tattgcagga atccggataa agcctcatcc | 2520 |
| | | cctcccctgc ttatcaagtt gataaggttt | |
| | | tcctcaaaga ttttgcctct cttaatgtca | 2580 |

| SEQ ID NO. | Description | Sequence | |
|---|---|---|---|
| | | ttgaacactt tcctcgcgca gttccttata | |
| | | aacattgtct ccttatcatc agaaaaaata | 2640 |
| | | gcttcaattt tcctctgtag acggtaccct | |
| | | ctagacccat caacccagtc tttgacatct | 2700 |
| | | tgttcttcaa tagctccaaa cggagtctct | |
| | | ctgtatccag agtatctaat caattggttg | 2760 |
| | | actctaatgg aaatctttga cactatatga | |
| | | gtgctaaccc cattagcaat acattgatca | 2820 |
| | | caaattgtgt ctatggtctc tgacagttgt | |
| | | gttggagttt tacacttaac gttgtgtaga | 2880 |
| | | gcagcagaca caaacttggt gagtaaagga | |
| | | gtctcttcac ccatgacaaa aaatcttgac | 2940 |
| | | ttaaactcag caacaaaagt tcctatcaca | |
| | | ctctttgggc tgataaactt gtttaattta | 3000 |
| | | gaagataaga attcatggaa gcacaccatt | |
| | | tccagcagtt ctgtcctgtc ttgaaacttt | 3060 |
| | | tcatcactaa ggcaaggaat ttttataagg | |
| | | ctaacctggt catcgctgga ggtataagtg | 3120 |
| | | acaggtatca catcatacaa taagtcaagt | |
| | | gcataacaca gaaattgttc agtaattagc | 3180 |
| | | ccatataaat ctgatgtgtt gtgcaagatt | |
| | | ccctggccca tgtccaagac agacattata | 3240 |
| | | tggctgggga cctggtccct tgactgcaga | |
| | | tactggtgaa aaaactcttc accaacacta | 3300 |
| | | gtacagtcac aacccattaa acctaaagat | |
| | | ctcttcaatt tccctacaca gtaggcttct | 3360 |
| | | gcaacattaa ttggaacttc aacgaccgta | |
| | | tgaagatgcc atttgagaat gttcattact | 3420 |
| | | ggttcaagat tcacctttgt tctatctctg | |
| | | ggattcttca attctaatgt gtacaaaaaa | 3480 |
| | | gaaaggaaaa gtgctgggct catagttggt | |
| | | ccccatttgg agtggtcata tgaacaggac | 3540 |
| | | aagtcaccat tgttaacagc cattttcata | |
| | | tcacagattg cacgttcgaa ttccttttct | 3600 |
| | | gaattcaagc atgtgtattt cattgaacta | |
| | | cccacagctt ctgagaagtc ttcaactaac | 3660 |
| | | ctggtcatca gcttagtgtt gaggtctccc | |
| | | acatacagtt ctctatttga gccaacctgc | 3720 |
| | | tccttataac ttagtccaaa tttcaagttc | |
| | | cctgtatttg agctgatgct tgtgaactct | 3780 |
| | | gtaggagagt cgtctgaata gaaacataaa | |
| | | ttccgtaggg ctgcatttgt aaaataactt | 3840 |
| | | ttgtctagct tatcagcaat ggcttcagaa | |
| | | ttgctttccc tggtactaag ccgaacctca | 3900 |
| | | tcctttagtc tcagaacttc actggaaaag | |
| | | cccaatctag atctacttct atgctcataa | 3960 |
| | | ctacccaatt tctgatcata atgtccttga | |
| | | attaaaagat acttgaagca ttcaaagaat | 4020 |
| | | tcatcttctt ggtaggctat tgttgtcaaa | |
| | | ttttttaata acaaacccaa agggcagatg | 4080 |
| | | tcctgcggtg cttcaagaaa ataagtcaat | |
| | | ttaaatggag atagataaac agcatcacat | 4140 |
| | | aactcttttat acacatcaga cctgagcaca | |
| | | tctggatcaa aatccttcac ctcatgcatt | 4200 |
| | | gacacctctg ctttaatctc tctcaacact | |
| | | ccaaaagggg cccacaatga ctcaagagac | 4260 |
| | | tctcgctcat caacagatgg atttttgat | |
| | | ttcaacttgg tgatctcaac ttttgtcccc | 4320 |
| | | tcactattag ccatcttggc tagtgtcatt | |
| | | tgtacgtcat ttctaatacc ctcaaaggcc | 4380 |
| | | cttacttgat cctctgttaa actctcatac | |
| | | atcactgata attcttcttg attggttctg | 4440 |
| | | gttcttgaac cggtgctcac aagacctgtt | |
| | | agattttta atattaagta gtccatggaa | 4500 |
| | | tcaggatcaa gattatacct gccttttgtt | |
| | | ttaaacctct cagccatagt agaaacgcat | 4560 |
| | | gttgaaacaa gtttctcctt atcataaaca | |
| | | gaaagaatat ttccaagttc gtcgagcttg | 4620 |
| | | gggattacca cacttttatt gcttgacaga | |
| | | tccagagctg tgctagtgat gttaggcctg | 4680 |
| | | tagggattgc ttttcagttc acctgtaact | |
| | | ttaagtcttc ctctattgaa gagagaaatg | 4740 |
| | | cagaaggaca aaatctcttt acacactcct | |
| | | ggaatttgag tatctgagga agtcttagcc | 4800 |
| | | tctttggaaa agaatctgtc caatcctctt | |
| | | atcatggtgt cctcttgttc cagtgttaga | 4860 |

| SEQ ID NO. | Description | Sequence | |
|---|---|---|---|
| | | ctcccactta gagggggtt tacaacaaca | |
| | | caatcaaact tgactttggg ctcaataaac | 4920 |
| | | ttctcaaaac actttatttg atctgtcagg | |
| | | cgatcaggtg tctctttggt taccaagtga | 4980 |
| | | cacagataac taacatttaa tagatattta | |
| | | aaccttcttg caaagtaaag atctgcatct | 5040 |
| | | tccccttcac ccaaaattgt ctggaaaagt | |
| | | tccacagcca tcctctgaat cagcacctct | 5100 |
| | | gatccagaca tgcagtcgac ccttaacttt | |
| | | gacatcaaat ccacatgatg gatttgattt | 5160 |
| | | gcatatgcca tcaagaaata tcttagacct | |
| | | tgtaaaaatg tctggttcct tttggaaggg | 5220 |
| | | gaacagagta cagctaacac taacaatctt | |
| | | aatattggcc ttgtcattgt catgagttcg | 5280 |
| | | tggctaaaat ccaaccagct ggtcatttcc | |
| | | tcacacattt caattaacac atcctccgaa | 5340 |
| | | aatataggca ggaaaaatct ctttggatca | |
| | | cagtaaaaag agccttgttc ttccaatacc | 5400 |
| | | ccattgatgg atagatagat agaatagcac | |
| | | cttgacttct cacctgtttt ttggtaaaac | 5460 |
| | | aagagaccaa atgtattctt tgtcagatga | |
| | | aatctttgta cataacactc tcttagtcta | 5520 |
| | | acattcccaa aatatctaga atactctctt | |
| | | tcattgatta acaatcggga ggaaaatgat | 5580 |
| | | gtcttcatcg agttgaccaa tgcaagggaa | |
| | | atggaggaca aaatcctaaa taatttcttc | 5640 |
| | | tgctcacctt ccactaagct gctgaatggc | |
| | | tgatgtctac agattttctc aaattccttg | 5700 |
| | | ttaatagtat atctcatcac tggtctgtca | |
| | | gaaacaagtg cctgagctaa aatcatcaag | 5760 |
| | | ctatccatat cagggtgttt tattagtttt | |
| | | tccagctgtg accagagatc ttgatgagag | 5820 |
| | | ttcttcaatg ttctggaaca cgcttgaacc | |
| | | cacttggggc tggtcatcaa tttcttcctt | 5880 |
| | | attagtttaa tcgcctccag aatatctaga | |
| | | agtctgtcat tgactaacat taacatttgt | 5940 |
| | | ccaacaacta ttcccgcatt tcttaacctt | |
| | | acaattgcat catcatgcgt tttgaaaaga | 6000 |
| | | tcacaaagta aattgagtaa aactaagtcc | |
| | | agaaacagta aagtgtttct cctggtgttg | 6060 |
| | | aaaactttta gaccttcac tttgttacac | |
| | | acggaaaggg cttgaagata acacctctct | 6120 |
| | | acagcatcaa tagatataga attctcatct | |
| | | gactggcttt ccatgttgac ttcatctatt | 6180 |
| | | ggatgcaatg cgatagagta gactacatcc | |
| | | atcaacttgt ttgcacaaaa agggcagctg | 6240 |
| | | ggcacatcac tgtctttgtg gcttcctaat | |
| | | aagatcaagt catttataag cttagacttt | 6300 |
| | | tgtgaaaatt tgaatttccc caactgcttg | |
| | | tcaaaaatct ccttcttaaa ccaaaacctt | 6360 |
| | | aactttatga gttcttctct tatgacagat | |
| | | tctctaatgt ctcctctaac cccaacaaag | 6420 |
| | | agggattcat ttaacctctc atcataaccc | |
| | | aaagaattct ttttcaagca ttcgatgttt | 6480 |
| | | tctaatccca agctctggtt ttttgtgttg | |
| | | gacaaactat ggatcaatcg ctggtattct | 6540 |
| | | tgttcttcaa tattaatctc ttgcataaat | |
| | | tttgatttct ttaggatgtc gatcagcaac | 6600 |
| | | caccgaactc tttcaacaac ccaatcagca | |
| | | aggaatctat tgctgtagct agatctgcca | 6660 |
| | | tcaaccacag gaaccaacgt aatccctgcc | |
| | | cttagtaggt cggactttag gtttaagagc | 6720 |
| | | tttgacatgt cactcttcca ttttctctca | |
| | | aactcatcag gattgaccct aacaaaggtt | 6780 |
| | | tccaatagga tgagtgtttt ccctgtgagt | |
| | | ttgaagccat ccggaatgac ttttggaagg | 6840 |
| | | gtgggacata gtatgccata gtcagacagg | |
| | | atcacatcaa caaacttctg atctgaattg | 6900 |
| | | atctgacagg cgtgtgcctc acaggactca | |
| | | agctctacta aacttgacag aagtttgaac | 6960 |
| | | ccttccaaca acagagagct ggggtgatgt | |
| | | tgagataaaa agatgtccct ttggtatgct | 7020 |

| SEQ ID NO. | Description | Sequence | |
|---|---|---|---|
| | | agctcctgtc tttctggaaa atgctttcta<br>ataaggcttt ttatttcatt tactgattcc<br>tccatgctca agtgccgcct aggatcctcg gtgcg | 7080<br><br>7115 |
| 24 | Amino acid sequence of a P815 mouse mastocytoma-derived self antigen P1A | Met Ser Asp Asn Lys Lys Pro Asp Lys Ala<br>His Ser Gly Ser Gly Gly Asp Gly Asp Gly<br>Asn Arg Cys Asn Leu Leu His Arg Tyr Ser<br>Leu Glu Glu Ile Leu Pro Tyr Leu Gly Trp<br>Leu Val Phe Ala Val Val Thr Thr Ser Phe<br>Leu Ala Leu Gln Met Phe Ile Asp Ala Leu<br>Tyr Glu Glu Gln Tyr Glu Arg Asp Val Ala<br>Trp Ile Ala Arg Gln Ser Lys Arg Met Ser<br>Ser Val Asp Glu Asp Glu Asp Asp Glu Asp<br>Asp Glu Asp Asp Tyr Tyr Asp Asp Glu Asp<br>Asp Asp Asp Asp Ala Phe Tyr Asp Asp Glu<br>Asp Asp Glu Glu Glu Leu Glu Asn Leu<br>Met Asp Asp Glu Ser Glu Asp Glu Ala Glu<br>Glu Glu Met Ser Val Glu Met Gly Ala Gly<br>Ala Glu Glu Met Gly Ala Gly Ala Asn Cys<br>Ala Cys Val Pro Gly His His Leu Arg Lys<br>Asn Glu Val Lys Cys Arg Met Ile Tyr Phe<br>Phe His Asp Pro Asn Phe Leu Val Ser Ile<br>Pro Val Asn Pro Lys Glu Gln Met Glu Cys<br>Arg Cys Glu Asn Ala Asp Glu Glu Val Ala<br>Met Glu Glu Glu Glu Glu Glu Glu Glu Glu<br>Glu Glu Glu Glu Glu Met Gly Asn Pro Asp<br>Gly Phe Ser Pro | |

What is claimed:

1. An arenavirus genomic segment, wherein the genomic segment is engineered to carry a viral open reading frame ("ORF") in a position other than the wild-type position of the ORF, wherein the arenavirus genomic segment is selected from the group consisting of:
   (i) an S segment, wherein the ORF encoding the nucleoprotein ("NP") is under control of an arenavirus 5' untranslated region ("UTR");
   (ii) an S segment, wherein the ORF encoding the matrix protein Z ("Z protein") is under control of an arenavirus 5' UTR;
   (iii) an S segment, wherein the ORF encoding the RNA dependent RNA polymerase L ("L protein") is under control of an arenavirus 5' UTR;
   (iv) an S segment, wherein the ORF encoding the viral glycoprotein ("GP") is under control of an arenavirus 3' UTR;
   (v) an S segment, wherein the ORF encoding the L protein is under control of an arenavirus 3' UTR; and
   (vi) an S segment, wherein the ORF encoding the Z protein is under control of an arenavirus 3' UTR.

2. The arenavirus genomic segment of claim 1, wherein the arenavirus 3' UTR is the 3' UTR of the arenavirus S segment, and wherein the arenavirus 5' UTR is the 5' UTR of the arenavirus S segment.

3. A cDNA of the arenavirus genomic segment of claim 1.

4. A DNA expression vector comprising the cDNA of claim 3.

5. A host cell comprising the vector of claim 4.

6. An arenavirus particle comprising the arenavirus genomic segment of claim 1 and a second arenavirus genomic segment so that the arenavirus particle comprises an S segment and an L segment.

7. The arenavirus particle of claim 6, wherein the arenavirus particle is:
   (i) infectious and replication competent;
   (ii) attenuated; or
   (iii) infectious but unable to produce further infectious progeny in non-complementing cells.

8. The arenavirus particle of claim 7, wherein:
   (i) at least one of the four ORFs encoding GP, NP, Z protein, and L protein is removed or functionally inactivated;
   (ii) at least one of the four ORFs encoding GP, NP, Z protein, and L protein is removed and replaced with a heterologous ORF from an organism other than an arenavirus;
   (iii) only one of the four ORFs encoding GP, NP, Z protein and L protein is removed and replaced with a heterologous ORF from an organism other than an arenavirus;
   (iv) the ORF encoding GP is removed and replaced with a heterologous ORF from an organism other than an arenavirus;
   (v) the ORF encoding NP is removed and replaced with a heterologous ORF from an organism other than an arenavirus;
   (vi) the ORF encoding the Z protein is removed and replaced with a heterologous ORF from an organism other than an arenavirus; or
   (vii) the ORF encoding the L protein is removed and replaced with a heterologous ORF from an organism other than an arenavirus.

9. The arenavirus particle of claim 8, wherein the heterologous ORF encodes an antigen derived from an infectious organism, tumor, or allergen.

10. The arenavirus particle of claim 9, wherein the heterologous ORF encoding an antigen is selected from human immunodeficiency virus antigens, hepatitis C virus antigens, varizella zoster virus antigens, cytomegalovirus antigens, *Mycobacterium tuberculosis* antigens, and tumor associated antigens.

11. A vaccine comprising the arenavirus particle of claim 8 and a pharmaceutically acceptable carrier.

12. A pharmaceutical composition comprising an arenavirus particle of claim 8 and a pharmaceutically acceptable carrier.

13. The arenavirus genomic segment of claim 1, wherein the arenavirus genomic segment is derived from lymphocytic choriomeningitis virus ("LCMV").

14. A tri-segmented arenavirus particle comprising one L segment and two S segments, wherein one of the two S segments is selected from the group consisting of:

(i) an S segment, wherein the ORF encoding the NP is under control of an arenavirus 5' UTR, (ii) an S segment, wherein the ORF encoding the Z protein is under control of an arenavirus 5' UTR, (iii) an S segment, wherein the ORF encoding the L protein is under control of an arenavirus 5' UTR, (iv) an S segment, wherein the ORF encoding the GP is under control of an arenavirus 3' UTR, (v) an S segment, wherein the ORF encoding the L protein is under control of an arenavirus 3' UTR, and (vi) an S segment, wherein the ORF encoding the Z protein is under control of an arenavirus 3' UTR.

15. The tri-segmented arenavirus particle of claim 14, wherein inter-segmental recombination of the two S segments, uniting two arenavirus ORFs on only one instead of two separate segments, abrogates viral promoter activity.

16. The tri-segmented arenavirus particle of claim 14, wherein one of the two S segments is an S segment, wherein the ORF encoding the GP is under control of an arenavirus 3' UTR.

17. The tri-segmented arenavirus particle of claim 16, wherein the arenavirus 3' UTR is the 3' UTR of the arenavirus S segment, and wherein the arenavirus 5' UTR is the 5' UTR of the arenavirus S segment.

18. The tri-segmented arenavirus particle of claim 14, wherein the two S segments comprise (i) one or two heterologous ORFs from an organism other than an arenavirus; or (ii) one or two duplicated arenavirus ORFs; or (iii) one heterologous ORF from an organism other than an arenavirus and one duplicated arenavirus ORF.

19. The tri-segmented arenavirus particle of claim 18, wherein the heterologous ORF encodes an antigen derived from an infectious organism, tumor, or allergen.

20. The tri-segmented arenavirus particle of claim 19, wherein the heterologous ORF encoding an antigen is selected from human immunodeficiency virus antigens, hepatitis C virus antigens, varizella zoster virus antigens, cytomegalovirus antigens, *Mycobacterium tuberculosis* antigens, and tumor associated antigens.

21. The tri-segmented arenavirus particle of claim 14, wherein the tri-segmented arenavirus particle comprises all four arenavirus ORFs, and wherein the tri-segmented arenavirus particle is infectious and replication competent.

22. A tri-segmented arenavirus particle comprising one L segment and two S segments, wherein a first S segment is engineered to carry an ORF encoding GP in a position under control of an arenavirus 3' UTR and an ORF encoding a first gene of interest in a position under control of an arenavirus 5' UTR and a second S segment is engineered to carry an ORF encoding NP in a position under control of an arenavirus 3' UTR and an ORF encoding a second gene of interest in a position under control of an arenavirus 5' UTR.

23. A tri-segmented arenavirus particle comprising one L segment and two S segments, wherein a first S segment is engineered to carry an ORF encoding GP in a position under control of an arenavirus 5' UTR and an ORF encoding a first gene of interest in a position under control of an arenavirus 3' UTR and a second S segment is engineered to carry an ORF encoding NP in a position is under control of an arenavirus 5' UTR and an ORF encoding a second gene of interest in a position under control of an arenavirus 3' UTR.

24. The tri-segmented arenavirus particle of claim 22 or 23, wherein the gene of interest encodes an antigen derived from an infectious organism, tumor, or allergen.

25. The tri-segmented arenavirus particle of claim 24, wherein the gene of interest encodes an antigen selected from human immunodeficiency virus antigens, hepatitis C virus antigens, varizella zoster virus antigens, cytomegalovirus antigens, *Mycobacterium tuberculosis* antigens, and tumor associated antigens.

26. A cDNA of the tri-segmented arenavirus particle genome of claim 14 or 22 or 23.

27. A DNA expression vector comprising the cDNA of claim 26.

28. A host cell comprising the vector of claim 27.

29. A vaccine comprising a tri-segmented arenavirus particle of any one of claim 14, 22, or 23 and a pharmaceutically acceptable carrier.

30. A pharmaceutical composition comprising a tri-segmented arenavirus particle of any one of the claims 14, 22, or 23 and a pharmaceutically acceptable carrier.

31. The tri-segmented arenavirus particle of any one of claim 14, 22, or 23, wherein the tri-segmented arenavirus particle is derived from LCMV.

* * * * *